US009745607B2

(12) United States Patent
Conradie et al.

(10) Patent No.: US 9,745,607 B2
(45) Date of Patent: Aug. 29, 2017

(54) METHODS OF PRODUCING 6-CARBON CHEMICALS USING 2,6-DIAMINOPIMELATE AS PRECURSOR TO 2-AMINOPIMELATE

(71) Applicant: INVISTA North America S.á r.l., Wilmington, DE (US)

(72) Inventors: Alex Van Eck Conradie, Eaglescliffe (GB); Adriana Leonora Botes, Rosedale East (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 14/714,164

(22) Filed: May 15, 2015

(65) Prior Publication Data

US 2015/0361462 A1 Dec. 17, 2015

Related U.S. Application Data

(60) Provisional application No. 61/993,532, filed on May 15, 2014.

(51) Int. Cl.
| | |
|---|---|
| C12P 13/00 | (2006.01) |
| C12N 15/52 | (2006.01) |
| C12P 13/04 | (2006.01) |
| C12N 9/02 | (2006.01) |
| C12N 9/10 | (2006.01) |
| C12P 7/42 | (2006.01) |

(52) U.S. Cl.
CPC .......... *C12P 13/001* (2013.01); *C12N 9/0008* (2013.01); *C12N 9/1096* (2013.01); *C12N 15/52* (2013.01); *C12P 13/005* (2013.01); *C12P 13/04* (2013.01); *C12P 7/42* (2013.01); *C12Y 102/99006* (2013.01)

(58) Field of Classification Search
CPC ......... C12P 13/001; C12P 13/005; C12P 7/42; C12N 9/1025
See application file for complete search history.

(56) References Cited

U.S. PATENT DOCUMENTS

| | | | |
|---|---|---|---|
| 2,439,513 A | 4/1948 | Hamblet et al. |
| 2,557,282 A | 6/1951 | Hamblet et al. |
| 2,791,566 A | 5/1957 | Jeffers |
| 2,840,607 A | 6/1958 | Attane, Jr. et al. |
| 2,971,010 A | 2/1961 | Gilby, Jr. et al. |
| 3,023,238 A | 2/1962 | Chapman et al. |
| 3,338,959 A | 8/1967 | Sciance et al. |
| 3,365,490 A | 1/1968 | Arthur et al. |
| 3,515,751 A | 6/1970 | Oberster |
| 3,719,561 A | 3/1973 | Tanaka et al. |
| 4,058,555 A | 11/1977 | Mims |
| 6,255,451 B1 | 7/2001 | Koch et al. |
| 6,372,939 B1 | 4/2002 | Bunnel et al. |
| 8,088,607 B2 | 1/2012 | Buggard et al. |

| | | |
|---|---|---|
| 2004/0054235 A1 | 3/2004 | Fodor et al. |
| 2010/0035309 A1 | 2/2010 | Havemen et al. |
| 2010/0151536 A1 | 6/2010 | Baynes et al. |
| 2010/0203600 A1 | 8/2010 | Dubois |
| 2010/0317069 A1 | 12/2010 | Burk et al. |
| 2011/0171699 A1 | 7/2011 | Raemakers-Franken et al. |
| 2011/0256599 A1 | 10/2011 | Hu et al. |
| 2012/0064252 A1 | 3/2012 | Beatty |
| 2012/0101009 A1 | 4/2012 | Beatty |
| 2013/0065279 A1 | 3/2013 | Burk et al. |
| 2013/0183728 A1 | 7/2013 | Botes |
| 2013/0210090 A1 | 8/2013 | Pearlman et al. |
| 2013/0217081 A1 | 8/2013 | Pearlman et al. |
| 2013/0224807 A1 | 8/2013 | Pearlman et al. |
| 2014/0186902 A1 | 7/2014 | Botes et al. |
| 2014/0186904 A1 | 7/2014 | Botes et al. |
| 2014/0193861 A1 | 7/2014 | Botes et al. |
| 2014/0193862 A1 | 7/2014 | Botes et al. |
| 2014/0193863 A1 | 7/2014 | Botes et al. |
| 2014/0193864 A1 | 7/2014 | Botes et al. |
| 2014/0193865 A1 | 7/2014 | Botes et al. |
| 2014/0196904 A1 | 7/2014 | Fontenelle et al. |
| 2014/0199737 A1 | 7/2014 | Botes et al. |
| 2014/0248673 A1 | 9/2014 | Botes et al. |

(Continued)

FOREIGN PATENT DOCUMENTS

| | | |
|---|---|---|
| EP | 2647718 | 10/2013 |
| WO | WO 2008/006037 | 1/2008 |
| WO | WO 2008/145737 | 12/2008 |

(Continued)

OTHER PUBLICATIONS

"Enterococcus faecalis V583 bifuntional acetaldehyde-CoA/Alcohol Dehydrogenase," biocyc.org, retrieved on Jun. 19, 2014, http://biocyc.org/EFAE226185/N_EW-IMAGE?type=ENZYME&object=GH11-877-MONOMER, 9 pages.

"Information on EC 1.2.1.57—butanal dehydrogenase," brenda-enzymes.org, retrieved on Jun. 19, 2014, http://www.brenda-enzymes.org/php/result_flat.php4?ecno=1.2.1.57, 6 pages.

"BRENDA—The comprehensive Enzyme Information System," Jul. 2011, retrieved on Sep. 19, 2014, http://web.archive.org/web/20111009205602/http://www.brenda-enzymes.org/, 1 page.

Aimin et al., "*Nocardia* sp. carboxylic acid reductase: cloning, expression, and characterization of a new aldehyde oxidoreductase family," Appl. Environ. Microbiol., 2004, 70:1874-1881.

(Continued)

*Primary Examiner* — Gregory Listvoyb
(74) *Attorney, Agent, or Firm* — Finnegan, Henderson, Farabow, Garrett & Dunner, LLP; Carla A. Mouta-Bellum

(57) ABSTRACT

This document describes biochemical pathways for producing 2-aminopimelate from 2,6-diaminopimelate, and methods for converting 2-aminopimelate to one or more of adipic acid, adipate semialdehyde, caprolactam, 6-aminohexanoic acid, 6-hexanoic acid, hexamethylenediamine, or 1,6-hexanediol by decarboxylating 2-aminopimelate into a six carbon chain aliphatic backbone and enzymatically forming one or two terminal functional groups, comprised of carboxyl, amine or hydroxyl group, in the backbone.

34 Claims, 30 Drawing Sheets

(56) References Cited

U.S. PATENT DOCUMENTS

| | | |
|---|---|---|
| 2015/0111262 A1 | 4/2015 | Botes et al. |
| 2015/0267211 A1 | 9/2015 | Botes et al. |

FOREIGN PATENT DOCUMENTS

| | | |
|---|---|---|
| WO | WO 2009/113853 | 9/2009 |
| WO | WO 2009/113855 | 9/2009 |
| WO | WO 2009/140159 | 11/2009 |
| WO | WO 2009/140695 | 11/2009 |
| WO | WO 2009/140696 | 11/2009 |
| WO | WO 2009/151728 | 12/2009 |
| WO | WO 2010/068944 | 6/2010 |
| WO | WO 2010/068953 | 6/2010 |
| WO | WO 2010/071759 | 6/2010 |
| WO | WO 2010/104390 | 9/2010 |
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO 2013/028519 | 2/2013 |
| WO | WO 2013/082542 | 6/2013 |
| WO | WO 2013/090837 | 6/2013 |
| WO | WO 2013/096898 | 6/2013 |
| WO | WO 2014/031724 | 2/2014 |
| WO | WO 2014/105788 | 7/2014 |

OTHER PUBLICATIONS

Akita et al., "Highly stable meso-diaminopimelate dehydrogenase from an Ureibacillus thermosphaericus strain A1 isolated from a Japanese compost: purification, characterization and sequencing," AMB Express, 2011 1:43, 8 pages.

Alber et al., "Malonyl-coenzyme A reductase in the modified 3-hydroxypropionate cycle for autotrophic carbon fixation in archaeal *Metallosphaera* and *Sulfolobus* spp," J. Bacteriology, 2006, 188:8551-8559.

Aloulou et al., "Purification and biochemical characterization of the LIP2 lipase from Yarrowia lipolytica," Biochim. Biophys. Acta, 2007, 1771:228-237.

Anton et al., Polyamides, Fibers, Encyclopedia of Polymer Science and Engineering, 2001, 11:409-445.

Atsumi et al., "Acetolactate synthase from *Bacillus subtilis* serves as a 2-ketoisovalerate decarboxylase from isobutanol synthesis in *Escherichi coli*," Applied and Environ. Microbiol., 2009, 75(19):6306-6311.

Azuma et al., "Naphthalene—a constituent of Magnolia flowers," Phytochemistry, 1996, 42:999-1004.

Barker et al., "Enzymatic reactions in the degradation of 5-aminovalerate by Clostridium aminovalercum," J Biol Chem., 1987, 262(19):8994-9003.

Becker et al., "Metabolic flux engineering of L-lysine production in Corynebacterium glutamicum—over expression and modification of G6P dehydrogenase," J Biotechnol. 2007, 132(2):99-109.

Bellmann et al., "Expression control and specificity of the basic amino acid exporter LysE of Corynebacterium glutamicum," Microbiology 2001, 147:1765-1774.

Bennett et al., "Purification and properties of ϵ-caprolactone hydrolases from Acinetobacter NCIB 9871 and Nocardia globevula CL1," Journal of General Microbiology, 1988 134: 161-168.

Bergler et al., "Protein EnvM is the NADH-dependent enoyl-ACP reductase (FabI) of *Escherichia coli*," J. Bio Chem, 1993, 269(8):5493-5496.

Bernstein et al., "Transfer of the high-GC cyclohexane carboxylate degradation pathway from Rhodopseudomonas palustris to *Escherichia coli* for production of biotin," Metabolic Engineering, May 2008, 10(3-4):131-140.

Berthold et al., "Structure of the branched-chain keto acid decarboxylase (KdcA) from Lactococcus lactis provides insights into the structural basis for the chemoselective and enantioselective carboligation reaction," Acta Crystallographica Sec. D, 2007, D63:1217-1224.

Binieda et al., "Purification, characterization, DNA Sequence and cloning of a pimeloyl-CoA synthetase from Pseudomonas medocin 35," Biochem J., 1999, 340:793-801.

Bond-Watts et al., "Biochemical and Structural Characterization of the trans-Enoly-CoA Reductase from Treponema denticola," Biochemistry, 2012, 51:6827-6837.

Bordes et al., "Isolation of a thermostable variant of Lip2 lipase from Yarrowia lipolytica by directed evolution and deeper insight into the denaturation mechanisms," Journal of Biotechnology, 2011, 156: 117-124.

Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.

Boylan et al., "Functional identification of the fatty acid reductase components encoded in the luminescence operon of Vibrio fischeri," Journal of Bacteriology, 1985, 163(3):1186-1190.

Boylan et al., "Lux C, D and E genes of the Vibrio fischeri luminescence operon code for the reductase, transferase, and synthetase enzymes involved in aldehyde biosynthesis," Photochemistry and photobiology, 1989, 49:681-688.

Bramer et al., "The methylcitric acid pathway in Ralstonia eutropha: new genes identified involved in propionate metabolism," Microbiology 2001, 147:2203-2214.

Breithaupt et al., "Crystal structure of 12-oxophytodienoate reductase 3 from tomato: self-inhibition by dimerization," Proc Natl. Acad Sci. USA, 2006, 103:14337-14342.

Brigham et al., "Engineering Ralstonia eutropha for Production of Isobutanol from CO2, H2, and O2," Advanced Biofuels and Bioproducts 2013, Chapter 39, pp. 1065-1090.

Brzostowicz et al., "mRNA differential display in a microbial enrichment culture: simultaneous identification of three cyclohexanonemonooxygenases from three species," Applied and Environmental Microbiology, 2003, 69: 334-342.

Brzostowicz et al., "Identification of two gene clusters involved in cyclohexanone oxidation in Brevibacterium epidermidis strain HCU," Applied and Microbiological Biotechnology, 2002, 58:781-789.

Buckel et al., "Glutaconate CoA-transferase from Acidaminococcus fermentans," Eur J. Biochem, 1981, 118:315-321.

Budde et al., "Roles of Multiple Acetoacetyl Coenzyme A Reductases in Polyhydroxybutyrate Biosynthesis in Ralstonis eutropha H16," J Bacteriol. 2010, 192(20):5319-5328.

Bugg et al., "The emerging role for bacteria in lignin degradation and bio-product formation," Curr Opin Biotechnol 2011, 22(3):394-400.

Buhler et al., "Occurrence and the possible physiological role of 2-enoate reductases," FEBS Letters, 1980, 109:244-246.

Bult et al., "Complete genome sequence of the methanogenicarchaeon, Methanococcus jannaschii," Science, 1996, 273: 1058-1073.

Bunik et al., "Kinetic properties of the 2-oxoglutarate dehydrogenase complex from Azotobacter vinelandii evidence for the formation of a precatalytic complex with 2-oxoglutarate," Eur J Biochem., 267(12):3583-3591, Jun. 2000.

Cantu et al., "Thioesterases: A new perspective based on their primary and tertiary structures," Protein Science 2010, 19:1281-1295.

Chayabutra and Ju, "Degradation of n-hexadecane and its metabolites by Pseudomonas aeruginosa under microaerobic and anaerobic denitrifying conditions," Appl Environ Microbiol., 66(2):493-498, Feb. 2000.

Cheesbrough and Kolattukudy, "Alkane biosynthesis by decarbonylation of aldehydes catalyzed by a particulate preparation from Pisum sativum," PNAS USA, 1984, 81(21):6613-7.

(56) References Cited

OTHER PUBLICATIONS

Chen et al., "Termites fumigate their nests with naphthalene," Nature, 1998, 392:558-559.
Cheng et al., "Genetic Analysis of a Gene Cluster for Cyclohexanol Oxidation in *Acinetobacter* sp. Strain SE19 by In Vitro Transposition," Journal of Bacteriology, 2000, 182(17):4744-4751.
Coon, "Omega oxygenases: nonheme-iron enzymes and P450 cytochromes," Biochemical & Biophysical Research Communications, 2005,338:378-385.
Cronan and Lin, "Synthesis of the αω-dicarboxylic acid precursor of biotin by the canonical fatty acid biosynthetic pathway," Current Opinion in Chem Biol., 2011, 15:407-413.
Cryle and Schlichting, "Structural insights from a P450 Carrier Protein complex reveal how specificity is achieved in the P450BioI ACP complex," Proceedings of the National Academy of Sciences, Oct. 2008, 105(41):15696-15701.
Cryle et al., "Carbon-carbon bond cleavage by cytochrome P450BioI (CYP107H1) E1," Chemical Communications, Jan. 2004, 86-87.
Cryle, "Selectivity in a barren landscape: the P450BioI-ACP complex," Biochemical Society Transactions, Aug. 2010, 38(4):934-939.
Da Silva et al., "Glycerol: A promising and abundant carbon source for industrial microbiology," Biotechnology Advances, 2009, 27:30-39.
Daisy et al., "Naphthalene, an insect repellent, is produced by Muscodor vitigenus, a novel endophytic fungus," Microbiology, 2002, 148:3737-3741.
Dalby, "Optimizing enzyme function by directed evolution," Current Opinion in Structural Biology, 2003, 13, 500-505.
Davis et al., "Overproduction of acetyl-CoA carboxylase activity increases the rate of fatty acid biosynthesis in *Escherichia coli*," J. Biol. Chem., 2000, 275(37): 28593-28598.
Day et al., "Partial purification and properties of acyl-CoA reductase from *Clostridum butyricum*," Archives of Biochemistry and Biophysics, 1978, 190(1):322-331.
Deana et al., "Substrate specificity of a dicarboxyl-CoA: Dicarboxylic acid coenzyme . A transferase from rat liver mitochondria," Biochem Int., 1992, 26:767-773.
Dekishima et al., "Extending Carbon Chain Length of 1-Butanol Pathway for 1-Hexanol Synthesis from Glucose by Engineered *Escherichia coli*," J. Am. Chem. Soc., Aug. 2011, 133(30):11399-11401.
Dellomonaco et al., "Engineered reversal of the [beta]-oxidation cycle for the synthesis of fuels and chemicals," Nature, Jan. 2011, 476(7360):355-359.
Deshmukh and Mungre, "Purification and properties of 2-aminoadipate: 2-oxoglutarate aminotransferase from bovine kidney," Biochem J, 1989, 261(3):761-768.
Doan et al., "Functional expression of five Arabidopsis fatty acyl-CoA reductase genes in *Escherichia coli*," J. Plant Physiology, 2009, 166:787-796.
Dobritzsch et al., "High resolution crystal structure of pyruvate decarboxylase from Zymomonas mobilis. Implications for substrate activation in pyruvate decarboxylases," J. Biol. Chem., 1998, 273:20196-20204.
Donoghue and Trudgill, "The Metabolism of Cyclohexanol by Acinetobacter NCIB9871," Eur J Bochem., 1975, 60:1-7.
Drevland et al., "Enzymology and Evolution of the Pyruvate Pathway to 2-Oxobutyrate in Methanocaldococcus jannaschii," J. Bacteriol., Apr. 2007, 189(12):4391-4400.
Drevland et al., "Methanogen homoaconitase catalyzes both hydrolyase reactions in coenzyme B biosynthesis," J Biol Chem., Oct. 2008, 283: 28888-28896.
Egmond et al., "Fusarium solani pisi cutinase," Biochimie, Nov. 2000, 82(11):1015-1021.
Eikmanns and Buckel, "Properties of 5-hydroxyvalerate CoA-transferase from *Clostridium aminovalericum*," Biol. Chem, 1990, 371:1077-1082.
Elkins et al., "Substrate Specificity of the RND-Type Multidrug Efflux Pumps AcrB and AcrD of *Esherichia coli* is Determined Predominately by Two Large Periplasmic Looops," J Bacteriol. 2002, 184(23):6490-6499.
Elshahed et al., "Benzoate Fermentation by the Anaerobic bacterium Syntrophus aciditrophicus in the Absence of Hydrogen-Using Microorganisms," Applied and Environ Microbiology, 2001, 67(12):5520-5525.
Elshahed et al., "Metabolism of Benzoate, Cyclohex-1-ene Carboxylate, and Cyclohexane Carboxylate by Syntrophus aciditrophicus Strain SB in Syntrophic Association with H2-Using Microorganisms," Applied and Environ. Microbiol., Apr. 2001, 67(4):1728-1738.
Eurich et al., "Cloning and characterization of three fatty alcohol oxidase genes from Candida tropicalis strain ATCC 20336," Applied & Environmental Microbiology, 2004, 70(8): 4872-4879.
Ferreira et al. "A member of the sugar transporter family, St11p is the glycerol/H= symporter in *Saccharomyces cerevisiae*," Molecular Biology of the Cell, American Society for Cell Biology, Apr. 1, 2005, 16(4):2068-2076.
Fickers et al., "Carbon and nitrogen sources modulate lipase production in the yeast Yarrowia lipolytica," Journal of Applied Microbiology , 2004, 96:742-9.
Fickers et al., "The lipases from Yarrowia lipolytica: Genetics, production, regulation, biochemical characterization and biotechnological applications," Biotechnology Advances, 2011, 29: 632-644.
Fonknechten et al., "Clostridium sticklandii, a specialist in amino acid degradation: revisiting its metabolism through its genome sequence," BMC Genomics, 2010, 11:1-12.
Fuchs et al., "Microbial degradation of aromatic compounds—from one strategy to four," Nat Rev Microbiol., Oct. 3, 2011;9(11):803-816, Oct. 2011.
Fukui et al., "Expression and Characterization of ®-Specific Enoly Coenzyme A Hydratase Involved in Polyhydroxyalkanoate Biosynthesis by Aeromonas caviae," J Bacteriol. 1998, 180(3):667-673.
Funhoff et al., "CYP153A6, a Soluble P450 Oxygenase Catalyzing Terminal-Alkane Hydroxylation," J Bacteriol. 2006, 188(14):5220-5227.
Funhoff et al., "Expression and Characterization of (R)-Specific Enoyl Coenzyme A Hydratase Involved in Polyhydroxyalkanoate Biosynthesis by Aeromonas caviae," J. Bacteriol., 2006, 188(14):5220-5227.
Gallus and Schink, "Anaerobic degradation of pimelate by newly isolated denitrifying bacteria," Microbiology, 1994, 140:409-416.
Gao et al: "A novel meso-diaminopimelate dehydrogenase from Symbiobacterium thermophilum: overexpression, characterization, and potential for D-amino acid synthesis," Applied and Environmental Microbiology, 2012, 78:8595-8600.
Gasmi et al., "A molecular approach to optimize hIFN α2b expression and secretion in Yarrowia lipolytica," Appl Microbiol Biotechnol, 2011, 89:109-119.
GenBank Accession No. AAA23536, Apr. 26, 1993, 1 page.
GenBank Accession No. AAA24664.1, Mar. 25, 1993, 1 page.
Genbank Accession No. AAA24665.1, Apr. 26, 1993, 1 page.
Genbank Accession No. AAA57874.1, Nov. 21, 2011, 2 pages.
GenBank Accession No. AAA69178.1, Jul. 1, 1995, 1 page.
GenBank Accession No. AAA92347.1, Mar. 15, 1996, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct. 23, 2009, 2 pages.
GenBank Accession No. AAB99100, Aug. 27, 1996, 2 pages.
GenBank Accession No. AAB99277.1, Oct. 23, 2009.
GenBank Accession No. AAC23921, Apr. 23, 2003, 2 pages.
GenBank Accession No. AAC76437.1, dated Oct. 2010, 2 pages.
Genbank Accession No. AAF02538.1, Oct. 20, 1999, 2 pages.
Genbank Accession No. AAG08191.1, Jan. 31, 2014, 2 pages.
Genbank Accession No. AAK73167.2, retrieved May 19, 2014, 1 page.
Genbank Accession No. AAN37290.1, retrieved May 19, 2014, 1 page.
GenBank Accession No. AAO77182, Mar. 28, 2003, 1 page.

(56) References Cited

OTHER PUBLICATIONS

Genbank Accession No. AAQ59697.1, Jan. 31, 2014, 2 pages.
GenBank Accession No. AAS11092.1, Mar. 5, 2010, 1 page.
Genbank Accession No. AAS43086.1, dated Nov. 2011, 1 page.
Genbank Accession No. AAT43726, retrieved May 19, 2014, 1 page.
GenBank Accession No. AAW66853.1, Feb. 12, 2005, 1 page.
Genbank Accession No. AAY39893.1, Jan. 31, 2014, 2 pages.
GenBank Accession No. AB005294, Feb. 2000, 2 pages.
Genbank Accession No. ABA81135.1, Jan. 28, 2014, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
Genbank Accession No. ABE47158.1, Jan. 26, 2014, 1 page.
Genbank Accession No. ABE47159.1, Jan. 28, 2014, 2 pages.
Genbank Accession No. ABE47160.1, Jan. 28, 2014, 1 page.
Genbank Accession No. ABI83656.1, Jan. 3, 2007, 1 page.
GenBank Accession No. ABJ63754.1, dated Mar. 2010, 1 page.
Genbank Accession No. ABK71854.1, Jan. 31, 2014, 2 pages.
Genbank Accession No. ABK75684.1, Jan. 31, 2014, 2 pages.
Genbank Accession No. ACC40567.1, Jan. 31, 2014, 2 pages.
Genbank Accession No. ACJ06772.1, Dec. 4, 2009, 1 page.
Genbank Accession No. ADG98140.1, Jan. 28, 2014, 2 pages.
GenBank Accession No. ADK19581.1, Sep. 20, 2010, 2 pages.
GenBank Accession No. AE000666.1, Jan. 5, 2006, 309 pages.
GenBank Accession No. AEA39183.1, Apr. 4, 2011, 1 page.
GenBank Accession No. AJ012480.1, Apr. 2005, 2 pages.
GenBank Accession No. AY143338, Apr. 2003, 5 pages.
GenBank Accession No. AY495697, Mar. 2004, 3 pages.
Genbank Accession No. BAB91331.1, retrieved May 19, 2014, 1 page.
Genbank Accession No. BAC06606, Aug. 1, 2002, 1 page.
GenBank Accession No. BAD69624, Sep. 2005, 1 page.
GenBank Accession No. BAF92773, Nov. 27, 2007, 1 page.
Genbank Accession No. BAF94304.1, retrieved May 19, 2014, 1 page.
Genbank Accession No. CAA44858.1, Apr. 28, 1992, 1 page.
Genbank Accession No. CAA81612.1, Apr. 18, 2005, 2 pages.
Genbank Accession No. CAA90836.1, Apr. 18, 2005, 2 pages.
GenBank Accession No. CAB13029.2, Nov. 20, 1997, 2 pages.
GenBank Accession No. CAC48239.1, Apr. 15, 2005, 2 page.
GenBank Accession No. CAE26094.1, Apr. 17, 2005, 2 pages.
GenBank Accession No. CAE26097.1, Apr. 17, 2005, 2 pages.
Genbank Accession No. CAH04396.1, Apr. 7, 2005, 1 page.
GenBank Accession No. CAH04397.1, Apr. 7, 2005, 2 pages.
GenBank Accession No. CAH04398.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. D87518, Jul. 31, 1997, 2 pages.
Genbank Accession No. EFV11917.1, Sep. 9, 2013, 2 pages.
GenBank Accession No. EIV11143.1, Jun. 19, 2012, 2 pages.
GenBank Accession No. HQ418483.1, Apr. 4, 2011, 2 pages.
GenBank Accession No. JA114119.1, Apr. 19, 2011, 1 page.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. MJ0663, Oct. 1, 2014, 4 pages.
GenBank Accession No. NC_013156.1, Jun. 10, 2013, 2 pages.
GenBank Accession No. NC_14122.1, Jun. 10, 2013, 2 pages.
GenBank Accession No. NC_015562.1, Jun. 10, 2013, 2 Pages.
GenBank Accession No. NM_001246944, Dec. 2011, 2 pages.
GenBank Accession No. NM_01247852, Dec. 2011, 2 pages.
GenBank Accession No. NM_133240, Feb. 25, 2002, 2 pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. S48141, May 1993, 2 pages.
GenBank Accession No. XM_001827609, Mar. 2011, 2 pages.
GenBank Accession No. YP_001394144.1, Jul. 26, 2007, 1 page.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.
GenBank Accession No. YP$_{13}$ 400611, Nov. 10, 2005, 2 pages.
GenBank Accession No. YP_959486, Jan. 3, 2007, 2 pages.
GenBank Accession No. YP_959769, Jan. 3, 2007, 2 pages.
Gerbling et al., "A new acyl-CoA synthetase, located in higher plant cytosol," J Plant Physiol, 1994, 143:561-564.
Gloeckler et al., "Cloning and characterization of the *Bacillus sphaericus* genes controlling the bioconversion of pimlate into dethiobiotin," Gene, 1990, 87:63-70.
Gloerich et al., "Peroxisomal trans-2-enoyl-CoA reductase is involved in phytol degradation," FEBS Letters 2006, 580:2092-2096.
Gocke et al., "Comparative characterization of ThPP-dependent decarboxylases," J. Mol. Cat. B: Enzymatic, 2009, 61:30-35.
Gonzalez-Lopez, "Genetic control of extracellular protease synthesis in the yeast Yarrowia lipolytica," Genetics, 2002, 160: 417-427.
Graupner et al., "Identification of the gene encoding sulfopyruvate decarboxylase, an enzyme involved in biosynthesis of coenzyme M," J Bacteriol., 2000, 182: 4862-4867.
Guerrillot et al., "Purification and Characterization of Two Aldehyde Dehydrogenases from Pseudomonas aeruginosa," Eur. J. Biochem. 1977, 81:185-192.
Hall, "The Contribution of Horizontal Gene Transfer to the Evolution of Fungi," Duke University Libraries, May 10, 2007, 163 pages.
Hall, "Asymmetric bioreduction of activated alkenes using cloned 12-oxophytodienoate reductase isoenzymes OPR-1 and OPR-3 from Lycopersicon esculentum (tomato): a striking change of stereoselectivity," Agnew Chem Int. Ed., 2007, 46:3934-3937.
Han et al., "Oxaloacetate hydrolase, the C—C bond lyase of oxalate secreting fungi," J. Biol. Chem. 2007, 282:9581-9590.
Harrison and Harwood, "The pimFABCDE operon from Phodopseudomonas palustris mediates dicarboxylic acid degradation and participates in anaerobic benzoate degradation," Microbiology, 2005, 151:727-736.
Harwood and Parales, "The beta-ketoadipate pathway and the biology of self-identity," Ann. Rev. Microbiol., 1996, 50:553-590.
Harwood et al., "Anaerobic metabolism of aromatic compounds via the benzoyl-CoA pathway," FEMS Microbiology Reviews, 1999, 22:439-458.
Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
Haywood et al., "Characterization of two 3-ketothiolases possessing differing substrate specificities in the polyhydroxyalkanoate synthesizing organism Alcaligenes eutrophus," FEMS Microbiology Letters 1988, 52(1-2):91-96.

(56) References Cited

OTHER PUBLICATIONS

He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from Bacillus subtilis," J Biol Chem., 275(51):40128-40133, Dec. 22, 2000.
Hermann et al, "Industrial production of amino acids by coryneform bacteria," J Biotechnol. 2003, 104(1-3):155-172.
Hess et al., "Extremely thermostable esterases from the thermoacidophilic euryarchaeon Picrophilus torridus," Extremophiles, 2008, 12:351-364.
Ho and Weiner, "Isolation and characterization of an aldehyde dehydrogenase encoded by the aldB gene of *Escherichia coli*," J. Bacteriol., 2005, 187(3):1067-1073.
Hoffmeister et al., "Mitochondrial trans-2-enoyl-CoA reductase of wax ester fermentation from Euglena gracilis defines a new family of enzymes involved in lipid synthesis," J Biol Chem., 280(6):4329-4338. Epub Nov. 29, 2004.
Hofvander et al., "A prokaryotic acyl-CoA reductase performing reduction of fatty acyl-CoA to fatty alcohol," FEBS Letters, 2001, 585:3538-3543.
Holden et al., "Chorismate lyase: kinetics and engineering for stability," Biochim Biophys Acta., Jan. 31, 2002, 1594(1):160-167.
Hooks et al., "Long-chain acyl-CoA oxidases of Arabidopsis," Plant J., 1999, 20:1-13.
Horning et al., "α-Ketoglutaric Acid," Organic Syntheses, 1955, 3: 510-512.
Hotta et al., "Extremely Stable and Versatile Carboxylesterase from a Hyperthermophilic Archaeon," Applied and Environmental Microbiology, 2002, 68(8):3925-3931.
Howell et al., "Alpha-keto acid chain elongation reactions involved in the biosynthesis of coenzyme B (7-mercaptoheptanoyl threonine phosphate) in methanogenicArchaea," Biochemistry, 1989, 37: 10108-10117.
Howell et al., "Identification of enzymes homologous to isocitrate dehydrogenase that are involved in coenzyme Band leucine biosynthesis in methanoarchaea," J Bacteriol., Sep. 2000, 182: 5013-5016.
Hugler et al., "Malonyl-coenzyme A reductase from Chloroflexus aurantiacus, a key enzyme of the 3-hydroxypropionate cycle for autotrophic CO(2) fixation," J. Bacteriology, 2002, 184:2404-2410.
Huhn et al., "Identification of the membrane protein SucE and its role in succinate transport in Corynebacterium glutamicum," Appl Microbiol Biotechnol. 2011, 89(2):327-335.
Hunt et al., "Characterization of an acyl-CoA thioesterase that functions as a major regulator of peroxisomal lipid metabolism," J. Biol Chem, 2002, 277:1128-1138.
International Preliminary Report on Patentability for International Application No. PCT/US 2012/069934, mailed Jun. 17, 2014, 15 pages.
International Preliminary Report on Patentability in International Application No. PCT/US 2012/042777, mailed Jan. 10, 2013, 22 pages.
International Preliminary Report on Patentability in International Application No. PCT/US 2012/044984, mailed Jan. 28, 2014, 11 pages.
International Preliminary Report on Patentability for International Application No. PCT/US 2013/075058, mailed Jun. 25, 2015, 11 pages.
International Preliminary Report on Patentability for International Application No. PCT/US 2013/075087, mailed Jun. 25, 2015, 11 pages.
International Preliminary Report on Patentability for International Application No. PCT/US 2013/077445, mailed Jul. 9, 2015, 11 pages.
International Preliminary Report on Patentability for International Application No. PCT/US 2013/077420, mailed Jul. 9, 2015, 14 pages.
International Preliminary Report on Patentability for International Application No. PCT/US 2013/077419, mailed Jul. 9, 2015, 13 pages.
International Preliminary Report on Patentability for International Application No. PCT/US 2013/077430, mailed Jul. 9, 2015, 18 pages.
International Preliminary Report on Patentability for International Application No. PCT/US 2013/077413, mailed Jul. 9, 2015, 13 pages.
International Preliminary Report on Patentability for International Application No. PCT/US 2013/077411, mailed Jul. 9, 2015, 12 pages.
International Preliminary Report on Patentability for International Application No. PCT/US 2013/077423, mailed Jul. 9, 2015, 14 pages.
International Search Report and Written Opinion in International Application No. PCT/US 2014/052950, mailed Dec. 3, 2014, 15 pages.
International Search Report and Written Opinion for International Application No. PCT/US 2012/069934, mailed Jan. 17, 2014, 21 pages.
International Search Report and Written Opinion in International Application No. PCT/US 2012/042747, mailed Jan. 14, 2013, 19 pages.
International Search Report and Written Opinion in International Application No. PCT/US 2012/042777, mailed Sep. 11, 2012, 9 pages.
International Search Report and Written Opinion in International Application No. PCT/US 2012/044984, mailed Dec. 17, 2013, 17 pages.
International Search Report and Written Opinion in International Application No. PCT/US 2012/071472, mailed Dec. 17, 2013, 17 pages.
International Search Report and Written Opinion in International Application No. PCT/US2013/075058, mailed Sep. 15, 2014, 17 pages.
International Search Report and Written Opinion in International Application No. PCT/US2013/075087, mailed Aug. 4, 2014, 18 pages.
International Search Report and Written Opinion in International Application No. PCT/US2013/077411, mailed Sep. 24, 2014, 18 pages.
International Search Report and Written Opinion in International Application No. PCT/US2013/077413, mailed Jul. 22, 2014, 20 pages.
International Search Report and Written Opinion in International Application No. PCT/US2013/077419, mailed Jun. 16, 2014, 19 pages.
International Search Report and Written Opinion in International Application No. PCT/US2013/077420, mailed Jul. 21, 2014, 21 pages.
International Search Report and Written Opinion in International Application No. PCT/US2013/077423, mailed Jul. 21, 2014, 22 pages.
International Search Report and Written Opinion in International Application No. PCT/US2013/077430, mailed Nov. 10, 2014, 23 pages.
International Search Report and Written Opinion in International Application No. PCT/US2013/077445, mailed Sep. 15, 2014, 17 pages.
International Search Report and Written Opinion in International Application No. PCT/US2014/053222, mailed Mar. 4, 2015, 18 pages.
International Search Report and Written Opinion in International Application No. PCT/US2015/031227, mailed Jul. 31, 2015, 40 pages.
Invitation to Pay Additional Fees in International Application No. PCT/US2013/075058, mailed Jul. 7, 2014, 7 pages.
Invitation to Pay Additional Fees in International Application No. PCT/US2013/07745, mailed Jul. 7, 2014, 9 pages.
Invitation to Pay Additional Fees in International Application No. PCT/US2014/053222, mailed Dec. 15, 2014, 8 pages.

(56) References Cited

OTHER PUBLICATIONS

Invitation to Pay Fees in International Application No. PCT/US2013/075087, mailed May 16, 2014, 9 pages.
Invitation to Pay Fees in International Application No. PCT/US2013/077411, mailed Jul. 16, 2014, 9 pages.
Invitation to Pay Fees in International Application No. PCT/US2013/077413, mailed May 12, 2014, 9 pages.
Invitation to Pay Fees in International Application No. PCT/US2013/077419, mailed Apr. 16, 2014, 9 pages.
Invitation to Pay Fees in International Application No. PCT/US2013/077420, mailed May 13, 2014, 9 pages.
Invitation to Pay Fees in International Application No. PCT/US2013/077423, mailed May 13, 2014, 10 pages.
Invitation to Pay Fees in International Application No. PCT/US2013/077430, mailed Aug. 25, 2014, 9 pages.
Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbiology, 2002, 68:1192-1195.
Ishikawa et al., "The pathway via D-galacturonate/L-galactonate is significant for ascorbate biosynthesis in Euglena gracilis: identification and functional characterization of aldonolactonase," Journal of Biologiocal Chemistry, 2008, 283:31133-31141.
Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Appl Environ Microbiol., 2002, 68(11):5671-5684, 14 pages.
Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," Appl. Environ. Microbiol., 1999, 65(11):5158-5162.
Izumi et al., "Structure and Mechanism of HpcG, a Hydratase in the Homoprotocatechuate Degradation Pathway of *Escherichia coli*," J. Mol. Biol., 2007, 370:899-911.
Izumi et al., "The pimeloyl-CoA synthetase responsible for the first step in biotin biosynthesis by microorganisms," Agr. Biol. Chem., 1974, 38:2257-2262.
Jacob et al., "Glutaconate CoA-transferase from *Acidamiococcus fermentans*: the crystal structure reveals homology with other CoA-transferases," Structure, 1997, 5:415-426.
Jang et al., "Bio-based production of C2—C6 platform chemicals," Biotechnol. & Bioengineering, 2012, 109(10):2437-2459.
Jarboe, "YqhD: a broad-substrate range aldehyde reductase with various applications in production of biorenewable fuels and chemicals," Appl Microbiol Biotechnol., 2011, 89(2):249-257.
Jaremko et al., "The initial metabolic conversion of levulinic acid in Cupriavidus nectar," J. Biotechnol., 2011, 155(3):293-298.
Jeyakanthan et al., "Substrate specificity determinants of the methanogen homoaconitase enzyme: structure and function of the small subunit," Biochemistry, 2010, 49:2687-2696.
Jing et al., "Phylogenetic and experimental characterization of an acyl-ACP thioesterase family reveals significant diversity in enzymatic specificity and activity," BMC Biochemistry, 2011, 12:44, 16 pages.
Joon-Young et al., "Production of 1,2-Propanediol from Glycerol in *Saccharomyces cerevisiae*," J. Microbiology and Biotechnology, May 19, 2011, 21(8):846-853.
Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.
Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.
Kaulmann et al., "Substrate spectrum of omega-transaminase from Chromobacterium violaceum DSM30191 and its potential for biocatalysis," Enzyme Microb Technol. 2007, 41:628-637.

Kikuchi et al., "Characterization of a second lysine decarboxylase isolated from *Escherichia coli*," J Bacteriol, 1997, 179(14): 4486-4489.
Kim et al., "Cloning and characterization of a cyclohexanone monooxygenase gene from *Arthrobacter* sp. L661," Biotechnology Bioprocess Engineering, 2008, 13:40-47.
Kim, "Purification and properties of a diamine alpha-ketoglutarate transaminase from *Escherichia coli*," J Biol Chem 1964, 239(3):783-786.
Kitzing et al., "The 1.3 A crystal structure of the flavoprotein YqjM reveals a novel class of Old Yellow Enzymes," J. Biol. Chem., 2005, 280:27904-27913.
Kizer, "Application of Functional Genomics to Pathway Optimization for Increased Isoprenoid Production," Applied and Environmental Microbiology, 2008, 74(10)3229-3241.
Klatte et al., "Redox self-sufficient whole cell biotransformation for amination of alcohols," Bioorg & Medicinal Chem, May 2014, 22: 5578-5585.
Koch et al., "Products of Enzymatic Reduction of Benzoyl-CoA, A Key Reaction in Anaerobic Aromatic Metabolism," Eur. J. Biochemistry, Jan. 1993, 211(3):649-661.
Koch et al., "In Vivo Evolution of Butane Oxidation by Terminal Alkane Hydroxylases A1kB and CYP153A6," Appl. Environ. Microbiol., 2009, 75(2):337-344.
Kockelkorn and Fuchs, "Malonic semialdehyde reductase, succinic semialdehyde reductase, and succinyl-coenzyme A reductase from Metallosphaera sedula: enzymes of the autotrophic 3-hydroxypropionate/4-hydroxybutyrate cycle in Sulfolobales," J. Bacteriology, 2009, 191:6352-6362.
Kolattukudy, "Enzymatic synthesis of fatty alcohols in *Brassica oleracea*," Archives of Biochemistry and Biophysics, 1971, 142(2):701-709.
Köpke et al., "2,3-Butanediol Production by Acetogenic Bacteria, an Alternative Route to Chemical Synthesis, Using Industrial Waste Gas," Appl Environ Microbiol., 2011, 77(15):5467-5475.
Kulkarni and Kanekar, "Bioremediation of epsilon-caprolactam from nylon-6 waste water by use of Pseudomonas aeruginosa MCM B-407," Curr. Microbiol., 1998, 37:191-194.
Kung et al., "Cyclohexane carboxyl-coenzyme A (CoA) and cyclohex-1-ene-1-carboxyl-CoA dehydrogenases, two enzymes involved in the fermentation of benzoate and crotonate in Syntrophus aciditrophicus," J Bacteriol., 195(14):3193-3200, Epub May 10, 2013.
Lan et al., "Oxygen-tolerant coenzyme A-acylating aldehyde dehydrogenase facilitates efficient photosynthetic n-butanol biosynthesis in cyanobacteria," Energy Environ Sci, 2013, 6:2672-2681.
Larroy et al., "Characterization of the *Saccharomyces cerevisiae* YMR318C (ADH6) gene product as a broad specificity NADPH-dependent alcohol dehydrogenase: relevance in aldehyde reduction," Biochem J., 2002, 361(Pt 1):163-172.
Le Dall et al., "Multiple-copy integration in the yeast Yarrowia lipolytica," Current Genetics, 1994 26:38-44.
Lea et al., "Long-chain acyl-CoA dehydrogenase is a key enzyme in the mitochondrial B-oxidation of unsaturated fatty acids," Biochmica et Biophysica Acta, 2000, 1485: 121-128.
Lee and Meighen, "Cysteine-286 as the site of acylation of the LUX-specific fatty acyl-CoA reductase," Biochim Biophys Acta, 1997, 1338:215-222.
Lee et al., "Metabolic Engineering of Pentose Phosphate Pathway in Ralstonia eutropha for Enhanced Biosynthesis of Poly-13-hydroxybutyrate," Biotechnology Progress, 2003, 19(5):1444-1449.
Lee et al., "Synthesis of pure meso-2,3-butanediol from crude glycerol using an engineered metabolic pathway in *Escherichia coli*," Appl Biochem Biotechnol., 2012, 166(7):1801-1813.
Li et al., "Cupriavidus necator JMP 134 rapidly reduces furfural through a Zn-dependent alcohol dehydrogenase," Biodegradation, 2011, 22:1215-1225.
Lim et al., "Amplification of the NADPH-related genes zwf and gnd for the oddball biosynthesis of PHB in an *E. coli* transformant harboring a cloned phbCAB operon," J Bioscience and Bioengineering, 2002, 93(6):543-549.
Lin and Cronan, "Closing in on complete pathways of biotin biosynthesis," Molecular Biosystems, 2011, 7:1811-1821.

(56) References Cited

OTHER PUBLICATIONS

Lin et al., "Biotin Sythesis Begins by Hijacking the Fatty Acid Synthetic Pathway," Nature Chem Biol., Sep. 2010, 6:682-688.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin, "Biotin Synthesis in *Escherichia coli*," PhD Dissertation, University of Illinois at Urbana-Champaign, 2012, 140 pages.
Liu and Chen, "Production and characterization of medium-chain-length polyhydroxyalkanoate with high 3-hydroxytetradecanoate monomer content by fadB and fadA knockout mutant of Pseudomonas putida KT2442," Appl. Microbiol. Biotechnol., 2007, 76(5):1153-1159.
Liu et al., "Two novel metal-independent long-chain alkyl alcohol dehydrogenases from Geobacillus thermodenitrificans NG80-2," Microbiology, 2009, 155:2078-2085.
Lopez-Sanchez et al., "Tetralin-Induced and ThnR-Regulated Aldehyde Dehydrogenase and β-Oxidation Genes in *Sphingomonas macrogolitabida* Strain TFA," Appl. Environ. Microbiol., 2010, 76(1):110-118.
Luo et al., "Production of 3-hydroxypropionic acid through propionaldehyde dehydrogenase PduP mediated biosynthetic pathway in Klebsiella pneumoniae," Bioresource Technology, 2012, 103:1-6.
Lütke-Eversloh & Steinbüchel, "Biochemical and molecular characterization of a succinate semialdehyde dehydrogenase involved in the catabolism of 4-hydroxybutyric acid in Ralstonia eutropha," FEMS Microbiology Letters, 1999, 181(1):63-71.
Mack and Buckel, "Conversion of glutaconate CoA-transferase from Acidaminococcus fermentans into an acyl-CoA hydrolase by site-directed mutagenesis," FEBS Letters, 1997, 405:209-212.
Maeda et al., "Purification and characterization of a biodegradable plastic-degrading enzyme from Aspergillus oryzae," Applied and Environmental Biotechnology, 2005, 67: 778-788.
Mahadik et al., "Production of acidic lipase by Aspergillus niger in solid state fermentation," Process Biochemistry, 2002, 38: 715-721.
Martin and Prather, "High-titer production of monomeric hydroxyvalerates from levulinic acide Pseudomonas putida," J. Biotechnol., 2009, 139: 61-67.
Martinez et al., "Fusarium solani cutinase is a lipolytic enzyme with a catalytic serine accessible to solvent," Nature, 1992, 356:615-618.
Matsumoto et al., "A new pathway for poly(3-hydroxybutyrate) production in *Escherichia coli* and Corynebacterium glutamicum by functional expression of a new acetoacetyl-coenzyme A synthase," Biosci. Biotechnol. Biochem., 2011, 75(2):364-366.
Mawal and Deshmukh, "Alpha-aminoadipate and kynurenine aminotransferase activities from rat kidney. Evidence for separate identity," J. Biol Chem, 1991, 266(4):2573-2575.
McAndrew et al., "Structural basis for substrate fatty acyl chain specificity: crystal structure of human very-long-chain acyl-CoA dehydrogenase," J. Biol. Chem., 2008, 283:9435-9443.
Meijnen et al., "Improved p-hydroxybenzoate production by engineered Pseudomonas putida S12 by using a mixed-substrate feeding strategy," Appl. Microbiol. Biotechnol., 2011, 90:885-893.
Mhetras et al., "Purification and characterization of acidic lipase from Aspergillus niger NCIM 1207," Bioresource Technology, 2009, 100: 1486-1490.
Millar et al., "CUT1, an Arabidopsis Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.
Miyazaki et al., "Alpha-Aminoadipate aminotransferase from an extremely thermophilic bacterium, Thermus thermophilus," Microbiology, 2004, 150(7): 2327-2334.
Mo et al., "Connecting extracellular metabolomic measurements to intracellular flux states in yeast," BMC Systems Biology, 2009, 3(37):1-17.
Mouttaki et al "Cyclohexane Carboxylate and Benzoate Formation from Crotonate in Sytrophus aciditrophicus," Applied and Environ Microbiology, Feb. 2007, 73(3):930-938.
Murphy et al., "Fusarium polycaprolactone depolymerase is cutinase," Appl. Environm. Microbiol., 1996, 62:456-460.
Mutti et al., "Amination of ketones by employing two new (S)-selective w-transaminases and the His-tagged w-TA from Vibrio fluvialis," Eur. J. Org. Chem, 2012, 1003-1007 (Abstract).
Naggert et al., "Cloning, sequencing, and characterization of *Escherichia coli* thioesterase II," J. Biol. Chem., 1991, 266(17):11044-11050.
Neyfakh, "The Multidrug Efflux Transporter of Bacillus subtilis is a Structural and Functional Homolog of the *Staphylococcus* NorA Protein," Antimicrob Agents Chemother, 1992, 36(2):484-485.
Ng et al., "Quinolone Resistance Mediated by norA: Physiologic Characterization and Relationship to flqB, a Quinolone Resistance Locus on the *Staphylococcus aureus* Chromosome," Antimicrob Agents Chemother, 1994, 38(6):1345-1355.
Nicol et al., "Bioconversion of crude glycerol by fungi," Applied Microbiology and Biotechnology, Feb. 10, 2012, 93(5):1865-1875.
Nieder and Shapiro, "Physiological function of the Pseudomonas putida PpG6 (*Pseudomonas oleovorans*) alkane hydroxylase: monoterminal oxidation of alkanes and fatty acids," J. Bacteriol., 1975, 122(1):93-98.
Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," J. Biochem., 1984, 95:1315-1321.
Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiol., 2005, 71(8):4297-4306.
Ohashi et al., "Continuous production of lactic acid from molasses by perfusion culture of Lactococcus lactis using a stirred ceramic membrane reactor," J. Bioscience and Bioengineering, 1999, 87(5):647-654.
Okuhara et al., "Formation of Glutaric and Adipic Acids from n-Alkanes with Odd and Even Numbers of Carbons by Candida tropicalis OH23," Agr. Biol. Chem., 1971, 35(9):1376-1380.
Onakunle et al., "The formation and substrate specificity of bacterial lactonases capable of enantioselective resolution of racemic lactones," Enzyme and Microbial Technology, 1997, 21: 245-251.
Oppenheim and Dickerson, "Adipic Acid," Kirk-Othmer Encyclopedia of Chemical Technology, 2003.
Ouchi et al., "Dual roles of a conserved pair, Arg23 and Ser20, in recognition of multiple substrates in alpha-aminoadipate aminotransferase from Thermus thermophilus," Biochem Biophys Res Commun, 2009, 388(1):21-27.
Palosaari and Rogers, "Purification and properties of the inducible coenzyme A-linked butyraldehyde dehydrogenase from Clostridium acetobutylicum," J. Bacteriol., 1988, 170(7):2971-2976.
Papanikolaou et al., "Citric acid production by Yarrowia lipolytica cultivated on olive-mill wastewater-based media," Bioresource Technol., 2008, 99(7):2419-2428.
Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.
Pelletier and Harwood et al., "2-Hydroxycyclohexanecarboxyl coenzyme A dehydrogenase, an enzyme characteristic of the anaerobic benzoate degradation pathway used by Rhodopseudomonas palustris," J Bacteriol., 182(10):2753-2760, May 2000.
Pérez-Pantoja et al., "Metabolic reconstruction of aromatic compounds degradation from the genome of the amazing pollutant-degrading bacterium Cupriavidus necator JMP134," FEMS Microbiol. Rev., 2008, 32:736-794.
Peterson et al., "The Thermal Stability of the Fusarium solani pisi Cutinase as a Function of pH," BioMed Research International, 2001, 1.2:62-69.
Pignede et al., "Autocloning and Amplification of LIP2 in Yarrowia lipolytica," Appl. Environ. Microbiol, 2000 66:3283-3289.

(56) References Cited

OTHER PUBLICATIONS

Pignede et al., "Characterization of an extracellular lipase encoded by LIP2 in Yarrowia lipolytica," Journal of Bacteriology, 2000, 182: 2802-2810.

Ploux et al., "Investigation of the first step of biotin biosynthesis in Bacillus sphaericus: Purification and characterization of the pimloyl-CoA synthase, and uptake of pimelate," Biochem J., 1992, 287:685-690.

Prabhu et al., "Lactate and Acrylate Metabolism by Megasphaera elsdenii under Batch and Steady-State Conditions," Applied and Environ. Microbiology, Sep. 2012, 78(24): 8564-8570.

Prather et al., "De novo biosynthetic pathways: rational design of microbial chemical factories," Current Opinion in Biotechnology, 2008, 19:468-474.

Prybylski et al., "Third-generation feed stocks for the clean and sustainable biotechnological production of bulk chemicals: synthesis of 2-hydroxyisobutyric acid," Energy, Sustainability and Society, 2012, 2:11.

Qian et al., "Metabolic engineering of *Escherichia coli* for the production of cadaverine: a five carbon diamine," Biotechnol Bioeng, 2011, 108(1):93-103.

Qiu et al., "Crystal structure and substrate specificity of the β-ketoacyl-acyl carrier protein synthase III (FabH) from *Staphylococcus aureus*," Protein Sci, 2005, 14(8):2087-2094.

Rajashekhara et al., "Propionyl-coenzyme A synthetases of Ralstonia solanacearum and *Salmonella choleraesuis* display atypical kenetics," FEBS Letters, 2004, 556:143-147.

Ramsay et al., "Use of a Nylon Manufacturing Waste as an Industrial Fermentation Substrate," Applied and Environmental Microbiology, 1986, 52(1):152-156.

Ray et al., "Cocrystal structures of diaminopimelate decarboxylase: mechanism, evolution, and inhibition of an antibiotic resistance accessory factor," Structure, 2002, 10(11):1499-1508.

Rea et al., "Structure and Mechanism of HpcH: A Metal Ion Dependent Class II Aldolase from the Homoprotocatechuate Degradation Pathway of *Escherichia coli*, " J. Mol. Biol., 2007, 373:866-876.

Reiser and Somerville, "Isolation of mutants of *Acinetobacter calcoaceticus* deficient in wax ester synthesis and complementation of on mutation with gene encoding a fatty acyl coenzyme A reductase," J. Bacteriol., 1997, 179:2969-2975.

Rizzarelli et al., "Evidence for Selective Hydrolysis of Aliphatic Copolyesters Induced by Lipase Catalysis," Biomacromolecules, 2004, 5:433-444.

Rohdich et al., "Enoate reductases of Clostridia. Cloning, sequencing, and expression," J. Biol. Chem., 2001, 276:5779-5787.

Roje, "Vitamin B biosynthesis in plants," Phytochemistry, 2007, 68:1904-1921.

Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.

Ryu et al., "A novel synthesis of .beta.-trichlorostannyl ketones from siloxycyclopropanes and their facile dehydrostannation affording 2-methylene ketones," JOC, 1986, 51:2389-2391.

Salcher and Lingens, "Regulation of phospho-2-keto-3-deoxyheptonate aldolase (DAHP synthase) and anthranilate synthase of Pseudomonas aureofaciens," J Gen Microbiol., 121(2):473-476, Dec. 1980.

Sambrook et al., Molecular Cloning—a Laboratory Manual, Cold Spring Harbor Laboratory Press, 2001.

Samsonova et al., "Molecular cloning and characterization of *Escherichia coli* K12 ygjG gene," BMC Microbiology, 2003, 3:2.

Sanders et al., "Characterization of the human ω-oxidation pathway for ω-hydroxy-very-long-chain fatty acids," FASEB Journal, 2008, 22(6):2064-2071.

Sanders et al., "Evidence for two enzymatic pathways for ω-oxidation of docosanoic acid in rat liver microsomes," J. Lipid Research, 2005, 46(5):1001-1008.

Satoh et al., "Enzyme-catalyzed poly(3-hydroxybutyrate) synthesis from acetate with CoA recycling and NADPH regeneration in vitro," J Bioscience and Bioengineering, 2003, 95(4):335-341.

Scheller et al., "Generation of the Soluble and Functional Cytosolic Domain of Microsomal Cytochrome P450 52A3," J Biol Chem., 1994, 269(17):12779-12783.

Schirmer et al., "Microbial Biosynthesis of Alkanes," Science, 2010, 329:559-562.

Schwartz et al., "A proteomic view of the facultatively chemolithoautotrophic lifestyle of Ralstonia eutropha H16," Proteomics, 2009, 9:5132-5142.

Seedorf et al., "The genome of Clostridium kluyveri, a strict anaerobe with unique metabolic features," Proc. Natl. Acad. Sci. USA, 2008, 105(6):2128-2133.

Shapiro et al., "Remarkable Diversity in the Enzymes Catalyzing the Last Step in Synthesis of the Pimelate Moiety of Biotin," PLoSOne, Nov. 2012, 7(11):e49440, 11 pages.

Shen et al., "Driving Forces Enable High-Titer Anaerobic 1-Butanol Synthesis in *Escherichia coli*," Appl. Environ. Microbiol., 2011, 77(9):2905-2915.

Shikata et al., "A novel ADP-forming succinyl-CoA synthetase in Thermococcus kodakaraensis structurally related to the archaeal nucleoside diphosphate-forming acetyl-CoA synthetases," J. Biol. Chem, 2007, 282(37):26963-26970.

Siegert et al., "Exchanging the substrate specificities of pyruvate decarboxylase from Zymomonas mobilis and benzoylformate decarboxylase from Pseudomonas putida," Port. Eng. Des. Sel., 2005, 18:345-357.

Simon et al., "Chiral Compounds Synthesized by Biocatalytic Reductions [New Synthetic Methods (51)]," Angew Chem Ed Engl., 1985, 24:539-553.

Simon, "Properties and mechanistic aspects of newly found redox enzymes from anaerobes suitable for bioconversions on preparatory scale," Pure and Appl. Chem, 1992, 64:1181-1186.

Slater et al., "Multiple β-Ketothiolases Mediate Poly(β-Hydroxyalkanoate) Copolymer Synthesis in Ralstonia eutropha," J Bacteriol., 1998, 180(8):1979-1987.

Smith et al., "Complete genome sequence of Methanobacterium thermoautotrophicum deltaH: functional analysis and comparative genomics," J Bacteriol., 1997, 179: 7135-7155.

Smith et al., "Structural analysis of ligand binding and catalysis in chorismate lyase," Archives of Biochemistry and Biophysics, Jan. 2006, 445(1):72-80.

Stok et al., "Expression, Purification, and Characterization of BioI: A Carbon-Carbon Bond Cleaving Cytochrome P450 Involved in Biotin Biosynthesis in Bacillus Subtilis," Archives of Biochemistry and Biophysics, Dec. 2000, 384(2):351-360.

Strassner et al., "A homolog of old yellow enzyme in tomato. Spectral properties and substrate specificity of the recombinant protein," J. Biol. Chem. 1999, 274:35067-35073.

Stueckler, "Stereocomplementary bioreduction of alpha,beta-unsaturated dicarboxylic acids and dimethyl esters using enoate reductases: enzyme- and substrate-based stereocontrol," Org. Lett., 2007, 9:5409-5411.

Suzuki et al., "Acetylputrescine deacetylase from Micrococcus luteus K-11," BBA—General Subjects, 1986, 882(1):140-142.

Kobayashi et al., "Antimicrobial Activity of Meropenem Against Main Bacterial Species Isolated from Patient Blood in 2006," Jpn J. Antibiot. 2007, 60(6):378-86 (with English abstract).

Suzuki et al., "GriC and GriD Constitute a Carboxylic Acid Reductase Involved in Grixazone Biosynthesis in Streptomyces griseus," J. Antibiot., 2007, 60(6):380-387.

Tomita et al., "Mechanism for multiple-substrates recognition of alpha-aminoadipate aminotransferase from Thermus thermophilus," Proteins, 2009, 75(2):348-359.

Tseng et al., "Biosynthesis of chiral 3-hydroxyvalerate from single propionate-unrelated carbon sources in metabolically engineered *E. coli*," Microbial Cell Factories, 2010, 9:96.

Uniprot Accession No. I5YEB8, Sep. 5, 2012, 1 page.

US Non-Final Office Action in U.S. Appl. No. 13/524,883, mailed Nov. 29, 2013, 13 pages.

US Non-Final Office Action in U.S. Appl. No. 13/715,981, mailed Jun. 27, 2014, 23 pages.

(56) References Cited

OTHER PUBLICATIONS

US Notice of Allowance in U.S. Appl. No. 13/524,883, mailed May 29, 2014, 7 pages.
US Notice of Allowance in U.S. Appl. No. 13/715,981, mailed Dec. 16, 2014, 23 pages.
US Notice of Allowance in U.S. Appl. No. 13/715,981, mailed Apr. 6, 2015, 10 pages.
US Non-Final Office Action in U.S. Appl. No. 13/715,826, mailed Jan. 30, 2015, 24 pages.
US Non-Final Office Action in U.S. Appl. No. 14/106,033, mailed Apr. 6, 2015, 37 pages.
US Non-Final Office Action in U.S. Appl. No. 14/138,827, mailed Apr. 24, 2015, 35 pages.
US Non-Final Office Action in U.S. Appl. No. 14/138,971, mailed Jun. 9, 2015, 44 pages.
US Non-Final Office Action in U.S. Appl. No. 14/138,904, mailed Jun. 9, 2015, 50 pages.
US Non-Final Office Action in U.S. Appl. No. 14/490,270, mailed Jul. 17, 2015, 49 pages.
US Notice of Allowance in U.S. Appl. No. 14/106,124, mailed Dec. 24, 2014, 31 pages.
Vamecq et al., "The microsomal dicarboxylyl-CoA synthetase," Biochem J., 1985, 230:683-693.
Van Beilen and Funhoff, "Expanding the alkane oxygenase toolbox: new enzymes and Applications," Curr. Opin. Biotechnol., 2005, 16:308-314.
Venkitasubramanian et al., "Aldehyde oxidoreductase as a biocatalyst: Reductions of vanillic acid," Enzyme and Microbial Technology, 2008, 42:130-137.
Vioque et al., Resolution and purification of an aldehyde-generating and an alcohol-generating fatty-acyl-CoA reductase from Pea leaves (*Pisum sativum* L), Archives of Biochemistry and Biophysics, 1997, 340(1):64-72.
Vyazmensky et al., "Isolation and Characterization of Subunits of Acetohydroxy Acid Synthase Isozyme III and Reconstruction of the Holoenzyme," Biochemistry, 1996, 35:10339-10346.
Wahlen et al., "Purification, characterization and potential bacterial wax production role of an NADPH-dependent fatty aldehyde reductase from Marinobacter aquaeolei VT8," Appl. Environ Microbiol, 2009, 75:2758-2764.
Wang and Kolattukudy, "Solubilization and purification of aldehyde-generation fatty acyl-CoA reductase from green alga Botryococcus braunii," FEBS Letters, 1995, 370:15-18.
Wee et al., "Biotechnological Production of Lactic Acid and Its Recent Applications," Food Technol. Biotechnol., 2006, 44(2):163-172.
Westin et al., "Molecular cloning and characterization of two mouse peroxisome proliferator-activated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From *Escherichia coli*," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7-mercaptoheptanoyl)threonine phosphate] of methanogenic bacteria," Biochemistry, 1989, 28: 860-865.
White, "Steps in the conversion of a-ketosuberate to 7-mercaptoheptanoic acid in methanogenic bacteria," Biochemistry, 1989, 28: 9417-9423.
Widmann et al., "Structural classification by the Lipase Engineering Database: a case study of Candida antarctica lipase A," BMC Genomics, 2010, 11:123-130.

Willis et al., "Characterization of a fatty acyl-CoA reductase from *Marinobacter aquaeolei* VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.
Wischgoll et al., "Structural basis for promoting and preventing decarboxylation in glutaryl-coenzyme, A dehydrogenases," Biochemistry, 2010, 49:5350-5357.
Woolridge et al., "Efflux of the natural polyamine spermidine facilitated by the Bacillus subtilis multidrug transporter Blt," J Biol Chem., 1997, 272(14):8864-8866.
Xiong et al., "A bio-catalytic approach to aliphatic ketones," Sci Rep., 2:311, Epub Mar. 13, 2012.
Yang et al., "Value-added uses for crude glycerol—a byproduct of biodiesel production," Biotechnology for Biofuels, 2012, 5:13.
Yonaha et al., "4-Aminobutyrate : 2-oxoglutarate aminotransferase of Streptomyces griseus: Purification and properties," Eur. J. Biochem., 1985, 146:101-106.
Zhang et al., "Expanding metabolism for biosynthesis of non-natural alcohols," Proc Natl Acad Sci U S A., 105(52):20653-20658 Epub Dec. 8, 2008.
Zhao et al., "Prediction and characterization of enzymatic activities guided by sequence similarity and genome neighborhood networks," E-Life, Jun. 2014, 3: 1-32.
Zhuang et al., "Divergence of function in the hot dog fold enzyme superfamily: the bacterial thioesterase YciA," Biochemistry, 2008, 47(9):2789-2796.
Zomorrodi et al., "Improving the iMM904 S. Cerevisiae metabolic model using essentiality and synthetic lethality data," BMC Systems Biology, Dec. 2010, 4(1):1-15.
International Search Report and Written Opinion in International Application No. PCT/US2015/036074, mailed Sep. 9, 2015, 14 pages.
Invitation to Pay Fees in International Application No. PCT/US2015/036086, mailed Sep. 16, 2015, 7 pages.
"Metabolic engineering," Wikipedia, 8 Jun. 2014 (Jun. 8, 2014), XP002744570, Retrieved from the Internet: URL:https://en.wikipedia.org/w/index.php?title=Metabolicengineering&oldid=612026466 [retrieved on Sep. 15, 2015] last paragraph.
Akatsuka et al., "The Serratia marcescens bioH gene encodes an esterase," GENE, Jan. 2003, 302:185-192.
Eriksen et al., "Protein Design for Pathway Engineering," Journal of Structural Biology, Apr. 2013, 185(2):234-242.
Invitation to Pay Fees in International Application No. PCT/US2015/036015, mailed Oct. 2, 2015, 9 pages.
Invitation to Pay Fees in International Application No. PCT/US2015/036092, mailed Sep. 21, 2015, 8 pages.
Invitation to Pay Fees in International Application No. PCT/US2015/036067, mailed Sep. 18, 2015, 12 pages.
Klapa and Stephanopoulos, "Bioreaction Engineering: Modeling and Control," 2000, Springer Verlag, Heidelberg, pp. 106-124.
Moreno-Sanchez et al., "Experimental validation of metabolic pathway modeling—An illustration with glycolytic segments from Entamoeba histolytica," FEBS Journal, Jul. 2008, 275(13):3454-3469.
Palsson, "The challenges of in silico biology," Nature Biotechnology, Nature Publishing Group, US, Nov. 2000, 18(1):1147-1150.
Price et al., "Genome-scale models of microbial cells: evaluating the consequences of constraints," Nature Reviews. Microbiology, Nature Publishing Group, GB, Nov. 2004, 2(11):886-897.
Uniprot Accession No. O32472, Jun. 11, 2014, 2 pages.
Uniprot Accession No. P69909, Jan. 4, 2005, 1 page.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A953, Jun. 11, 2014, 4 pages.
Uniprot Accession No. P0A6Q6, Jun. 11, 2014, 3 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.

(56) References Cited

OTHER PUBLICATIONS

Uniprot Accession No. Q73Q47, May 14, 2014, 2 pages.
Uniprot Accession No. Q818X2, Jun. 11, 2014, 2 pages.
Yadav et al., "The future of metabolic engineering and synthetic biology: Towards a systematic practice," Metabolic Engineering, Feb. 2012, 14(3):233-241.
Adkins, J. et al., "Engineering microbial chemical factories to produce renewable 'biomonomers,'" *Front Microbiol.*, 2012, 3: 313 (12 pages).
Blombach, B. et al., "Current knowledge on isobutanol production with *Escherichia coli, Bacillus subtilis* and *Corynebacterium glutamicum,*" *Bioeng Bugs.*, 2011, 2(6): 346-350.
Chan, S. et al "Production of succinic acid from sucrose and sugarcane molasses by metabolically engineered *Escherichia coli,*" *Bioresour Technol.*, 2012, 103(1): 329-336.
Choi, Y.J. et al., "Metabolic engineering of *Escherichia coli* for the production of 1-propanol," *Metab Eng.*, 2012, 14(5):477-86.
Lee, S. et al., "Heterologous co-expression of accA, fabD, and thioesterase genes for improving long-chain fatty acid production in *Pseudomonas aeruginosa* and *Escherichia coli,*" *Appl Biochem Biotechnol.*, 2012, 167(1)24-38.
Rathnasingh, C. et al., "Development and evaluation of efficient recombinant *Escherichia coil* strains for the production of 3-hydroxypropionic acid from glycerol," *Biotechnol Bioeng.*, 2009, 104(4):729-39.
ExPASy, "Enzyme class 1.1.1," archived Mar. 28, 2014, retrieved Oct. 15, 2016, Internet Archive, [http://web.archive.org/web/20140328194148/http://enzyme.expasy.org/EC/1.1.1.-] (6 pages).
ExPASy, "Enzyme entry: EC 1.1.1.2," archived Oct. 2, 2012, retrieved Oct. 15, 2016, Internet Archive, [http://web.archive.org/web/20121002162820/http://enzyme.expasy.org/EC/1.1.1.2] (2 pages).
ExPASy, "Enzyme entry: EC 1.1.337," archived Sep. 8, 2015, retrieved Oct. 15, 2016, Internet Archive, [http://web.archive.org/web/20150908052936/http://enzyme.expasy.org/EC/1.1.1.337] (2 pages).
ExPASy, "Enzyme class 1.2.1," archived May 7, 2013, retrieved Oct. 15, 2016, Internet Archive, [http://web.archive.org/web/20130507002847/http://enzyme.expasy.org/EC/1.2.1.-] (2 pages).
ExPASy, "Enzyme entry: EC 1.2.1.3," archived Aug. 20, 2013, retrieved Oct. 15, 2016, Internet Archive, [http://web.archive.org/web/20130820074435/http://enzyme.expasy.org/EC/1.2.1,3] (2 pages).
ExPASy, "Enzyme entry: EC 1.4.1.16," archived Aug. 3, 2013, retrieved Oct. 15, 2016, Internet Archive, [http://web.archive.org/web/20130803051244/http://enzyme.expasy.org/EC/1.4.1.16] (1 page).
ExPASy, "Enzyme entry: EC 1.6.99.1 ," archived Sep. 28, 2012, retrieved Oct. 15, 2016, Internet Archive, [http://web.archive.org/web/20120928222836/http://enzyme.expasy.org/EC/1.6.99.1] (2 pages).
ExPASy, "Enzyme entry: EC 2.2.1.6," archived Dec. 5, 2013, retrieved Oct. 15, 2016, Internet Archive, [http://web.archive.org/web/20131205040425/http://enzyme.expasy.org/EC/2.2.1.6] (2 pages).
ExPASy, "Enzyme entry: EC 2.3.1.32," archived Oct. 6, 2012, retrieved Oct. 15, 2016, Internet Archive, [http://web.archive.org/web/20121006030936/http://enzyme.expasy.org/EC/2.3.1,32] (2 pages).
ExPASy, "Enzyme class 2.6.1," archived Dec. 6, 2013, retrieved Oct. 15, 2016, Internet Archive, [http://web.archive.org/web/20131206150707/http://enzyme.expasy.org/EC/2.6.1.-] (2 pages).
ExPASy, "Enzyme entry: EC 2.6.1.39," archived Oct. 13, 2012, retrieved Oct. 15, 2016, Internet Archive, [http://web.archive.org/web/20121013065547/http://enzyme.expasy.org/EC/2.6.1.39] (2 pages).
ExPASy, "Enzyme class 2.8.3," archived Oct. 17, 2012, retrieved Oct. 15, 2016, Internet Archive, [http://web.archive.org/web/20121017070332/http://enzyme,expasy.org/EC/2.8.3.-] (2 pages).
ExPASy, "Enzyme entry: EC 2.8.3.12" archived Sep. 15, 2012, retrieved Oct. 15, 2016, Internet Archive, [http://web.archive.org/web/20120915015651/http://enzyme.expasy.org/EC/2.8.3.12] (w pages).
ExPASy "Enzyme entry: EC 3.5.1.17," archived Oct. 12, 2012, retrieved Oct. 15, 2016, Internet Archive, [http://web.archive.org/web/20121012222326/http://enzyme.expasy.org/EC/3.5.1.17] (2 pages).
ExPASy, "Enzyme class 3.5.2," archived Apr. 27, 2014, retrieved Oct. 15, 2016, Internet Archive, [http://web.archive.org/web/20140427211205/http://enzyme.expasy.org/EC/3.5.2.-] (2 pages).
ExPASy, "Enzyme class 4.2.1," archived Jul. 14, 2013, retrieved Oct. 15, 2016, Internet Archive, [http://web.archive.org/web/20130714074913/http://enzyme.expasy.org/EC/4.2.1-] (3 pages).
ExPASy, "Enzyme entry: EC 6.2.1.5," archived May 27, 2012, retrieved Oct. 15, 2016, Internet Archive, [http://web.archive.org/web/20120527143835/http://enzyme.expasy.org/EC/6.2.1.5] (5 pages).
Marchler-Bauer, A. et al., "CDD: specific functional annotation with the Conserved Domain Database," *Nucleic Acids Res.* 37,suppl 1: D205-D210 (2009).
Davids, T., et al. "Strategies for the discovery and engineering of enzymes for biocatalysis," *Curr. Opin. Chem. Biol.* 17(2): 215-220 (2013).
Akhtar, M. et al., "Carboxylic acid reductase is a versatile enzyme for the conversion of fatty acids into fuels and chemical commodities," *Proc. Natl. Acad. Sci. USA* 110(1): 87-92 (2013).
Barker, H. et al., "Pathway of lysine degradation in *Fusobacterium nucleatum,*" *J. Bacteriol.* 152(1): 201-207 (1982).
Chen, D. et al., "A novel lysine 2,3-aminomutase encoded by the yodO gene of *Bacillus subtilis*: characterization and the observation of organic radical intermediates," *Biochem. J.* 348(3): 539-549 (2000).
Chaparro-Riggers, J. et al., "Comparison of three enoate reductases and their potential use for biotransformations." *Adv. Synth. Catal.* 349(8-9): 1521-1531 (2007).
Kim, J. et al., "Dehydration of (R)-2-hydroxyacyl-CoA to enoyl-CoA in the fermentation of α-amino acids by anaerobic bacteria," *FEMS Microbiology Reviews* 28(4): 465-468 (2004).

FIG. 20A

| SEQ ID NO | Organism | GENBANK reference | Amino acid sequence |
|---|---|---|---|
| 1 | Lactobacillus brevis | ABJ63754.1 | MAAANEFSETHRVVYYEADDTGOLTLAMLLNLFVLVSEDONDALGLSTAFVQSHGVGWVVT QYHLHIDELPRTGAQVTIKTRATAYNRYFAYREYWLLDDAGQVLAYGEGIWVTMSYATRK ITTIPAEVMAPYHSEEQJTRLPRLPRPDHFDEAVNQJLKPYTVRYFDIDGNGHVNNAHYFD WMLDVLPATFLRAHHPTDVKIRFENEVQYGHGVTSELSQAAALTTQJHMIKVGDLTAVKAT IQWDNR |
| 2 | Lactobacillus plantarum | CCC78182.1 | MATLGANASLYSEQHRITYECDRTGRATLTTLIDIAVLASEDCQSDALGLTTEMVQSHGV GWVVTQYAIDITRMPRQDEVVTIAVRGSAYNPYFAYREFWIRDADGCQLAYFISIWVMMS QTTRRIVKILPELVAPYQSEVVKRIPRLPRPISFEATDTTITKPYHVRFFDHDPNRHVNN AHYFDWLVDTLPATFLLQHDLVHVDVVRYENEVKYGQTVTAHANILPSEVADQVTTSHLE VDDEKCCEVTJCQWRTLPEPJQ |
| 3 | Mycobacterium marinum | ACC40567.1 | MSPJTREEERLERRJCQDLYANDPQFAAAKPATAITAAIERPGLPLPQHETVMTGYADRPA LAQRSVEFVTDAGTGHTTLRLLPHFETISYGELWDRISALADVLSTEQTVKPGDRVCLLG FNSVDYATIDMTLARLGAVAVPLQTSAAITCLQPIVAETQPTMIAASVDALADATELALS GQTATRVLVFDHHRQVDAHRAAVESARERLAGSAVVETLAEAIARGDVPRGASAGSAPGT DVSDDSLALLIYTSGSTGAPKGAMYPRRNVATFWRKRTWFEGGYEPSITLNFMPMSHVMG RCJLYGTLCNGGTAYFVAKSDISTLFEDLALVRPTELTFVPRVWDMVFDEFQSEVDRRLV DGADRVALEAQVKAEIRMDVLGGRYTSALTGSAPISDEMKAWVEELLOMHLVEGYGSTEA GMILIDGAIRRPAVLDYKLVDVPDLGYFLTDRPHPRGELLVKTDSLFPGYYCJRAEVTADV FDADGFYRTGDIMAEVGPECJFVYLDRRMNVLKLSCQGEFVTVSKLEAVFGDSSPLVRCJJYY GNSARAYLLAVIVPTQFALDAVPVEELKARJGDSLQEVAKAAGICSYEIPRDFHETTPW TLENGLLTGJRKLARPCQLKKHYGELLEQJYTDLAHGQADELRSLRCQSGADAPVLVTVCRA AAALLGGSASDVQPDAHFTDLGGDSLSALSFTNLLHEIFDIEVPVGVIVSPANDLCQALAD YVEAARKPGSSRPTFASVHGASNGQVTEVHAGDLSLDKFIDAATLAEAPRLPAANTCJVRT VLLTGATGFLGRYLALEWLERMDILVDGKLICIVRAKSDTEARARLDKTFDSGDPELLAHY RALAGDHLEVLAGDKGEADIGLDRQTWQRLADTVDLIVDPAALVNHVLPYSQLFGPNALG TAELLRLJALTSKILPYSYTSTIGVADQJPPSAFTEDADIRVISATRAVDDSYANGYSNSK WAGEVLLREAHDLCGLPVAVFRCDMILADTTWAGQLNVPDMFTRMHLSLAATGJAPGSFY ELAADGARQRAHYDGLPVEFIAEAISTLGAQSQDGFHTYHVMNPYDDGIGLDEFVDWLNE SGCPJQRIADYGDWLQRFETALRALPDRQRHSSLLPLLHNYRQPERPVRGSJAPTDRFRA AVQEAKIGPDKIPHVGAPHVKYVSDLRLLGLL |

FIG. 20B

| SEQ ID NO | Organism | GENBANK reference | Amino acid sequence |
|---|---|---|---|
| 4 | Mycobacterium smegmatis | ABK71854.1 | MTSDVHDATDGVTETALDDEQSTRRIAELYATDPEFAAAAPLPAVVDAAHKPGLRLAEIL QTLFTGYGDRPALGYRARELATDEGGRTVTRLLPRFDTLTYAQVWSRVQAVAAALRHNFA QPNYPGDAVATIGFASPDYLTEDLVCAYLGLVSVPLQHNAPVSRLAPILAEVEPRILTVS AEYLDLAVESVRDVNSVSQLVVFDHHPEVDGHRDALARAREQLAGKGIAVTTLDAIADEG AGLPAEPHYTADHEDQRLAMILYTSGSTGAPKGAMYTEAMVARLWTMSFHTGDPTPVINVM FMPLNHLGGRIPISTAVQNGGTSYFVPESDMSTLFEDLALVRPTELGLVPRSVADMLYQHH LATVDRLVTQGADELTAEKQAGAELREQVLGGRVITGFVSTAPLAAEMRAFLDITLGAHI VDGYGLTETGSAVTRDGVIVRPPVIDYKLIIDVPELLGSYFSTIDKPYPRGELLVRSQILTPGYY KRPEVTASVFDRDGYYHTGDVMAETAPDHLVYVDRRNNVLKLAQGEFVAVANLEAVFSGA ALVRQIIFVYGNSERSFLLAVVVPTPEALEQYDPAALKAALADSLQRTARDAELQSYEVPA DFIVETEPFSAANGLLSGVGKLLRPNLKDRYGQRLEQMYADIAATQANQLRELRRAAATQ PVIDTLTQAAATILGTGSEVASDAHFTDLGGDSLSALTLSNLLSDFFGFEVPVGTIVNPA TNLAQLAQHEAQRTAGDRRPSFTTVHGADATEIRASELTLDKFIDAETLRAAPGLPKVT TEPRTVLLSGANGWLGRFLTLQWLERLAPVGGTLITIVRGRDDAAARARLTQAYDTDPEL SRRFAELADRHLRVVAGDIIGDPNLGLTPEIWHHRLAAEVDLVVHPAALVNHVLPYRQLFGP NVVGTAEVIKLALTERIKPVTYLSTVSVAMGIPDFEEDGDIRTVSPVRPLDGGYANGYGN SKWAGEVLLREAHDLCGLPVATFRSDMILAHPRYRGQVNVFDMFTRLLLSLLITGVAPRS FYIGDGERPRAHYPGLTVDFVAEAVTTLGACQREGYVSYDVMNPHDDGISLDVFDWLIR AGHPIDRVDDYDDWVRRFETALTALPEKRRAQTVLPLLHAFRAPQAPLRGAPEPTEVFHA AVRTAKVGPGDIPHLDEALIEKYIRDLREFGLI |

FIG. 20C

| SEQ ID NO | Organism | GENBANK reference | Amino acid sequence |
|---|---|---|---|
| 5 | Segniliparus rugosus | EFV11917.1 | MGDGEERAKRFFQRIGELSATDPQFAAAAPDPAVVEAVSDPSLSFTRYLDTLMRGYAERP ALAHRVGAGYETISYGELWARVGAIAAAWQADGLAPGDFVATVGFTSPDYVAVDLAAARS GLVSVPLQAGASLAQLVGILEETEPKVLAASASSLEGAVACALAAPSVQRLVFDLRGPD ASESAADERRGALADAFEEQLARAGRAVVVETLADLAARGEALPEAPLFEPAEGEDPLAIL IYTSGSTGAPKGAMYSQRLVSQLWGRTPVVPGMPNISLHYMPLSHSYGRAVLAGALSAGG TAHFTANSDLSTLFEDIALARPTFLALVPRVCEMLFQESQRGQDVAELRERVLGGRLLVA VCGSAPLSPEMRAFMEEVLGFPLLDGYGSTEALGVMRNGIIQRPPVIDYKLVDSVPELGYR TTDKPYPRGELCJRSTSLISGYYKRPEITAEVFDAQGYYKTGDVMAELAPDHLVYVDRSK NVLKLSQGEFVAVARKLEAAYGTSPYVKQIFVVGNSERSFLLAVVVPNAEVLGARDQEEAK PLIAASLQKIAKEAGLQSYEVPRDFLIETEPFTTQNGLLSEVGKLLRPKLKARYGEALEA RYDEIAHGQADELRALRDGAGQRPVVETVVRAAVAISGSSEGAEVGPEANFADLGGDSLSA LSLANLLHDVFEVEVPVRIHGPTASLAGIAKHLEAERAGASAPTAASVHGAGATRIRAS ELTLEKFLPEDLLAAAKGLPAADQYRTVLLTGANGWLGRFLALEQLERLARSGQDGGKLI CLVRGKDAAAARRRIEETLGTDPALAARFAELAEGRLEVPGDVGEPKFGLDDAAWDRLA EEVDVIVHPAALVNHVLPYHQLFGPNVVGTAEIIRLAITAKRKPVTYLSTVAVAAGVEPS SFEEGDIRAVVPERPLGDGYANGYGNSKWAGEVLLREAHELVGLPVAVFRSDMILAHTR YTGQLNVPDQQFTRLVLSLLATGIAPKSFYQQGAAGERQRAHYDGIPVDFTAEAITTLGAE PSWFDGGAGFRSFDVFNPHHDGVGLDEFVDWLIEAGHPISRIDDHKEWFARFETAVRGLP EAQRQHSLLPLLRAYSFPHPPVDGSVYPTGKFQGAVKAAQYGSDHDVPHLGKALIVKYAD DLKALGLL |

FIG. 20D

| SEQ ID NO | Organism | GENBANK reference | Amino acid sequence |
|---|---|---|---|
| 6 | Mycobacterium massiliense | EIV11143.1 | MTNETNPQQEQLSRRIESLRESDPQFRAAQPDPAVAEQVLRPGLHLSEAIAALMTGYAER PALGERARELVIDQDGRTTLRLLPRFDTTTYGELWSRTTSVAAAWHHDATHPVKAGDLVA TLGFTSIDYTVLDLAIMILGGVAVPLQTSAPASQWTTHLAEAEPNTLAVSIELIGAAMES VRATPSJKQVVVFDYTPEVDDQREAFEAASTQLAGTGIALETLDAVIARGAALPAAPLYA PSAGDDPLALLIYTSGSTGAPKGAMHSENIVRRVWWIREDVMAGITENLPMIGINFMPMSHI MGRGTLTSTLSTGGTGYFAASSDMSTLFEDMELIRPTALALVPRVCDMVFQRFQTEVDRR LASGDTASAEAVAAEVKADIRDNLFGGRVSAVMWGSAPLSEELGEFIESCFELMLTDGYG STEAGMVFRDGIVQRPPVIDVKLVDVPELGYFSTDKPHPRGELLLKTDGMFLGYYKRPEV TASVFDADGFYMTGDIVAFLAHDNEIIDRRMNVLKLSQGEFVAVATLEAEYANSPVVHQ IYVYGSSERSYLLAVVVPTPEAVAAAKGDAAALKTTIADSLQDIAKEIQLQSYEVPRDFI IEPQPFTQGNGLLTGIAKLARPNLKAHYGPRLEQMYAEIAEQQAAELRALHGVDPDKPAL ETVLKAAQALLGVSSAELAADAHFTDLGGDSLSALSFSDLLRDIFAVEVPVGVIVSAAND LGGVAKFVDEQRHSGGTRPTAETVHGAGHTEIRAADLTLDKFIDEATLHAAPSLPKAAGI PHTVLLTGSNGYLGHYLALEWLERLDKTDGKLVIVRGKNAEAAYGRLEEAFDTGDTELL AHFRSLADKHLEVLAGDIGDPNLGLDADTVDVIVHPAALVNHVLPYNQLFGPN VVGTAEIIKLAITTKIKPVTYLSTVAVAAYVDPTTFDEESDIRLISAVRPIDDGYANGYG NAKWAGEVLLREAHDLCGLPVAVFRSDMILAHSRYTGQLNVPDQFTRLJLSLIATGIAPG SFYQAQTTGERPLAHYDGLPGDFTAEAITLGTQVPEGSEGFVTYDCVNPHADGISLDNF VDWLIEAGYPIARIDNYTEWFTRFDTAIRGLSEKQKQHSLLPLLHAFEQPSAAENHGVVP AKRFQHAVQAAGIGPVGQDGTTDIPHLSRRLIVKYAKDLEQLGLL |

FIG. 20E

| SEQ ID NO | Organism | GENBANK reference | Amino acid sequence |
|---|---|---|---|
| 7 | Segniliparus rotundus | ADG98140.1 | MTQSHTQGPQASAAHSRLARRAEELLATDPQAAATLPDPEVVRQATRPGLRLAERVDAIL SGYADRPALGQRSFQTYKDPITGRSSVELLPTFDTHYRELRERATAHASDLAHHPQAPA KPGDFLASKGFISVDYVAIDIAGVFAGLTAVPLQTGATLATLATAETAPTLFAASIEH LPTAVDAVLATPSVRRLLVFDYRAGSDEDREAVEAAKRKIADAGSSVLVDVLDEVIARGK SAPKAPLPPATDAGDDSLLHYTSGSTGTPKGAMYPERNVAHFWGGVWAAAFDEDAAPP VPAINITFLPLSHVASRLSLMPTLARGGLMHFVAKSDLSTLFEDLKLARPTNLFLVPRVV EMLYQHYQSELDRRGVQDGTREAEAVKDDLRTGLLGGRILTAGFGSAPLSAELAGFIESL LQIHLVDGYGSSTEAGPVWRDGYLVKPPVTDYKLIDVPELGYFSTDSPHPRGELAIKTQII LPGYYKRPETTAEVFDEDQGFYLTGDVVAQIGPEQFAYVDRRKNVLKLSQGEFVTLAKLEA AYSSSPLVRQLFVYGSSERSYLLAVIVPTPDALKKFGVGEAAKAALGESLQKIARDEGLQ SYEVPRDFHETDPFTVENGLLSDDARKSLRPKLKEHYGERLEAMYKELADGQANELRDIR RGVQQRPTLETVRRAAAAAMLGASAAEIKPDAHFTELGGDSLSALTFSMFLHDLFEVDVPV GVIVSAANTLGSVAEHDAQLAGGRARPTFATVHGKGSTTIKASDLTLDKFIDEQTLEAA KHLPKPADPPRTVLLTGANGWLGRFLALEWLERLAPAGGKLITIVRGKDAAQAKARLDAA YESGDPKLAGHYQDLAATTLEVLAGDFSEPRLGLDEATWNRLADEVDFHSHPGALVNHVL PYNQLFGPNVAGVAEIHKLAITTRIKPVTYLSTVAVAAGVEPSALDEDGDIRTVSAERSV DEGYANGYGNSKWGGEVLLREAHDRTGLPVRVFRSDMILAHQKYTGQVNATDQFTRLVQS LLATGLAPKSFYELDAQGNRQRAHYDGIPVDFTAESITTLGGDGLEGYRSYNVFNPHRDG VGLDEFVDWLIEAGHPITRIDDYDQWLSRFETSLRGLPESKRQASVLPLLHAFARPGPAV DGSPFRNTVFRTDVQKAKIGAEHDIPHLGKALVLKYADDHKQLGLL |
| 8 | Chromobacterium violaceum | AAQ59697.1 | MQKQRTTSQWRELDAAHHLHPFTDTASLNQAGARVMTREGGVYLWDSEGNKIDGMAGILW CVNVGYGRKDFAEAARRQMEELPFYNTFFKTTHPAVVELSSLLAEVTPAGFDRVFYTNSG SESVDTMIRMVRRYWDVQGKPEKKTLIGRWNGYHGSTIGGASLGGMKYMHEQGDLPIPGM AHIEQPWMVYKHGKDMTPDEFGVVAARWLEEKILEIGADKVAAFVGEPIQGAGGVIVPPAT YWPEIERICRKYDVLLVADEVICGFGRTGEWFGHQHFGFQPDLFTAAKGLSSGYLPIGAV FVGKRVAEGLIAGGDFNHGFTYSGHPVCAAVAHANVAALREGIVQRVKDDIGPYMQKRW RETFSRFEHVDDVRGVGMAVQAFTLVKNKAKRELFPDFGEIGTLCRDIFFRNNLIMRACGD HIVSAPPLVMTRAEVDEMLAVAERCLEEFEQTLKARGLA |
| 9 | Pseudomonas aeruginosa | AAG08191.1 | MNARLHATSPLGDADLVRADQAHYMHGYHVFDDHRVNGSLNIAAGDGAYYDTAGNRYLD AVGGMWCTNIGLGREEMARTVAEQTRLLAYSNPFCDMANPRAIELCRKLAELAPGDLDHV FLTTGGSTAVDTAIRLMHYYQNCRGKRAKKHVFTRINAYHGSTFLGMSLGGKSADRPAEF DFLDERIHHLACPYYYRAPEGLGEAEFLDGLVDEFERKILELGADRVGARSEPVFGSGG VIVPPAGYHRRMWELCQRYDVLYISDEVTSFGRLGHFFASQAVFGVGPDIKLTAKGLTS GYQPLGACIFSRRIWEVIAEPDKGRCFSHGFTYSGHPVACAAALKNIEHEREGLLAHAD EVGRYFEERLQSLRDLPIVGDVRGMRFMACVEFVADKASKALFPESLNIGEWVHLRAQKR GLLVRPIVHLNVMSPPLLTREQVDTVVRLRESIEETVEDLVRAGHR |

FIG. 20F

| SEQ ID NO | Organism | GENBANK reference | Amino acid sequence |
|---|---|---|---|
| 10 | Pseudomonas syringae | AAY39893.1 | MSANNPQTLEWQALSSEHHLAPFSDYKQLKEKGPRHTRAEGVYLWDSEGNKILDGMSGL WCVAIGYGREELADAASKQMRELPYYNLFFCQTAHPPVLELAKAISDIAPEGMNHVFFTGS GSEGMDTMLRMVRHYWALKGQPNKKTHSRVNGYHGSTVAGASLGGMTYMHECQGDLPLPG VVHPQPYWFGEGGDMTPDEFGWAAECLEKKILELGVENVGAFIAEPIQGAGGVIVPPD SYWPKIREHLSRYDLFAADEVICGFGRTSEWFGSDFYGLRPDMMTHAKGLTSGYVPNGG LIVRDEIVAVLNEGGDFNHGFTYSGHPVAAAVALENIRILREEKIVEVRVSETAPYLQKR LRELSDHPLVGEVRGVGLLGAIELVKDKTTRERYTDKGAGMICRTFCFDNGLHMRAVGDT MHAPPLVISFAQIDELVEKARICLDLTLAVLQG |
| 11 | Rhodobacter sphaeroides | ABA81135.1 | MTRNDATNAAGAVGAAMRDHILLPAQEMAKILGKSAQPVLTHAEGIYVHTEDGRRLIDGPA GMWCAQVGYGREEIVDAMAHQAMVLPYASPWYMATSPAARLAEKIATLTPGDLNRIFFTT GGSTAVDSALRFSEFYNNVLGRPQKKRIHVRYDGYHGSTALLTAACTGRTGNWPNFDIAQD RISFLSSPNPRHAGNRSQEAFLDDLVCQEFEDRIESLGPDTIAAFLAEPILASGGVIPPA GYHARFKAICEKHDLYISDEVVTGFGRCGEWFASEKVFGVVPDHTFAKGVTSGYVPLG GLAISEAVLARISGENAKGSWFTNGYTYSNQPVACAAALAMIELMEREGIVDQAREMADY FAAALASLRDLPGVAETRSVGLVGCVQCLLDPTRADGTAEDKAFTLKIDERCFELGLIVR PLGDLCVISPPLHSRAQIDEMVAIMRCQAITEVSAAHGLTAKEPAAV |
| 12 | Escherichia coli | AAA57874.1 | MNRLPSSASALACSAHALNLIEKRTLDHEEMKALNREVIEYFKEHVNPGFLEYRKSVTAG GDYGAVEWQAGSLNTLVDTGQSQEFIDCLGGFGIFNVGHRNPVVVSAVQNQLAKQPLHSQE LLDPLRAMLAKTLAALTPGKLKYSFFCNSGTESVEAALKLAKAYQSPRGKFTHATSGAF HGKSLGALSATAKSTFRKPFMPLLPGFRHVPFGNIEAMRTALNECKKTGDDVAAVILEPI QGEGGVILPPPGYLTAVRKLCDEFGALMILDEVQTGMGRTGKMFACEHENVQPDHLCLAK ALGGGVMPIGATIATEEVFSVLFDNPLHTTFGGNPLACAAALATINVLLEQNLPAQAE QKGDMLLDGFRQLAREVPDLVQEARGKGMLMAIEFVDNEIGYNFASEMFRQRVLVAGTLN NAKTIRIEPPLTLTIEQCELVIKAARKALAAMRVSVEEA |
| 13 | Vibrio Fluvialis | AEA39183.1 | MNKPQSWEARAETYSLVGFTDMPSLHQRGTVVTHGEGPYIVDVNGRRYLDANSGLWNMV AGFDHKGLIDAAKACYERFPGYHAFFGRMSDQTVMLSEKLVEVSPFDSGRVFYTNSGSEA NDTMVKMLWFLHAAEGKPQKRKILTRWNAYHGVTAVSASMTGKPYNSVFGLPLPGFVHLT CPHYWRYGEEGETEEQFVARLARELEETIQREGADTIAGFFAEPVMGAGGVIPPAKGYFQ AILPILRKYDIPVISDEVICGFGRTGNTWGCVTYDFTPDAHISSKNLTAGFPMGAVILG PELSKRLETAIEAIEEFPHGFTASGHPVGCAIALKAIDVWMNEGLAENVRRLAPRFEERL KHIAERPNIGEYRGIGFMWALEAVKDKASKTPFDGNLSVSERIANTCTDLGLICRPLGQS VVLCPPHLTEAQMDEMFQKLEKALDKVFAEVA |
| 14 | Bacillus subtilis | CAA44858.1 | MKIYGIYMDRPLSQEENERFMSFISPEKREKCRRFYHKEDAHRTLLGDVLVRSVISRQYQ LDKSDIRFSTQEYGKPCPIDLPDAHFNSHSGRWVICAFDSQPIGIDIEKTKPISLEIAK RFFSKTEYSGLLAKDKDEQTDYFHLWSMKESFIKQEGKGLSLPLDSFSVRLHQDGCQVSI ELPDSHSPCYIKTYEVDPGYKMAVCAAHPDFPEDITMVSYEELL |

FIG. 20G

| SEQ ID NO | Organism | GENBANK reference | Amino acid sequence |
|---|---|---|---|
| 15 | Nocardia sp. NRRL 5646 | ABI83656.1 | MHETILPAGVESAELLEYPEDLKAHPAEEHLIAKSVEKRRRDFIGARHCARLALAELGEP PVAIGKGERGAPIWPRGVVGSLTHCOGYRAAAVAHKMRFSIGDAEPHATLPEGVLDSV SLPPEREWLKTTDSALHLDRLLFCAKEATYKAWWPLTARWLGFEEAHTFEIEDGSADSG NGTFHSELLVPGQINDGGTPLLSFDGRWLIADGFILTAIAYA |
| 16 | Bacillus subtilis | BAA12619.1 | MARKLFTPTTKDMATLKNRIVMSPMCMYSSHEKDGKLTPFHMAHYISRAIGQVGLIIVEA SAVNPQGRITDQDLGIWSDEHEGFAKLTEQVKEQGSKIGIQLAHAGRKAELEGDHFAPS AIAFDEQSATPVEMSAEKVKETVQEFKQAAARAEAGFDVIEHAAHGYLIHEFLSPLSN HRTDEYGGSPENRYRFLREHDEVKQVWDGPLFVRVSASDYTDKGLDIADHIGFAKWMKE QGVDLIDCSSGALVHADHNVFPGYCQVSFAEKIREQADMATGAVGMHTDGSMAEEHLQNGR ADLIFIGRELLRDPFFARTAAKQLNTEIPAPVQYERGW |
| 17 | Pseudomonas putida | AAN66878.1 | MSALFEPYTLKDVTLRNRIAPPMCCYMAEDGMINDWHHVHLAGLLARGGAGLLVVEATAV APEGRHTPGCAGIWSDAHAQAFVPVVQIAHAGRKASANRPWEGDDHIA AEDDARGWETIAPSAIAFGAHLPKVPREMTLDDIARVKQDFVDAARRARDAGFEWIEHLFA HGYLGQSFFSEHSNKRTDAYGGSFONRSRFLLETLAAVREVWPENLPLTARFGVLEYDGR DECQTLEESIELARRFKAGGLDLLSVSVGFTIPDTNIPWGPAFMGPIAERVRREAKLPVTS AWGFGTPQLAEAALQANQLDLVSVGRAHLADPHWAYFAAKELGVEKASWTLPAPYAHWLE RYR |
| 18 | Kluyveromyces lactis | AAA98815 | MSFMNFEPKPLADTDIEKPIKIGNTELKHRVVMPALTRMRALHPGNVPNPDWAVEYYRQR SQYPGTMHITEGAFPSAQSGGYDNAPGVWSEEQLAQWRKIFKAIHDNKSFVWVQLWVLGR QAFADNLARDGLRYDSASDEVMGEDEKERAIRSNNPQHGITKDEIKQYIRDYVDAAKKC IDAGAGDGVEIHSANGYLLNQFLDPISNKRTDEYGGSIENRARFVLEVVDAVVDAVGAERT SIRFSPYGVFGTMSGGSDPVLVAQFAYVLAELEKRAKAGKRLAYVDLVEPRVTSPFQPEF EGWYKGGTNEFVYSVWKGNVLRVGNYALDPDAAITDSKNPNTLIGYGRAFIANPDLVERL EKGLPLNQYDRPSFYKMSAEGYHDPTYEEAVAKGYKK |
| 19 | Lactobacillus casei | AGP69310.1 | MSGYHFLKPFTFKHQTITLKNRIVPPMTTRLSFEDGTVTRDEHRYYQQRAGGVGMFITG TANVNALGKGFEGELSVADDRFFPGLSKLAAAMKTGGTKAHLQIFSAGRMSNSKILRGEFCQ PVSASAVAAPRAGYETPRALTSAEILEATIHDFGOAVRRAILAGEFDGIELHGANTYLHQQF YSPNSNRRTDEWGGORDKRMREFPLAVVHEAEKVIATIADRPFLLGYRISPEELECPGITL DDTLALIDALKQTKIDYLHVSQSDVVWRTSLRNFPEDTAIMNEQIRDHVAGAFPVIVVGGIK TPADAEKAAEESFDLVAIGHEMIREPHWVQKVLDHDEKAIRYQIAPADLEELGIAPTFLDF IESISGGAKGVPLTTAQSVTSSNVTQD |
| 20 | Saccharomyces pastorianus | CAA37656.1 | MSFVKDFKPQALGDTNLFKPIKIGNNELLHRAVIPPLTRMRALHPGNIPNRDWAVEYYTQ RACQRPGTMIITEGAHISPDAGGYDNAPGVWSEEQMVEWTKIFNAIHEKKSFVWVQLWVLG WAAFPDNLARDGLRYDSASDNVFMDAEQEAKAKKANNPQHSLTKDEIKCYHKEYVQAAKN SIAAGADGVEIHSANGYLLNQFLDPHSNTRTDEYGGSIENRARFTLEVVDALVEAIGHEK VGLRLSPYGVFNSMSGGAETGIVAQYAYVAGELEKRAKAGKRLAFVHLVEPRVTNPFLTE GEGEYEGSSNDFVYSIWKGPVIRAGNFALHPEVVREEVKDKRTLIGYGRFFISNPDLVDR LEKGLPLNKYDRDTFYQMSAHGYIDYPTYEEALKLGWDKK |

FIG. 20H

| SEQ ID NO | Organism | GENBANK reference | Amino acid sequence |
|---|---|---|---|
| 21 | Thermoanaerobacter pseudethanolicus | ABY93685.1 | MSILHMPLEKICHTIKNRIMMSPMCMYSASTDGMPNDWHIVHYATRAIGGVGLIMQEATA VESRGRITDHDLGWNDEQVKELKKIVDICKANGAVMGIQLAHAGRKCNISYEDVVGPSP IKAGDRYKLPRELSVEEKSIVKAFGEAAKRANLAGYDVVEIHAAHGYLIHEFLSPLSNK RKDEYGNSIENRARFLIEVIDEVRKNWPENKPIFVRVSADDYMEGGINIDMMAVEYINMIK DKVBLIDVSSGGLINVDINLYPGYCQVKYAETIKKRCNIKTSAVGLITTQELAEEHLSNER ADLVALGRELLRNPYWVLHTYTSKEDWPKQYERAFKK |
| 22 | Enterobacter cloacae | AAB38683.1 | MSAEKLFTPLKVGAVTAPNRVFMAPLTRLRSIEPGDIPTLMGEYYRQRASAGLIHSEAT GISAQAKGYAGAPGLHSPEQIAAWKKITAGVHAEDGRIAVQLWHTGRISHSSIQPGGQAP VSASALNANTRTSLRDENGNAIRVDTTTPRALELDEIPGIVNDFRQAVANAREAGFDLVE LHSAHGYLLHQFLSPSSNQRTDQYGGSVENRARLVLEVVDAVCNEWSADRIGIRVSPIGT FQNVDNGPNEEADALYLIEELAKRGIAYLHMSETDLAGGKPYSEAFRQKVRERFHGVIIG AGAYTAEKAEDLIGKGLIDAVAFGRDYHANPDLVARLQKKAELNPQRPESFYGGGAEGYT DYPSL |
| 23 | Fusobacterium nucleatum subsp. nucleatum | AAL93968.1 | MKSLIRLRMSSHDAHYGGNLVDGARMLQLFGDVATELLIQLDGDEGLFKAYDSVEFMAPV FAGDYIEAEGEIVNVGNSSRKMVFEARKVIVPRPDISDSAADVLAEPIVVCRATGTCVTP KDKQRGKK |
| 24 | Acidaminococcus fermentans | CAA42196.1 | MSIYTLGIDVGSTASKCIILKDGKEIVAKSLVAVGTGTSGPARSIISEVLENAHMKKEDMA FTLATGYGRNSLEGIADKQMSELSCHAMGASFIWPNVHTVIDIGGQDVKVHVENGTMTN FQMNDKCAAGTGRFLDVMANILEVKVSDLAELGAKSTKRVAISSTCTVFAESEVISQLSK GTDKIDIIAGIHRSVASRVIGLANRVGIVKDVVMTGGVAQNYGVVRGALEEGLGVEIKTSP LAQYNGALGAALYAYKKAAK |
| 25 | Clostridium symbiosum | AAD31677.1 & AAD31675.1 | MSINALLDEFKVKAATPKQQLAEYKAQGKKVGVLPYYAPEELVYAAGMVPMGIWGSNNK TISRAKEYCATFYCTIAQLALEMLLDGTMDQLDGHTPTICDTLRPMSQNFRVAMGDKMA VIFLAQPQNRFEDFGLQFSVDQYTNVKKELEKVAGKEITNEAIQDAIKVYNKSRAARRKF VELASAHCDVITPTKRSAVLKSFFMEKPEYIEKLEELNAELEKLPVCDWQGTKVVTSGI ICDNPKLLEIFEENNIAIAADDVGHESRSFRVDAPEDEADALMALAKQFANMDYDVLLYD PKSTENRRGEFIANMVKESGAQGLVLFMCQFCDPEEMEYPYLKALNNAGIPHIKLGIDQ QMRDFGQASTAIQAFADVLEMQK MSGIYTLGIDVGSTASKCIVLKDGKEIVAKSLIHDVGAGTSGPQRAIEAVLNEAGMKKEDM AYTLATGYGRTSLMDGIADKQMSELSCHAKGATFLPNVHTVIDIGGQDVKVLHIDNGAM TNFQMNDKCAAGTGRFLDVMARVLEVKVEDLGRLGAMSRKKVGISSTCTVFAESEVISQL AMGTDKCDIDGIHRSVAHRVTGLAHRIGVVPDVVMTGGVAQNEGVVAQLQDELGCPINT SPLTQYNGALGAALLAWQAASRQSNS |

FIG. 20I

| SEQ ID NO | Organism | GENBANK reference | Amino acid sequence |
|---|---|---|---|
| 26 | Bacillus subtilis | AAB72059.1 | MKNKWYKPKRHWKEIELWKDVPEEKWNDWLWQLTHTVRTLDDLKKVINLTEDEEEGVRIS TKTIPLNTPYYASLMDPDNPRCPVRMQSVPLSEEMHKTKYDLEDPLHEDEDSPVPGLTH RYPDRVLFLVTNQCSAYCYCTRRFSGQJGMGVPKKQLDAAIAYRETPEIRDCLISGG DGLLINDQLEYILKELRSIPHLEVIRIGTRAPVVFPQRITDHLCEILKKYHPVWLNTHF NTSIEMTEESVEACEKLVNAGVPVGNQAVVLAGINDSVPMKKLMHDLVKIRVRPYYIYQ CDLSEGIGHFRAPVSKGLEIIEGLRGHTSGYAVPTFVVDAPGGGGKIALQPNVVLSQSPD KVILRNFEGVHTSYPEPENYIPNQADAYFESVPPETADKKEPIGLSAIFADKEVSFTPEN VDRIKRREAYIANPEHETLKDRREKRDQLKEKFLACJQKKQKETECGGDSS |
| 27 | Peptoclostridium difficile | AAV40818.1 | MYTMGLDIGSTASKGIVLKNGEDIVASETISSGTGTTGPSRVLEKLYGKTGLAREDKKV VVTGYGRMNYSDADKQJSELSCHARGVNFHPETRTHDIGGQDAKVLKLDNNGRLLNFL MNDKCAAGTGRFLDVMAKIHEVDVSELGSISMNSQNEVSISSTCTVFAESEVISHLSENA KIEDHVAGIHTSVAKRVSSLVKRIGVQRNVVMVGGVARNSGIVRAAMAREINTEHVPDIP QLTGALGAALYAFDEAKESQKEVKNI |
| 28 | Peptoclostridium difficile | AAV40819.1 & AAV40820.1 | MSEKKEARVMINDLLAEQYANAFKAKEEGRPVGWSTSVFPQELAEVFDLNVLYPENQAAG VAAKKGSLELCEIAESKGYSIDLCAVARTNFGLLENGGCEALDMPAPDFLLCCNNICNQV IKWYENISRELDIPLIMIDTTFMNEDEVTQSRIDYIKAQFEEAIKQLEIHSGKKFDPKKF EEVMKISAENGRLIWKYSMSLPADSSPSPMNGFDLFTYMAVIVCARGKKETTEAFKLIEE LEDNMKTGKSSFRGEEKYRIMMEGIPCWPYIGYKMKTLAKFGVNMTGSSVYPHAWALQYEV NDLDGMAVAYSTMFNNVNLDRMTKYRVDSLVEGKCDGAFYHMNRSCKLMSLIQYEMQRRA AEETGLPYAGHFDGIDQADPRAFTNAQHETRIQGLVEVMEERKKLNRGEI MEAILSKMKEVVENPNAAVKKYKSETGKKAIGCFPVVCPEEIHAAGMLPVGIWGGQTEL DLAKQYFPAFACSIMQSCLEYGLKGAYDELSGVIIPPGMCDTLICLGQNWWKSAVPHKYIS LVHPQNRKLEAGVKYLISEYKGVKRELEEICGYEEEAKIHESIEVYNEHRKTMRDFVEV AYKHSNTIKPSIRKSLVIKSGFFMRKEEHTELVKDLIAKLNAMPEEVCSGKKVLLTGILAD SKOILDILEDNNISVVADDLAQETRQFRTDVPAGDDALERLARQWSNIEGCSLAYDPKKK RGSLIVDEVKKDIDGVIFCMMKFCDPEEYDVPLVRKDIEDSGIPTLYVEIDQQTQMNEQ ARTRIQTFAEMMSLA |
| 29 | Escherichia coli | AAA23833.1 | MDQKILTDFRSELLDSSRFGAKAISTIAESKRFPLHEMRDDVAFQIINDELYLDGNARQNI ATFCQTWDDENVHKLMDLSIMKNWIDKEEYPQSAAIDLRCVNMVADLWHAPAPKNGQAVG TNTIGSSEACMLGGMAMKVRWRKRMEAAGKPTDKPNLVCGPVQICVWHKFARYWDVELREI PMRRPGQLFMDPKRMIEACDENTIGSVVPTFGVTYFGNYEFPQPLHDALDKFQADTGIDIDM HIDAASGGFLAPFVAPCIWVWDFRLPRVKSISASGHKFGLAPLGCGWVIWRDEEALPQELV FNVDYLGGQGGQIGTFAINFSRPAGQVIAQYYEFLRLGREGYTKVQNASYQVAAYLADEIAKL GPYEFICTGRPDEGIPAVCFKLKDGEDPGYTLYDLSERLRLRGWQVPAFTLGGEATDIVV MRIMCRRGFEMDFAELLLEDYKASLKYLSDHPKLQGIAQQNSFKHT |

FIG. 20J

| SEQ ID NO | Organism | GENBANK reference | Amino acid sequence |
|---|---|---|---|
| 30 | Escherichia coli | AAA23536.1 | MNVIALNHMEGVYFKEEPIRELHRALERLNFQIVYPNDRDDLLKLIENNARLCGVIFDWD KYNLELCEEISKMNENLPLYAFANTYSTLDVSLNDLRLQISFFEYALGAAEDIANKIKQT TDEVINTILPLTKALFKVVREGKYTFCTPGHMGGTAFQKSPVGSLFYDFFGPNTMKSDI SISVSELGSLLDHSGPHKEAEQYARVFNADRSYRMVTNGTSTANKIVGMYSAPAGSTILI DRNCHKSLTHLMMMSDVTPIYFRPTRNAYGILGGIPQSEFQHATIAKRVKETPNATWPVH AVITNSTYDGLLYNTDFIKKTLDVKSIHFDSAWVPYTNFSPIYEGKCGMSGGRVEGKVIY ETQSTHKLLAAFSQASMIHVKGDVNEETFNEAYMMAHTTTSPHYGIVASTETAAAMMKGNA GKRLINGSIERAIKFRKEIKRLRTESDGWFFDVWQPDHIDTTECWPLRSDSTWHGFKNID NEHMYLDPIKVTLLTPGMEKDGTMSDFGIPASIVAKYLREDPEFYENMRIQELAQNHIKLVHH IDKTKALSLLRALTDFKRAFDINLRVKNMLPSLYREDPEFYENMRIQELAQNHIKLVHH NLPDLMYRAFEVLPTMVMTPYAAFQKELHGMTEEVYLDEMVGRINANMILPYPPGVPLVM PGEMITEESRPVLEFLQMLCEIGAHYPGFETDIHGAYRCADGRYTVKVLKEESKK |
| 31 | Escherichia coli | AAA62785.1 | MSKLKIAVSDSCPDCFTTQRECTYINESRNIDVAAVSLNDVTCGKLDEIDATEYGIPV FIATENQEFRVPAEYLPRISGVFENCESRREFYGRQLETAASHYETQLRPPFFRALVDYVN QGNSAFDCPGHQGGEFFRRHPAGNQFVEVFGEALFRADLCNADVAMGDLLIHEGAPCIAQ CHAAKVFNADKTYFVLNGTSSSNKVVLNALLTPGDLVLFDRNNHKSNHHGALLQAGATPV YLETARNPYGFIGGIDAHCFEESYLRELIAEVAPQRAKEARPFRLAVIQLGTYDGTIYNA RQVVDKIGHLCDYILFDSAWVGYEQFIPKMADCSPLLLDLNENDPGILVTQSVHKQQAGF SQTSQIHKKDSHIKGQCQRYVPHKRMNAFMMHASTSPFVPLFAALNINAKMHEGVSGRNM WMEDCVVNGINARKLILDNCQHRPVPELVDGKPWQSYETAQIAVDLRFFQFVPGEHWHS FEGYAENQYFVDPCKLLLTPGIDARNGEYEAFGVPATILANFLRENGVVPEKCDLNSIL FLLTPAEDMAKLQQLVALLVREFEKLLESDAPLAEVLPSIYKQHEERYAGYTLRQLCQEMH DLYARHNVKQLQKEMFRKEHFPRVSMNPGEANYALRGEVELVRLPDAEGRIAAEGALPY PPGVLCVVPGEIWGGAVLRYFSALEEGINLLPGFAPELQGVYIEEHDGRKQVWCYVIKPR DAQSTLLKGEKL |
| 32 | Escherichia coli | BAA21656.1 | MNIIIAIMGPHGVFYKDEPIKELESALVAQGFQIIWPQNSVDLLKFIEHNPRICGVIFDWD EYSLDLCSDINQLNEYLPLYAFINTHSTMDVSVQDMRMAALWFFEYALGQAEDIARMRQY TDEYLDNITPPFTKALFTYVKERKYTFCTPGHMGGTAYCKSPVGCLFYDFFGGNTLKADV SISVTELGSLLDHTGPHLEAEEYIARTFGAEQSVIVTNGTSTSNKIVGMYAAPSGSTILI DRNCHKSLAHLLMMNDVVPVWIKPTRNALGILGGIPRREFTRDSIEEKVAATTQAQWPVH AVITNSTYDGLLYNTDFIKQTLDVPSIHFDSAWVPYTHFHPYQGKSGMSGGERVAGKVIF ETQSTHKMLAALSQASLIHKGEYDEEAFNEAFMMHTTTSPSYPIVASVETAAAMLRGNP GKRLINRSVERALHFRKEVQRLREESDGWFFDIWQPPQVDEACWPVAPGEQWHGFNDAD ADHMFLDPVKVTILTPGMDEQNMSEEGIPAALVAKFLDERGIVVEKTGPYNLLFLFSIG IDKTKAMGLLRGLTEFKRSYDLNLRIKNMLPDLVAEDPFYRNMRIQDLAQGIHKLIRKH DLPGLMLRAFDTLPEMIMTPHQAWQRQIKGEVETIALEQLVGRVSANMILPYPPGVPLLM PGEMLTKESRTVLDFLLMLCSVGQHYPGFETDIHGAKQDEDGVYRVRVLKMAG |

FIG. 20K

| SEQ ID NO | Organism | GENBANK reference | Amino acid sequence |
|---|---|---|---|
| 33 | Escherichia coli | AAA83861.1 | MPHSLFSTDTDLTAENLLRLPAEFGCPVWVYDAQIIRRQIAALKQFDVVRFAQKACSNIH ILRLMREQGVKVDSVSLGEIERALAAGYNPCTHPDBVFTADVIDQATLERVSELQIPVN AGSVDMLDQLGQVSPGHRVWLRVNPGFGHGHSQKTNTGGENSKHGIWYTDLPAALDVIQR HHLQLVGIHMHIGSGVDYAHLEQVCGAMVRQVIEFGQDLQAISAGGGLSVPYQQGEEAVD TEHYYGLWNAAREQIARHLGHPVKLEIEPGRFLVAQSGVLITQVRSVKQMGSRHFVLVDA GFNDLMRPAMYGSYHHSSALAADGRSLEHAPTVETVVAGPLCESGDVFTQQEGGNVETRA LPEVKAGDYLVLHDTGAYGASMSSNYNSRPLLPEVLFDNGQARLIRRQTIEELLALELL |
| 34 | Salmonella typhimurium | CAC48239.1 | MQNPYTVADYLLDRLAGCGIGHLFGVPGDYNLQFLDHVIEDHPTLRWVGCANELNAAYAAD GYARMSGAGALLTTFGVGELSAINGIAGSYAEYVPVLHVGAPCSAAQQRGELMHHTLGD GDFRHFYRMSQAISAASAILDEQNACFEIDRVLGEMLAARRPGYIMLPADVAKKTAIPPT QALALPVHEAQSGVETAFRYHAROCLMNSRRIALLADFLAGRFGLRPLLQRWMAETPIAH ATLLMGKGLFDEQHPNFVGTYSAGASSKEVRQAIEDADRVICVGTRFVDTLTAGFTQQLP AERTLEIQPYASRIGETWFNLPMAQAVSTLRELCLECAFAPPPTRSAGQPVRIDKGELTQ ESFWQTLQQYLKPGDILVDQGTAAFGAAALSLPDGAEVVLQPLWGSIGYSLPAAFGAQT ACPDRRVILIGDGAAQLTIQEMIGSMLRDGQAPVIELLNNDGYTVERAIHGAAQRYNDIA SWRWTQIPPALNAAQCAECWRVTQAICLAEVLERLARPQRLSFIEVMLPKADLPELLRTV TRAILEARNGG |

```
                             SEQUENCE LISTING

<160> NUMBER OF SEQ ID NOS: 34

<210> SEQ ID NO 1
<211> LENGTH: 246
<212> TYPE: PRT
<213> ORGANISM: Lactobacillus brevis

<400> SEQUENCE: 1

Met Ala Ala Asn Glu Phe Ser Glu Thr His Arg Val Val Tyr Tyr Glu
  1               5                  10                  15

Ala Asp Asp Thr Gly Gln Leu Thr Leu Ala Met Leu Ile Asn Leu Phe
             20                  25                  30

Val Leu Val Ser Glu Asp Gln Asn Asp Ala Leu Gly Leu Ser Thr Ala
         35                  40                  45

Phe Val Gln Ser His Gly Val Gly Trp Val Val Thr Gln Tyr His Leu
     50                  55                  60

His Ile Asp Glu Leu Pro Arg Thr Gly Ala Gln Val Thr Ile Lys Thr
 65                  70                  75                  80

Arg Ala Thr Ala Tyr Asn Arg Tyr Phe Ala Tyr Arg Glu Tyr Trp Leu
                 85                  90                  95

Leu Asp Asp Ala Gly Gln Val Leu Ala Tyr Gly Glu Gly Ile Trp Val
            100                 105                 110

Thr Met Ser Tyr Ala Thr Arg Lys Ile Thr Thr Ile Pro Ala Glu Val
        115                 120                 125

Met Ala Pro Tyr His Ser Glu Glu Gln Thr Arg Leu Pro Arg Leu Pro
    130                 135                 140

Arg Pro Asp His Phe Asp Glu Ala Val Asn Gln Thr Leu Lys Pro Tyr
145                 150                 155                 160

Thr Val Arg Tyr Phe Asp Ile Asp Gly Asn Gly His Val Asn Asn Ala
                165                 170                 175

His Tyr Phe Asp Trp Met Leu Asp Val Leu Pro Ala Thr Phe Leu Arg
            180                 185                 190

Ala His His Pro Thr Asp Val Lys Ile Arg Phe Glu Asn Glu Val Gln
        195                 200                 205

Tyr Gly His Gln Val Thr Ser Glu Leu Ser Gln Ala Ala Leu Thr
    210                 215                 220

Thr Gln His Met Ile Lys Val Gly Asp Leu Thr Ala Val Lys Ala Thr
225                 230                 235                 240

Ile Gln Trp Asp Asn Arg
                245

<210> SEQ ID NO 2
<211> LENGTH: 261
<212> TYPE: PRT
<213> ORGANISM: Lactobacillus plantarum

<400> SEQUENCE: 2

Met Ala Thr Leu Gly Ala Asn Ala Ser Leu Tyr Ser Glu Gln His Arg
  1               5                  10                  15

Ile Thr Tyr Tyr Glu Cys Asp Arg Thr Gly Arg Ala Thr Leu Thr Thr
             20                  25                  30
```

Leu Ile Asp Ile Ala Val Leu Ala Ser Glu Asp Gln Ser Asp Ala Leu
            35                  40                  45

Gly Leu Thr Thr Glu Met Val Gln Ser His Gly Val Gly Trp Val Val
 50                  55                  60

Thr Gln Tyr Ala Ile Asp Ile Thr Arg Met Pro Arg Gln Asp Glu Val
 65                  70                  75                  80

Val Thr Ile Ala Val Arg Gly Ser Ala Tyr Asn Pro Tyr Phe Ala Tyr
                 85                  90                  95

Arg Glu Phe Trp Ile Arg Asp Ala Asp Gly Gln Gln Leu Ala Tyr Ile
                100                 105                 110

Thr Ser Ile Trp Val Met Met Ser Gln Thr Thr Arg Arg Ile Val Lys
                115                 120                 125

Ile Leu Pro Glu Leu Val Ala Pro Tyr Gln Ser Glu Val Val Lys Arg
            130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
                180                 185                 190

Ala Thr Phe Leu Leu Gln His Asp Leu Val His Val Asp Val Arg Tyr
            195                 200                 205

Glu Asn Glu Val Lys Tyr Gly Gln Thr Val Thr Ala His Ala Asn Ile
            210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
            260

<210> SEQ ID NO 3
<211> LENGTH: 1174
<212> TYPE: PRT
<213> ORGANISM: Mycobacterium marinum

<400> SEQUENCE: 3

Met Ser Pro Ile Thr Arg Glu Glu Arg Leu Glu Arg Arg Ile Gln Asp
 1                   5 10 15

Leu Tyr Ala Asn Asp Pro Gln Phe Ala Ala Ala Lys Pro Ala Thr Ala
20 25 30

Ile Thr Ala Ala Ile Glu Arg Pro Gly Leu Pro Leu Pro Gln Ile Ile
35 40 45

Glu Thr Val Met Thr Gly Tyr Ala Asp Arg Pro Ala Leu Ala Gln Arg
50 55 60

Ser Val Glu Phe Val Thr Asp Ala Gly Thr Gly His Thr Thr Leu Arg
65 70 75 80

Leu Leu Pro His Phe Glu Thr Ile Ser Tyr Gly Glu Leu Trp Asp Arg
85 90 95

Ile Ser Ala Leu Ala Asp Val Leu Ser Thr Glu Gln Thr Val Lys Pro
100 105 110

Gly Asp Arg Val Cys Leu Leu Gly Phe Asn Ser Val Asp Tyr Ala Thr
115 120 125

Ile Asp Met Thr Leu Ala Arg Leu Gly Ala Val Ala Val Pro Leu Gln
130 135 140

```
Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
            165                 170                 175

Leu Ala Leu Ser Gly Gln Thr Ala Thr Arg Val Leu Val Phe Asp His
        180                 185                 190

His Arg Gln Val Asp Ala His Arg Ala Ala Val Glu Ser Ala Arg Glu
            195                 200                 205

Arg Leu Ala Gly Ser Ala Val Val Glu Thr Leu Ala Glu Ala Ile Ala
        210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
        275                 280                 285

Thr Leu Asn Phe Met Pro Met Ser His Val Met Gly Arg Gln Ile Leu
290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
            340                 345                 350

Ser Glu Val Asp Arg Arg Leu Val Asp Gly Ala Asp Arg Val Ala Leu
        355                 360                 365

Glu Ala Gln Val Lys Ala Glu Ile Arg Asn Asp Val Leu Gly Gly Arg
370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
        435                 440                 445

Leu Thr Asp Arg Pro His Pro Arg Gly Glu Leu Leu Val Lys Thr Asp
    450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
        515                 520                 525

Gly Asp Ser Pro Leu Val Arg Gln Ile Tyr Ile Tyr Gly Asn Ser Ala
530                 535                 540

Arg Ala Tyr Leu Leu Ala Val Ile Val Pro Thr Gln Glu Ala Leu Asp
545                 550                 555                 560
```

```
Ala Val Pro Val Glu Glu Leu Lys Ala Arg Leu Gly Asp Ser Leu Gln
            565                 570                 575
Glu Val Ala Lys Ala Ala Gly Leu Gln Ser Tyr Glu Ile Pro Arg Asp
        580                 585                 590
Phe Ile Ile Glu Thr Thr Pro Trp Thr Leu Glu Asn Gly Leu Leu Thr
            595                 600             605
Gly Ile Arg Lys Leu Ala Arg Pro Gln Leu Lys Lys His Tyr Gly Glu
    610                 615                 620
Leu Leu Glu Gln Ile Tyr Thr Asp Leu Ala His Gly Gln Ala Asp Glu
625                 630                 635                 640
Leu Arg Ser Leu Arg Gln Ser Gly Ala Asp Ala Pro Val Leu Val Thr
                645                 650                 655
Val Cys Arg Ala Ala Ala Ala Leu Leu Gly Gly Ser Ala Ser Asp Val
            660                 665                 670
Gln Pro Asp Ala His Phe Thr Asp Leu Gly Gly Asp Ser Leu Ser Ala
        675                 680                 685
Leu Ser Phe Thr Asn Leu Leu His Glu Ile Phe Asp Ile Glu Val Pro
    690                 695                 700
Val Gly Val Ile Val Ser Pro Ala Asn Asp Leu Gln Ala Leu Ala Asp
705                 710                 715                 720
Tyr Val Glu Ala Ala Arg Lys Pro Gly Ser Ser Arg Pro Thr Phe Ala
                725                 730                 735
Ser Val His Gly Ala Ser Asn Gly Gln Val Thr Glu Val His Ala Gly
            740                 745                 750
Asp Leu Ser Leu Asp Lys Phe Ile Asp Ala Ala Thr Leu Ala Glu Ala
        755                 760                 765
Pro Arg Leu Pro Ala Ala Asn Thr Gln Val Arg Thr Val Leu Leu Thr
    770                 775                 780
Gly Ala Thr Gly Phe Leu Gly Arg Tyr Leu Ala Leu Glu Trp Leu Glu
785                 790                 795                 800
Arg Met Asp Leu Val Asp Gly Lys Leu Ile Cys Leu Val Arg Ala Lys
                805                 810                 815
Ser Asp Thr Glu Ala Arg Ala Arg Leu Asp Lys Thr Phe Asp Ser Gly
            820                 825                 830
Asp Pro Glu Leu Leu Ala His Tyr Arg Ala Leu Ala Gly Asp His Leu
        835                 840                 845
Glu Val Leu Ala Gly Asp Lys Gly Glu Ala Asp Leu Gly Leu Asp Arg
    850                 855                 860
Gln Thr Trp Gln Arg Leu Ala Asp Thr Val Asp Leu Ile Val Asp Pro
865                 870                 875                 880
Ala Ala Leu Val Asn His Val Leu Pro Tyr Ser Gln Leu Phe Gly Pro
                885                 890                 895
Asn Ala Leu Gly Thr Ala Glu Leu Leu Arg Leu Ala Leu Thr Ser Lys
            900                 905                 910
Ile Lys Pro Tyr Ser Tyr Thr Ser Thr Ile Gly Val Ala Asp Gln Ile
        915                 920                 925
Pro Pro Ser Ala Phe Thr Glu Asp Ala Asp Ile Arg Val Ile Ser Ala
    930                 935                 940
Thr Arg Ala Val Asp Asp Ser Tyr Ala Asn Gly Tyr Ser Asn Ser Lys
945                 950                 955                 960
Trp Ala Gly Glu Val Leu Leu Arg Glu Ala His Asp Leu Cys Gly Leu
                965                 970                 975
Pro Val Ala Val Phe Arg Cys Asp Met Ile Leu Ala Asp Thr Thr Trp
```

-continued

```
                980             985             990
Ala Gly Gln Leu Asn Val Pro Asp Met Phe Thr Arg Met Ile Leu Ser
            995                 1000                1005

Leu Ala Ala Thr Gly Ile Ala Pro Gly Ser Phe Tyr Glu Leu Ala Ala
            1010                1015                1020

Asp Gly Ala Arg Gln Arg Ala His Tyr Asp Gly Leu Pro Val Glu Phe
1025                1030                1035                1040

Ile Ala Glu Ala Ile Ser Thr Leu Gly Ala Gln Ser Gln Asp Gly Phe
                1045                1050                1055

His Thr Tyr His Val Met Asn Pro Tyr Asp Asp Gly Ile Gly Leu Asp
            1060                1065                1070

Glu Phe Val Asp Trp Leu Asn Glu Ser Gly Cys Pro Ile Gln Arg Ile
            1075                1080                1085

Ala Asp Tyr Gly Asp Trp Leu Gln Arg Phe Glu Thr Ala Leu Arg Ala
            1090                1095                1100

Leu Pro Asp Arg Gln Arg His Ser Ser Leu Leu Pro Leu His Asn
1105                1110                1115                1120

Tyr Arg Gln Pro Glu Arg Pro Val Arg Gly Ser Ile Ala Pro Thr Asp
            1125                1130                1135

Arg Phe Arg Ala Ala Val Gln Glu Ala Lys Ile Gly Pro Asp Lys Asp
            1140                1145                1150

Ile Pro His Val Gly Ala Pro Ile Ile Val Lys Tyr Val Ser Asp Leu
            1155                1160                1165

Arg Leu Leu Gly Leu Leu
            1170

<210> SEQ ID NO 4
<211> LENGTH: 1173
<212> TYPE: PRT
<213> ORGANISM: Mycobacterium smegmatis

<400> SEQUENCE: 4

Met Thr Ser Asp Val His Asp Ala Thr Asp Gly Val Thr Glu Thr Ala
1               5                   10                  15

Leu Asp Asp Glu Gln Ser Thr Arg Ile Ala Glu Leu Tyr Ala Thr
            20                  25                  30

Asp Pro Glu Phe Ala Ala Ala Pro Leu Pro Ala Val Val Asp Ala
            35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
            115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175
```

```
Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380

Leu Arg Glu Gln Val Leu Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
        435                 440                 445

Ile Asp Val Pro Glu Leu Gly Tyr Phe Ser Thr Asp Lys Pro Tyr Pro
    450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
```

```
                595                 600                 605
Phe Ser Ala Ala Asn Gly Leu Leu Ser Gly Val Gly Lys Leu Leu Arg
610                     615                 620

Pro Asn Leu Lys Asp Arg Tyr Gly Gln Arg Leu Glu Gln Met Tyr Ala
625                     630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
                660                 665                 670

Ile Leu Gly Thr Gly Ser Glu Val Ala Ser Asp Ala His Phe Thr Asp
                675                 680                 685

Leu Gly Gly Asp Ser Leu Ser Ala Leu Thr Leu Ser Asn Leu Leu Ser
690                     695                 700

Asp Phe Phe Gly Phe Glu Val Pro Val Gly Thr Ile Val Asn Pro Ala
705                     710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
                740                 745                 750

Glu Ile Arg Ala Ser Glu Leu Thr Leu Asp Lys Phe Ile Asp Ala Glu
                755                 760                 765

Thr Leu Arg Ala Ala Pro Gly Leu Pro Lys Val Thr Thr Glu Pro Arg
770                     775                 780

Thr Val Leu Leu Ser Gly Ala Asn Gly Trp Leu Gly Arg Phe Leu Thr
785                     790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
                820                 825                 830

Ala Tyr Asp Thr Asp Pro Glu Leu Ser Arg Arg Phe Ala Glu Leu Ala
                835                 840                 845

Asp Arg His Leu Arg Val Val Ala Gly Asp Ile Gly Asp Pro Asn Leu
850                     855                 860

Gly Leu Thr Pro Glu Ile Trp His Arg Leu Ala Ala Glu Val Asp Leu
865                     870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
                900                 905                 910

Leu Thr Glu Arg Ile Lys Pro Val Thr Tyr Leu Ser Thr Val Ser Val
                915                 920                 925

Ala Met Gly Ile Pro Asp Phe Glu Glu Asp Gly Asp Ile Arg Thr Val
930                     935                 940

Ser Pro Val Arg Pro Leu Asp Gly Gly Tyr Ala Asn Gly Tyr Gly Asn
945                     950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
                980                 985                 990

Arg Tyr Arg Gly Gln Val Asn Val Pro Asp Met Phe Thr Arg Leu Leu
                995                 1000                1005

Leu Ser Leu Leu Ile Thr Gly Val Ala Pro Arg Ser Phe Tyr Ile Gly
                1010                1015                1020
```

-continued

```
Asp Gly Glu Arg Pro Arg Ala His Tyr Pro Gly Leu Thr Val Asp Phe
1025                1030                1035                1040

Val Ala Glu Ala Val Thr Thr Leu Gly Ala Gln Gln Arg Glu Gly Tyr
            1045                1050                1055

Val Ser Tyr Asp Val Met Asn Pro His Asp Asp Gly Ile Ser Leu Asp
        1060                1065                1070

Val Phe Val Asp Trp Leu Ile Arg Ala Gly His Pro Ile Asp Arg Val
    1075                1080                1085

Asp Asp Tyr Asp Asp Trp Val Arg Arg Phe Glu Thr Ala Leu Thr Ala
    1090                1095                1100

Leu Pro Glu Lys Arg Arg Ala Gln Thr Val Leu Pro Leu Leu His Ala
1105                1110                1115                1120

Phe Arg Ala Pro Gln Ala Pro Leu Arg Gly Ala Pro Glu Pro Thr Glu
                1125                1130                1135

Val Phe His Ala Ala Val Arg Thr Ala Lys Val Gly Pro Gly Asp Ile
            1140                1145                1150

Pro His Leu Asp Glu Ala Leu Ile Asp Lys Tyr Ile Arg Asp Leu Arg
        1155                1160                1165

Glu Phe Gly Leu Ile
    1170

<210> SEQ ID NO 5
<211> LENGTH: 1148
<212> TYPE: PRT
<213> ORGANISM: Segniliparus rugosus

<400> SEQUENCE: 5

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu Ala His
    50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Trp Gln Ala Asp Gly Leu Ala Pro
                85                  90                  95

Gly Asp Phe Val Ala Thr Val Gly Phe Thr Ser Pro Asp Tyr Val Ala
            100                 105                 110

Val Asp Leu Ala Ala Ala Arg Ser Gly Leu Val Ser Val Pro Leu Gln
        115                 120                 125

Ala Gly Ala Ser Leu Ala Gln Leu Val Gly Ile Leu Glu Glu Thr Glu
    130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Glu Gln Leu Ala Arg Ala Gly Arg Ala Val Val
        195                 200                 205

Val Glu Thr Leu Ala Asp Leu Ala Ala Arg Gly Glu Ala Leu Pro Glu
```

```
                    210                 215                 220
Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                    245                 250                 255

Gln Arg Leu Val Ser Gln Leu Trp Gly Arg Thr Pro Val Val Pro Gly
                260                 265                 270

Met Pro Asn Ile Ser Leu His Tyr Met Pro Leu Ser His Ser Tyr Gly
            275                 280                 285

Arg Ala Val Leu Ala Gly Ala Leu Ser Ala Gly Gly Thr Ala His Phe
290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
                340                 345                 350

Leu Gly Gly Arg Leu Leu Val Ala Val Cys Gly Ser Ala Pro Leu Ser
            355                 360                 365

Pro Glu Met Arg Ala Phe Met Glu Glu Val Leu Gly Phe Pro Leu Leu
370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
                420                 425                 430

Ile Arg Ser Thr Ser Leu Ile Ser Gly Tyr Tyr Lys Arg Pro Glu Ile
            435                 440                 445

Thr Ala Glu Val Phe Asp Ala Gln Gly Tyr Tyr Lys Thr Gly Asp Val
450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
                500                 505                 510

Gly Asn Ser Glu Arg Ser Phe Leu Leu Ala Val Val Val Pro Asn Ala
            515                 520                 525

Glu Val Leu Gly Ala Arg Asp Gln Glu Glu Ala Lys Pro Leu Ile Ala
530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
                580                 585                 590

Arg Tyr Gly Glu Ala Leu Glu Ala Arg Tyr Asp Glu Ile Ala His Gly
            595                 600                 605

Gln Ala Asp Glu Leu Arg Ala Leu Arg Asp Gly Ala Gly Gln Arg Pro
610                 615                 620

Val Val Glu Thr Val Val Arg Ala Ala Val Ala Ile Ser Gly Ser Glu
625                 630                 635                 640
```

```
Gly Ala Glu Val Gly Pro Glu Ala Asn Phe Ala Asp Leu Gly Gly Asp
            645                 650                 655
Ser Leu Ser Ala Leu Ser Leu Ala Asn Leu Leu His Asp Val Phe Glu
            660                 665                 670
Val Glu Val Pro Val Arg Ile Ile Ile Gly Pro Thr Ala Ser Leu Ala
            675                 680                 685
Gly Ile Ala Lys His Ile Glu Ala Glu Arg Ala Gly Ala Ser Ala Pro
            690                 695                 700
Thr Ala Ala Ser Val His Gly Ala Gly Ala Thr Arg Ile Arg Ala Ser
705                 710                 715                 720
Glu Leu Thr Leu Glu Lys Phe Leu Pro Glu Asp Leu Ala Ala Ala
            725                 730                 735
Lys Gly Leu Pro Ala Ala Asp Gln Val Arg Thr Val Leu Leu Thr Gly
            740                 745                 750
Ala Asn Gly Trp Leu Gly Arg Phe Leu Ala Leu Glu Gln Leu Glu Arg
            755                 760                 765
Leu Ala Arg Ser Gly Gln Asp Gly Gly Lys Leu Ile Cys Leu Val Arg
    770                 775                 780
Gly Lys Asp Ala Ala Ala Arg Arg Ile Glu Glu Thr Leu Gly
785                 790                 795                 800
Thr Asp Pro Ala Leu Ala Ala Arg Phe Ala Glu Leu Ala Glu Gly Arg
            805                 810                 815
Leu Glu Val Val Pro Gly Asp Val Gly Glu Pro Lys Phe Gly Leu Asp
            820                 825                 830
Asp Ala Ala Trp Asp Arg Leu Ala Glu Glu Val Asp Val Ile Val His
            835                 840                 845
Pro Ala Ala Leu Val Asn His Val Leu Pro Tyr His Gln Leu Phe Gly
    850                 855                 860
Pro Asn Val Val Gly Thr Ala Glu Ile Ile Arg Leu Ala Ile Thr Ala
865                 870                 875                 880
Lys Arg Lys Pro Val Thr Tyr Leu Ser Thr Val Ala Val Ala Ala Gly
            885                 890                 895
Val Glu Pro Ser Ser Phe Glu Glu Asp Gly Asp Ile Arg Ala Val Val
            900                 905                 910
Pro Glu Arg Pro Leu Gly Asp Gly Tyr Ala Asn Gly Tyr Gly Asn Ser
            915                 920                 925
Lys Trp Ala Gly Glu Val Leu Leu Arg Glu Ala His Glu Leu Val Gly
    930                 935                 940
Leu Pro Val Ala Val Phe Arg Ser Asp Met Ile Leu Ala His Thr Arg
945                 950                 955                 960
Tyr Thr Gly Gln Leu Asn Val Pro Asp Gln Phe Thr Arg Leu Val Leu
            965                 970                 975
Ser Leu Leu Ala Thr Gly Ile Ala Pro Lys Ser Phe Tyr Gln Gln Gly
            980                 985                 990
Ala Ala Gly Glu Arg Gln Arg Ala His Tyr Asp Gly Ile Pro Val Asp
            995                 1000                1005
Phe Thr Ala Glu Ala Ile Thr Thr Leu Gly Ala Glu Pro Ser Trp Phe
            1010                1015                1020
Asp Gly Gly Ala Gly Phe Arg Ser Phe Asp Val Phe Asn Pro His His
    1025                1030                1035                1040
Asp Gly Val Gly Leu Asp Glu Phe Val Asp Trp Leu Ile Glu Ala Gly
            1045                1050                1055
```

His Pro Ile Ser Arg Ile Asp Asp His Lys Glu Trp Phe Ala Arg Phe
            1060            1065            1070

Glu Thr Ala Val Arg Gly Leu Pro Glu Ala Gln Arg Gln His Ser Leu
        1075            1080            1085

Leu Pro Leu Leu Arg Ala Tyr Ser Phe Pro His Pro Val Asp Gly
        1090            1095            1100

Ser Val Tyr Pro Thr Gly Lys Phe Gln Gly Ala Val Lys Ala Gln
1105            1110            1115            1120

Val Gly Ser Asp His Asp Val Pro His Leu Gly Lys Ala Leu Ile Val
            1125            1130            1135

Lys Tyr Ala Asp Asp Leu Lys Ala Leu Gly Leu Leu
            1140            1145

<210> SEQ ID NO 6
<211> LENGTH: 1185
<212> TYPE: PRT
<213> ORGANISM: Mycobacterium massiliense

<400> SEQUENCE: 6

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Gly Val Ala Val
    130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
            180                 185                 190

Phe Asp Tyr Thr Pro Glu Val Asp Asp Gln Arg Glu Ala Phe Glu Ala
        195                 200                 205

Ala Ser Thr Gln Leu Ala Gly Thr Gly Ile Ala Leu Glu Thr Leu Asp
    210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
            260                 265                 270

Arg Trp Trp Ile Arg Glu Asp Val Met Ala Gly Thr Glu Asn Leu Pro
        275                 280                 285

```
Met Ile Gly Leu Asn Phe Met Pro Met Ser His Ile Met Gly Arg Gly
        290                 295                 300
Thr Leu Thr Ser Thr Leu Ser Thr Gly Gly Thr Gly Tyr Phe Ala Ala
305                 310                 315                 320
Ser Ser Asp Met Ser Thr Leu Phe Glu Asp Met Glu Leu Ile Arg Pro
                325                 330                 335
Thr Ala Leu Ala Leu Val Pro Arg Val Cys Asp Met Val Phe Gln Arg
                340                 345                 350
Phe Gln Thr Glu Val Asp Arg Arg Leu Ala Ser Gly Asp Thr Ala Ser
            355                 360                 365
Ala Glu Ala Val Ala Ala Glu Val Lys Ala Asp Ile Arg Asp Asn Leu
        370                 375                 380
Phe Gly Gly Arg Val Ser Ala Val Met Val Gly Ser Ala Pro Leu Ser
385                 390                 395                 400
Glu Glu Leu Gly Glu Phe Ile Glu Ser Cys Phe Glu Leu Asn Leu Thr
                405                 410                 415
Asp Gly Tyr Gly Ser Thr Glu Ala Gly Met Val Phe Arg Asp Gly Ile
                420                 425                 430
Val Gln Arg Pro Pro Val Ile Asp Tyr Lys Leu Val Asp Val Pro Glu
            435                 440                 445
Leu Gly Tyr Phe Ser Thr Asp Lys Pro His Pro Arg Gly Glu Leu Leu
        450                 455                 460
Leu Lys Thr Asp Gly Met Phe Leu Gly Tyr Tyr Lys Arg Pro Glu Val
465                 470                 475                 480
Thr Ala Ser Val Phe Asp Ala Asp Gly Phe Tyr Met Thr Gly Asp Ile
                485                 490                 495
Val Ala Glu Leu Ala His Asp Asn Ile Glu Ile Ile Asp Arg Arg Asn
                500                 505                 510
Asn Val Leu Lys Leu Ser Gln Gly Glu Phe Val Ala Val Ala Thr Leu
            515                 520                 525
Glu Ala Glu Tyr Ala Asn Ser Pro Val Val His Gln Ile Tyr Val Tyr
        530                 535                 540
Gly Ser Ser Glu Arg Ser Tyr Leu Leu Ala Val Val Pro Thr Pro
545                 550                 555                 560
Glu Ala Val Ala Ala Lys Gly Asp Ala Ala Ala Leu Lys Thr Thr
                565                 570                 575
Ile Ala Asp Ser Leu Gln Asp Ile Ala Lys Glu Ile Gln Leu Gln Ser
                580                 585                 590
Tyr Glu Val Pro Arg Asp Phe Ile Ile Glu Pro Gln Pro Phe Thr Gln
            595                 600                 605
Gly Asn Gly Leu Leu Thr Gly Ile Ala Lys Leu Ala Arg Pro Asn Leu
        610                 615                 620
Lys Ala His Tyr Gly Pro Arg Leu Glu Gln Met Tyr Ala Glu Ile Ala
625                 630                 635                 640
Glu Gln Gln Ala Ala Glu Leu Arg Ala Leu His Gly Val Asp Pro Asp
                645                 650                 655
Lys Pro Ala Leu Glu Thr Val Leu Lys Ala Ala Gln Ala Leu Leu Gly
                660                 665                 670
Val Ser Ser Ala Glu Leu Ala Ala Asp Ala His Phe Thr Asp Leu Gly
            675                 680                 685
Gly Asp Ser Leu Ser Ala Leu Ser Phe Ser Asp Leu Leu Arg Asp Ile
        690                 695                 700
```

-continued

```
Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
        755                 760                 765

His Ala Ala Pro Ser Leu Pro Lys Ala Gly Ile Pro His Thr Val
    770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
            820                 825                 830

Asp Thr Gly Asp Thr Glu Leu Leu Ala His Phe Arg Ser Leu Ala Asp
        835                 840                 845

Lys His Leu Glu Val Leu Ala Gly Asp Ile Gly Asp Pro Asn Leu Gly
    850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
            900                 905                 910

Thr Thr Lys Ile Lys Pro Val Thr Tyr Leu Ser Thr Val Ala Val Ala
        915                 920                 925

Ala Tyr Val Asp Pro Thr Thr Phe Asp Glu Glu Ser Asp Ile Arg Leu
    930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
            980                 985                 990

Ser Arg Tyr Thr Gly Gln Leu Asn Val Pro Asp Gln Phe Thr Arg Leu
        995                 1000                1005

Ile Leu Ser Leu Ile Ala Thr Gly Ile Ala Pro Gly Ser Phe Tyr Gln
    1010                1015                1020

Ala Gln Thr Thr Gly Glu Arg Pro Leu Ala His Tyr Asp Gly Leu Pro
1025                1030                1035                1040

Gly Asp Phe Thr Ala Glu Ala Ile Thr Thr Leu Gly Thr Gln Val Pro
                1045                1050                1055

Glu Gly Ser Glu Gly Phe Val Tyr Asp Cys Val Asn Pro His Ala
            1060                1065                1070

Asp Gly Ile Ser Leu Asp Asn Phe Val Asp Trp Leu Ile Glu Ala Gly
        1075                1080                1085

Tyr Pro Ile Ala Arg Ile Asp Asn Tyr Thr Glu Trp Phe Thr Arg Phe
    1090                1095                1100

Asp Thr Ala Ile Arg Gly Leu Ser Glu Lys Gln Lys Gln His Ser Leu
1105                1110                1115                1120

Leu Pro Leu Leu His Ala Phe Glu Gln Pro Ser Ala Ala Glu Asn His
```

```
                       1125                1130                1135
Gly Val Val Pro Ala Lys Arg Phe Gln His Ala Val Gln Ala Ala Gly
                1140                1145                1150

Ile Gly Pro Val Gly Gln Asp Gly Thr Thr Asp Ile Pro His Leu Ser
                1155                1160                1165

Arg Arg Leu Ile Val Lys Tyr Ala Lys Asp Leu Glu Gln Leu Gly Leu
                1170                1175                1180

Leu
1185

<210> SEQ ID NO 7
<211> LENGTH: 1186
<212> TYPE: PRT
<213> ORGANISM: Segniliparus rotundus

<400> SEQUENCE: 7

Met Thr Gln Ser His Thr Gln Gly Pro Gln Ala Ser Ala Ala His Ser
 1               5                  10                  15

Arg Leu Ala Arg Arg Ala Ala Glu Leu Leu Ala Thr Asp Pro Gln Ala
            20                  25                  30

Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
    210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Ala Phe Asp Glu Asp Ala Ala Pro Pro Val Pro Ala Ile
    290                 295                 300
```

```
Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
                340                 345                 350

Leu Phe Leu Val Pro Arg Val Glu Met Leu Tyr Gln His Tyr Gln
        355                 360                 365

Ser Glu Leu Asp Arg Arg Gly Val Gln Asp Gly Thr Arg Glu Ala Glu
370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
                420                 425                 430

Glu Ala Gly Pro Val Trp Arg Asp Gly Tyr Leu Val Lys Pro Pro Val
                435                 440                 445

Thr Asp Tyr Lys Leu Ile Asp Val Pro Glu Leu Gly Tyr Phe Ser Thr
450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
                500                 505                 510

Glu Gln Phe Ala Tyr Val Asp Arg Arg Lys Asn Val Leu Lys Leu Ser
                515                 520                 525

Gln Gly Glu Phe Val Thr Leu Ala Lys Leu Glu Ala Ala Tyr Ser Ser
                530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Lys Ala Ala Leu Gly Glu Ser Leu Gln Lys
                580                 585                 590

Ile Ala Arg Asp Glu Gly Leu Gln Ser Tyr Glu Val Pro Arg Asp Phe
                595                 600                 605

Ile Ile Glu Thr Asp Pro Phe Thr Val Glu Asn Gly Leu Leu Ser Asp
                610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
                660                 665                 670

Arg Arg Ala Ala Ala Met Leu Gly Ala Ser Ala Ala Glu Ile Lys
                675                 680                 685

Pro Asp Ala His Phe Thr Asp Leu Gly Gly Asp Ser Leu Ser Ala Leu
                690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
```

```
                725                 730                 735
Ile Asp Ala Gln Leu Ala Gly Gly Arg Ala Arg Pro Thr Phe Ala Thr
                740                 745                 750

Val His Gly Lys Gly Ser Thr Thr Ile Lys Ala Ser Asp Leu Thr Leu
                755                 760                 765

Asp Lys Phe Ile Asp Glu Gln Thr Leu Glu Ala Ala Lys His Leu Pro
    770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
                820                 825                 830

Ala Lys Ala Arg Leu Asp Ala Ala Tyr Glu Ser Gly Asp Pro Lys Leu
                835                 840                 845

Ala Gly His Tyr Gln Asp Leu Ala Ala Thr Thr Leu Glu Val Leu Ala
                850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
                885                 890                 895

Asn His Val Leu Pro Tyr Asn Gln Leu Phe Gly Pro Asn Val Ala Gly
                900                 905                 910

Val Ala Glu Ile Ile Lys Leu Ala Ile Thr Thr Arg Ile Lys Pro Val
                915                 920                 925

Thr Tyr Leu Ser Thr Val Ala Val Ala Ala Gly Val Glu Pro Ser Ala
    930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
                965                 970                 975

Val Leu Leu Arg Glu Ala His Asp Arg Thr Gly Leu Pro Val Arg Val
                980                 985                 990

Phe Arg Ser Asp Met Ile Leu Ala His Gln Lys Tyr Thr Gly Gln Val
    995                 1000                1005

Asn Ala Thr Asp Gln Phe Thr Arg Leu Val Gln Ser Leu Leu Ala Thr
    1010                1015                1020

Gly Leu Ala Pro Lys Ser Phe Tyr Glu Leu Asp Ala Gln Gly Asn Arg
1025                1030                1035                1040

Gln Arg Ala His Tyr Asp Gly Ile Pro Val Asp Phe Thr Ala Glu Ser
                1045                1050                1055

Ile Thr Thr Leu Gly Gly Asp Gly Leu Glu Gly Tyr Arg Ser Tyr Asn
                1060                1065                1070

Val Phe Asn Pro His Arg Asp Gly Val Gly Leu Asp Glu Phe Val Asp
                1075                1080                1085

Trp Leu Ile Glu Ala Gly His Pro Ile Thr Arg Ile Asp Asp Tyr Asp
                1090                1095                1100

Gln Trp Leu Ser Arg Phe Glu Thr Ser Leu Arg Gly Leu Pro Glu Ser
1105                1110                1115                1120

Lys Arg Gln Ala Ser Val Leu Pro Leu Leu His Ala Phe Ala Arg Pro
                1125                1130                1135

Gly Pro Ala Val Asp Gly Ser Pro Phe Arg Asn Thr Val Phe Arg Thr
                1140                1145                1150
```

Asp Val Gln Lys Ala Lys Ile Gly Ala Glu His Asp Ile Pro His Leu
            1155                1160                1165

Gly Lys Ala Leu Val Leu Lys Tyr Ala Asp Ile Lys Gln Leu Gly
    1170                1175                1180

Leu Leu
1185

<210> SEQ ID NO 8
<211> LENGTH: 459
<212> TYPE: PRT
<213> ORGANISM: Chromobacterium violaceum

<400> SEQUENCE: 8

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Ser Glu
            35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
        290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val

-continued

```
                    325                 330                 335
Ala Ala Leu Arg Asp Glu Gly Ile Val Gln Arg Val Lys Asp Asp Ile
                340                 345                 350
Gly Pro Tyr Met Gln Lys Arg Trp Arg Glu Thr Phe Ser Arg Phe Glu
                355                 360                 365
His Val Asp Asp Val Arg Gly Val Gly Met Val Gln Ala Phe Thr Leu
            370                 375                 380
Val Lys Asn Lys Ala Lys Arg Glu Leu Phe Pro Asp Phe Gly Glu Ile
385                 390                 395                 400
Gly Thr Leu Cys Arg Asp Ile Phe Phe Arg Asn Asn Leu Ile Met Arg
                405                 410                 415
Ala Cys Gly Asp His Ile Val Ser Ala Pro Leu Val Met Thr Arg
                420                 425                 430
Ala Glu Val Asp Glu Met Leu Ala Val Ala Glu Arg Cys Leu Glu Glu
                435                 440                 445
Phe Glu Gln Thr Leu Lys Ala Arg Gly Leu Ala
                450                 455

<210> SEQ ID NO 9
<211> LENGTH: 468
<212> TYPE: PRT
<213> ORGANISM: Pseudomonas aeruginosa

<400> SEQUENCE: 9

Met Asn Ala Arg Leu His Ala Thr Ser Pro Leu Gly Asp Ala Asp Leu
1               5                   10                  15
Val Arg Ala Asp Gln Ala His Tyr Met His Gly Tyr His Val Phe Asp
                20                  25                  30
Asp His Arg Val Asn Gly Ser Leu Asn Ile Ala Ala Gly Asp Gly Ala
            35                  40                  45
Tyr Ile Tyr Asp Thr Ala Gly Asn Arg Tyr Leu Asp Ala Val Gly Gly
        50                  55                  60
Met Trp Cys Thr Asn Ile Gly Leu Gly Arg Glu Glu Met Ala Arg Thr
65                  70                  75                  80
Val Ala Glu Gln Thr Arg Leu Leu Ala Tyr Ser Asn Pro Phe Cys Asp
                85                  90                  95
Met Ala Asn Pro Arg Ala Ile Glu Leu Cys Arg Lys Leu Ala Glu Leu
                100                 105                 110
Ala Pro Gly Asp Leu Asp His Val Phe Leu Thr Thr Gly Gly Ser Thr
            115                 120                 125
Ala Val Asp Thr Ala Ile Arg Leu Met His Tyr Tyr Gln Asn Cys Arg
        130                 135                 140
Gly Lys Arg Ala Lys Lys His Val Ile Thr Arg Ile Asn Ala Tyr His
145                 150                 155                 160
Gly Ser Thr Phe Leu Gly Met Ser Leu Gly Gly Lys Ser Ala Asp Arg
                165                 170                 175
Pro Ala Glu Phe Asp Phe Leu Asp Glu Arg Ile His His Leu Ala Cys
                180                 185                 190
Pro Tyr Tyr Tyr Arg Ala Pro Glu Gly Leu Gly Glu Ala Glu Phe Leu
            195                 200                 205
Asp Gly Leu Val Asp Glu Phe Glu Arg Lys Ile Leu Glu Leu Gly Ala
        210                 215                 220
Asp Arg Val Gly Ala Phe Ile Ser Glu Pro Val Phe Gly Ser Gly Gly
225                 230                 235                 240
```

-continued

```
Val Ile Val Pro Pro Ala Gly Tyr His Arg Arg Met Trp Glu Leu Cys
            245                 250                 255

Gln Arg Tyr Asp Val Leu Tyr Ile Ser Asp Glu Val Val Thr Ser Phe
        260                 265                 270

Gly Arg Leu Gly His Phe Phe Ala Ser Gln Ala Val Phe Gly Val Gln
    275                 280                 285

Pro Asp Ile Ile Leu Thr Ala Lys Gly Leu Thr Ser Gly Tyr Gln Pro
290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 10
<211> LENGTH: 454
<212> TYPE: PRT
<213> ORGANISM: Pseudomonas syringae

<400> SEQUENCE: 10

Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140
```

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
            165                 170                 175

Pro Ile Pro Gly Val Val His Ile Pro Gln Pro Tyr Trp Phe Gly Glu
        180                 185                 190

Gly Gly Asp Met Thr Pro Asp Glu Phe Gly Ile Trp Ala Ala Glu Gln
    195                 200                 205

Leu Glu Lys Lys Ile Leu Glu Leu Gly Val Glu Asn Val Gly Ala Phe
210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
        355                 360                 365

Leu Val Gly Glu Val Arg Gly Val Gly Leu Leu Gly Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
            420                 425                 430

Gln Ile Asp Glu Leu Val Glu Lys Ala Arg Thr Cys Leu Asp Leu Thr
        435                 440                 445

Leu Ala Val Leu Gln Gly
    450

<210> SEQ ID NO 11
<211> LENGTH: 467
<212> TYPE: PRT
<213> ORGANISM: Rhodobacter sphaeroides

<400> SEQUENCE: 11

Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys

-continued

```
                50                  55                  60
Ala Gln Val Gly Tyr Gly Arg Arg Glu Ile Val Asp Ala Met Ala His
 65                  70                  75                  80

Gln Ala Met Val Leu Pro Tyr Ala Ser Pro Trp Tyr Met Ala Thr Ser
                 85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
            115                 120                 125

Ala Leu Arg Phe Ser Glu Phe Tyr Asn Asn Val Leu Gly Arg Pro Gln
        130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
210                 215                 220

Leu Ala Glu Pro Ile Leu Ala Ser Gly Gly Val Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
        275                 280                 285

Ala Lys Gly Val Thr Ser Gly Tyr Val Pro Leu Gly Gly Leu Ala Ile
        290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Leu Ala Ser Leu
        355                 360                 365

Arg Asp Leu Pro Gly Val Ala Glu Thr Arg Ser Val Gly Leu Val Gly
        370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
        435                 440                 445

Ala Ile Thr Glu Val Ser Ala Ala His Gly Leu Thr Ala Lys Glu Pro
    450                 455                 460

Ala Ala Val
465
```

```
<210> SEQ ID NO 12
<211> LENGTH: 459
<212> TYPE: PRT
<213> ORGANISM: Escherichia coli

<400> SEQUENCE: 12

Met Asn Arg Leu Pro Ser Ser Ala Ser Ala Leu Ala Cys Ser Ala His
  1               5                  10                  15

Ala Leu Asn Leu Ile Glu Lys Arg Thr Leu Asp His Glu Glu Met Lys
             20                  25                  30

Ala Leu Asn Arg Glu Val Ile Glu Tyr Phe Lys Glu His Val Asn Pro
         35                  40                  45

Gly Phe Leu Glu Tyr Arg Lys Ser Val Thr Ala Gly Gly Asp Tyr Gly
     50                  55                  60

Ala Val Glu Trp Gln Ala Gly Ser Leu Asn Thr Leu Val Asp Thr Gln
 65                  70                  75                  80

Gly Gln Glu Phe Ile Asp Cys Leu Gly Gly Phe Gly Ile Phe Asn Val
                 85                  90                  95

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
        115                 120                 125

Leu Ala Lys Thr Leu Ala Ala Leu Thr Pro Gly Lys Leu Lys Tyr Ser
    130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
                245                 250                 255

Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
```

```
              370                 375                 380
Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
                420                 425                 430

Leu Thr Ile Glu Gln Cys Glu Leu Val Ile Lys Ala Ala Arg Lys Ala
            435                 440                 445

Leu Ala Ala Met Arg Val Ser Val Glu Glu Ala
        450                 455
```

<210> SEQ ID NO 13
<211> LENGTH: 453
<212> TYPE: PRT
<213> ORGANISM: Vibrio fluvialis

<400> SEQUENCE: 13

```
Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val Asn Gly Arg Arg
            35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
            195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285
```

Ala Gly Phe Phe Pro Met Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
450

<210> SEQ ID NO 14
<211> LENGTH: 224
<212> TYPE: PRT
<213> ORGANISM: Bacillus subtilis

<400> SEQUENCE: 14

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

```
Pro Asp Phe Pro Glu Asp Ile Thr Met Val Ser Tyr Glu Glu Leu Leu
    210                 215                 220

<210> SEQ ID NO 15
<211> LENGTH: 222
<212> TYPE: PRT
<213> ORGANISM: Nocardia sp. NRRL 5646

<400> SEQUENCE: 15

Met Ile Glu Thr Ile Leu Pro Ala Gly Val Glu Ser Ala Glu Leu Leu
  1               5                  10                  15

Glu Tyr Pro Glu Asp Leu Lys Ala His Pro Ala Glu Glu His Leu Ile
             20                  25                  30

Ala Lys Ser Val Glu Lys Arg Arg Asp Phe Ile Gly Ala Arg His
         35                  40                  45

Cys Ala Arg Leu Ala Leu Ala Glu Leu Gly Glu Pro Pro Val Ala Ile
     50                  55                  60

Gly Lys Gly Glu Arg Gly Ala Pro Ile Trp Pro Arg Gly Val Val Gly
 65                  70                  75                  80

Ser Leu Thr His Cys Asp Gly Tyr Arg Ala Ala Val Ala His Lys
                 85                  90                  95

Met Arg Phe Arg Ser Ile Gly Ile Asp Ala Glu Pro His Ala Thr Leu
            100                 105                 110

Pro Glu Gly Val Leu Asp Ser Val Ser Leu Pro Pro Glu Arg Glu Trp
            115                 120                 125

Leu Lys Thr Thr Asp Ser Ala Leu His Leu Asp Arg Leu Leu Phe Cys
130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
            195                 200                 205

Leu Ile Ala Asp Gly Phe Ile Leu Thr Ala Ile Ala Tyr Ala
    210                 215                 220

<210> SEQ ID NO 16
<211> LENGTH: 338
<212> TYPE: PRT
<213> ORGANISM: Bacillus subtilis

<400> SEQUENCE: 16

Met Ala Arg Lys Leu Phe Thr Pro Ile Thr Ile Lys Asp Met Thr Leu
  1               5                  10                  15

Lys Asn Arg Ile Val Met Ser Pro Met Cys Met Tyr Ser Ser His Glu
             20                  25                  30

Lys Asp Gly Lys Leu Thr Pro Phe His Met Ala His Tyr Ile Ser Arg
             35                  40                  45

Ala Ile Gly Gln Val Gly Leu Ile Ile Val Glu Ala Ser Ala Val Asn
     50                  55                  60

Pro Gln Gly Arg Ile Thr Asp Gln Asp Leu Gly Ile Trp Ser Asp Glu
 65                  70                  75                  80

His Ile Glu Gly Phe Ala Lys Leu Thr Glu Gln Val Lys Glu Gln Gly
                 85                  90                  95
```

```
Ser Lys Ile Gly Ile Gln Leu Ala His Ala Gly Arg Lys Ala Glu Leu
                100                 105                 110

Glu Gly Asp Ile Phe Ala Pro Ser Ala Ile Ala Phe Asp Glu Gln Ser
            115                 120                 125

Ala Thr Pro Val Glu Met Ser Ala Glu Lys Val Lys Glu Thr Val Gln
130                 135                 140

Glu Phe Lys Gln Ala Ala Arg Ala Lys Glu Ala Gly Phe Asp Val
145                 150                 155                 160

Ile Glu Ile His Ala Ala His Gly Tyr Leu Ile His Glu Phe Leu Ser
                165                 170                 175

Pro Leu Ser Asn His Arg Thr Asp Glu Tyr Gly Gly Ser Pro Glu Asn
            180                 185                 190

Arg Tyr Arg Phe Leu Arg Glu Ile Ile Asp Glu Val Lys Gln Val Trp
        195                 200                 205

Asp Gly Pro Leu Phe Val Arg Val Ser Ala Ser Asp Tyr Thr Asp Lys
    210                 215                 220

Gly Leu Asp Ile Ala Asp His Ile Gly Phe Ala Lys Trp Met Lys Glu
225                 230                 235                 240

Gln Gly Val Asp Leu Ile Asp Cys Ser Ser Gly Ala Leu Val His Ala
                245                 250                 255

Asp Ile Asn Val Phe Pro Gly Tyr Gln Val Ser Phe Ala Glu Lys Ile
            260                 265                 270

Arg Glu Gln Ala Asp Met Ala Thr Gly Ala Val Gly Met Ile Thr Asp
        275                 280                 285

Gly Ser Met Ala Glu Glu Ile Leu Gln Asn Gly Arg Ala Asp Leu Ile
    290                 295                 300

Phe Ile Gly Arg Glu Leu Leu Arg Asp Pro Phe Phe Ala Arg Thr Ala
305                 310                 315                 320

Ala Lys Gln Leu Asn Thr Glu Ile Pro Ala Pro Val Gln Tyr Glu Arg
                325                 330                 335

Gly Trp

<210> SEQ ID NO 17
<211> LENGTH: 363
<212> TYPE: PRT
<213> ORGANISM: Pseudomonas putida

<400> SEQUENCE: 17

Met Ser Ala Leu Phe Glu Pro Tyr Thr Leu Lys Asp Val Thr Leu Arg
1               5                   10                  15

Asn Arg Ile Ala Ile Pro Pro Met Cys Gln Tyr Met Ala Glu Asp Gly
            20                  25                  30

Met Ile Asn Asp Trp His His Val Leu Ala Gly Leu Ala Arg Gly
        35                  40                  45

Gly Ala Gly Leu Leu Val Val Glu Ala Thr Ala Val Ala Pro Glu Gly
    50                  55                  60

Arg Ile Thr Pro Gly Cys Ala Gly Ile Trp Ser Asp Ala His Ala Gln
65                  70                  75                  80

Ala Phe Val Pro Val Val Gln Ala Ile Lys Ala Ala Gly Ser Val Pro
                85                  90                  95

Gly Ile Gln Ile Ala His Ala Gly Arg Lys Ala Ser Ala Asn Arg Pro
            100                 105                 110

Trp Glu Gly Asp Asp His Ile Ala Ala Asp Ala Arg Gly Trp Glu
        115                 120                 125
```

Thr Ile Ala Pro Ser Ala Ile Ala Phe Gly Ala His Leu Pro Lys Val
130                 135                 140

Pro Arg Glu Met Thr Leu Asp Asp Ile Ala Arg Val Lys Gln Asp Phe
145                 150                 155                 160

Val Asp Ala Ala Arg Arg Ala Arg Asp Ala Gly Phe Glu Trp Ile Glu
            165                 170                 175

Leu His Phe Ala His Gly Tyr Leu Gly Gln Ser Phe Phe Ser Glu His
            180                 185                 190

Ser Asn Lys Arg Thr Asp Ala Tyr Gly Gly Ser Phe Asp Asn Arg Ser
        195                 200                 205

Arg Phe Leu Leu Glu Thr Leu Ala Val Arg Glu Val Trp Pro Glu
        210                 215                 220

Asn Leu Pro Leu Thr Ala Arg Phe Gly Val Leu Glu Tyr Asp Gly Arg
225                 230                 235                 240

Asp Glu Gln Thr Leu Glu Glu Ser Ile Glu Leu Ala Arg Arg Phe Lys
            245                 250                 255

Ala Gly Gly Leu Asp Leu Leu Ser Val Ser Val Gly Phe Thr Ile Pro
            260                 265                 270

Asp Thr Asn Ile Pro Trp Gly Pro Ala Phe Met Gly Pro Ile Ala Glu
            275                 280                 285

Arg Val Arg Arg Glu Ala Lys Leu Pro Val Thr Ser Ala Trp Gly Phe
290                 295                 300

Gly Thr Pro Gln Leu Ala Glu Ala Leu Gln Ala Asn Gln Leu Asp
305                 310                 315                 320

Leu Val Ser Val Gly Arg Ala His Leu Ala Asp Pro His Trp Ala Tyr
            325                 330                 335

Phe Ala Ala Lys Glu Leu Gly Val Glu Lys Ala Ser Trp Thr Leu Pro
            340                 345                 350

Ala Pro Tyr Ala His Trp Leu Glu Arg Tyr Arg
            355                 360

<210> SEQ ID NO 18
<211> LENGTH: 398
<212> TYPE: PRT
<213> ORGANISM: Kluyveromyces lactis

<400> SEQUENCE: 18

Met Ser Phe Met Asn Phe Glu Pro Lys Pro Leu Ala Asp Thr Asp Ile
1               5                   10                  15

Phe Lys Pro Ile Lys Ile Gly Asn Thr Glu Leu Lys His Arg Val Val
            20                  25                  30

Met Pro Ala Leu Thr Arg Met Arg Ala Leu His Pro Gly Asn Val Pro
        35                  40                  45

Asn Pro Asp Trp Ala Val Glu Tyr Tyr Arg Gln Arg Ser Gln Tyr Pro
    50                  55                  60

Gly Thr Met Ile Ile Thr Glu Gly Ala Phe Pro Ser Ala Gln Ser Gly
65                  70                  75                  80

Gly Tyr Asp Asn Ala Pro Gly Val Trp Ser Glu Glu Gln Leu Ala Gln
            85                  90                  95

Trp Arg Lys Ile Phe Lys Ala Ile His Asp Asn Lys Ser Phe Val Trp
            100                 105                 110

Val Gln Leu Trp Val Leu Gly Arg Gln Ala Phe Ala Asp Asn Leu Ala
        115                 120                 125

Arg Asp Gly Leu Arg Tyr Asp Ser Ala Ser Asp Glu Val Tyr Met Gly

```
                130                 135                 140
Glu Asp Glu Lys Glu Arg Ala Ile Arg Ser Asn Asn Pro Gln His Gly
145                 150                 155                 160

Ile Thr Lys Asp Glu Ile Lys Gln Tyr Ile Arg Asp Tyr Val Asp Ala
                165                 170                 175

Ala Lys Lys Cys Ile Asp Ala Gly Ala Asp Gly Val Glu Ile His Ser
                180                 185                 190

Ala Asn Gly Tyr Leu Leu Asn Gln Phe Leu Asp Pro Ile Ser Asn Lys
                195                 200                 205

Arg Thr Asp Glu Tyr Gly Gly Ser Ile Glu Asn Arg Ala Arg Phe Val
                210                 215                 220

Leu Glu Val Val Asp Ala Val Val Asp Ala Val Gly Ala Glu Arg Thr
225                 230                 235                 240

Ser Ile Arg Phe Ser Pro Tyr Gly Val Phe Gly Thr Met Ser Gly Gly
                245                 250                 255

Ser Asp Pro Val Leu Val Ala Gln Phe Ala Tyr Val Leu Ala Glu Leu
                260                 265                 270

Glu Lys Arg Ala Lys Ala Gly Lys Arg Leu Ala Tyr Val Asp Leu Val
                275                 280                 285

Glu Pro Arg Val Thr Ser Pro Phe Gln Pro Glu Phe Glu Gly Trp Tyr
                290                 295                 300

Lys Gly Gly Thr Asn Glu Phe Val Tyr Ser Val Trp Lys Gly Asn Val
305                 310                 315                 320

Leu Arg Val Gly Asn Tyr Ala Leu Asp Pro Asp Ala Ala Ile Thr Asp
                325                 330                 335

Ser Lys Asn Pro Asn Thr Leu Ile Gly Tyr Gly Arg Ala Phe Ile Ala
                340                 345                 350

Asn Pro Asp Leu Val Glu Arg Leu Glu Lys Gly Leu Pro Leu Asn Gln
                355                 360                 365

Tyr Asp Arg Pro Ser Phe Tyr Lys Met Ser Ala Glu Gly Tyr Ile Asp
                370                 375                 380

Tyr Pro Thr Tyr Glu Glu Ala Val Ala Lys Gly Tyr Lys Lys
385                 390                 395

<210> SEQ ID NO 19
<211> LENGTH: 387
<212> TYPE: PRT
<213> ORGANISM: Lactobacillus casei

<400> SEQUENCE: 19

Met Ser Gly Tyr His Phe Leu Lys Pro Phe Thr Phe Lys His Gln Thr
1               5                   10                  15

Ile Thr Leu Lys Asn Arg Ile Val Ile Pro Pro Met Thr Thr Arg Leu
                20                  25                  30

Ser Phe Glu Asp Gly Thr Val Thr Arg Asp Glu Ile Arg Tyr Tyr Gln
                35                  40                  45

Gln Arg Ala Gly Gly Val Gly Met Phe Ile Thr Gly Thr Ala Asn Val
                50                  55                  60

Asn Ala Leu Gly Lys Gly Phe Glu Gly Glu Leu Ser Val Ala Asp Asp
65                  70                  75                  80

Arg Phe Ile Pro Gly Leu Ser Lys Leu Ala Ala Met Lys Thr Gly
                85                  90                  95

Gly Thr Lys Ala Ile Leu Gln Ile Phe Ser Ala Gly Arg Met Ser Asn
                100                 105                 110
```

```
Ser Lys Ile Leu Arg Gly Glu Gln Pro Val Ser Ala Ser Ala Val Ala
            115                 120                 125

Ala Pro Arg Ala Gly Tyr Glu Thr Pro Arg Ala Leu Thr Ser Ala Glu
130                 135                 140

Ile Glu Ala Thr Ile His Asp Phe Gly Gln Ala Val Arg Arg Ala Ile
145                 150                 155                 160

Leu Ala Gly Phe Asp Gly Ile Glu Leu His Gly Ala Asn Thr Tyr Leu
                165                 170                 175

Ile Gln Gln Phe Tyr Ser Pro Asn Ser Asn Arg Arg Thr Asp Glu Trp
            180                 185                 190

Gly Gly Asp Arg Asp Lys Arg Met Arg Phe Pro Leu Ala Val Val His
        195                 200                 205

Glu Ala Glu Lys Val Ile Ala Thr Ile Ala Asp Arg Pro Phe Leu Leu
210                 215                 220

Gly Tyr Arg Ile Ser Pro Glu Glu Leu Glu Gln Pro Gly Ile Thr Leu
225                 230                 235                 240

Asp Asp Thr Leu Ala Leu Ile Asp Ala Leu Lys Gln Thr Lys Ile Asp
                245                 250                 255

Tyr Leu His Val Ser Gln Ser Asp Val Trp Arg Thr Ser Leu Arg Asn
            260                 265                 270

Pro Glu Asp Thr Ala Ile Met Asn Glu Gln Ile Arg Asp His Val Ala
        275                 280                 285

Gly Ala Phe Pro Val Ile Val Gly Gly Ile Lys Thr Pro Ala Asp
290                 295                 300

Ala Glu Lys Ala Ala Glu Ser Phe Asp Leu Val Ala Ile Gly His Glu
305                 310                 315                 320

Met Ile Arg Glu Pro His Trp Val Gln Lys Val Leu Asp His Asp Glu
                325                 330                 335

Lys Ala Ile Arg Tyr Gln Ile Ala Pro Ala Asp Leu Glu Glu Leu Gly
            340                 345                 350

Ile Ala Pro Thr Phe Leu Asp Phe Ile Glu Ser Ile Ser Gly Gly Ala
        355                 360                 365

Lys Gly Val Pro Leu Thr Thr Ala Gln Ser Val Thr Ser Ser Asn Val
370                 375                 380

Thr Gln Asp
385

<210> SEQ ID NO 20
<211> LENGTH: 400
<212> TYPE: PRT
<213> ORGANISM: Saccharomyces pastorianus

<400> SEQUENCE: 20

Met Ser Phe Val Lys Asp Phe Lys Pro Gln Ala Leu Gly Asp Thr Asn
  1               5                  10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Leu His Pro Gly Asn Ile
        35                  40                  45

Pro Asn Arg Asp Trp Ala Val Glu Tyr Tyr Thr Gln Arg Ala Gln Arg
50                  55                  60

Pro Gly Thr Met Ile Ile Thr Glu Gly Ala Phe Ile Ser Pro Gln Ala
65                  70                  75                  80

Gly Gly Tyr Asp Asn Ala Pro Gly Val Trp Ser Glu Glu Gln Met Val
                85                  90                  95
```

Glu Trp Thr Lys Ile Phe Asn Ala Ile His Glu Lys Lys Ser Phe Val
                100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Phe Met
130                 135                 140

Asp Ala Glu Gln Glu Ala Lys Ala Lys Lys Ala Asn Asn Pro Gln His
145                 150                 155                 160

Ser Leu Thr Lys Asp Glu Ile Lys Gln Tyr Ile Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Thr Arg Thr Asp Glu Tyr Gly Gly Ser Ile Glu Asn Arg Ala Arg Phe
    210                 215                 220

Thr Leu Glu Val Val Asp Ala Leu Val Glu Ala Ile Gly His Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Ala Gly Glu
            260                 265                 270

Leu Glu Lys Arg Ala Lys Ala Gly Lys Arg Leu Ala Phe Val His Leu
        275                 280                 285

Val Glu Pro Arg Val Thr Asn Pro Phe Leu Thr Gly Glu Gly Glu
    290                 295                 300

Tyr Glu Gly Gly Ser Asn Asp Phe Val Tyr Ser Ile Trp Lys Gly Pro
305                 310                 315                 320

Val Ile Arg Ala Gly Asn Phe Ala Leu His Pro Glu Val Val Arg Glu
                325                 330                 335

Glu Val Lys Asp Lys Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

Lys Tyr Asp Arg Asp Thr Phe Tyr Gln Met Ser Ala His Gly Tyr Ile
370                 375                 380

Asp Tyr Pro Thr Tyr Glu Glu Ala Leu Lys Leu Gly Trp Asp Lys Lys
385                 390                 395                 400

<210> SEQ ID NO 21
<211> LENGTH: 337
<212> TYPE: PRT
<213> ORGANISM: Thermoanaerobacter pseudethanolicus

<400> SEQUENCE: 21

Met Ser Ile Leu His Met Pro Leu Lys Ile Lys Asp Ile Thr Ile Lys
1               5                   10                  15

Asn Arg Ile Met Met Ser Pro Met Cys Met Tyr Ser Ala Ser Thr Asp
                20                  25                  30

Gly Met Pro Asn Asp Trp His Ile Val His Tyr Ala Thr Arg Ala Ile
            35                  40                  45

Gly Gly Val Gly Leu Ile Met Gln Glu Ala Thr Ala Val Glu Ser Arg
        50                  55                  60

Gly Arg Ile Thr Asp His Asp Leu Gly Ile Trp Asn Asp Glu Gln Val

```
                65                  70                  75                  80
Lys Glu Leu Lys Lys Ile Val Asp Ile Cys Lys Ala Asn Gly Ala Val
                    85                  90                  95

Met Gly Ile Gln Leu Ala His Ala Gly Arg Lys Cys Asn Ile Ser Tyr
            100                 105                 110

Glu Asp Val Val Gly Pro Ser Pro Ile Lys Ala Gly Asp Arg Tyr Lys
            115                 120                 125

Leu Pro Arg Glu Leu Ser Val Glu Glu Ile Lys Ser Ile Val Lys Ala
        130                 135                 140

Phe Gly Glu Ala Ala Lys Arg Ala Asn Leu Ala Gly Tyr Asp Val Val
145                 150                 155                 160

Glu Ile His Ala Ala His Gly Tyr Leu Ile His Glu Phe Leu Ser Pro
                165                 170                 175

Leu Ser Asn Lys Arg Lys Asp Glu Tyr Gly Asn Ser Ile Glu Asn Arg
            180                 185                 190

Ala Arg Phe Leu Ile Glu Val Ile Asp Glu Val Arg Lys Asn Trp Pro
        195                 200                 205

Glu Asn Lys Pro Ile Phe Val Arg Val Ser Ala Asp Asp Tyr Met Glu
    210                 215                 220

Gly Gly Ile Asn Ile Asp Met Met Val Glu Tyr Ile Asn Met Ile Lys
225                 230                 235                 240

Asp Lys Val Asp Leu Ile Asp Val Ser Ser Gly Gly Leu Leu Asn Val
                245                 250                 255

Asp Ile Asn Leu Tyr Pro Gly Tyr Gln Val Lys Tyr Ala Glu Thr Ile
            260                 265                 270

Lys Lys Arg Cys Asn Ile Lys Thr Ser Ala Val Gly Leu Ile Thr Thr
        275                 280                 285

Gln Glu Leu Ala Glu Glu Ile Leu Ser Asn Glu Arg Ala Asp Leu Val
    290                 295                 300

Ala Leu Gly Arg Glu Leu Leu Arg Asn Pro Tyr Trp Val Leu His Thr
305                 310                 315                 320

Tyr Thr Ser Lys Glu Asp Trp Pro Lys Gln Tyr Glu Arg Ala Phe Lys
                325                 330                 335

Lys

<210> SEQ ID NO 22
<211> LENGTH: 365
<212> TYPE: PRT
<213> ORGANISM: Enterobacter cloacae

<400> SEQUENCE: 22

Met Ser Ala Glu Lys Leu Phe Thr Pro Leu Lys Val Gly Ala Val Thr
1               5                   10                  15

Ala Pro Asn Arg Val Phe Met Ala Pro Leu Thr Arg Leu Arg Ser Ile
            20                  25                  30

Glu Pro Gly Asp Ile Pro Thr Pro Leu Met Gly Glu Tyr Tyr Arg Gln
        35                  40                  45

Arg Ala Ser Ala Gly Leu Ile Ile Ser Glu Ala Thr Gln Ile Ser Ala
    50                  55                  60

Gln Ala Lys Gly Tyr Ala Gly Ala Pro Gly Leu His Ser Pro Glu Gln
65                  70                  75                  80

Ile Ala Ala Trp Lys Lys Ile Thr Ala Gly Val His Ala Glu Asp Gly
                85                  90                  95

Arg Ile Ala Val Gln Leu Trp His Thr Gly Arg Ile Ser His Ser Ser
```

```
                100                 105                 110
Ile Gln Pro Gly Gly Gln Ala Pro Val Ser Ala Ser Ala Leu Asn Ala
        115                 120                 125
Asn Thr Arg Thr Ser Leu Arg Asp Glu Asn Gly Asn Ala Ile Arg Val
        130                 135                 140
Asp Thr Thr Pro Arg Ala Leu Glu Leu Asp Glu Ile Pro Gly Ile
145                 150                 155                 160
Val Asn Asp Phe Arg Gln Ala Val Ala Asn Ala Arg Glu Ala Gly Phe
                165                 170                 175
Asp Leu Val Glu Leu His Ser Ala His Gly Tyr Leu Leu His Gln Phe
        180                 185                 190
Leu Ser Pro Ser Ser Asn Gln Arg Thr Asp Gln Tyr Gly Gly Ser Val
        195                 200                 205
Glu Asn Arg Ala Arg Leu Val Leu Glu Val Val Asp Ala Val Cys Asn
        210                 215                 220
Glu Trp Ser Ala Asp Arg Ile Gly Ile Arg Val Ser Pro Ile Gly Thr
225                 230                 235                 240
Phe Gln Asn Val Asp Asn Gly Pro Asn Glu Glu Ala Asp Ala Leu Tyr
                245                 250                 255
Leu Ile Glu Glu Leu Ala Lys Arg Gly Ile Ala Tyr Leu His Met Ser
        260                 265                 270
Glu Thr Asp Leu Ala Gly Gly Lys Pro Tyr Ser Glu Ala Phe Arg Gln
        275                 280                 285
Lys Val Arg Glu Arg Phe His Gly Val Ile Ile Gly Ala Gly Ala Tyr
        290                 295                 300
Thr Ala Glu Lys Ala Glu Asp Leu Ile Gly Lys Gly Leu Ile Asp Ala
305                 310                 315                 320
Val Ala Phe Gly Arg Asp Tyr Ile Ala Asn Pro Asp Leu Val Ala Arg
                325                 330                 335
Leu Gln Lys Lys Ala Glu Leu Asn Pro Gln Arg Pro Glu Ser Phe Tyr
        340                 345                 350
Gly Gly Gly Ala Glu Gly Tyr Thr Asp Tyr Pro Ser Leu
        355                 360                 365

<210> SEQ ID NO 23
<211> LENGTH: 128
<212> TYPE: PRT
<213> ORGANISM: Fusobacterium nucleatum subsp. nucleatum

<400> SEQUENCE: 23

Met Lys Ser Leu Ile Arg Leu Arg Met Ser His Asp Ala His Tyr
1               5                   10                  15
Gly Gly Asn Leu Val Asp Gly Ala Arg Met Leu Gln Leu Phe Gly Asp
                20                  25                  30
Val Ala Thr Glu Leu Leu Ile Gln Leu Asp Gly Asp Glu Gly Leu Phe
        35                  40                  45
Lys Ala Tyr Asp Ser Val Glu Phe Met Ala Pro Val Phe Ala Gly Asp
        50                  55                  60
Tyr Ile Glu Ala Glu Gly Glu Ile Val Asn Val Gly Asn Ser Ser Arg
65                  70                  75                  80
Lys Met Val Phe Glu Ala Arg Lys Val Ile Val Pro Arg Pro Asp Ile
                85                  90                  95
Ser Asp Ser Ala Ala Asp Val Leu Ala Glu Pro Ile Val Val Cys Arg
        100                 105                 110
```

```
Ala Thr Gly Thr Cys Val Thr Pro Lys Asp Lys Gln Arg Gly Lys Lys
            115                 120                 125
```

<210> SEQ ID NO 24
<211> LENGTH: 260
<212> TYPE: PRT
<213> ORGANISM: Acidaminococcus fermentans

<400> SEQUENCE: 24

```
Met Ser Ile Tyr Thr Leu Gly Ile Asp Val Gly Ser Thr Ala Ser Lys
  1               5                  10                  15

Cys Ile Ile Leu Lys Asp Gly Lys Glu Ile Val Ala Lys Ser Leu Val
                 20                  25                  30

Ala Val Gly Thr Gly Thr Ser Gly Pro Ala Arg Ser Ile Ser Glu Val
             35                  40                  45

Leu Glu Asn Ala His Met Lys Lys Glu Asp Met Ala Phe Thr Leu Ala
         50                  55                  60

Thr Gly Tyr Gly Arg Asn Ser Leu Glu Gly Ile Ala Asp Lys Gln Met
 65                  70                  75                  80

Ser Glu Leu Ser Cys His Ala Met Gly Ala Ser Phe Ile Trp Pro Asn
                 85                  90                  95

Val His Thr Val Ile Asp Ile Gly Gly Gln Asp Val Lys Val Ile His
                100                 105                 110

Val Glu Asn Gly Thr Met Thr Asn Phe Gln Met Asn Asp Lys Cys Ala
            115                 120                 125

Ala Gly Thr Gly Arg Phe Leu Asp Val Met Ala Asn Ile Leu Glu Val
        130                 135                 140

Lys Val Ser Asp Leu Ala Glu Leu Gly Ala Lys Ser Thr Lys Arg Val
145                 150                 155                 160

Ala Ile Ser Ser Thr Cys Thr Val Phe Ala Glu Ser Glu Val Ile Ser
                165                 170                 175

Gln Leu Ser Lys Gly Thr Asp Lys Ile Asp Ile Ile Ala Gly Ile His
            180                 185                 190

Arg Ser Val Ala Ser Arg Val Ile Gly Leu Ala Asn Arg Val Gly Ile
        195                 200                 205

Val Lys Asp Val Val Met Thr Gly Gly Val Ala Gln Asn Tyr Gly Val
210                 215                 220

Arg Gly Ala Leu Glu Glu Gly Leu Gly Val Glu Ile Lys Thr Ser Pro
225                 230                 235                 240

Leu Ala Gln Tyr Asn Gly Ala Leu Gly Ala Ala Leu Tyr Ala Tyr Lys
                245                 250                 255

Lys Ala Ala Lys
            260
```

<210> SEQ ID NO 25
<211> LENGTH: 650
<212> TYPE: PRT
<213> ORGANISM: Clostridium symbiosum

<400> SEQUENCE: 25

```
Met Ser Ile Asn Ala Leu Leu Asp Glu Phe Lys Val Lys Ala Ala Thr
  1               5                  10                  15

Pro Lys Gln Gln Leu Ala Glu Tyr Lys Ala Gln Gly Lys Lys Val Ile
                 20                  25                  30

Gly Val Leu Pro Tyr Tyr Ala Pro Glu Glu Leu Val Tyr Ala Ala Gly
             35                  40                  45
```

```
Met Val Pro Met Gly Ile Trp Gly Ser Asn Asn Lys Thr Ile Ser Arg
     50                  55                  60
Ala Lys Glu Tyr Cys Ala Thr Phe Tyr Cys Thr Ile Ala Gln Leu Ala
 65              70                  75                  80
Leu Glu Met Leu Leu Asp Gly Thr Met Asp Gln Leu Asp Gly Ile Ile
                 85                  90                  95
Thr Pro Thr Ile Cys Asp Thr Leu Arg Pro Met Ser Gln Asn Phe Arg
                100                 105                 110
Val Ala Met Gly Asp Lys Met Ala Val Ile Phe Leu Ala Gln Pro Gln
            115                 120                 125
Asn Arg Phe Glu Asp Phe Gly Leu Gln Phe Ser Val Asp Gln Tyr Thr
130                 135                 140
Asn Val Lys Lys Glu Leu Glu Lys Val Ala Gly Lys Glu Ile Thr Asn
145                 150                 155                 160
Glu Ala Ile Gln Asp Ala Ile Lys Val Tyr Asn Lys Ser Arg Ala Ala
                165                 170                 175
Arg Arg Lys Phe Val Glu Leu Ala Ser Ala His Cys Asp Val Ile Thr
            180                 185                 190
Pro Thr Lys Arg Ser Ala Val Leu Lys Ser Phe Phe Phe Met Glu Lys
            195                 200                 205
Pro Glu Tyr Ile Glu Lys Leu Glu Glu Leu Asn Ala Glu Leu Glu Lys
            210                 215                 220
Leu Pro Val Cys Asp Trp Gln Gly Thr Lys Val Val Thr Ser Gly Ile
225                 230                 235                 240
Ile Cys Asp Asn Pro Lys Leu Leu Glu Ile Phe Glu Glu Asn Asn Ile
                245                 250                 255
Ala Ile Ala Ala Asp Asp Val Gly His Glu Ser Arg Ser Phe Arg Val
            260                 265                 270
Asp Ala Pro Glu Asp Glu Ala Asp Ala Leu Met Ala Leu Ala Lys Gln
            275                 280                 285
Phe Ala Asn Met Asp Tyr Asp Val Leu Leu Tyr Asp Pro Lys Ser Thr
            290                 295                 300
Glu Asn Arg Arg Gly Glu Phe Ile Ala Asn Met Val Lys Glu Ser Gly
305                 310                 315                 320
Ala Gln Gly Leu Val Leu Phe Met Gln Gln Phe Cys Asp Pro Glu Glu
                325                 330                 335
Met Glu Tyr Pro Tyr Leu Lys Lys Ala Leu Asn Asn Ala Gly Ile Pro
            340                 345                 350
His Ile Lys Leu Gly Ile Asp Gln Gln Met Arg Asp Phe Gly Gln Ala
            355                 360                 365
Ser Thr Ala Ile Gln Ala Phe Ala Asp Val Leu Glu Met Gln Lys Met
370                 375                 380
Ser Gly Ile Tyr Thr Leu Gly Ile Asp Val Gly Ser Thr Ala Ser Lys
385                 390                 395                 400
Cys Ile Val Leu Lys Asp Gly Lys Glu Ile Val Ala Lys Ser Leu Ile
                405                 410                 415
Asp Val Gly Ala Gly Thr Ser Gly Pro Gln Arg Ala Ile Glu Ala Val
            420                 425                 430
Leu Asn Glu Ala Gly Met Lys Lys Glu Asp Met Ala Tyr Thr Leu Ala
            435                 440                 445
Thr Gly Tyr Gly Arg Thr Ser Leu Met Asp Gly Ile Ala Asp Lys Gln
            450                 455                 460
Met Ser Glu Leu Ser Cys His Ala Lys Gly Ala Thr Phe Leu Phe Pro
```

```
                465                 470                 475                 480
        Asn Val His Thr Val Ile Asp Ile Gly Gly Gln Asp Val Lys Val Leu
                        485                 490                 495
        His Ile Asp Asn Gly Ala Met Thr Asn Phe Gln Met Asn Asp Lys Cys
                        500                 505                 510
        Ala Ala Gly Thr Gly Arg Phe Leu Asp Val Met Ala Arg Val Leu Glu
                        515                 520                 525
        Val Lys Val Glu Asp Leu Gly Arg Leu Gly Ala Met Ser Arg Lys Lys
                        530                 535                 540
        Val Gly Ile Ser Ser Thr Cys Thr Val Phe Ala Glu Ser Glu Val Ile
        545                 550                 555                 560
        Ser Gln Leu Ala Met Gly Thr Asp Lys Cys Asp Ile Ile Asp Gly Ile
                        565                 570                 575
        His Arg Ser Val Ala His Arg Val Thr Gly Leu Ala His Arg Ile Gly
                        580                 585                 590
        Val Val Pro Asp Val Val Met Thr Gly Gly Val Ala Gln Asn Glu Gly
                        595                 600                 605
        Val Val Lys Ala Leu Gln Asp Glu Leu Gly Cys Pro Ile Asn Thr Ser
                        610                 615                 620
        Pro Leu Thr Gln Tyr Asn Gly Ala Leu Gly Ala Ala Leu Leu Ala Trp
        625                 630                 635                 640
        Gln Ala Ala Ser Arg Arg Gln Ser Asn Ser
                        645                 650

<210> SEQ ID NO 26
<211> LENGTH: 471
<212> TYPE: PRT
<213> ORGANISM: Bacillus subtilis

<400> SEQUENCE: 26

Met Lys Asn Lys Trp Tyr Lys Pro Lys Arg His Trp Lys Glu Ile Glu
        1               5                   10                  15
        Leu Trp Lys Asp Val Pro Glu Glu Lys Trp Asn Asp Trp Leu Trp Gln
                        20                  25                  30
        Leu Thr His Thr Val Arg Thr Leu Asp Asp Leu Lys Lys Val Ile Asn
                        35                  40                  45
        Leu Thr Glu Asp Glu Glu Gly Val Arg Ile Ser Thr Lys Thr Ile
        50                  55                  60
        Pro Leu Asn Ile Thr Pro Tyr Tyr Ala Ser Leu Met Asp Pro Asp Asn
        65                  70                  75                  80
        Pro Arg Cys Pro Val Arg Met Gln Ser Val Pro Leu Ser Glu Glu Met
                        85                  90                  95
        His Lys Thr Lys Tyr Asp Leu Glu Asp Pro Leu His Glu Asp Glu Asp
                        100                 105                 110
        Ser Pro Val Pro Gly Leu Thr His Arg Tyr Pro Asp Arg Val Leu Phe
                        115                 120                 125
        Leu Val Thr Asn Gln Cys Ser Met Tyr Cys Arg Tyr Cys Thr Arg Arg
                        130                 135                 140
        Arg Phe Ser Gly Gln Ile Gly Met Gly Val Pro Lys Lys Gln Leu Asp
        145                 150                 155                 160
        Ala Ala Ile Ala Tyr Ile Arg Glu Thr Pro Glu Ile Arg Asp Cys Leu
                        165                 170                 175
        Ile Ser Gly Gly Asp Gly Leu Leu Ile Asn Asp Gln Ile Leu Glu Tyr
                        180                 185                 190
```

```
Ile Leu Lys Glu Leu Arg Ser Ile Pro His Leu Glu Val Arg Ile
            195                 200                 205

Gly Thr Arg Ala Pro Val Val Phe Pro Gln Arg Ile Thr Asp His Leu
210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
                260                 265                 270

Gly Ile Asn Asp Ser Val Pro Ile Met Lys Lys Leu Met His Asp Leu
            275                 280                 285

Val Lys Ile Arg Val Arg Pro Tyr Tyr Ile Tyr Gln Cys Asp Leu Ser
290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val Asp Ala Pro Gly Gly Gly Lys Ile Ala Leu Gln Pro Asn
                340                 345                 350

Tyr Val Leu Ser Gln Ser Pro Asp Lys Val Ile Leu Arg Asn Phe Glu
            355                 360                 365

Gly Val Ile Thr Ser Tyr Pro Glu Pro Glu Asn Tyr Ile Pro Asn Gln
370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
                420                 425                 430

Asn Pro Glu His Glu Thr Leu Lys Asp Arg Arg Glu Lys Arg Asp Gln
            435                 440                 445

Leu Lys Glu Lys Lys Phe Leu Ala Gln Gln Lys Lys Gln Lys Glu Thr
450                 455                 460

Glu Cys Gly Gly Asp Ser Ser
465                 470

<210> SEQ ID NO 27
<211> LENGTH: 266
<212> TYPE: PRT
<213> ORGANISM: Peptoclostridium difficile

<400> SEQUENCE: 27

Met Tyr Thr Met Gly Leu Asp Ile Gly Ser Thr Ala Ser Lys Gly Val
 1               5                  10                  15

Ile Leu Lys Asn Gly Glu Asp Ile Val Ala Ser Glu Thr Ile Ser Ser
                20                  25                  30

Gly Thr Gly Thr Thr Gly Pro Ser Arg Val Leu Glu Lys Leu Tyr Gly
            35                  40                  45

Lys Thr Gly Leu Ala Arg Glu Asp Ile Lys Lys Val Val Val Thr Gly
        50                  55                  60

Tyr Gly Arg Met Asn Tyr Ser Asp Ala Asp Lys Gln Ile Ser Glu Leu
65                  70                  75                  80

Ser Cys His Ala Arg Gly Val Asn Phe Ile Ile Pro Glu Thr Arg Thr
                85                  90                  95
```

```
Ile Ile Asp Ile Gly Gly Gln Asp Ala Lys Val Leu Lys Leu Asp Asn
            100                 105                 110

Asn Gly Arg Leu Leu Asn Phe Leu Met Asn Asp Lys Cys Ala Ala Gly
        115                 120                 125

Thr Gly Arg Phe Leu Asp Val Met Ala Lys Ile Ile Glu Val Asp Val
    130                 135                 140

Ser Glu Leu Gly Ser Ile Ser Met Asn Ser Gln Asn Glu Val Ser Ile
145                 150                 155                 160

Ser Ser Thr Cys Thr Val Phe Ala Glu Ser Glu Val Ile Ser His Leu
                165                 170                 175

Ser Glu Asn Ala Lys Ile Glu Asp Ile Val Ala Gly Ile His Thr Ser
            180                 185                 190

Val Ala Lys Arg Val Ser Ser Leu Val Lys Arg Ile Gly Val Gln Arg
        195                 200                 205

Asn Val Val Met Val Gly Gly Val Ala Arg Asn Ser Gly Ile Val Arg
    210                 215                 220

Ala Met Ala Arg Glu Ile Asn Thr Glu Ile Ile Val Pro Asp Ile Pro
225                 230                 235                 240

Gln Leu Thr Gly Ala Leu Gly Ala Ala Leu Tyr Ala Phe Asp Glu Ala
                245                 250                 255

Lys Glu Ser Gln Lys Glu Val Lys Asn Ile
            260                 265

<210> SEQ ID NO 28
<211> LENGTH: 783
<212> TYPE: PRT
<213> ORGANISM: Peptoclostridium difficile

<400> SEQUENCE: 28

Met Ser Glu Lys Lys Glu Ala Arg Val Val Ile Asn Asp Leu Leu Ala
1               5                   10                  15

Glu Gln Tyr Ala Asn Ala Phe Lys Ala Lys Glu Gly Arg Pro Val
            20                  25                  30

Gly Trp Ser Thr Ser Val Phe Pro Gln Glu Leu Ala Glu Val Phe Asp
        35                  40                  45

Leu Asn Val Leu Tyr Pro Glu Asn Gln Ala Ala Gly Val Ala Ala Lys
    50                  55                  60

Lys Gly Ser Leu Glu Leu Cys Glu Ile Ala Glu Ser Lys Gly Tyr Ser
65                  70                  75                  80

Ile Asp Leu Cys Ala Tyr Ala Arg Thr Asn Phe Gly Leu Leu Glu Asn
                85                  90                  95

Gly Gly Cys Glu Ala Leu Asp Met Pro Ala Pro Asp Phe Leu Leu Cys
            100                 105                 110

Cys Asn Asn Ile Cys Asn Gln Val Ile Lys Trp Tyr Glu Asn Ile Ser
        115                 120                 125

Arg Glu Leu Asp Ile Pro Leu Ile Met Ile Asp Thr Thr Phe Asn Asn
    130                 135                 140

Glu Asp Glu Val Thr Gln Ser Arg Ile Asp Tyr Ile Lys Ala Gln Phe
145                 150                 155                 160

Glu Glu Ala Ile Lys Gln Leu Glu Ile Ile Ser Gly Lys Lys Phe Asp
                165                 170                 175

Pro Lys Lys Phe Glu Glu Val Met Lys Ile Ser Ala Glu Asn Gly Arg
            180                 185                 190

Leu Trp Lys Tyr Ser Met Ser Leu Pro Ala Asp Ser Ser Pro Ser Pro
```

```
            195                 200                 205
Met Asn Gly Phe Asp Leu Phe Thr Tyr Met Ala Val Ile Val Cys Ala
210                 215                 220

Arg Gly Lys Lys Glu Thr Thr Glu Ala Phe Lys Leu Leu Ile Glu Glu
225                 230                 235                 240

Leu Glu Asp Asn Met Lys Thr Gly Lys Ser Ser Phe Arg Gly Glu Glu
                245                 250                 255

Lys Tyr Arg Ile Met Met Glu Gly Ile Pro Cys Trp Pro Tyr Ile Gly
                260                 265                 270

Tyr Lys Met Lys Thr Leu Ala Lys Phe Gly Val Asn Met Thr Gly Ser
                275                 280                 285

Val Tyr Pro His Ala Trp Ala Leu Gln Tyr Glu Val Asn Asp Leu Asp
290                 295                 300

Gly Met Ala Val Ala Tyr Ser Thr Met Phe Asn Asn Val Asn Leu Asp
305                 310                 315                 320

Arg Met Thr Lys Tyr Arg Val Asp Ser Leu Val Glu Gly Lys Cys Asp
                325                 330                 335

Gly Ala Phe Tyr His Met Asn Arg Ser Cys Lys Leu Met Ser Leu Ile
                340                 345                 350

Gln Tyr Glu Met Gln Arg Arg Ala Ala Glu Glu Thr Gly Leu Pro Tyr
                355                 360                 365

Ala Gly Phe Asp Gly Asp Gln Ala Asp Pro Arg Ala Phe Thr Asn Ala
370                 375                 380

Gln Phe Glu Thr Arg Ile Gln Gly Leu Val Glu Val Met Glu Glu Arg
385                 390                 395                 400

Lys Lys Leu Asn Arg Gly Glu Ile Met Glu Ala Ile Leu Ser Lys Met
                405                 410                 415

Lys Glu Val Val Glu Asn Pro Asn Ala Ala Val Lys Lys Tyr Lys Ser
                420                 425                 430

Glu Thr Gly Lys Lys Ala Ile Gly Cys Phe Pro Val Tyr Cys Pro Glu
                435                 440                 445

Glu Ile Ile His Ala Ala Gly Met Leu Pro Val Gly Ile Trp Gly Gly
450                 455                 460

Gln Thr Glu Leu Asp Leu Ala Lys Gln Tyr Phe Pro Ala Phe Ala Cys
465                 470                 475                 480

Ser Ile Met Gln Ser Cys Leu Glu Tyr Gly Leu Lys Gly Ala Tyr Asp
                485                 490                 495

Glu Leu Ser Gly Val Ile Ile Pro Gly Met Cys Asp Thr Leu Ile Cys
                500                 505                 510

Leu Gly Gln Asn Trp Lys Ser Ala Val Pro His Ile Lys Tyr Ile Ser
                515                 520                 525

Leu Val His Pro Gln Asn Arg Lys Leu Glu Ala Gly Val Lys Tyr Leu
530                 535                 540

Ile Ser Glu Tyr Lys Gly Val Lys Arg Glu Leu Glu Glu Ile Cys Gly
545                 550                 555                 560

Tyr Glu Ile Glu Glu Ala Lys Ile His Glu Ser Ile Glu Val Tyr Asn
                565                 570                 575

Glu His Arg Lys Thr Met Arg Asp Phe Val Glu Val Ala Tyr Lys His
                580                 585                 590

Ser Asn Thr Ile Lys Pro Ser Ile Arg Ser Leu Val Ile Lys Ser Gly
                595                 600                 605

Phe Phe Met Arg Lys Glu Glu His Thr Glu Leu Val Lys Asp Leu Ile
610                 615                 620
```

```
Ala Lys Leu Asn Ala Met Pro Glu Glu Val Cys Ser Gly Lys Val
625                 630                 635                 640

Leu Leu Thr Gly Ile Leu Ala Asp Ser Lys Asp Ile Leu Asp Ile Leu
            645                 650                 655

Glu Asp Asn Asn Ile Ser Val Val Ala Asp Asp Leu Ala Gln Glu Thr
                660                 665                 670

Arg Gln Phe Arg Thr Asp Val Pro Ala Gly Asp Asp Ala Leu Glu Arg
            675                 680                 685

Leu Ala Arg Gln Trp Ser Asn Ile Glu Gly Cys Ser Leu Ala Tyr Asp
690                 695                 700

Pro Lys Lys Lys Arg Gly Ser Leu Ile Val Asp Glu Val Lys Lys
705                 710                 715                 720

Asp Ile Asp Gly Val Ile Phe Cys Met Met Lys Phe Cys Asp Pro Glu
                725                 730                 735

Glu Tyr Asp Tyr Pro Leu Val Arg Lys Asp Ile Glu Asp Ser Gly Ile
            740                 745                 750

Pro Thr Leu Tyr Val Glu Ile Asp Gln Gln Thr Gln Asn Asn Glu Gln
            755                 760                 765

Ala Arg Thr Arg Ile Gln Thr Phe Ala Glu Met Met Ser Leu Ala
770                 775                 780
```

<210> SEQ ID NO 29
<211> LENGTH: 466
<212> TYPE: PRT
<213> ORGANISM: Escherichia coli

<400> SEQUENCE: 29

```
Met Asp Gln Lys Leu Leu Thr Asp Phe Arg Ser Glu Leu Leu Asp Ser
1               5                   10                  15

Arg Phe Gly Ala Lys Ala Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
```

```
                    210                 215                 220
Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
                260                 265                 270

Ser Gly His Lys Phe Gly Leu Ala Pro Leu Gly Cys Gly Trp Val Ile
                275                 280                 285

Trp Arg Asp Glu Glu Ala Leu Pro Gln Glu Leu Val Phe Asn Val Asp
            290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
                340                 345                 350

Leu Ala Asp Glu Ile Ala Lys Leu Gly Pro Tyr Glu Phe Ile Cys Thr
            355                 360                 365

Gly Arg Pro Asp Glu Gly Ile Pro Ala Val Cys Phe Lys Leu Lys Asp
            370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
                420                 425                 430

Phe Ala Glu Leu Leu Leu Glu Asp Tyr Lys Ala Ser Leu Lys Tyr Leu
            435                 440                 445

Ser Asp His Pro Lys Leu Gln Gly Ile Ala Gln Gln Asn Ser Phe Lys
            450                 455                 460

His Thr
465

<210> SEQ ID NO 30
<211> LENGTH: 715
<212> TYPE: PRT
<213> ORGANISM: Escherichia coli

<400> SEQUENCE: 30

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
                20                  25                  30

Ile Val Tyr Pro Asn Asp Arg Asp Leu Leu Lys Leu Ile Glu Asn
            35                  40                  45

Asn Ala Arg Leu Cys Gly Val Ile Phe Asp Trp Asp Lys Tyr Asn Leu
        50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110
```

```
Ile Ala Asn Lys Ile Lys Gln Thr Thr Asp Glu Tyr Ile Asn Thr Ile
            115                 120                 125
Leu Pro Pro Leu Thr Lys Ala Leu Phe Lys Tyr Val Arg Glu Gly Lys
        130                 135                 140
Tyr Thr Phe Cys Thr Pro Gly His Met Gly Gly Thr Ala Phe Gln Lys
145                 150                 155                 160
Ser Pro Val Gly Ser Leu Phe Tyr Asp Phe Phe Gly Pro Asn Thr Met
                165                 170                 175
Lys Ser Asp Ile Ser Ile Ser Val Glu Leu Gly Ser Leu Leu Asp
            180                 185                 190
His Ser Gly Pro His Lys Glu Ala Glu Gln Tyr Ile Ala Arg Val Phe
        195                 200                 205
Asn Ala Asp Arg Ser Tyr Met Val Thr Asn Gly Thr Ser Thr Ala Asn
210                 215                 220
Lys Ile Val Gly Met Tyr Ser Ala Pro Ala Gly Ser Thr Ile Leu Ile
225                 230                 235                 240
Asp Arg Asn Cys His Lys Ser Leu Thr His Leu Met Met Met Ser Asp
                245                 250                 255
Val Thr Pro Ile Tyr Phe Arg Pro Thr Arg Asn Ala Tyr Gly Ile Leu
            260                 265                 270
Gly Gly Ile Pro Gln Ser Glu Phe Gln His Ala Thr Ile Ala Lys Arg
        275                 280                 285
Val Lys Glu Thr Pro Asn Ala Thr Trp Pro Val His Ala Val Ile Thr
        290                 295                 300
Asn Ser Thr Tyr Asp Gly Leu Leu Tyr Asn Thr Asp Phe Ile Lys Lys
305                 310                 315                 320
Thr Leu Asp Val Lys Ser Ile His Phe Asp Ser Ala Trp Val Pro Tyr
                325                 330                 335
Thr Asn Phe Ser Pro Ile Tyr Glu Gly Lys Cys Gly Met Ser Gly Gly
            340                 345                 350
Arg Val Glu Gly Lys Val Ile Tyr Glu Thr Gln Ser Thr His Lys Leu
        355                 360                 365
Leu Ala Ala Phe Ser Gln Ala Ser Met Ile His Val Lys Gly Asp Val
        370                 375                 380
Asn Glu Glu Thr Phe Asn Glu Ala Tyr Met Met His Thr Thr Thr Ser
385                 390                 395                 400
Pro His Tyr Gly Ile Val Ala Ser Thr Glu Thr Ala Ala Ala Met Met
                405                 410                 415
Lys Gly Asn Ala Gly Lys Arg Leu Ile Asn Gly Ser Ile Glu Arg Ala
            420                 425                 430
Ile Lys Phe Arg Lys Glu Ile Lys Arg Leu Arg Thr Glu Ser Asp Gly
        435                 440                 445
Trp Phe Phe Asp Val Trp Gln Pro Asp His Ile Asp Thr Thr Glu Cys
        450                 455                 460
Trp Pro Leu Arg Ser Asp Ser Trp His Gly Phe Lys Asn Ile Asp
465                 470                 475                 480
Asn Glu His Met Tyr Leu Asp Pro Ile Lys Val Thr Leu Leu Thr Pro
                485                 490                 495
Gly Met Glu Lys Asp Gly Thr Met Ser Asp Phe Gly Ile Pro Ala Ser
            500                 505                 510
Ile Val Ala Lys Tyr Leu Asp Glu His Gly Ile Val Val Glu Lys Thr
        515                 520                 525
Gly Pro Tyr Asn Leu Leu Phe Leu Phe Ser Ile Gly Ile Asp Lys Thr
```

530                 535                 540
Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                    580                 585                 590

Ile His Lys Leu Ile Val His His Asn Leu Pro Asp Leu Met Tyr Arg
                595                 600                 605

Ala Phe Glu Val Leu Pro Thr Met Val Met Thr Pro Tyr Ala Ala Phe
                610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                    645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
                675                 680                 685

Phe Glu Thr Asp Ile His Gly Ala Tyr Arg Gln Ala Asp Gly Arg Tyr
                690                 695                 700

Thr Val Lys Val Leu Lys Glu Glu Ser Lys Lys
705                 710                 715

<210> SEQ ID NO 31
<211> LENGTH: 732
<212> TYPE: PRT
<213> ORGANISM: Escherichia coli

<400> SEQUENCE: 31

Met Ser Lys Leu Lys Ile Ala Val Ser Asp Ser Cys Pro Asp Cys Phe
1               5                   10                  15

Thr Thr Gln Arg Glu Cys Ile Tyr Ile Asn Glu Ser Arg Asn Ile Asp
                20                  25                  30

Val Ala Ala Ile Val Leu Ser Leu Asn Asp Val Thr Cys Gly Lys Leu
            35                  40                  45

Asp Glu Ile Asp Ala Thr Gly Tyr Gly Ile Pro Val Phe Ile Ala Thr
50                  55                  60

Glu Asn Gln Glu Arg Val Pro Ala Glu Tyr Leu Pro Arg Ile Ser Gly
65                  70                  75                  80

Val Phe Glu Asn Cys Glu Ser Arg Arg Glu Phe Tyr Gly Arg Gln Leu
                85                  90                  95

Glu Thr Ala Ala Ser His Tyr Glu Thr Gln Leu Arg Pro Pro Phe Phe
            100                 105                 110

Arg Ala Leu Val Asp Tyr Val Asn Gln Gly Asn Ser Ala Phe Asp Cys
        115                 120                 125

Pro Gly His Gln Gly Gly Glu Phe Phe Arg Arg His Pro Ala Gly Asn
    130                 135                 140

Gln Phe Val Glu Tyr Phe Gly Glu Ala Leu Phe Arg Ala Asp Leu Cys
145                 150                 155                 160

Asn Ala Asp Val Ala Met Gly Asp Leu Leu Ile His Glu Gly Ala Pro
                165                 170                 175

Cys Ile Ala Gln Gln His Ala Ala Lys Val Phe Asn Ala Asp Lys Thr
            180                 185                 190

```
Tyr Phe Val Leu Asn Gly Thr Ser Ser Asn Lys Val Leu Asn
            195                 200                 205

Ala Leu Leu Thr Pro Gly Asp Leu Val Leu Phe Asp Arg Asn His
210                 215                 220

Lys Ser Asn His His Gly Ala Leu Leu Gln Ala Gly Ala Thr Pro Val
225                 230                 235                 240

Tyr Leu Glu Thr Ala Arg Asn Pro Tyr Gly Phe Ile Gly Gly Ile Asp
                245                 250                 255

Ala His Cys Phe Glu Glu Ser Tyr Leu Arg Glu Leu Ile Ala Glu Val
            260                 265                 270

Ala Pro Gln Arg Ala Lys Glu Ala Arg Pro Phe Arg Leu Ala Val Ile
            275                 280                 285

Gln Leu Gly Thr Tyr Asp Gly Thr Ile Tyr Asn Ala Arg Gln Val Val
        290                 295                 300

Asp Lys Ile Gly His Leu Cys Asp Tyr Ile Leu Phe Asp Ser Ala Trp
305                 310                 315                 320

Val Gly Tyr Glu Gln Phe Ile Pro Met Met Ala Asp Cys Ser Pro Leu
                325                 330                 335

Leu Leu Asp Leu Asn Glu Asn Asp Pro Gly Ile Leu Val Thr Gln Ser
            340                 345                 350

Val His Lys Gln Gln Ala Gly Phe Ser Gln Thr Ser Gln Ile His Lys
        355                 360                 365

Lys Asp Ser His Ile Lys Gly Gln Gln Arg Tyr Val Pro His Lys Arg
370                 375                 380

Met Asn Asn Ala Phe Met Met His Ala Ser Thr Ser Pro Phe Tyr Pro
385                 390                 395                 400

Leu Phe Ala Ala Leu Asn Ile Asn Ala Lys Met His Glu Gly Val Ser
                405                 410                 415

Gly Arg Asn Met Trp Met Asp Cys Val Val Asn Gly Ile Asn Ala Arg
            420                 425                 430

Lys Leu Ile Leu Asp Asn Cys Gln His Ile Arg Pro Phe Val Pro Glu
        435                 440                 445

Leu Val Asp Gly Lys Pro Trp Gln Ser Tyr Glu Thr Ala Gln Ile Ala
450                 455                 460

Val Asp Leu Arg Phe Phe Gln Phe Val Pro Gly Glu His Trp His Ser
465                 470                 475                 480

Phe Glu Gly Tyr Ala Glu Asn Gln Tyr Phe Val Asp Pro Cys Lys Leu
                485                 490                 495

Leu Leu Thr Thr Pro Gly Ile Asp Ala Arg Asn Gly Glu Tyr Glu Ala
            500                 505                 510

Phe Gly Val Pro Ala Thr Ile Leu Ala Asn Phe Leu Arg Glu Asn Gly
        515                 520                 525

Val Val Pro Glu Lys Cys Asp Leu Asn Ser Ile Leu Phe Leu Leu Thr
530                 535                 540

Pro Ala Glu Asp Met Ala Lys Leu Gln Gln Leu Val Ala Leu Leu Val
545                 550                 555                 560

Arg Phe Glu Lys Leu Leu Glu Ser Asp Ala Pro Leu Ala Glu Val Leu
                565                 570                 575

Pro Ser Ile Tyr Lys Gln His Glu Glu Arg Tyr Ala Gly Tyr Thr Leu
            580                 585                 590

Arg Gln Leu Cys Gln Glu Met His Asp Leu Tyr Ala Arg His Asn Val
        595                 600                 605

Lys Gln Leu Gln Lys Glu Met Phe Arg Lys Glu His Phe Pro Arg Val
```

```
                 610                 615                 620

Ser Met Asn Pro Gln Glu Ala Asn Tyr Ala Tyr Leu Arg Gly Glu Val
625                 630                 635                 640

Glu Leu Val Arg Leu Pro Asp Ala Glu Gly Arg Ile Ala Ala Glu Gly
                645                 650                 655

Ala Leu Pro Tyr Pro Pro Gly Val Leu Cys Val Val Pro Gly Glu Ile
                660                 665                 670

Trp Gly Gly Ala Val Leu Arg Tyr Phe Ser Ala Leu Glu Glu Gly Ile
            675                 680                 685

Asn Leu Leu Pro Gly Phe Ala Pro Glu Leu Gln Gly Val Tyr Ile Glu
        690                 695                 700

Glu His Asp Gly Arg Lys Gln Val Trp Cys Tyr Val Ile Lys Pro Arg
705                 710                 715                 720

Asp Ala Gln Ser Thr Leu Leu Lys Gly Glu Lys Leu
                725                 730

<210> SEQ ID NO 32
<211> LENGTH: 713
<212> TYPE: PRT
<213> ORGANISM: Escherichia coli

<400> SEQUENCE: 32

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
    210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255
```

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
            275                 280                 285

Val Ala Ala Thr Thr Gln Ala Gln Trp Pro Val His Ala Val Ile Thr
290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
            355                 360                 365

Leu Ala Ala Leu Ser Gln Ala Ser Leu Ile His Ile Lys Gly Glu Tyr
            370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
            420                 425                 430

Leu His Phe Arg Lys Glu Val Gln Arg Leu Arg Glu Glu Ser Asp Gly
            435                 440                 445

Trp Phe Phe Asp Ile Trp Gln Pro Pro Gln Val Asp Glu Ala Glu Cys
450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
                485                 490                 495

Gly Met Asp Glu Gln Gly Asn Met Ser Glu Glu Gly Ile Pro Ala Ala
            500                 505                 510

Leu Val Ala Lys Phe Leu Asp Glu Arg Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
            595                 600                 605

Ala Phe Asp Thr Leu Pro Glu Met Ile Met Thr Pro His Gln Ala Trp
            610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly

```
                    675                 680                 685
Phe Glu Thr Asp Ile His Gly Ala Lys Gln Asp Glu Asp Gly Val Tyr
    690                 695                 700
Arg Val Arg Val Leu Lys Met Ala Gly
705                 710
```

<210> SEQ ID NO 33
<211> LENGTH: 420
<212> TYPE: PRT
<213> ORGANISM: Escherichia coli

<400> SEQUENCE: 33

```
Met Pro His Ser Leu Phe Ser Thr Asp Thr Asp Leu Thr Ala Glu Asn
 1               5                  10                  15
Leu Leu Arg Leu Pro Ala Glu Phe Gly Cys Pro Val Trp Val Tyr Asp
                20                  25                  30
Ala Gln Ile Ile Arg Arg Gln Ile Ala Leu Lys Gln Phe Asp Val
                35                  40                  45
Val Arg Phe Ala Gln Lys Ala Cys Ser Asn Ile His Ile Leu Arg Leu
    50                  55                  60
Met Arg Glu Gln Gly Val Lys Val Asp Ser Val Ser Leu Gly Glu Ile
65                  70                  75                  80
Glu Arg Ala Leu Ala Ala Gly Tyr Asn Pro Gln Thr His Pro Asp Asp
                85                  90                  95
Ile Val Phe Thr Ala Asp Val Ile Asp Gln Ala Thr Leu Glu Arg Val
                100                 105                 110
Ser Glu Leu Gln Ile Pro Val Asn Ala Gly Ser Val Asp Met Leu Asp
                115                 120                 125
Gln Leu Gly Gln Val Ser Pro Gly His Arg Val Trp Leu Arg Val Asn
    130                 135                 140
Pro Gly Phe Gly His Gly His Ser Gln Lys Thr Asn Thr Gly Gly Glu
145                 150                 155                 160
Asn Ser Lys His Gly Ile Trp Tyr Thr Asp Leu Pro Ala Ala Leu Asp
                165                 170                 175
Val Ile Gln Arg His His Leu Gln Leu Val Gly Ile His Met His Ile
                180                 185                 190
Gly Ser Gly Val Asp Tyr Ala His Leu Glu Gln Val Cys Gly Ala Met
                195                 200                 205
Val Arg Gln Val Ile Glu Phe Gly Gln Asp Leu Gln Ala Ile Ser Ala
    210                 215                 220
Gly Gly Gly Leu Ser Val Pro Tyr Gln Gln Gly Glu Glu Ala Val Asp
225                 230                 235                 240
Thr Glu His Tyr Tyr Gly Leu Trp Asn Ala Ala Arg Glu Gln Ile Ala
                245                 250                 255
Arg His Leu Gly His Pro Val Lys Leu Glu Ile Glu Pro Gly Arg Phe
                260                 265                 270
Leu Val Ala Gln Ser Gly Val Leu Ile Thr Gln Val Arg Ser Val Lys
                275                 280                 285
Gln Met Gly Ser Arg His Phe Val Leu Val Asp Ala Gly Phe Asn Asp
    290                 295                 300
Leu Met Arg Pro Ala Met Tyr Gly Ser Tyr His His Ile Ser Ala Leu
305                 310                 315                 320
Ala Ala Asp Gly Arg Ser Leu Glu His Ala Pro Thr Val Glu Thr Val
                325                 330                 335
```

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
        420

<210> SEQ ID NO 34
<211> LENGTH: 550
<212> TYPE: PRT
<213> ORGANISM: Salmonella typhimurium

<400> SEQUENCE: 34

Met Gln Asn Pro Tyr Thr Val Ala Asp Tyr Leu Leu Asp Arg Leu Ala
1               5                   10                  15

Gly Cys Gly Ile Gly His Leu Phe Gly Val Pro Gly Asp Tyr Asn Leu
            20                  25                  30

Gln Phe Leu Asp His Val Ile Asp His Pro Thr Leu Arg Trp Val Gly
        35                  40                  45

Cys Ala Asn Glu Leu Asn Ala Ala Tyr Ala Ala Asp Gly Tyr Ala Arg
    50                  55                  60

Met Ser Gly Ala Gly Ala Leu Leu Thr Thr Phe Gly Val Gly Glu Leu
65                  70                  75                  80

Ser Ala Ile Asn Gly Ile Ala Gly Ser Tyr Ala Glu Tyr Val Pro Val
                85                  90                  95

Leu His Ile Val Gly Ala Pro Cys Ser Ala Ala Gln Gln Arg Gly Glu
            100                 105                 110

Leu Met His His Thr Leu Gly Asp Gly Asp Phe Arg His Phe Tyr Arg
        115                 120                 125

Met Ser Gln Ala Ile Ser Ala Ala Ser Ala Ile Leu Asp Glu Gln Asn
130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
            180                 185                 190

Gly Val Glu Thr Ala Phe Arg Tyr His Ala Arg Gln Cys Leu Met Asn
        195                 200                 205

Ser Arg Arg Ile Ala Leu Leu Ala Asp Phe Leu Ala Gly Arg Phe Gly
210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
            260                 265                 270

Ala Ile Glu Asp Ala Asp Arg Val Ile Cys Val Gly Thr Arg Phe Val
        275                 280                 285

```
Asp Thr Leu Thr Ala Gly Phe Thr Gln Gln Leu Pro Ala Glu Arg Thr
        290             295             300
Leu Glu Ile Gln Pro Tyr Ala Ser Arg Ile Gly Glu Thr Trp Phe Asn
305             310             315                     320
Leu Pro Met Ala Gln Ala Val Ser Thr Leu Arg Glu Leu Cys Leu Glu
                325             330             335
Cys Ala Phe Ala Pro Pro Thr Arg Ser Ala Gly Gln Pro Val Arg
                340             345             350
Ile Asp Lys Gly Glu Leu Thr Gln Glu Ser Phe Trp Gln Thr Leu Gln
        355             360             365
Gln Tyr Leu Lys Pro Gly Asp Ile Ile Leu Val Asp Gln Gly Thr Ala
        370             375             380
Ala Phe Gly Ala Ala Ala Leu Ser Leu Pro Asp Gly Ala Glu Val Val
385             390             395             400
Leu Gln Pro Leu Trp Gly Ser Ile Gly Tyr Ser Leu Pro Ala Ala Phe
                405             410             415
Gly Ala Gln Thr Ala Cys Pro Asp Arg Arg Val Ile Leu Ile Ile Gly
                420             425             430
Asp Gly Ala Ala Gln Leu Thr Ile Gln Glu Met Gly Ser Met Leu Arg
        435             440             445
Asp Gly Gln Ala Pro Val Ile Leu Leu Leu Asn Asn Asp Gly Tyr Thr
        450             455             460
Val Glu Arg Ala Ile His Gly Ala Ala Gln Arg Tyr Asn Asp Ile Ala
465             470             475             480
Ser Trp Asn Trp Thr Gln Ile Pro Pro Ala Leu Asn Ala Ala Gln Gln
                485             490             495
Ala Glu Cys Trp Arg Val Thr Gln Ala Ile Gln Leu Ala Glu Val Leu
                500             505             510
Glu Arg Leu Ala Arg Pro Gln Arg Leu Ser Phe Ile Glu Val Met Leu
        515             520             525
Pro Lys Ala Asp Leu Pro Glu Leu Leu Arg Thr Val Thr Arg Ala Leu
        530             535             540
Glu Ala Arg Asn Gly Gly
545             550
```

US 9,745,607 B2

METHODS OF PRODUCING 6-CARBON CHEMICALS USING 2,6-DIAMINOPIMELATE AS PRECURSOR TO 2-AMINOPIMELATE

CROSS-REFERENCE TO RELATED APPLICATIONS

This application claims priority to U.S. Application Ser. No. 61/993,532, filed on May 15, 2015, the disclosure of which is incorporated by reference in its entirety.

TECHNICAL FIELD

Disclosed herein are methods for biosynthesizing 2-aminopimelate in a recombinant host from 2,6-diaminopimelate using one or more of a polypeptide having 2-hydroxyacyl-CoA dehydratase activity, a polypeptide having mutase activity, a polypeptide having ammonia lyase activity, and a polypeptide having enoate reductase activity. The biosynthesized 2-aminopimelate can be enzymatically converted to a product selected from the group consisting of adipic acid, adipate semialdehyde, 6-aminohexanoic acid, 6-hydroxyhexanoic acid, caprolactam, hexamethylenediamine, and 1,6-hexanediol using, for example, one or more of a polypeptide having α-oxoacid decarboxylase activity classified under EC 4.1.1.-, a polypeptide having α-aminoacid decarboxylase activity classified under EC 4.1.1.-, a polypeptide having synthase activity, and a polypeptide having the activity of a dehydrogenase complex; and one or more optional polypeptides having an activity such as aldehyde dehydrogenase activity, alcohol dehydrogenase activity, CoA-transferase activity, carboxylate reductase activity, α-aminotransferase activity, thioesterase activity, hydrolase activity, ω-transaminase activity, N-acetyltransferase activity, or deacylase activity, and combinations thereof.

BACKGROUND

Nylons are polyamides which are sometimes synthesized by the condensation polymerisation of a diamine with a dicarboxylic acid. Similarly, nylons may be produced by the condensation polymerisation of lactams. A ubiquitous nylon is nylon 6,6, which is produced by reaction of hexamethylenediamine (HMD) and adipic acid. Nylon 6 is produced by a ring opening polymerisation of caprolactam. Therefore, adipic acid, hexamethylenediamine, and caprolactam are important intermediates in the production of nylons (Anton & Baird, Polyamides Fibers, Encyclopedia of Polymer Science and Technology, 2001).

Industrially, adipic acid and caprolactam are produced via air oxidation of cyclohexane. The air oxidation of cyclohexane produces, in a series of steps, a mixture of cyclohexanone (K) and cyclohexanol (A), designated as KA oil. Nitric acid oxidation of KA oil produces adipic acid (Musser, Adipic acid, Ullmann's Encyclopedia of Industrial Chemistry, 2000). Caprolactam is produced from cyclohexanone via its oxime and subsequent acid rearrangement (Fuchs, Kieczka and Moran, Caprolactam, Ullmann's Encyclopedia of Industrial Chemistry, 2000).

Industrially, hexamethylenediamine (HMD) is produced by hydrocyanation of C6 Building Block to adiponitrile, followed by hydrogenation to HMD (Herzog and Smiley, Hexamethylenediamine, Ullmann's Encyclopedia of Industrial Chemistry, 2012).

Given a reliance on petrochemical feedstocks; biotechnology offers an alternative approach via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

Accordingly, against this background, it is clear that there is a need for sustainable methods for producing adipic acid, caprolactam, 6-aminohexanoic acid, hexamethylenediamine and 1,6-hexanediol (hereafter "C6 building blocks") wherein the methods are biocatalyst-based (Jang et al., Biotechnology & Bioengineering, 2012, 109(10), 2437-2459).

However, no wild-type prokaryote or eukaryote naturally overproduces or excretes C6 building blocks to the extracellular environment. Nevertheless, the metabolism of adipic acid and caprolactam has been reported (Ramsay et al., Appl. Environ. Microbiol., 1986, 52(1), 152-156; Kulkarni and Kanekar, Current Microbiology, 1998, 37, 191-194).

The dicarboxylic acid, adipic acid, is converted efficiently as a carbon source by a number of bacteria and yeasts via β-oxidation into central metabolites. β-oxidation of adipate to 3-oxoadipate facilitates further catabolism via, for example, the ortho-cleavage pathway associated with aromatic substrate degradation. The catabolism of 3-oxoadipyl-CoA to acetyl-CoA and succinyl-CoA by several bacteria and fungi has been characterised comprehensively (Harwood and Parales, Annual Review of Microbiology, 1996, 50, 553-590). Both adipate and 6-aminohexanoic acid are intermediates in the catabolism of caprolactam, finally degraded via 3-oxoadipyl-CoA to central metabolites.

Potential metabolic pathways have been suggested for producing adipic acid from biomass-sugar: (1) biochemically from glucose to cis,cis muconic acid via the ortho-cleavage aromatic degradation pathway, followed by chemical catalysis to adipic acid; (2) a reversible adipic acid degradation pathway via the condensation of succinyl-CoA and acetyl-CoA and (3) combining β-oxidation, fatty acid synthase, and ω-oxidation. However, no information using these strategies has been reported (Jang et al., Biotechnology & Bioengineering, 2012, 109(10), 2437-2459).

An optimality principle states that microorganisms regulate their biochemical networks to support maximum biomass growth. Beyond the need for expressing heterologous pathways in a host organism, directing carbon flux towards C6 building blocks that serve as carbon sources rather than as biomass growth constituents, contradicts the optimality principle. For example, transferring the 1-butanol pathway from *Clostridium* species into other production strains has often fallen short by an order of magnitude compared to the production performance of native producers (Shen et al., Appl. Environ. Microbiol., 2011, 77(9), 2905-2915).

The efficient synthesis of a six or seven carbon aliphatic backbone as central precursor is a key consideration in synthesizing C6 building blocks prior to forming terminal functional groups, such as carboxyl, amine or hydroxyl groups, on the C6 aliphatic backbone.

SUMMARY

This document is based, at least in part, on the discovery that it is possible to construct biochemical pathways for producing a seven carbon chain aliphatic backbone as a central precursor, which can be decarboxylated to a six carbon aliphatic backbone in which one or two functional groups, i.e., carboxyl, amine or hydroxyl, can be formed, leading to the synthesis of adipic acid, adipate semialdehyde, 6-aminohexanoic acid, 6-hydroxyhexanoate, hexamethylenediamine, caprolactam, or 1,6-hexanediol (hereafter "C6 building blocks). Adipic acid and adipate, 6-hydroxyhexanoic acid and 6-hydroxyhexanoate, and 6-aminohexanoic acid and 6-aminohexanoate are used interchangeably herein to refer to the compound in any of its neutral or ionized forms, including any salt forms thereof. It is understood by those skilled in the art that the specific form will depend on pH. These pathways, metabolic engineering, and cultivation strategies described herein use meso-2,6 diaminopimelate as a central metabolite, which can be enzymatically converted to (S) 2-aminopimelate or (R) 2-aminopimelate.

In the face of an optimality principle, surprisingly it has been discovered that appropriate non-natural pathways, feedstocks, host microorganisms, attenuation strategies to the host's biochemical network and cultivation strategies may be combined to efficiently produce one or more C6 building blocks.

In one aspect, this document features a method of biosynthesizing 2-aminopimelate in a recombinant host. The method includes enzymatically converting 2,6-diaminopimelate to 2-aminopimelate in the host using at least one polypeptide having an activity selected from the group consisting of 2-hydroxyacyl-CoA dehydratase activity, mutase activity, ammonia lyase activity, and enoate reductase activity. In some embodiments, the method can include enzymatically converting 2,6-diaminopimelate to (S) 2-aminopimelate. In some embodiments, the method can include enzymatically converting 2,6-diaminopimelate to (R) 2-aminopimelate. The method can include using a polypeptide having 2-hydroxyacyl-CoA dehydratase activity and a polypeptide having enoate reductase activity to enzymatically convert 2,6-diaminopimelate to 2-aminopimelate. The polypeptide having 2-hydroxyacyl-CoA dehydratase activity can have at least 70%, at least 80%, or at least 90% sequence identity to the amino acid sequence set forth in SEQ ID NO: 25 or SEQ ID NO: 28. The polypeptide having enoate reductase activity can have at least 70%, at least 80%, or at least 90% sequence identity to the amino ac id sequence set forth in any one of SEQ ID NOs: 16-22. The method can include using a polypeptide having mutase activity, a polypeptide having ammonia lyase activity, a said polypeptide having enoate reductase activity to enzymatically convert 2,6-diaminopimelate to 2-aminopimelate. The polypeptide having ammonia lyase activity can have at least 70%, at least 80%, or at least 90% sequence identity to the amino acid sequence set forth in SEQ ID NO: 23. The polypeptide having mutase activity has at least 70%, at least 80%, or at least 90% sequence identity to the amino acid sequence set forth in SEQ ID NO: 26.

The method disclosed can further include using at least one polypeptide having an activity selected from the group consisting of diaminopimelate dehydrogenase activity, 2-hydroxycarboxylate dehydrogenase activity, CoA-transferase activity, 2-hydroxyacid dehydratase activity, and carboxylate reductase activity to enzymatically convert 2,6-diaminopimelate to 2-aminopimelate. The methods disclosed can further include using using at least one polypeptide having an activity selected from the group consisting of CoA ligase activity, CoA-transferase activity, carboxylate reductase activity, and aldehyde dehydrogenase activity to enzymatically convert 2,6-diaminopimelate to 2-aminopimelate.

In some embodiments, the central precursor comprises a C7 aliphatic backbone such as (S)-2-aminopimelate or (R)-2-aminopimelate, for enzymatic conversion to one or more C6 building blocks. Such C7 aliphatic backbones can be formed from a lysine biosynthesis precursor such as meso-2,6 diaminopimelate. See FIG. 1 and FIG. 2.

In some embodiments, a terminal carboxyl group can be enzymatically formed using a thioesterase, a CoA-transferase or CoA-ligase, or an aldehyde dehydrogenase. See FIG. 3.

In some embodiments, a terminal amine group can be enzymatically formed using an (R) alpha-aminodecarboxylase (classified, for example, under EC 4.1.1.- such as EC 4.1.1.20), (S) alpha-aminodecarboxylase (classified, for example, under EC 4.1.1.- such as EC 4.1.1.15, EC 4.1.1.17 or EC 4.1.1.18) or a transaminase (classified, for example, under EC 2.6.1.-). See FIG. 4, FIG. 5, FIG. 6, and FIG. 7.

In some embodiments, a terminal hydroxyl group can be enzymatically formed using a NADPH-specific or NADH-specific alcohol dehydrogenase. See FIG. 8.

In some embodiments, the principal carbon source fed to the fermentation derived from a biological feedstock or a non-biological feedstock In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

In some embodiments, the host microorganism is a prokaryote. For example, the prokaryote can be from the bacterial genus *Escherichia* such as *Escherichia coli*; from the bacterial genus *Clostridia* such as *Clostridium ljungdahlii, Clostridium autoethanogenum* or *Clostridium kluyveri*; from the bacterial genus *Corynebacteria* such as *Corynebacterium glutamicum*; from the bacterial genus *Cupriavidus* such as *Cupriavidus necator* or *Cupriavidus metallidurans*; from the bacterial genus *Pseudomonas* such as *Pseudomonas fluorescens, Pseudomonas putida* or *Pseudomonas oleavorans*; from the bacterial genus *Delftia* such as *Delftia acidovorans*; from the bacterial genus *Bacillus* such as *Bacillus subtillis*; from the bacterial genus *Lactobacillus* such as *Lactobacillus delbrueckii*; or from the bacterial genus *Lactococcus* such as *Lactococcus lactis*. Such prokaryotes also can be a source of genes to construct recombinant host cells described herein that are capable of producing one or more C6 building blocks.

In some embodiments, the host microorganism is a eukaryote (e.g., a fungus such as a yeast). For example, the eukaryote can be from the fungus genus *Aspergillus* such as *Aspergillus niger*; from the yeast genus *Saccharomyces* such as *Saccharomyces cerevisiae*; from the yeast genus *Pichia* such as *Pichia pastoris*; from the yeast genus *Yarrowia* such as *Yarrowia lipolytica*; from the yeast genus *Issatchenkia* such as *Issathenkia orientalis*; from the yeast genus *Debaryomyces* such as *Debaryomyces hansenii*; from the yeast genus *Arxula* such as *Arxula adenoinivorans*; or from the yeast genus *Kluyveromyces* such as *Kluyveromyces lactis*. Such eukaryotes also can be a source of genes to construct recombinant host cells described herein that are capable of producing one or more C6 building blocks.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g. cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

Many of the enzymes described herein catalyze reversible reactions, and the reaction of interest may be the reverse of the described reaction. The schematic pathways shown in FIGS. 1-8 illustrate the reaction of interest for each of the intermediates.

In some embodiments, the host microorganism's tolerance to high concentrations of a C6 building block is improved through continuous cultivation in a selective environment.

In some embodiments, the host microorganism's biochemical network is attenuated or augmented to (1) ensure the intracellular availability of oxaloacetate, (2) create an NADPH imbalance that may only be balanced via the formation of one or more C6 building blocks, (3) prevent degradation of central metabolites or central precursors leading to and including C6 building blocks and (4) ensure efficient efflux from the cell.

In some embodiments, the cultivation strategy entails either achieving an aerobic or micro-aerobic cultivation condition.

In some embodiments, the cultivation strategy entails nutrient limitation either via nitrogen, phosphate or oxygen limitation.

In some embodiments, the cultivation strategy entails preventing the incorporation of fatty acids into lipid bodies or other carbon storage units.

In some embodiments, one or more C6 building blocks are produced by a single type of microorganism, e.g., a recombinant host containing one or more exogenous nucleic acids, using, for example, a fermentation strategy.

In some aspects, the methods disclosed further comprising enzymatically converting 2-aminopimelate to a product selected from the group consisting of adipic acid, adipate semialdehyde, 6-aminohexanoic acid, 6-hydroxyhexanoic acid, caprolactam, hexamethylenediamine, and 1,6-hexanediol. The method includes enzymatically converting 2-aminopimelate to one or more of said products using (i) at least one polypeptide having an activity selected from the group consisting of α-oxoacid decarboxylase activity classified under EC 4.1.1.-, α-aminoacid decarboxylase activity classified under EC 4.1.1.-, synthase activity, and activity of a dehydrogenase complex; and (ii) one or more optional polypeptides having an activity selected from the group consisting of aldehyde dehydrogenase activity, alcohol dehydrogenase activity, CoA-transferase activity, carboxylate reductase activity, α-aminotransferase activity, thioesterase activity, hydrolase activity, ω-transaminase activity, N-acetyltransferase activity, and deacylase activity. The polypeptide having α-oxoacid decarboxylase activity can be classified under EC 4.1.1.43, EC 4.1.1.71, EC 4.1.1.72 or EC 4.1.1.74. The polypeptide having α-aminoacid decarboxylase activity can be classified under EC 4.1.1.15, EC 4.1.1.17, EC 4.1.1.18, EC 4.1.1.19. The polypeptide having synthase activity is classified under EC 2.2.1.6, or the polypeptide having the activity of a dehydrogenase complex comprises activities can be classified under EC 1.2.4.2, EC 1.8.1.4 and EC 2.3.1.61.

For example, the methods disclosed herein further can included enzymatically converting 2-aminopimelate to adipic acid using at least one polypeptide having an activity selected from the group consisting of α-aminotransferase activity, 2-oxoacid decarboxylase activity, synthase activity, dehydrogenase complex activity, thioesterase activity, CoA-transeferase activity, CoA-ligase activity, and aldehyde dehydrogenase activity.

For example, the methods disclosed herein further can included enzymatically converting 2-aminopimelate to adipate semialdehyde using at least one polypeptide having an activity selected from the group consisting of α-aminotransferase activity, 2-oxoacid decarboxylase activity, and synthase activity.

For example, the methods disclosed herein further can included enzymatically converting 2-aminopimelate to 6-aminohexanoic acid using a polypeptide having α-aminoacid decarboxylase activity.

For example, the methods disclosed herein further can included enzymatically converting adipate semialdehyde to 6-aminohexanoic from using a ω-transaminase. The methods can further include biosynthesizing caprolactam from 6-aminohexanoic acid using a polypeptide having the activity of a hydrolase.

For example, the methods disclosed herein further can included enzymatically converting 6-aminohexanoic acid to hexamethylenediamine from using at least one polypeptide having an activity selected from the group consisting of carboxylate reductase activity, N-acetyltransferase activity, ω-transaminase activity, and deacylase activity.

For example, the method further can include enzymatically converting adipate semialdehyde to hexamethylenediamine using at least one polypeptide having an selected from the group consisting of carboxylate reductase activity and ω-transaminase activity.

For example, the methods disclosed herein further can included enzymatically converting 2-aminopimelate to 6-hydroxyhexanoic acid using at least one polypeptide having an activity selected from the group consisting of α-aminotransferase activity, 2-oxoacid decarboxylase activity, synthase activity, and alcohol dehydrogenase activity.

For example, the methods disclosed herein further can included enzymatically converting 6-hydroxyhexanoic acid to hexamethylenediamine using at least one polypeptide having an activity selected from the group consisting of carboxylate reductase activity, ω-transaminase activity, and alcohol dehydrogenase activity.

For example, the methods disclosed herein further can included enzymatically converting 6-hydroxyhexanoic acid to 1,6-hexanediol using a polypeptide having carboxylate reductase activity and a polypeptide having alcohol dehydrogenase activity.

The polypeptide having 2-oxoacid decarboxylase activity can have at least 70% sequence identity to the amino acid sequence set forth in SEQ ID NO:34, the polypeptide having α-aminoacid decarboxylase activity can have at least 70% sequence identity to the amino acid sequence set forth in any one of SEQ ID NOs: 29-34.

The polypeptide having carboxylate reductase activity can have at least 70% sequence identity to the amino acid sequence set forth in any one of SEQ ID NOs: 3-7.

The polypeptide having ω-transaminase activity can have at least 70% sequence identity to the amino acid sequence set forth in any one of SEQ ID NOs: 8-13.

The polypeptide having thioesterase activity can have at least 70% sequence identity to the amino acid sequence set forth in SEQ ID NO: 1 or SEQ ID NO: 2.

In some embodiments, the host comprises one or more of the following: the intracellular concentration of oxaloacetate for biosynthesis of a C6 building block is increased in the host by overexpressing recombinant genes forming oxaloacetate; wherein an imbalance in NADPH is generated that can be balanced via the formation of a C6 building block; wherein an exogenous lysine biosynthesis pathway synthesizing lysine from 2-oxoglutarate via 2-oxoadipate is introduced in a host using the meso 2,6 diaminopimelate pathway for lysine synthesis; wherein an exogenous lysine biosynthesis pathway synthesizing lysine from oxaloacetate to meso 2,6 diaminopimelate is introduced in a host using the 2-oxoadipate pathway for lysine synthesis; wherein endogenous degradation pathways of central metabolites and central precursors leading to and including C6 building blocks are attenuated in the host; or wherein the efflux of a C6 building block across the cell membrane to the extracellular media is enhanced or amplified by genetically engineering structural modifications to the cell membrane or increasing any associated transporter activity for a C6 building block.

This document also features a recombinant host that includes at least one exogenous nucleic acid encoding at least one polypeptide having an activity selected from the group consisting of 2-hydroxyacyl-CoA dehydratase activity, mutase activity, ammonia lyase activity, and enoate reductase activity, said host producing 2-aminopimelate from 2,6-diaminopimelate. For example, the recombinant host can include a polypeptide having exogenous 2-hydroxyacyl-CoA dehydratase activity and a polypeptide having enoate reductase activity. For example, the recombinant host can include a polypeptide having mutase activity, a polypeptide having ammonia lyase activity, and a polypeptide having enoate reductase activity. The polypeptide having enoate reductase activity can have at least 70% sequence identity to the amino acid sequence set forth in any one of SEQ ID NOs: 16-22. The polypeptide having 2-hydroxyacyl-CoA dehydratase activity can have at least 70% sequence identity to the amino acid sequence set forth in SEQ ID NO: 25 or SEQ ID NO: 28. The polypeptide having mutase activity can have at least 70% sequence identity to the amino acid sequence set forth in SEQ ID NO: 26. The polypeptide having ammonia lyase activity can have at least 70% sequence identity to the amino acid sequence set forth in SEQ ID NO: 23.

The host can further include at least one or more exogenous polypeptides having an activity selected from the group consisting of a) diaminopimelate dehydrogenase activity, 2-hydroxycarboxylate dehydrogenase activity, CoA-transferase activity, 2-hydroxyacid dehydratase activity, and carboxylate reductase activity; or b) CoA ligase activity, CoA-transferase activity, carboxylate reductase activity, and aldehyde dehydrogenase activity.

The host can further include at least one or more exogenous polypeptides having an activity selected from the group consisting of α-oxoacid decarboxylase activity classified under EC 4.1.1.-, α-aminoacid decarboxylase activity classified under EC 4.1.1.-, synthase activity, and activity of a dehydrogenase complex.

The host can further include at least one or more exogenous polypeptides having an activity selected from the group consisting of aldehyde dehydrogenase activity, alcohol dehydrogenase activity, CoA-transferase activity, carboxylate reductase activity, α-aminotransferase activity, thioesterase activity, hydrolase activity, ω-transaminase activity, N-acetyltransferase activity, and deacylase activity, the host producing a product selected from the group consisting of adipic acid, adipate semialdehyde, 6-aminohexanoic acid, 6-hydroxyhexanoic acid, caprolactam, hexamethylenediamine, and 1,6-hexanediol.

The host can further include at least one or more exogenous polypeptides having an activity selected from the group consisting of α-aminotransferase activity, 2-oxoacid decarboxylase activity, activity of a dehydrogenase complex, thioesterase activity, CoA-transeferase activity, CoA-ligase activity, and aldehyde dehydrogenase activity, the host producing adipic acid.

The host can further include at least one or more exogenous polypeptides having an activity selected from the group consisting of α-aminotransferase activity, 2-oxoacid decarboxylase activity, synthase activity, the host producing adipate semialdehyde.

The host can further include at least one or more exogenous polypeptides having an α-aminoacid decarboxylase activity, the host producing 6-aminohexanoic acid.

A recombinant host producing 6-aminohexanoic acid can include an exogenous polypeptide having ω-transaminase activity. A recombinant host producing 6-aminohexanoic acid further can include an exogenous polypeptide having hydrolase activity, the host producing caprolactam. The host can further include one or more of an exogenous polypeptide having carboxylate reductase activity, N-acetyltransferase activity, ω-transaminase activity, or deacylase activity, the host producing hexamethylenediamine.

The host cell can further include at least one exogenous polypeptide having carboxylate reductase activity and/or at least one exogenous polypeptide having ω-transaminase activity, the host producing hexamethylenediamine.

The host cell can further include at least one exogenous polypeptide having an activity selected from the group consisting of α-aminotransferase activity, α-oxoacid decarboxylase activity, alcohol dehydrogenase activity, or synthase activity, the host producing 6-hydroxyhexanoic acid.

The host cell can further include at least one exogenous polypeptide having an activity selected from the group consisting of carboxylate reductase activity, ω-transaminase activity, and alcohol dehydrogenase activity, the host producing hexamethylenediamine.

The host cell can further include at an exogenous polypeptide having carboxylate reductase activity and/or an exogenous polypeptide having alcohol dehydrogenase activity, the host producing 1,6-hexanediol.

In one aspect, this document features a method for producing a bioderived 6-carbon compound. The method for producing a bioderived 6-carbon compound can include culturing or growing a recombinant host as described herein under conditions and for a sufficient period of time to produce the bioderived 6-carbon compound, wherein, optionally, the bioderived 6-carbon compound is selected from the group consisting of adipic acid, adipate semialdehyde, 6-aminohexanoic acid, 6-hydroxyhexanoic acid, caprolactam, hexamethylenediamine, 1,6-hexanediol, and combinations thereof.

In one aspect, this document features composition comprising a bioderived 6-carbon compound as described herein and a compound other than the bioderived 6-carbon compound, wherein the bioderived 6-carbon compound is selected from the group consisting of adipic acid, adipate semialdehyde, 6-aminohexanoic acid, 6-hydroxyhexanoic acid, caprolactam, hexamethylenediamine, 1,6-hexanediol, and combinations thereof. For example, the bioderived 6-carbon compound is a cellular portion of a host cell or an organism.

This document also features a biobased polymer comprising the bioderived adipic acid, adipate semialdehyde, 6-aminohexanoic acid, 6-hydroxyhexanoic acid, caprolactam, hexamethylenediamine, 1,6-hexanediol, and combinations thereof.

This document also features a biobased resin comprising the bioderived adipic acid, adipate semialdehyde, 6-aminohexanoic acid, 6-hydroxyhexanoic acid, caprolactam, hexamethylenediamine, 1,6-hexanediol, and combinations thereof, as well as a molded product obtained by molding a biobased resin.

In another aspect, this document features a process for producing a biobased polymer that includes chemically reacting the bioderived adipic acid, adipate semialdehyde, 6-aminohexanoic acid, 6-hydroxyhexanoic acid, caprolactam, hexamethylenediamine, 1,6-hexanediol, with itself or another compound in a polymer producing reaction.

In another aspect, this document features a process for producing a biobased resin that includes chemically reacting the bioderived adipic acid, adipate semialdehyde, 6-aminohexanoic acid, 6-hydroxyhexanoic acid, caprolactam, hexamethylenediamine, 1,6-hexanediol, with itself or another compound in a resin producing reaction.

Any of the recombinant hosts described herein further can include attenuation of one or more of the following enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, NADH-consuming transhydrogenase, an NADH-specific glutamate dehydrogenase, a NADH/NADPH-utilizing glutamate dehydrogenase, a pimeloyl-CoA dehydrogenase; an acyl-CoA dehydrogenase accepting C6 building blocks and central precursors as substrates; a butyryl-CoA dehydrogenase; or an adipyl-CoA synthetase.

Any of the recombinant hosts described herein further can overexpress one or more genes encoding: 2-hydroxyacyl-CoA dehydratase; a mutase; a CoA-ligase; an ammonia lyase; an acetyl-CoA synthetase; an enoate reductase; a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; diaminopimelate dehydrogenase; 2-hydroxycarboxylate dehydrogenase, 2-hydroxyacid dehydratase, carboxylate reductase and/or a multidrug transporter.

Also, described herein is a biochemical network comprising a dehydrogenase, a CoA-transferase, a dehydratase, a reductase, a mutase, a CoA-ligase, an ammonia lyase, or a thioesterase and meso-2,6-diaminopimelate, wherein the dehydrogenase, the CoA-transferase, the dehydratase, the reductase, the mutase, the CoA-ligase, the ammonia lyase, or the thioesterase enzymatically converts the meso-2,6-diaminopimelate to 2-aminopimelate. The biochemical network can further include an α-aminotransferase, wherein the aminotransferase enzymatically converts 2-aminopimelate to 2-oxo-pimelate. The biochemical network can further include a decarboxylase, a synthase, or a dehydrogenase complex, wherein the decarboxylase, the synthase, or the dehydrogenase complex enzymatically converts 2-oxo-pimelate to adipyl-CoA or adipate semialdehyde. The biochemical network can further include a dehydrogenase, a CoA transferase, a CoA ligase, or a thioesterase, wherein the dehydrogenase, the CoA transferase, the CoA ligase, or the thioesterase enzymatically convert adipyl-CoA or adipate semialdehyde to adipic acid.

Also, described herein is a biochemical network comprising a dehydrogenase, a CoA-transferase, a dehydratase, a reductase, a mutase, a CoA-ligase, an ammonia lyase, or a thioesterase and meso-2,6-diaminopimelate, wherein the dehydrogenase, the CoA-transferase, the dehydratase, the reductase, the mutase, the CoA-ligase, the ammonia lyase, or the thioesterase enzymatically converts the meso-2,6-diaminopimelate to 2-aminopimelate. The biochemical network can further include a decarboxylase, wherein the decarboxylase enzymatically converts 2-aminopimelate to 6-aminohexanoic acid. The biochemical network can further include a hydrolase, a reductase (e.g., a carboxylate reductase), a transaminase, an N-acetyltransferase, or a deacetylase, wherein the hydrolase, the reductase, the transaminase, the N-acetyltransferase, or the deacetylase enzymatically convert 6-aminohexanoic acid into at least one of caprolactam or hexamethylenediamine.

Also, described herein is a biochemical network comprising a dehydrogenase, a CoA-transferase, a dehydratase, a reductase, a mutase, a CoA-ligase, an ammonia lyase, or a thioesterase and meso-2,6-diaminopimelate, wherein the dehydrogenase, the CoA-transferase, the dehydratase, the reductase, the mutase, the CoA-ligase, the ammonia lyase, or the thioesterase enzymatically converts the meso-2,6-diaminopimelate to 2-aminopimelate. The biochemical network can further include an aminotransferase, a synthase, a decarboxylase, or a dehydrogenase wherein the aminotransferase, the synthase, the decarboxylase, or the dehydrogenase enzymatically converts 2-aminopimelate to 6-hydroxyhexanoic acid. The biochemical network can further include a reductase (e.g., a carboxylate reductase), a transaminase, or an alcohol dehydrogenase, wherein the reductase, the transaminase, or the alcohol dehydrogenase enzymatically convert 6-hydroxyhexanoic acid into at least one of hexamethylenediamine and 1,6-hexanediol.

Also, described herein is a means for obtaining 2-aminopimelate using at least one of a dehydrogenase, a CoA-transferase, a dehydratase, a reductase, a mutase, a CoA-ligase, an ammonia lyase, or a thioesterase. The means can further include means for converting 2-aminopimelate to at least one of adipic acid, 6-aminohexanoic acid, caprolactam, hexamethylenediamine, 6-hydroxyhexanoic acid, and 1,6-hexanediol. The means can include a decarboxylase, a synthase, a dehydrogenase complex, a dehydrogenase, a CoA-transferase, a dehydratase, a reductase, a mutase, a CoA-ligase, a lyase, a thioesterase, an aminotransferase, a hydrolase, a transaminase, or an N-acetyltransferase.

Also described herein is (i) step for obtaining 2-aminopimelate using a dehydrogenase, a CoA-transferase, a dehydratase, a reductase, a mutase, a CoA-ligase, an ammonia lyase, or a thioesterase (ii) a step for obtaining adipic acid using a decarboxylase, a synthase, or a dehydrogenase complex; (iii) a step for obtaining 6-aminohexanoic acid using a decarboxylase; and (iv) a step for obtaining 6-hydroxyhexanoic acid using a at least one of a aminotransferase, a synthase, a decarboxylase, or a dehydrogenase.

In another aspect, this document features a composition comprising 2-aminopimelate and decarboxylase, a synthase, or a dehydrogenase complex. The composition can be cellular. The composition can further include a dehydrogenase, a CoA-transferase, a CoA-dehydratase, a dehydratase, a reductase, a mutase, a CoA-ligase, a lyase, a thioesterase, an aminotransferase, a hydrolase, a transaminase, or an N-acetyltransferase and at least one of adipic acid, 6-aminohexanoic acid, caprolactam, hexamethylenediamine, 6-hydroxyhexanoic acid, and 1,6-hexanediol. The composition can be cellular.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIG. 4 also contains a schematic of an exemplary biochemical pathway to caprolactam from 6-aminohexanoic acid.

FIGS. 20A-20K contains the amino acid sequences of a *Lactobacillus brevis* thioesterase (see GenBank Accession No. ABJ63754.1, SEQ ID NO: 1), an *Lactobacillus plantarum* thioesterase (see GenBank Accession No. CCC78182.1, SEQ ID NO: 2), *Mycobacterium marinum* carboxylate reductase (see Genbank Accession No. ACC40567.1, SEQ ID NO: 3), a *Mycobacterium smegmatis* carboxylate reductase (see Genbank Accession No. ABK71854.1, SEQ ID NO: 4), a *Segniliparus rugosus* carboxylate reductase (see Genbank Accession No. EFV11917.1, SEQ ID NO: 5), a *Mycobacterium massiliense* carboxylate reductase (see Genbank Accession No. EIV11143.1, SEQ ID NO: 6), a *Segniliparus rotundus* carboxylate reductase (see Genbank Accession No. ADG98140.1, SEQ ID NO: 7), a *Chromobacterium violaceum* ω-transaminase (see Genbank Accession No. AAQ59697.1, SEQ ID NO: 8), a *Pseudomonas aeruginosa* ω-transaminase (see Genbank Accession No. AAG08191.1, SEQ ID NO: 9), a *Pseudomonas syringae* ω-transaminase (see Genbank Accession No. AAY39893.1, SEQ ID NO: 10), a *Rhodobacter sphaeroides* ω-transaminase (see Genbank Accession No. ABA81135.1, SEQ ID NO: 11), an

Figure 1:
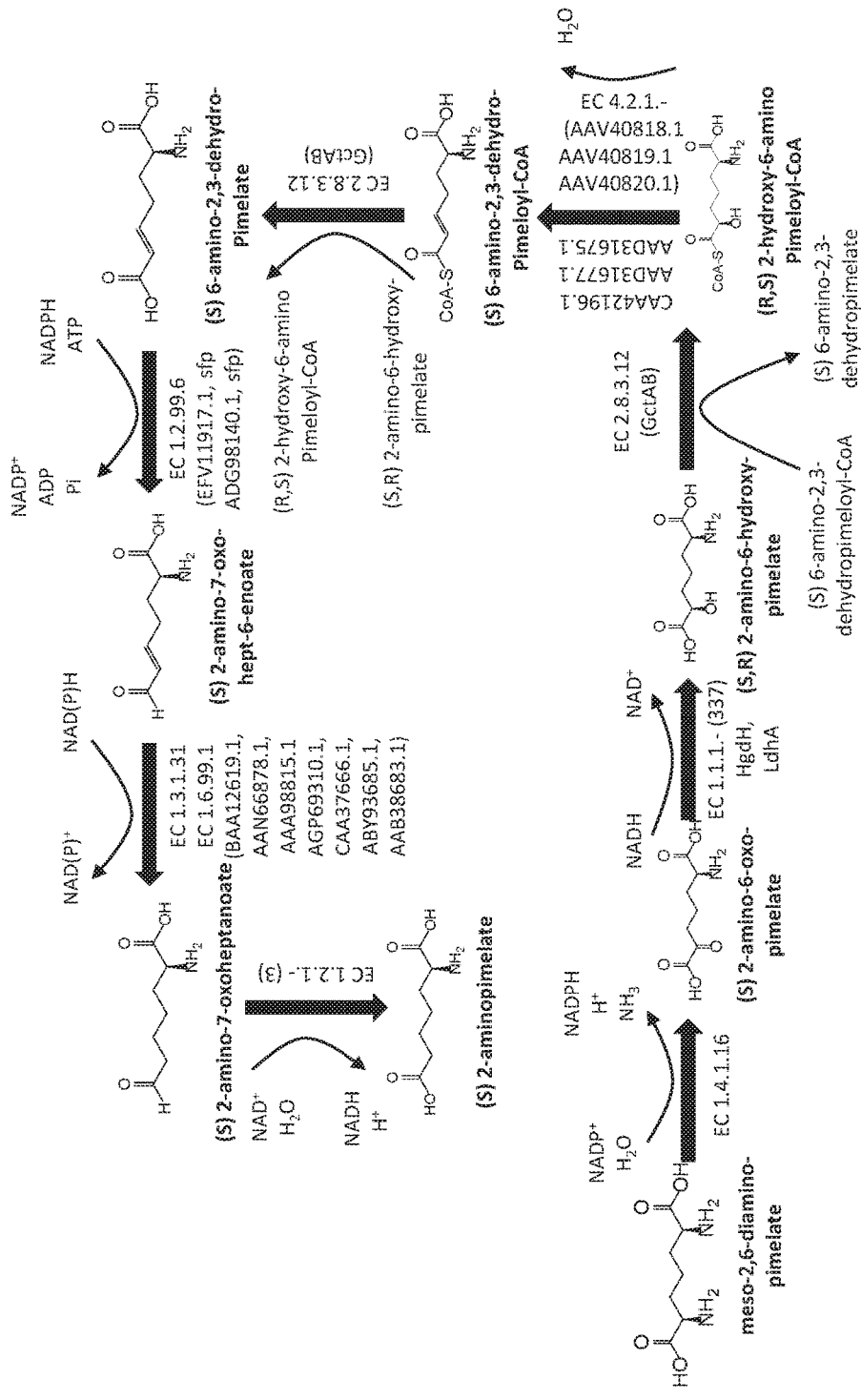
FIG. 1 is a schematic of an exemplary biochemical pathway leading to biosynthesis of (S) 2-aminopimelate using meso-2,6-diaminopimelate as a central metabolite.

*Escherichia coli* ω-transaminase (see Genbank Accession No. AAA57874.1, SEQ ID NO: 12), a *Vibrio fluvialis* ω-transaminase (see Genbank Accession No. AEA39183.1, SEQ ID NO: 13), a *Bacillus subtilis* phosphopantetheinyl transferase (see Genbank Accession No. CAA44858.1, SEQ ID NO:14), a *Nocardia* sp. NRRL 5646 phosphopantetheinyl transferase (see Genbank Accession No. ABI83656.1, SEQ ID NO:15), a *Bacillus subtilis* enoate reductase (see Genbank Accession No. BAA12619.1, SEQ ID NO: 16), a *Pseudomonas putida* enoate reductase (see Genbank Accession No. AAN66878.1, SEQ ID NO: 17), a *Kluyveromyces lactis* enoate reductase (see Genbank Accession No. AAA98815.1, SEQ ID NO: 18), a *Lactobacillus casei* enoate reductase (see Genbank Accession No. AGP69310.1, SEQ ID NO: 19), a *Saccharomyces pastorianus* enoate reductase (see Genbank Accession No. CAA37666.1, SEQ ID NO: 20), a *Thermoanaerobacter pseudethanolicus* enoate reductase (see Genbank Accession No. ABY93685.1, SEQ ID NO: 21), an *Enterobacter cloacae* enoate reductase (see Genbank Accession No. AAB38683.1, SEQ ID NO: 22), a *Fusobacterium nucleatum* ammonia lyase (see Genbank Accession No. AAL93968.1, SEQ ID NO: 23), an *Acidaminococcus fermentans* 2-hydroxyglutaryl-CoA dehydratase activator (see Genbank Accession No. CAA42196.1, SEQ ID NO: 24), a *Clostridium symbiosum* 2-hydroxyglutaryl-CoA dehydratase (see Genbank Accession No. AAD31677.1 & AAD31675.1, SEQ ID NO: 25), a *Bacillus subtilis* aminomutase (see Genbank Accession No. AAB72069.1, SEQ ID NO: 26), a *Peptoclostridium difficile* 2-Hydroxyisocaproyl-CoA dehydratase activator (see Genbank Accession No. AAV40818.1, SEQ ID NO: 27), a *Peptoclostridium difficile* 2-Hydroxyisocaproyl-CoA dehydratase (see Genbank Accession No. AAV40819.1 & AAV40820.1, SEQ ID NO: 28), an *Escherichia coli* glutamate decarboxylase (see Genbank Accession No. AAA23833.1, SEQ ID NO: 29), an *Escherichia coli* lysine decarboxylase (see Genbank Accession No. AAA23536.1, SEQ ID NO: 30), an *Escherichia coli* ornithine decarboxylase (see Genbank Accession No. AAA62785.1, SEQ ID NO: 31), an *Escherichia coli* lysine decarboxylase (see Genbank Accession No. BAA21656.1, SEQ ID NO: 32), an *Escherichia coli* diaminopimelate decarboxylase (see Genbank Accession No. AAA83861.1, SEQ ID NO: 33), and a *Salmonella typhimurium* indole-3-pyruvate decarboxylase (see Genbank Accession NO. CAC48239.1, SEQ ID: 34).

DETAILED DESCRIPTION

Described herein are enzymes, non-natural pathways, cultivation strategies, feedstocks, host microorganisms and attenuations to the host's biochemical network, which generates a seven carbon chain aliphatic backbone from central metabolites which can be decarboxylated to a six carbon aliphatic backbone into which one or two terminal functional groups may be formed leading to the synthesis of adipic acid, adipate semialdehyde, caprolactam, 6-aminohexanoic acid, 6-hydroxyhexanoic acid, hexamethylenediamine or 1,6-hexanediol (referred to as "C6 building blocks" herein). As used herein, the term "central precursor" is used to denote any metabolite in any metabolic pathway shown herein leading to the synthesis of one or more C6 building blocks. The term "central metabolite" is used herein to denote a metabolite that is produced in all microorganisms to support growth.

Host microorganisms described herein can include endogenous pathways that can be manipulated such that one or more C6 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host. Within an engineered pathway, the enzymes can be from a single source, i.e., from one species, or can be from multiple sources, i.e., different species or genera. Nucleic acids encoding the enzymes described herein have been identified from various organisms and are readily available in publicly available databases such as GenBank or EMBL. Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. Thus, as described herein recombinant hosts can include nucleic acids encoding one or more of a dehydrogenase, decarboxylase, reductase, dehydratase, CoA-transferase, CoA-ligase, thioesterase, hydrolase, ammonia lyase, mutase, synthase, aminotransferase, or transaminase as described in more detail below.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In some embodiments, depending on the host and the compounds produced by the host, one or more of the following polypeptides having 2-hydroxyacyl-CoA dehydratase activity, mutase activity, ammonia lyase activity, and enoate reductase activity may be expressed in the host in addition to one or more of: a polypeptide having α-oxoacid decarboxylase activity, a polypeptide having α-aminoacid decarboxylase activity, a polypeptide having synthase activity, a polypeptide having the activity of a dehydrogenase complex, a polypeptide having diaminopimelate dehydrogenase activity, a polypeptide having (R)-2-hydroxyisocaproate dehydrogenase activity, a polypeptide having (R)-2-hydroxyglutarate dehydrogenase activity, a polypeptide having glutaconate CoA-transferase activity, a polypeptide having 2-hydroxyisocaproyl-CoA dehydratase activity, a polypeptide having (R)-2-hydroxyglutryl-CoA dehydratase activity, a polypeptide having carboxylate reductase activity, a polypeptide having aldehyde dehydrogenase activity, a polypeptide having lysine 2, 3-aminomutase activity, a polypeptide having succinate-CoA ligase activity, a polypeptide having 3-aminobutyryl-CoA ammonia lyase activity, a polypeptide having thioesterase activity, a polypeptide having CoA-transferase activity, a polypeptide having alpha-aminotransferase activity, a polypeptide having branch-chain-2-oxoacid decarboxylase activity, a polypeptide having acetolactate synthase activity, a polypeptide having aldehyde dehydrogenase activity, a polypeptide having hydrolase activity, a polypeptide having ω-transaminase activity, a polypeptide having N-acetyltransferase activity, a polypeptide having lysine N-acetyltransferase activity, or a polypeptide having alcohol dehydrogenase activity. In recombinant hosts expressing a carboxylate reductase, a phosphopantetheinyl transferase also can be expressed as it enhances activity of the carboxylate reductase.

For example, a recombinant host can include at least one exogenous polypeptide having an activity selected from the group consisting of 2-hydroxyacyl-CoA dehydratase activity, mutase activity, ammonia lyase activity, and enoate reductase activity and produce 2-aminopimelate from 2,6-diaminopimelate.

For example, a host can include an exogenous polypeptide having 2-hydroxyacyl-CoA dehydratase activity and an exogenous polypeptide having enoate reductase activity and produce 2-aminopimelate (e.g., (S)-aminopimelate). Such a host further can include at least one polypeptide having an activity selected from the group consisting of diaminopimelate dehydrogenase activity, 2-hydroxycarboxylate dehydrogenase activity, CoA-transferase activity, 2-hydroxyacid dehydratase activity, and carboxylate reductase activity. See, e.g., FIG. 1.

For example, a recombinant host can include (i) an exogenous polypeptide having diaminopimelate dehydrogenase activity classified, for example, under EC 1.4.1.16, (ii) an exogenous polypeptide having 2-hydroxyisocaproate dehydrogenase activity or an exogenous polypeptide having (R)-2-hydroxyglutarate dehydrogenase activity classified, for example, under EC 1.1.1.- such as EC 1.1.1.337, (iii) an exogenous polypeptide having glutaconate CoA-transferase activity classified, for example, under EC 2.8.3.12, (iv) an exogenous polypeptide having 2-hydroxyisocaproyl-CoA dehydratase activity or a polypeptide having 2-hydroxyglu-tryl-CoA dehydratase activity classified, for example, under EC 4.2.1.-, (v) an exogenous polypeptide having carboxylate reductase activity classified, for example, under EC 1.2.99.6, (vi) an exogenous polypeptide having enoate reductase activity classified, for example, under EC 1.3.1.31 or EC 1.3.99.1, (vii) or an exogenous polypeptide having aldehyde dehydrogenase activity classified, for example, under EC 1.2.1.- such as EC 1.2.1.3 and produce (S) 2-aminopimelate. See, FIG. 1.

For example, a recombinant host can include an exogenous polypeptide having mutase activity, an exogenous polypeptide having ammonia lyase activity, and an exogenous polypeptide having enoate reductase activity and produce 2-aminopimelate (e.g., (R)-aminopimelate). Such a host further can include at least one polypeptide having an activity selected from the group consisting of CoA ligase activity, CoA-transferase activity, carboxylate reductase activity, and aldehyde dehydrogenase activity. See, FIG. 2.

For example, a recombinant host can include (i) an exogenous polypeptide having lysine 2,3-aminomutase activity classified, for example, under EC 5.4.3.2, (ii) an exogenous polypeptide having succinate-CoA ligase activity classified, for example, under EC 6.2.1.5 or a polypeptide having CoA-transferase activity classified, for example, under EC 2.8.3.-, (iii) an exogenous polypeptide having 3-aminobutyryl-CoA ammonia lyase activity classified, for example, under EC 4.3.1.14, (iv) an exogenous polypeptide having thioesterase activity classified, for example, under EC 3.1.2.- or polypeptide having CoA-transferase activity classified, for example, under EC 2.8.3.-, (v) an exogenous polypeptide having carboxylate reductase activity classified, for example, under EC 1.2.99.6, (vi) an exogenous polypeptide having enoate reductase activity classified, for example, under EC 1.3.1.31 or EC 1.6.99.1 or (vii) a polypeptide having aldehyde dehydrogenase activity classified, for example, under EC 1.2.1.- such as EC 1.2.1.3 and produce (R) 2-aminopimelate.

A recombinant host producing 2-aminopimelate also can include at least one exogenous polypeptide having an activity selected from the group consisting of α-oxoacid decarboxylase activity classified under EC 4.1.1.-, α-aminoacid decarboxylase activity classified under EC 4.1.1.-, synthase activity, and activity of a dehydrogenase complex. See, e.g., FIG. 3 and FIG. 4.

In some embodiments, a recombinant host producing 2-aminopimelate can include an exogenous polypeptide having 2-oxoacid decarboxylase activity classified, for example, under EC 4.1.1.- such as EC 4.1.1.43, EC 4.1.1.71, EC 4.1.1.72 or EC 4.1.1.74 or an exogenous polypeptide having acetolactate synthase activity classified, for example, under EC 2.2.1.6 and produce adipic acid. See, FIG. 3.

For example, a recombinant host producing 2-aminopimelate can include (i) an exogenous polypeptide having 2-oxoacid decarboxylase activity classified, for example, under EC 4.1.1.- such as EC 4.1.1.43, EC 4.1.1.71, EC 4.1.1.72 or EC 4.1.1.74 or an exogenous polypeptide having acetolactate synthase activity classified, for example, under EC 2.2.1.6 and (ii) an exogenous polypeptide having α-aminotransferase activity classified, for example, under EC 2.6.1.- such as EC 2.6.1.39, EC 2.6.1.42 or EC 2.6.1.21 and produce adipate semialdehyde or adipic acid. See, FIG. 3.

For example, a recombinant host producing 2-aminopimelate can include (i) an exogenous polypeptide having 2-oxoacid decarboxylase activity classified, for example, under EC 4.1.1.- such as EC 4.1.1.43, EC 4.1.1.71, EC 4.1.1.72 or EC 4.1.1.74 or an exogenous polypeptide having acetolactate synthase activity classified, for example, under EC 2.2.1.6, (ii) an exogenous polypeptide having α-aminotransferase activity classified, for example, under EC 2.6.1.- such as EC 2.6.1.39, EC 2.6.1.42 or EC 2.6.1.21, and (iii) an exogenous polypeptide having aldehyde dehydrogenase activity classified, for example, under EC 1.2.1.- such as EC 1.2.1.3, EC 1.2.1.16, EC 1.2.1.20, EC 1.2.1.63 or EC 1.2.1.79 and produce adipic acid. See, FIG. 3.

In some embodiments, a recombinant host producing 2-aminopimelate can include an exogenous polypeptide having acetolactate synthase activity classified, for example, under EC 2.2.1.6 and produce adipic acid. See, FIG. 3.

For example, a recombinant host producing 2-aminopimelate can include (i) an exogenous polypeptide having acetolactate synthase activity classified, for example, under EC 2.2.1.6 and an exogenous polypeptide having α-aminotransferase activity classified, for example, under EC 2.6.1.- such as EC 2.6.1.39, EC 2.6.1.42 or EC 2.6.1.21, and produce adipic acid. See, FIG. 3.

For example, a recombinant host producing 2-aminopimelate can include an exogenous polypeptide having acetolactate synthase activity classified, for example, under EC 2.2.1.6, an exogenous polypeptide having alpha-aminotransferase activity classified, for example, under EC 2.6.1.- such as EC 2.6.1.39, EC 2.6.1.42 or EC 2.6.1.21, and an exogenous polypeptide having aldehyde dehydrogenase activity classified, for example, under EC 1.2.1.- such as EC 1.2.1.3, EC 1.2.1.16, EC 1.2.1.20, EC 1.2.1.63 or EC 1.2.1.79 and produce adipic acid. See, FIG. 3.

In some embodiments, a recombinant host producing 2-aminopimelate can include an exogenous dehydrogenase complex comprised of enzyme activities classified, for example, EC 1.2.4.2, EC 1.8.1.4 or EC 2.3.1.61 and produce adipic acid. See, FIG. 3.

For example, a recombinant host producing 2-aminopimelate can include (i) an exogenous dehydrogenase complex comprised of enzyme activities classified, for example, EC 1.2.4.2, EC 1.8.1.4 or EC 2.3.1.61 and (ii) an exogenous polypeptide having α-aminotransferase activity classified, for example, under EC 2.6.1.- such as EC 2.6.1.39, EC 2.6.1.42 or EC 2.6.1.21 and produce adipic acid. See, FIG. 3.

For example, a recombinant host producing 2-aminopimelate can include an exogenous dehydrogenase complex comprised of enzyme activities classified, for example, EC 1.2.4.2, EC 1.8.1.4 or EC 2.3.1.61 and an exogenous polypeptide having thioesterase activity classified, for example, under EC 3.1.2.- and produce adipic acid. See, FIG. 3.

For example, a recombinant host producing 2-aminopimelate can include an exogenous dehydrogenase complex and an exogenous polypeptide having glutaconate CoA-transferase activity classified, for example, under EC 2.8.3.12 or an exogenous polypeptide having succinate CoA-ligase activity classified, for example, under EC 6.2.1.5 and produce adipic acid. See, FIG. 3.

For example, a recombinant host producing 2-aminopimelate can include (i) an exogenous dehydrogenase complex comprised of enzyme activities classified, for example, EC 1.2.4.2, EC 1.8.1.4 or EC 2.3.1.61, (ii) an exogenous polypeptide having alpha-aminotransferase activity classified, for example, under EC 2.6.1.- such as EC 2.6.1.39, EC 2.6.1.42 or EC 2.6.1.21, and (iii) an exogenous polypeptide having thioesterase activity classified, for example, under EC 3.1.2.-, a polypeptide having CoA-ligase activity classified, for example, under EC 6.2.1.5 or a polypeptide having CoA-transferase activity classified, for example, under EC 2.8.3.12 and produce adipic acid. See, FIG. 3.

For example, a recombinant host producing 2-aminopimelate can include an exogenous dehydrogenase complex, an exogenous polypeptide having alpha-aminotransferase activity, and an exogenous polypeptide having glutaconate CoA-transferase activity or an exogenous polypeptide having succinate CoA-ligase activity and produce adipic acid. See, FIG. 3.

In some embodiments, a recombinant host producing (S)-2-aminopimelate can include a polypeptide having decarboxylase activity classified, for example, under EC 4.1.1.- such as EC 4.1.1.15, EC 4.1.1.17, EC 4.1.1.18, EC 4.1.1.19 and produce 6-aminohexanoic acid, which can be converted to caprolactam using an exogenous polypeptide having amidohydrolase activity (classified, for example, under EC 3.5.2.-). See, FIG. 4.

In some embodiments, a recombinant host producing (R)-2-aminopimelate can include a polypeptide having decarboxylase activity classified, for example, under EC 4.1.1.- such as EC 4.1.1.20 and produce 6-aminohexanoic acid from (R)-2-aminopimelate, which can be converted to caprolactam using an exogenous polypeptide having hydrolase activity (classified, for example, under EC 3.5.2.-). See, FIG. 4.

A recombinant host producing 2-aminopimelate can include (i) an exogenous polypeptide having α-aminotransferase activity classified, for example, under EC 2.6.1- such as EC 2.6.1.21, EC 2.6.1.39 or EC 2.6.1.42 (ii) an exogenous polypeptide having decarboxylase activity classified, for example, under EC 4.1.1.- such as EC 4.1.1.43, EC 4.1.1.71, EC 4.1.1.71 or EC 4.1.1.74 or a polypeptide having acetolactate synthase activity classified, for example, under EC 2.2.1.6 and (iii) an exogenous polypeptide having ω-transaminase activity classified, for example, under EC 2.6.1.- such EC 2.6.1.18, EC 2.6.1.19, EC 2.6.1.48, EC 2.6.1.29, or EC 2.6.1.82 and produce 6-aminohexanoic acid. See, FIG. 4.

A recombinant host producing 6-aminohexanoic acid can further include (i) an exogenous polypeptide having carboxylate reductase activity classified, for example, under EC 1.2.99.6 (ii) an exogenous polypeptide having ω-transaminase activity classified, for example, under EC 2.6.1.- such as EC 2.6.1.18, EC 2.6.1.19, EC 2.6.1.48, EC 2.6.1.29, or EC 2.6.1.82 and produce hexamethylenediamine. See, FIG. 5.

A recombinant host producing 2-aminopimelate can include (i) an exogenous polypeptide having α-aminotransferase activity classified, for example, under EC 2.6.1.39 or EC 2.6.1.42, (ii) classified, for example, under EC 4.1.1.- such as EC 4.1.1.43, EC 4.1.1.71, EC 4.1.1.71 or EC 4.1.1.74 or a polypeptide having acetolactate synthase activity classified, for example, under EC 2.2.1.6, (iii) a polypeptide having carboxylate reductase activity classified, for example, under EC 1.2.99.6 and (iv) exogenous polypeptide having ω-transaminase activity classified, for example, under EC 2.6.1.- such EC 2.6.1.18, EC 2.6.1.19, EC 2.6.1.48, EC 2.6.1.29, or EC 2.6.1.82 and produce hexamethylenediamine. See, FIG. 5.

A recombinant host producing 6-aminohexanoic acid can further include (i) an exogenous polypeptide having N-acetyltransferase activity classified, for example, under EC 2.3.1.32 (ii) a polypeptide having carboxylate reductase activity classified, for example, under EC 1.2.99.6, (iii) a polypeptide having ω-transaminase activity classified, for example, under EC 2.6.1.- such as EC 2.6.1.18, EC 2.6.1.19, or EC 2.6.1.48, EC 2.6.1.29, or EC 2.6.1.82 and (iv) and a polypeptide having deacylase activity classified, for example, under EC 3.5.1.17 and produce hexamethylenediamine. See, FIG. 6.

In some embodiments, a recombinant host can include a polypeptide having α-aminotransferase activity classified, for example, under EC 2.6.1.- such as EC 2.6.1.39, EC 2.6.1.42 or EC 2.6.1.21 and produce 6-hydroxyhexanoic acid. See, FIG. 7.

For example, a recombinant host can include (i) a polypeptide having α-aminotransferase activity classified, for example, under EC 2.6.1.- such as EC 2.6.1.39, EC 2.6.1.42 or EC 2.6.1.21 and (ii) an exogenous polypeptide having 2-oxoacid decarboxylase activity classified, for example, under EC 4.1.1.- such as EC 4.1.1.43, EC 4.1.1.71, EC 4.1.1.72 or EC 4.1.1.74 or an exogenous polypeptide having acetolactate synthase activity classified, for example, under EC 2.2.1.6 and produce 6-hydroxyhexanoic acid. See, FIG. 8.

For example, a recombinant host can include (i) a polypeptide having α-aminotransferase activity classified, for example, under EC 2.6.1.- such as EC 2.6.1.39, EC 2.6.1.42 or EC 2.6.1.21 and (ii) an exogenous polypeptide having 2-oxoacid decarboxylase activity classified, for example, under EC 4.1.1.- such as EC 4.1.1.43, EC 4.1.1.71, EC 4.1.1.72 or EC 4.1.1.74 or an exogenous polypeptide having acetolactate synthase activity classified, for example, under EC 2.2.1.6, (iii) and a polypeptide having alcohol dehydrogenase activity classified, for example, under EC 1.1.1.- such as EC 1.1.1.2 or EC 1.1.1.258 and produce 6-hydroxyhexanoic acid. See, FIG. 8.

A recombinant host producing 6-hydroxyhexanoic acid can further include (i) a polypeptide having carboxylate reductase activity classified, for example, under EC 1.2.99.6, (ii) a polypeptide having ω-transaminase activity classified, for example, under EC 2.6.1.- such as EC 2.6.1.18, EC 2.6.1.19, or EC 2.6.1.48, EC 2.6.1.29, or EC 2.6.1.82, and (iii) a polypeptide having alcohol dehydrogenase activity classified, for example, under EC 1.1.1.- such as EC 1.1.1.1 and produce hexamethylenediamine. See, FIG. 7.

A recombinant host producing 6-hydroxyhexanoic acid can further include (i) an exogenous polypeptide having carboxylate reductase activity classified, for example, under EC 1.2.99.6 and (ii) an exogenous polypeptide having alcohol dehydrogenase activity classified, for example, under EC 1.1.1.- such as EC 1.1.1.1, EC 1.1.1.2, EC 1.1.1.21 or EC 1.1.1.184 and produce 1,6 hexanediol. See, FIG. 8.

Any of the enzymes described herein that can be used for production of one or more C6 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

Any of the enzymes described herein that can be used for production of one or more C6 building blocks can have at least 70% sequence identity (homology) (e.g., at least 75%, 80%, 85%, 90%, 95%, 97%, 98%, 99%, or 100%) to the amino acid sequence of the corresponding wild-type enzyme. For example, a thioesterase described herein can have at least 70% sequence identity (homology) (e.g., at least 75%, 80%, 85%, 90%, 95%, 97%, 98%, 99%, or 100%) to the amino acid sequence of a *Lactobacillus brevis* thioesterase (see GenBank Accession No. ABJ63754.1, SEQ ID NO: 1) or to the amino acid sequence of a *Lactobacillus plantarum* thioesterase (see GenBank Accession No. CCC78182.1, SEQ ID NO: 2). See FIG. 20A.

For example, a carboxylate reductase described herein can have at least 70% sequence identity (homology) (e.g., at least 75%, 80%, 85%, 90%, 95%, 97%, 98%, 99%, or 100%) to the amino acid sequence of a *Mycobacterium marinum* (see Genbank Accession No. ACC40567.1, SEQ ID NO: 3), a *Mycobacterium smegmatis* (see Genbank Accession No. ABK71854.1, SEQ ID NO: 4), a *Segniliparus rugosus* (see Genbank Accession No. EFV11917.1, SEQ ID NO: 5), a *Mycobacterium massiliense* (see Genbank Accession No. EIV11143.1, SEQ ID NO: 6), or a *Segniliparus rotundus* (see Genbank Accession No. ADG98140.1, SEQ ID NO: 7) carboxylate reductase. See, FIGS. 20A-20E.

For example, a ω-transaminase described herein can have at least 70% sequence identity (homology) (e.g., at least 75%, 80%, 85%, 90%, 95%, 97%, 98%, 99%, or 100%) to the amino acid sequence of a *Chromobacterium violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), a *Rhodobacter sphaeroides* (see Genbank Accession No. ABA81135.1, SEQ ID NO: 11), *an Escherichia coli* (see Genbank Accession No. AAA57874.1, SEQ ID NO: 12), or a *Vibrio fluvialis* (see Genbank Accession No. AEA39183.1, SEQ ID NO: 13) ω-transaminase. Some of these ω-transaminases are diamine ω-transaminases. See, FIG. 20E and FIG. 20F.

For example, a phosphopantetheinyl transferase described herein can have at least 70% sequence identity (homology) (e.g., at least 75%, 80%, 85%, 90%, 95%, 97%, 98%, 99%, or 100%) to the amino acid sequence of a *Bacillus subtilis* phosphopantetheinyl transferase (see Genbank Accession No. CAA44858.1, SEQ ID NO: 14) or a *Nocardia* sp. NRRL 5646 phosphopantetheinyl transferase (see Genbank Accession No. ABI83656.1, SEQ ID NO:15). See, FIG. 20F and FIG. 20G.

For example, an enoate reductase described herein can have at least 70% sequence identity (homology) (e.g., at least 75%, 80%, 85%, 90%, 95%, 97%, 98%, 99%, or 100%) to the amino acid sequence of a *Bacillus subtilis* enoate reductase (see Genbank Accession No. BAA12619.1, SEQ ID NO: 16), a *Pseudomonas putida* enoate reductase (see Genbank Accession No. AAN66878.1, SEQ ID NO: 17), a *Kluyveromyces lactis* enoate reductase (see Genbank Accession No. AAA98815.1, SEQ ID NO: 18), a *Lactobacillus casei* enoate reductase (see Genbank Accession No. AGP69310.1, SEQ ID NO: 19), a *Saccharomyces pastorianus* enoate reductase (see Genbank Accession No. CAA37666.1, SEQ ID NO: 20), a *Thermoanaerobacter pseudethanolicus* enoate reductase (see Genbank Accession No. ABY93685.1, SEQ ID NO: 21), a *Enterobacter cloacae* enoate reductase (see Genbank Accession No. AAB38683.1, SEQ ID NO: 22).

For example, an ammonia lyase described herein can have at least 70% sequence identity (homology) (e.g., at least 75%, 80%, 85%, 90%, 95%, 97%, 98%, 99%, or 100%) to the amino acid sequence of a *Fusobacterium nucleatum* ammonia lyase (see Genbank Accession No. AAL93968.1, SEQ ID NO: 23).

For example, a dehydratase activator described herein can have at least 70% sequence identity (homology) (e.g., at least 75%, 80%, 85%, 90%, 95%, 97%, 98%, 99%, or 100%)

to the amino acid sequence of an *Acidaminococcus fermentans* 2-hydroxyglutaryl-CoA dehydratase activator (see Genbank Accession No. CAA42196.1, SEQ ID NO: 24) or a *Peptoclostridium difficile* 2-Hydroxyisocaproyl-CoA dehydratase activator (see Genbank Accession No. AAV40818.1, SEQ ID NO: 27).

For example, a 2-hydroxyacyl-CoA dehydratase described herein can have at least 70% sequence identity (homology) (e.g., at least 75%, 80%, 85%, 90%, 95%, 97%, 98%, 99%, or 100%) to the amino acid sequence of a *Clostridium symbiosum* 2-hydroxyglutaryl-CoA dehydratase (see Genbank Accession No. AAD31677.1 & AAD31675.1, SEQ ID NO: 25), or a *Peptoclostridium difficile* 2-Hydroxyisocaproyl-CoA dehydratase (see Genbank Accession No. AAV40819.1 & AAV40820.1, SEQ ID NO: 28).

For example, an aminomutase described herein can have at least 70% sequence identity (homology) (e.g., at least 75%, 80%, 85%, 90%, 95%, 97%, 98%, 99%, or 100%) to the amino acid sequence of a *Bacillus subtilis* aminomutase (see Genbank Accession No. AAB72069.1, SEQ ID NO: 26).

For example, a decarboxylase described herein can have at least 70% sequence identity (homology) (e.g., at least 75%, 80%, 85%, 90%, 95%, 97%, 98%, 99%, or 100%) to the amino acid sequence of an *Escherichia coli* glutamate decarboxylase (see Genbank Accession No. AAA23833.1, SEQ ID NO: 29), an *Escherichia coli* lysine decarboxylase (see Genbank Accession No. AAA23536.1, SEQ ID NO: 30), an *Escherichia coli* ornithine decarboxylase (see Genbank Accession No. AAA62785.1, SEQ ID NO: 31), an *Escherichia coli* lysine decarboxylase (see Genbank Accession No. BAA21656.1, SEQ ID NO: 32), an *Escherichia coli* diaminopimelate decarboxylase (see Genbank Accession No. AAA83861.1, SEQ ID NO: 33), a *Salmonella typhimurium* indole-3-pyruvate decarboxylase (see Genbank Accession No. CAC48239.1, SEQ ID NO: 34).

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached In addition, the production of one or more C6 building blocks can be performed in vitro using the isolated enzymes described herein, using a lysate (e.g., a cell lysate) from a host microorganism as a source of the enzymes, or using a plurality of lysates from different host microorganisms as the source of the enzymes.

The reactions of the pathways described herein can be performed in one or more host strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from of the above types of host cells and used in a purified or semi-purified form. Moreover, such extracts include lysates (e.g. cell lysates) that can be used as sources of relevant enzymes. In the methods provided by the document, all the steps can be performed in host cells, all the steps can be performed using extracted enzymes, or some of the steps can be performed in cells and others can be performed using extracted enzymes.

In addition, the production of one or more C6 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Enzymes Generating the C7 Aliphatic Backbone for Conversion to C6 Building Blocks In some embodiments, (S)-2-amino-6-oxopimelate in FIG. 1 is substituted with the central precursor N-Acetyl-L-2-amino-6-oxopimelate.

In some embodiments, (S)-2-amino-6-oxopimelate in FIG. 1 is substituted with the central precursor N-Succinyl-2-L-amino-6-oxoheptanedioate.

In some embodiments, the C7 aliphatic backbone can be enzymatically formed from meso-2,6-diaminopimelate using one or more of a dehydrogenase, a CoA-transferase, a dehydratase, a reductase, a mutase, a CoA-ligase, an ammonia lyase and a thioesterase. See, e.g., FIGS. 1 and 2.

In some embodiments, the dehydrogenase is a diaminopimelate dehydrogenase classified, for example, under EC 1.4.1.16.

In some embodiments, the dehydrogenase is a (R)-2-hydroxyisocaproate dehydrogenase such as the gene product of LdhA or a 2-hydroxyglutarate dehydrogenase such as the gene product of HgdH.

In some embodiments, the CoA-transferase is a glutaconate CoA-transferase, classified, for example, under EC 2.8.3.12, such as the gene product of GctAB or a pimelate CoA-transferase classified, for example, under EC 2.8.3.- such as the gene product of thnH.

In some embodiments, the CoA-ligase is a succinate CoA-ligase classified, for example, under EC 6.2.1.5.

In some embodiments, the dehydratase is a 2-hydroxyisocaproyl-CoA dehydratase such as SEQ ID NO: 28 or a 2-hydroxyglutaryl-CoA dehydratase such as SEQ ID NO: 25.

In some embodiments, the thioesterase is classified, for example, under EC 3.1.2.-, such as that encoded by YciA, tesB, acot13, SEQ ID NO: 1 or SEQ ID NO: 2.

In some embodiments, the reductase is a carboxylate reductase classified, for example, under EC 1.2.99.6 such as the gene products of car & npt, GriC & GriD or SEQ ID NO: 5, 7.

In some embodiments, the reductase is an enoate reductase (old yellow enzyme) classified, for example, under EC 1.3.1.31 or EC 1.6.99.1 such as the gene product of SEQ ID NO: 16-22.

In some embodiments, the dehydrogenase is an aldehyde dehydrogenase classified, for example, under EC 1.2.1.- such as EC 1.2.1.3.

In some embodiments, the mutase is a lysine 2,3-aminomutase classified, for example, under EC 5.4.3.2 such as SEQ ID NO: 26.

In some embodiments, the ammonia lyase is a 3-butyryl-CoA ammonia lyase classified, for example, under EC 4.3.1.14 such as SEQ ID NO: 23.

Figure 2:
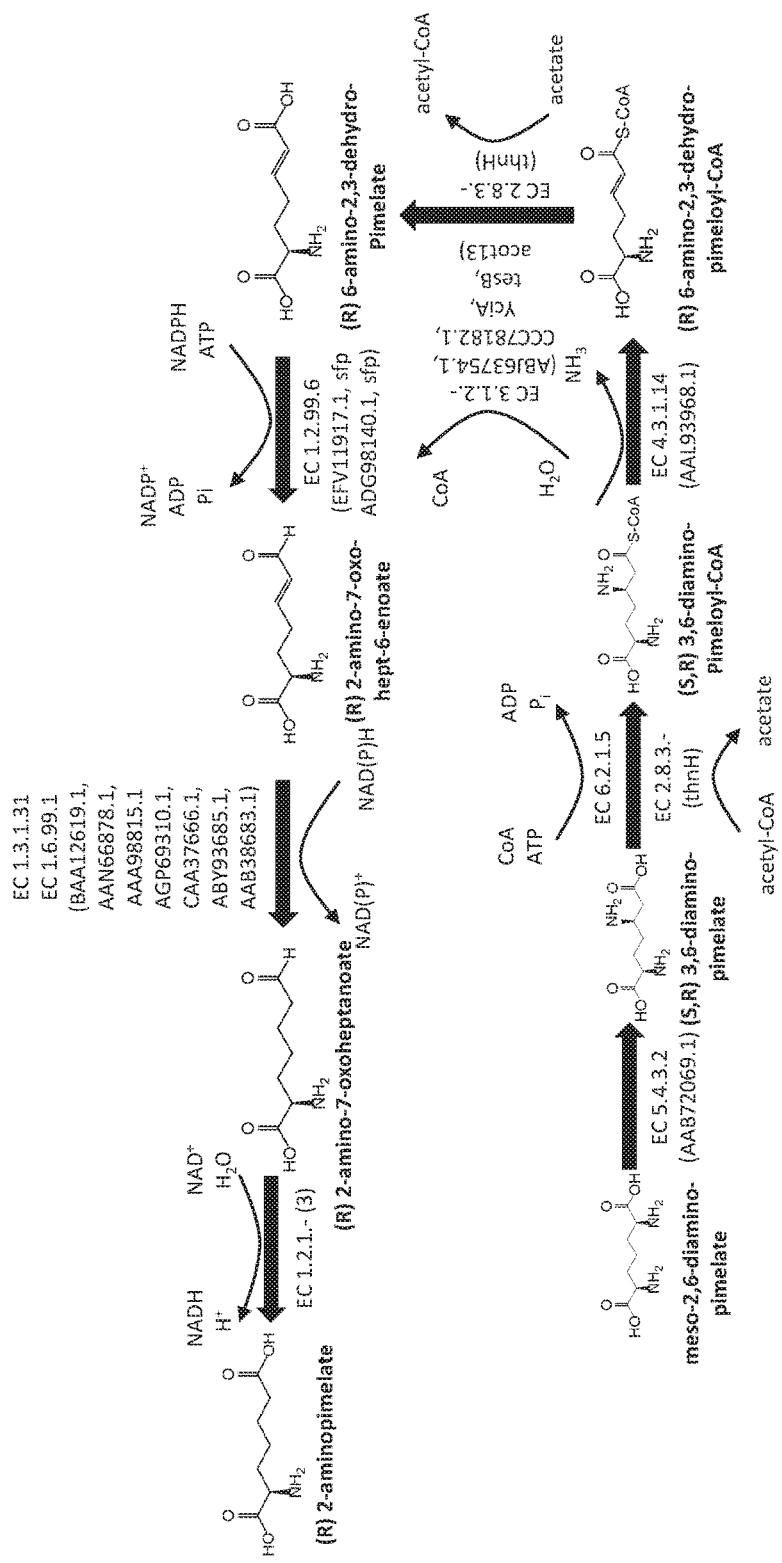
FIG. 2 is a schematic of an exemplary biochemical pathway leading to the biosynthesis of (R) 2-aminopimelate using meso-2,6-diaminopimelate as a central metabolite.
Figure 3:
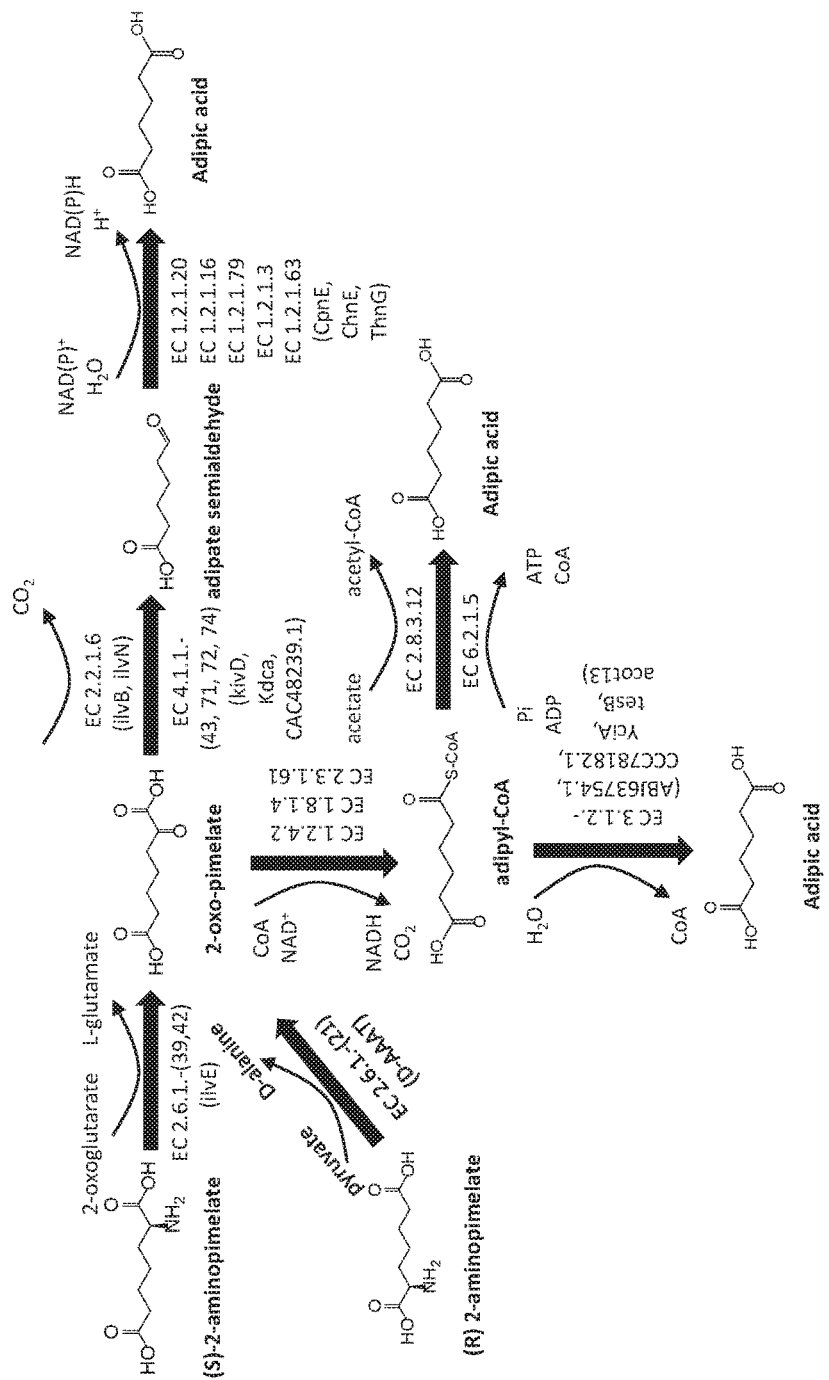
FIG. 3 is a schematic of exemplary biochemical pathways leading to adipic acid using either (S) 2-aminopimelate or (R) 2-aminopimelate as a central precursor.
Figure 4:
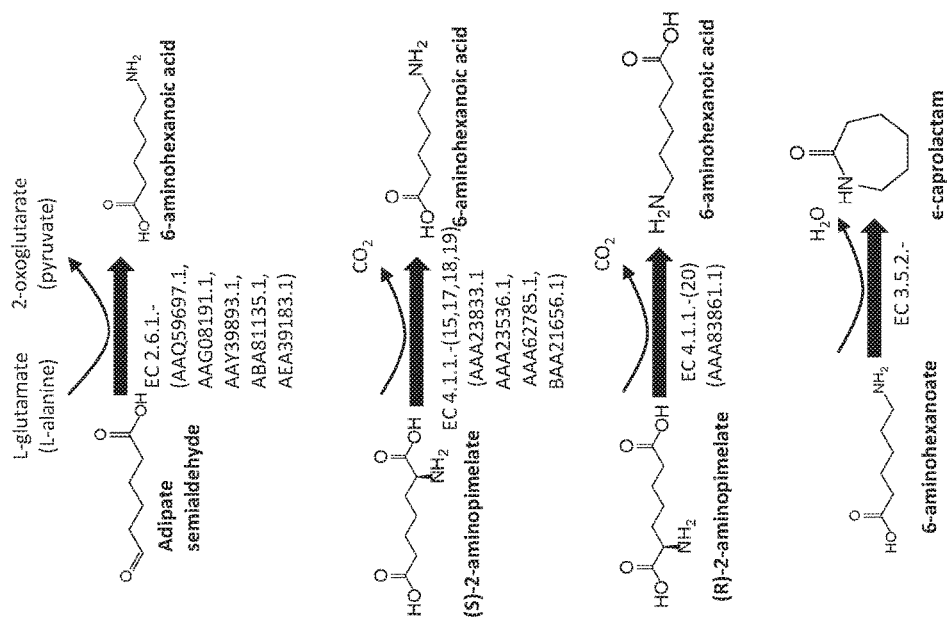
FIG. 4 is a schematic of exemplary biochemical pathways leading to 6-aminohexanoic acid using either (S) 2-aminopimelate, (R) 2-aminopimelate or adipate semialdehyde as a central precursor.

Enzymes Generating the Terminal Carboxyl Groups in the Biosynthesis of C6 Building Blocks As depicted in FIG. 1, FIG. 2, and FIG. 3, a terminal carboxyl group can be enzymatically formed using an aldehyde dehydrogenase, a thioesterase, a CoA-transferase, or a CoA-ligase.

In some embodiments, the first terminal carboxyl group leading to the synthesis of adipic acid is enzymatically formed by an aldehyde dehydrogenase classified, for example, under EC 1.2.1.3 (Guerrillot & Vandecasteele, Eur. J. Biochem., 1977, 81, 185-192). See, e.g., FIG. 3.

In some embodiments, the second terminal carboxyl group leading to the synthesis of a C6 building block is enzymatically formed by an acyl-CoA hydrolase or thioesterase classified under EC 3.1.2.-, such as the gene product of YciA, tesB, Acot13, SEQ ID NO: 1 or SEQ ID NO: 2 (see, for example, Cantu et al., Protein Science, 2010, 19, 1281-1295; Zhuang et al., Biochemistry, 2008, 47(9), 2789-2796; or Naggert et al., Journal of Biological Chemistry, 1991, 266(17), 11044-11050, Jing et al., BMC Biochemistry, 2011, 12, 44). See, e.g., FIG. 3.

In some embodiments, the second terminal carboxyl group leading to the synthesis of a C6 building block is enzymatically formed by a CoA-transferase such as a glutaconate CoA-transferase classified, for example, under EC 2.8.3.12. See, e.g., FIG. 3.

In some embodiments, the second terminal carboxyl group leading to the synthesis of a C6 building block is enzymatically formed by a reversible CoA-ligase such as succinate CoA-ligase classified under EC 6.2.1.5. See, e.g., FIG. 3.

In some embodiments, the second terminal carboxyl group leading to the synthesis of adipic acid is enzymatically formed by an aldehyde dehydrogenase classified, for example, under EC 1.2.1.63, such as the gene product of ChnE (Iwaki et al., Appl. Environ. Microbiol., 1999, 65(11), 5158-5162). See, e.g., FIG. 3.

Figure 5:
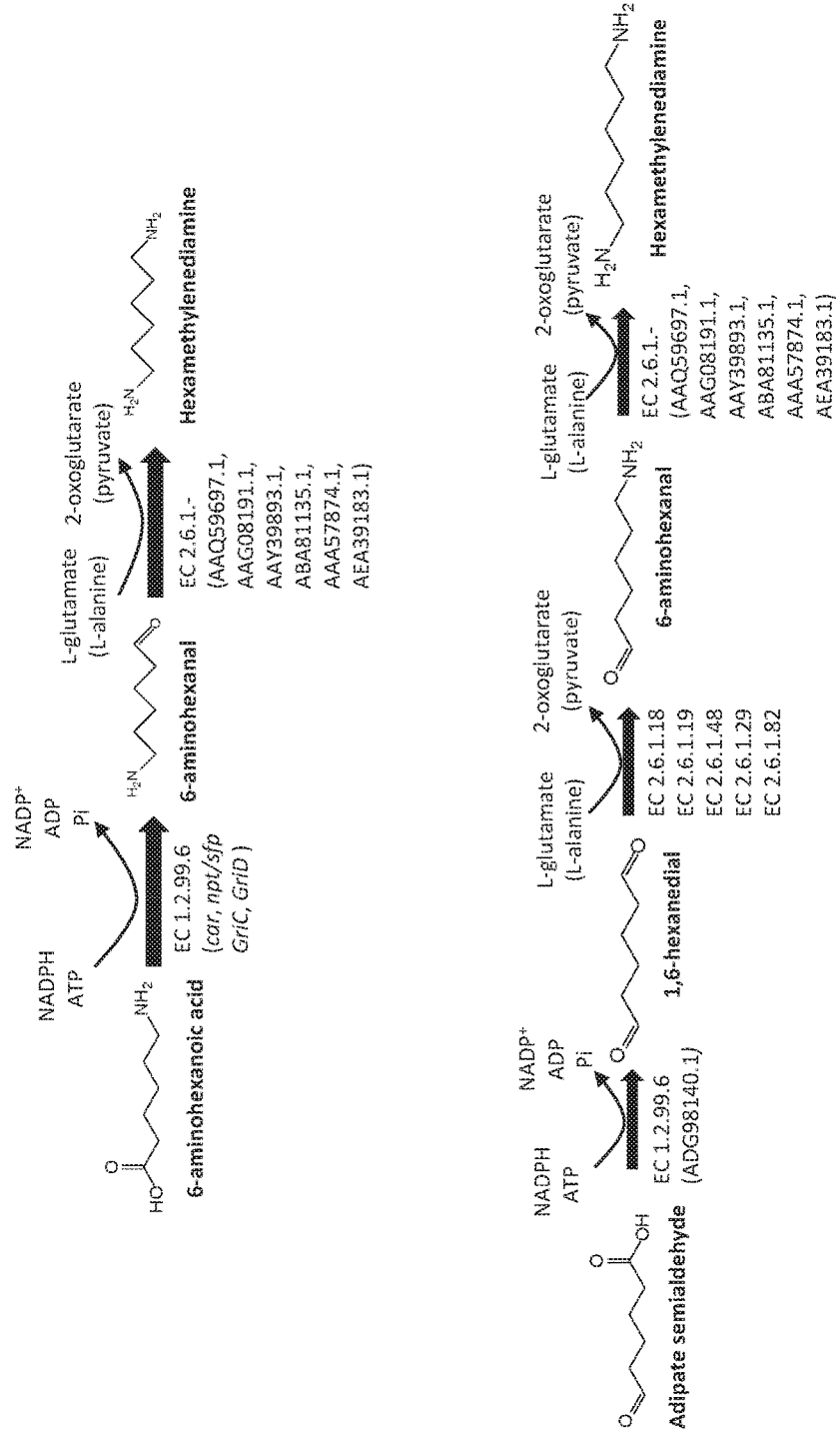
FIG. 5 is a schematic of exemplary biochemical pathways leading to hexamethylenediamine using 6-aminohexanoic acid or adipate semialdehyde as a central precursor.
Figure 6:
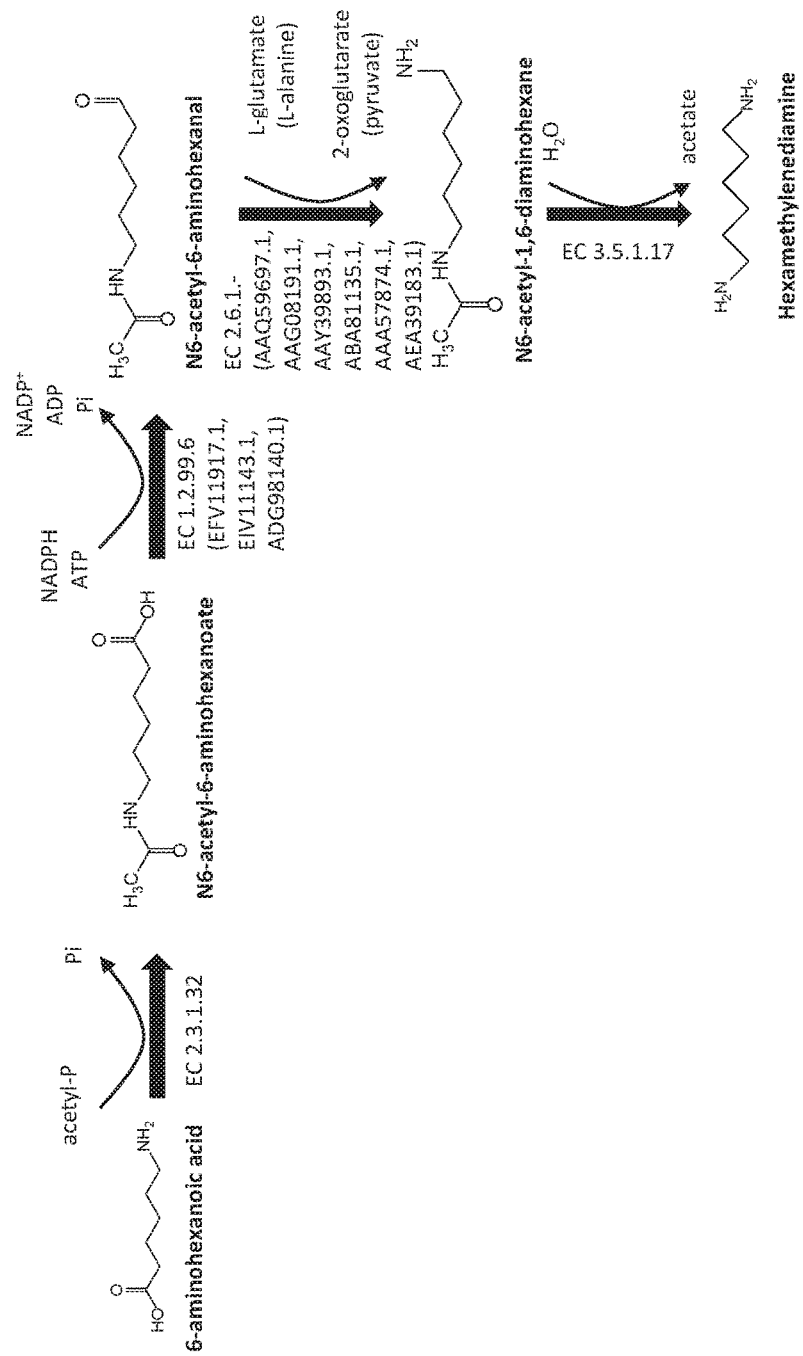
FIG. 6 is a schematic of an exemplary biochemical pathway leading to hexamethylenediamine using 6-aminohexanoic acid as a central precursor.
Figure 7:
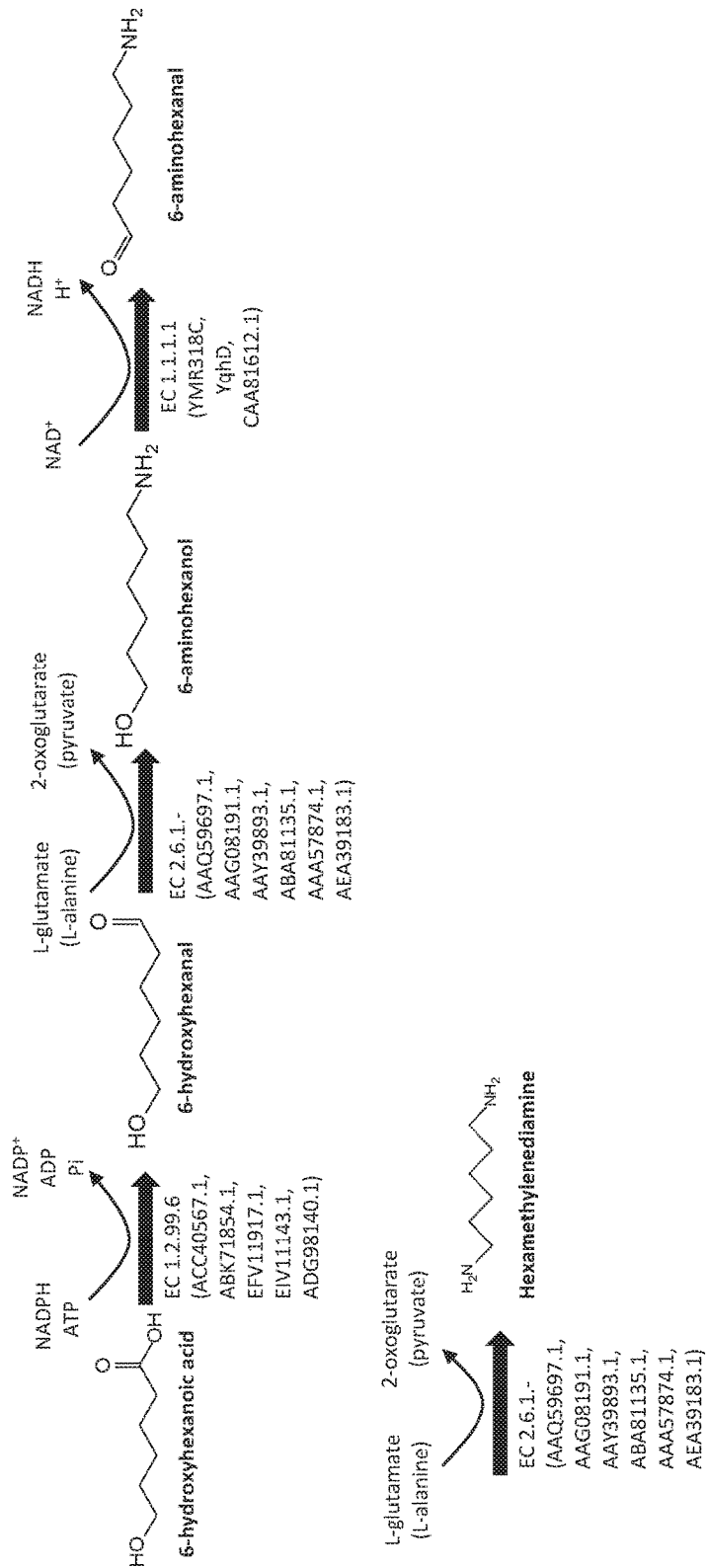
FIG. 7 is a schematic of an exemplary biochemical pathway leading to hexamethylenediamine using 6-hydroxyhexanoic acid as a central precursor.

Enzymes Generating the Terminal Amine Groups in the Biosynthesis of C6 Building Blocks As depicted in FIG. 5, FIG. 6, and FIG. 7 a terminal amine group can be enzymatically formed using a ω-transaminase.

In some embodiments, a terminal amine group is enzymatically formed by a ω-transaminase classified, for example, under EC 2.6.1.-, e.g., EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1), *Pseudomonas aeruginosa* (Genbank Accession No. AAG08191.1), *Pseudomonas syringae* (Genbank Accession No. AAY39893.1), *Rhodobacter sphaeroides* (Genbank Accession No. ABA81135.1), *Vibrio fluvialis* (Genbank Accession No. AEA39183.1), *Streptomyces griseus*, or *Clostridium viride*. See, FIG. 3.

An additional ω-transaminase that can be used in the methods and hosts described herein is from *Escherichia coli* (Genbank Accession No. AAA57874.1). Some of the ω-transaminases classified, for example, under EC 2.6.1.29 or EC 2.6.1.82 are diamine ω-transaminases.

In some embodiments, the first terminal amine group leading to the synthesis of 6-aminohexanoic acid is enzymatically formed by a ω-transaminase classified under EC 2.6.1.18, such as that obtained from *Vibrio fluvialis* or *Chromobacterium violaceum*, EC 2.6.1.19, such as that obtained from *Streptomyces griseus*, or EC 2.6.1.48, such as that obtained from *Clostridium viride*.

The reversible ω-transaminase from *Chromobacterium violaceum* has demonstrated analogous activity accepting 6-aminohexanoic acid as amino donor, thus forming the first terminal amine group in adipate seminaldehyde (Kaulmann et al., Enzyme and Microbial Technology, 2007, 41, 628-637).

The reversible 4-aminobubyrate: 2-oxoglutarate transaminase from *Streptomyces griseus* has demonstrated analogous activity for the conversion of 6-aminohexanoic acid to adipate semialdehyde (Yonaha et al., Eur. J. Biochem., 1985, 146, 101-106).

The reversible 5-aminovalerate transaminase from *Clostridium viride* has demonstrated analogous activity for the conversion of 6-aminohexanoic acid to adipate semialdehyde (Barker et al., The Journal of Biological Chemistry, 1987, 262(19), 8994-9003).

In some embodiments, the second terminal amine group leading to the synthesis of hexamethylenediamine is enzymatically formed by a transaminase classified under EC 2.6.1.29 or classified under EC 2.6.1.82, such as the gene product of YgjG.

The gene product of ygjG accepts a broad range of diamine carbon chain length substrates, such as putrescine, cadaverine and spermidine (Samsonova et al., BMC Microbiology, 2003, 3:2).

The diamine transaminase from *E. coli* strain B has demonstrated activity for 1,6 diaminohexane (Kim, The Journal of Chemistry, 1963, 239(3), 783-786)

Figure 8:
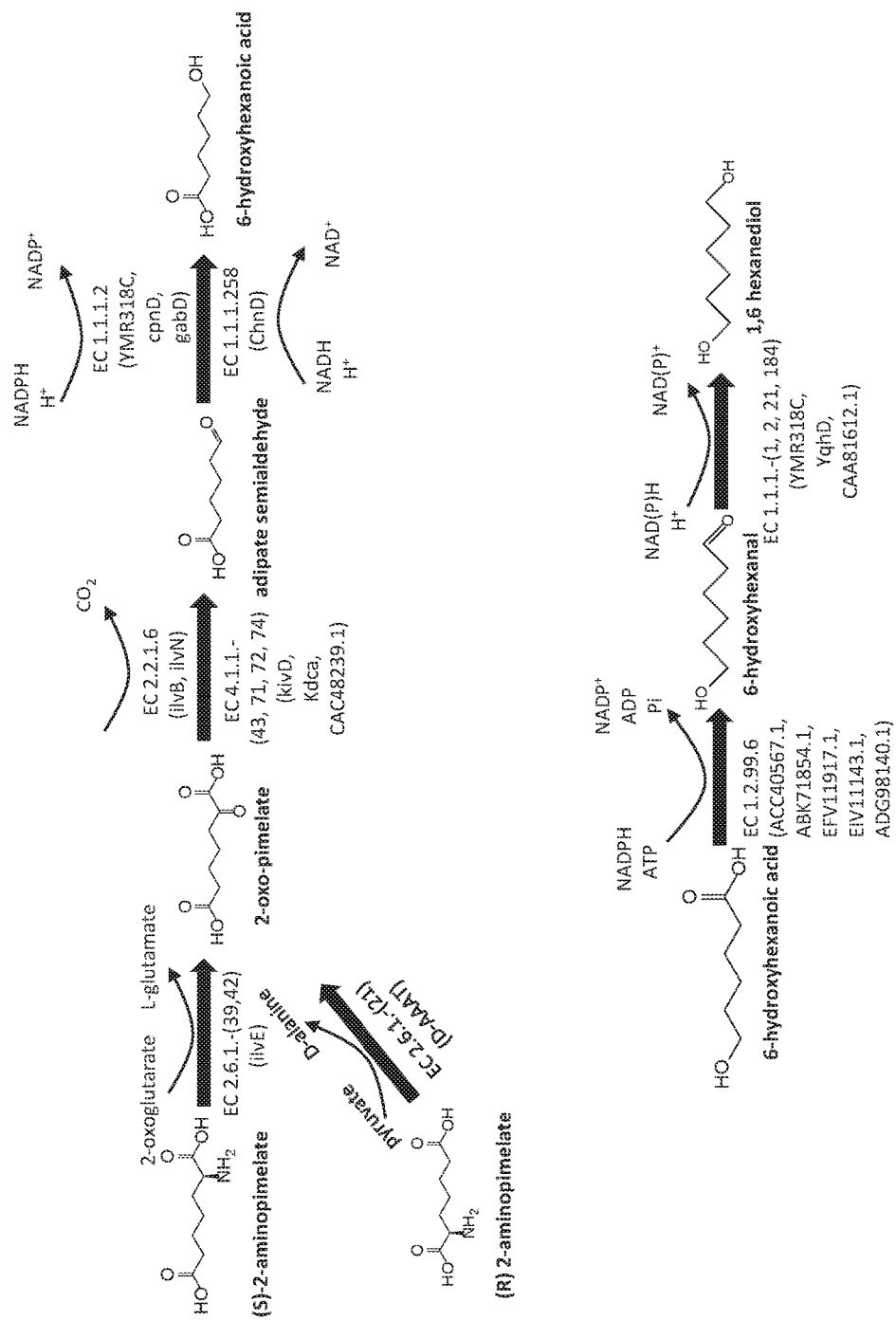
FIG. 8 is a schematic of (i) exemplary biochemical pathways leading to 6-hydroxyhexanoic acid using either (S) 2-aminopimelate or (R) 2-aminopimelate as a central precursor and (ii) exemplary biochemical pathways leading to 1,6-hexanediol using 6-hydroxyhexanoic acid as a central precursor.

Enzymes Generating the Terminal Hydroxyl Groups in the Biosynthesis of C6 Building Blocks As depicted in FIG. 8, the terminal hydroxyl group can be enzymatically forming using an alcohol dehydrogenase.

In some embodiments, the first terminal hydroxyl group leading to the synthesis of 1,6 hexanediol is enzymatically formed by an alcohol dehydrogenase classified, for example, under EC 1.1.1.2 such as the gene product of YMR318C or an alcohol dehydrogenase classified, for example, under EC 1.1.1.258 such as the gene product of ChnD.

In some embodiments, the second terminal hydroxyl group leading to the synthesis of 1,6 hexanediol is enzymatically formed by an alcohol dehydrogenase classified under EC 1.1.1.- (e.g., 1, 2, 21, or 184).

Biochemical Pathways

Pathways to (S) 2-aminopimate and (R) 2-aminopimelate as Precursor Leading to Central Precursors to C6 Building Blocks In some embodiments, (S) 2-aminopimelate is synthesized from the central metabolite, meso-2,6-diaminopimelate, by conversion of meso-2,6-diaminopimelate to (S)-2-amino-6-oxopimelate by a diaminopimelate dehydrogenase (classified for example under EC 1.4.1.16); followed by conversion of (S)-2-amino-6-oxopimelate to (S,R) 2-amino-6-hydroxypimelate by a (R)-2-hydroxyisocaproate dehydrogenase (classified for example under EC 1.1.1.337) such as the gene product of LdhA or a (R) 2-hydroxyglutarate dehydrogenase such as the gene product of HgdH; followed by conversion of (S,R) 2-amino-6-hydroxypimelate to (R,S) 2-hydroxy-6-aminopimeloyl-CoA by a glutaconate CoA-transferase (classified, for example, under EC 2.8.3.12) such as the gene product of GctAB; followed by conversion of (R,S) 2-hydroxy-6-aminopimeloyl-CoA to (S) 6-amino-2,3-dehydropimeloyl-CoA by a 2-hydroxyisocaproyl-CoA dehydratase such as SEQ ID NO: 28 activated SEQ ID NO: 27 or (R)-2-hydroxyglutryl-CoA dehydratase such as SEQ ID NO: 25 activated by SEQ ID NO: 24; followed by conversion of (S) 6-amino-2,3-dehydropimeloyl-CoA to (S) 6-amino-2,3-dehydropimelate by a glutaconate CoA-transferase (classified, for example, under EC 2.8.3.12); followed by conversion to (S) 2-amino-7-oxohept-6-enoate by a carboxylate reductase classified, for example, under EC 1.2.99.6) such as the gene product of car & npt, GriC & GriD or a carboxylate reductase such as SEQ ID NO: 5, 7; followed by conversion to (S) 2-amino-7-oxoheptanoate by an enoate reductase (classified, for example, under EC 1.3.1.31 or EC 1.6.99.1) such as the gene product of SEQ ID NO: 16-22; followed by conversion to (S) 2-aminopimelate by an aldehyde dehydrogenase (classified, for example, under EC 1.2.1.3). See FIG. 1.

In some embodiments, (S)-2-amino-6-oxopimelate in FIG. 1 is substituted with the central precursor N-Acetyl-L-2-amino-6-oxopimelate.

In some embodiments, (S)-2-amino-6-oxopimelate in FIG. 1 is substituted with the central precursor N-Succinyl-2-L-amino-6-oxoheptanedioate.

In some embodiments, (R) 2-aminopimelate is synthesized from the central metabolite, meso-2,6-diaminopimelate, by conversion of meso-2,6-diaminopimelate to (S,R) 3,6 diaminopimelate by a lysine 2,3-aminomutase (classified, for example, under EC 5.4.3.2) such SEQ ID NO: 26; followed by conversion of (S,R) 3,6 diaminopimelate to (S,R) 3,6 diaminopimeloyl-CoA by a succinate-CoA ligase (classified, for example, under EC 6.2.1.5); followed by conversion of (S,R) 3,6 diaminopimeloyl-CoA to (R) 6-amino-2,3-dehydropimeloyl-CoA by a 3-aminobutyryl-CoA ammonia lyase (classified, for example, under EC 4.3.1.14) such as SEQ ID NO: 23; followed by the conversion of (R) 6-amino-2,3-dehydropimeloyl-CoA to (R) 6-amino-2,3-dehydropimelate by a thioesterase (classified, for example, under EC 3.1.2.-) such as SEQ ID NO: 1-2 or the gene product of YciA, tesB or acot13 or by a CoA-transferase (classified, for example, under EC 2.8.3.-) such as the gene product of thnH; followed by conversion to (R) 2-amino-7-oxohept-6-enoate by a carboxylate reductase (classified, for example, under EC 1.2.99.6) such as the gene product of car & npt, GriC & GriD or the carboxylate reductase SEQ ID NO: 5,7; followed by conversion to (R) 2-amino-7-oxoheptanoate by an enoate reductase (classified, for example, under EC 1.3.1.31) such as SEQ ID NO: 16-22; followed by conversion to (R) 2-aminopimelate by an aldehyde dehydrogenase (classified, for example, under EC 1.2.1.3). See FIG. 2.

Pathways Using (S) 2-aminopimelate or (R) 2-aminopimelate as Central Precursor to Adipic Acid In some embodiments, adipic acid is synthesized from the central precursor (S) 2-aminopimelate or (R) 2-aminopimelate by conversion of (S) 2-aminopimelate to 2-oxopimelate by an L-specific alpha-aminotransferase (classified under EC 2.6.1.- such as EC 2.6.1.39 or EC 2.6.1.42) such as the gene product of ilvE or by conversion of (R) 2-aminopimelate to 2-oxopimelate by a D-specific alpha-aminotransferase (classified under EC 2.6.1.- such as EC 2.6.1.21) such as the gene product of D-AAAT; followed by conversion of 2-oxopimelate to adipate semialdehyde by a branch-chain-2-oxoacid decarboxylase (classified, for example, under EC 4.1.1.- such as EC 4.1.1.43, EC 4.1.1.71, EC 4.1.1.72 or EC 4.1.1.74) such as SEQ ID NO: 34 or the gene product of kivD or kdca or an acetolactate synthase (classified, for example, under EC 2.2.1.6) such as the gene product of ilvB & ilvN; followed by conversion of adipate semialdehyde to adipic acid by an aldehyde dehydrogenase (classified, for example, under EC 1.2.1.- such as EC 1.2.1.3, EC 1.2.1.16, EC 1.2.1.20, EC 1.2.1.63, EC 1.2.1.79) such as the gene product of ChnE, CpnE or ThnG. See FIG. 3.

In some embodiments, 2-oxopimelate obtained as described above is converted to adipyl-CoA by a dehydrogenase complex (classified, for example, under EC 1.2.4.2, EC 1.8.1.4, and EC 2.3.1.61); followed by conversion to adipic acid by a thioesterase (classified, for example, under EC 3.1.2.-) such as SEQ ID NO: 1-2 or the gene product of YciA, tesB or acot13 or by a glutaconate CoA-transferase (classified under, for example, EC 2.8.3.12) or a reversible succinate CoA-ligase (classified, for example, under EC 6.2.1.5). See FIG. 3.

Pathway Using (R) 2-aminopimelate or (S) 2-aminopimelate as Central Precursor to 6-aminohexanoate and ε-caprolactam In some embodiments, 6-aminohexanoic acid is synthesized from the central precursor (S) 2-aminopimelate, by conversion of (S) 2-aminopimelate to 6-aminohexanoic acid by a decarboxylase (classified, for example, under EC 4.1.1.- such as EC 4.1.1.15, EC 4.1.1.17, EC 4.1.1.18 or EC 4.1.1.19) such as SEQ ID NO: 29-32. See FIG. 4.

In some embodiments, 6-aminohexanoic acid is synthesized from the central precursor (R) 2-aminopimelate by conversion of (R) 2-aminopimelate to 6-aminohexanoic acid by a decarboxylase (classified, for example, under EC 4.1.1.- such as EC 4.1.1.20) such as SEQ ID NO: 33. See FIG. 4.

In some embodiments, ε-caprolactam is synthesized from the central precursor hexanoic acid by conversion of 6-aminohexanoic acid to ε-caprolactam by a hydrolase (classified, for example, under EC 3.5.2.-). See FIG. 4.

In some embodiments, 6-aminohexanoic acid is synthesized from the central precursor (S) 2-aminopimelate or (R) 2-aminopimelate by conversion of (S) 2-aminopimelate to 2-oxopimelate by an L-specific alpha-aminotransferase (classified under EC 2.6.1.- such as EC 2.6.1.39 or EC 2.6.1.42) such as the gene product of ilvE or by conversion of (R) 2-aminopimelate to 2-oxopimelate by a D-specific alpha-aminotransferase (classified under EC 2.6.1.- such as EC 2.6.1.21) such as the gene product of D-AAAT; followed by conversion of 2-oxopimelate to adipate semialdehyde by a branch-chain-2-oxoacid decarboxylase (classified, for example, under EC 4.1.1.- such as EC 4.1.1.43, EC 4.1.1.71, EC 4.1.1.72 or EC 4.1.1.74) such as SEQ ID NO: 34 or the gene product of kivD or kdca or an acetolactate synthase (classified, for example, under EC 2.2.1.6) such as the gene product of ilvB & ilvN; followed by conversion of adipate semialdehyde to 6-aminohexanoic acid by an ω-transaminase (classified, for example, under EC 2.6.1.- such as EC 2.6.1.18, EC 2.6.1.19, or EC 2.6.1.48, EC 2.6.1.29, or EC 2.6.1.82) such as SEQ ID NO 8-13. See FIGS. 1, 2 and 4.

Pathway Using 6-aminohexanoic Acid as Central Precursor to Hexamethylenediamine

In some embodiments, hexamethylenediamine is synthesized from the central precursor, 6-aminohexanoic acid, by conversion of 6-aminohexanoic acid to 6-aminohexanal by a carboxylate reductase (classified under, for example, EC 1.2.99.6) such as the gene product of car alongside the gene product of npt or the gene product of GriC & GriD (Suzuki et al., J. Antibiot., 2007, 60(6), 380-387); followed by conversion of 6-aminohexanal to hexamethylenediamine by a ω-transaminase (classified, for example, under EC 2.6.1.18, EC 2.6.1.19, 2.6.1.48, EC 2.6.1.29, or EC 2.6.1.82) such as SEQ ID NO: 8-13. See FIG. 5.

The carboxylate reductase encoded by the gene product of car and enhancer npt has broad substrate specificity, including terminal difunctional C4 and C5 carboxylic acids (Venkitasubramanian et al., Enzyme and Microbial Technology, 2008, 42, 130-137).

In some embodiments, 6-aminohexanoic acid is synthesized from the central precursor (S) 2-aminopimelate or (R) 2-aminopimelate by conversion of (S) 2-aminopimelate to 2-oxopimelate by an L-specific alpha-aminotransferase (classified under EC 2.6.1.- such as EC 2.6.1.39 or EC 2.6.1.42) such as the gene product of ilvE or by conversion of (R) 2-aminopimelate to 2-oxopimelate by a D-specific alpha-aminotransferase (classified under EC 2.6.1.- such as EC 2.6.1.21) such as the gene product of D-AAAT; followed by conversion of 2-oxopimelate to adipate semialdehyde by a branch-chain-2-oxoacid decarboxylase (classified, for example, under EC 4.1.1.- such as EC 4.1.1.43, EC 4.1.1.71, EC 4.1.1.72 or EC 4.1.1.74) such as SEQ ID NO: 34 or the gene product of kivD or kdca or an acetolactate synthase (classified, for example, under EC 2.2.1.6) such as the gene product of ilvB & ilvN; followed by conversion of adipate semialdehyde to 1,6 hexanedial by a carboxylate reductase (classified, for example, under EC 1.2.99.6) such as SEQ ID NO: 7; followed by conversion of 1,6-hexanedial to 6-aminohexanal by an ω-transaminase (classified, for example, under EC 2.6.1.- such as EC 2.6.1.18, EC 2.6.1.19, or EC 2.6.1.48, EC 2.6.1.29, or EC 2.6.1.82); followed by conversion of 6-aminohexanal to hexamethylenediamine by a ω-transaminase (classified, for example, under EC 2.6.1.- such as EC 2.6.1.18, EC 2.6.1.19, or EC 2.6.1.48, EC 2.6.1.29, or EC 2.6.1.82) such as SEQ ID NO: 8-13. See FIGS. 1, 2 and 5.

In some embodiments, hexamethylenediamine is synthesized from the central precursor, 6-aminohexanoic acid, by conversion of 6-aminohexanoic acid to N6-acetyl-6-aminohexanoic acid by a N-acetyltransferase classified, for example, under EC 2.3.1.32; followed by conversion of N6-acetyl-6-aminohexanoic acid to N6-acetyl-6-aminohexanal by a carboxylate reductase classified, for example, under EC 1.2.99.6 such as SEQ ID NO: 5-7 or the gene product of GriC & GriD (Suzuki et al., J. Antibiot., 2007, 60(6), 380-387); followed by conversion of N6-acetyl-6-aminohexanal to N6-acetyl-1,6-diaminohexane by a ω-transaminase (classified, for example, under EC 2.6.1.18, EC 2.6.1.19, EC 2.6.1.29, EC 2.6.1.48 or EC 2.6.1.82) such as SEQ ID NO: 8-13; followed by conversion of N6-acetyl-1,6-diaminohexane to hexamethylenediamine by a deacetylase (classified, for example, under EC 3.5.1.17). See FIG. 6.

Pathway Using 6-hydroxyhexanoic Acid as Central Precursor to Hexamethylenediamine In some embodiments, hexamethylenediamine is synthesized from the central precursor, 6-hydroxyhexanoic acid, by conversion of 6-hydroxyhexanoic acid to 6-hydroxyhexanal by a carboxylate reductase (classified, for example, under EC 1.2.99.6) such as SEQ ID NO: 3-7 or the gene product of car alongside the gene product of npt or the gene product of GriC & GriD (Suzuki et al., J. Antibiot., 2007, 60(6), 380-387); followed by conversion of 6-hydroxyhexanal to 1-amino-6-hydroxy-hexane by a transaminase (classified, for example, under EC 2.6.1.18, EC 2.6.1.19, EC 2.6.1.29, EC 2.6.1.48 or EC 2.6.1.82) such as SEQ ID NO: 8-13; followed by conversion of 1-amino-6-hydroxy-hexane to 6-aminohexanal by an alcohol dehydrogenase classified, for example, under EC 1.1.1.1 encoded by YMR318C, YqhD or the protein having GenBank Accession No. CAA81612.1 (from *Geobacillus stearothermophilus*); followed by conversion of 6-aminohexanal to hexamethylenediamine by a ω-transaminase (classified, for example, under EC 2.6.1.18, EC 2.6.1.19, 2.6.1.48, EC 2.6.1.29, or EC 2.6.1.82) such as SEQ ID NO: 8-13. See FIG. 7

Pathways Using (R) 2-aminopimelate or (S) 2-aminopimelate as Central Precursor to 1,6-hexanediol In some embodiments, adipic acid is synthesized from the central precursor (S) 2-aminopimelate or (R) 2-aminopimelate by conversion of (S) 2-aminopimelate to 2-oxopimelate by an L-specific alpha-aminotransferase (classified under EC 2.6.1.- such as EC 2.6.1.39 or EC 2.6.1.42) such as the gene product of ilvE or by conversion of (R) 2-aminopimelate to 2-oxopimelate by a D-specific alpha-aminotransferase (classified under EC 2.6.1.- such as EC 2.6.1.21) such as the gene product of D-AAAT; followed by conversion of 2-oxopimelate to adipate semialdehyde by a branch-chain-2-oxoacid decarboxylase (classified, for example, under EC 4.1.1.-such as EC 4.1.1.43, EC 4.1.1.71, EC 4.1.1.72 or EC 4.1.1.74) such as SEQ ID NO: 34 or the gene product of kivD or kdca or an acetolactate synthase (classified, for example, under EC 2.2.1.6) such as the gene product of ilvB & ilvN; followed by conversion of adipate semialdehyde to 6-hydroxyhexanoic acid by an alcohol dehydrogenase (classified, for example, under EC 1.1.1.- such as EC 1.1.1.2 or EC 1.1.1.258) such as encoded by YMR318C, ChnD, cpnD or gabD. See, FIG. 8.

In some embodiments, 1,6 hexanediol is synthesized from the central precursor 6-hydroxyhexanoic acid by conversion of 6-hydroxyhexanoic acid to 6-hydroxyhexanal by a carboxylate reductase (classified, for example, under EC 1.2.99.6) such as SEQ ID NO: 3-7; followed by conversion of 6-hydroxyhexanal to 1,6 hexanediol by an alcohol dehydrogenase (classified, for example, under EC 1.1.1.- such as EC 1.1.1.1, EC 1.1.1.2, EC 1.1.1.21, or EC 1.1.1.184) such as encoded by YMR318C, YqhD or CAA81612.1 (Liu et al., Microbiology, 2009, 155, 2078-2085).

Cultivation Strategy

In some embodiments, one or more C6 building blocks are biosynthesized in a recombinant host using anaerobic, aerobic or micro-aerobic cultivation conditions. In some embodiments, the cultivation strategy entails nutrient limitation such as nitrogen, phosphate or oxygen limitation.

In some embodiments in which (S) 2-aminopimelate is produced as a central precursor, a cultivation strategy entails either achieving an anaerobic or micro-aerobic cultivation condition.

In some embodiments in which (R) 2-aminopimelate is produced as a central precursor, a cultivation strategy entails either achieving an anaerobic, aerobic or micro-aerobic cultivation condition.

In some embodiments, a cell retention strategy using, for example, ceramic hollow fiber membranes is employed to achieve and maintain a high cell density during either fed-batch or continuous fermentation.

In some embodiments, the cultivation strategy entails culturing under conditions of nutrient limitation either via nitrogen, phosphate or oxygen limitation.

In some embodiments, the principal carbon source fed to the fermentation in the synthesis of one or more C6 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida, Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al, *J. Biotechnol.*, 2003, 104: 155-172; Wee et al., *Food Technol. Biotechnol.*, 2006, 44(2):163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Köpke et al., *Applied and Environmental Microbiology*, 2011, 77(15): 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1):152-156).

In some embodiments, the host microorganism is a prokaryote. For example, the prokaryote can be a bacterium from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C6 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C6 building blocks.

Metabolic Engineering

The present document provides methods involving less than all the steps described for all the above pathways. Such methods can involve, for example, one, two, three, four, five, six, seven, eight, nine, ten, or more of such steps. Where less than all the steps are included in such a method, the first step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined in section 4.5 are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined in section 4.5 are gene dosed (i.e., overexpressed by having a plurality of copies of the gene in the host organism), into the resulting genetically modified organism via episomal or chromosomal integration approaches.

In some embodiments, genome-scale system biology techniques such as Flux Balance Analysis are utilized to devise genome scale attenuation or knockout strategies for directing carbon flux to a C6 building block.

Attenuation strategies include, but are not limited to; the use of transposons, homologous recombination (double cross-over approach), mutagenesis, enzyme inhibitors and RNA interference (RNAi).

In some embodiments, fluxomic, metabolomic and transcriptomal data are utilized to inform or support genome-scale system biology techniques, thereby devising genome scale attenuation or knockout strategies in directing carbon flux to a C6 building block.

In some embodiments, the host microorganism's tolerance to high concentrations of a C6 building block is improved through continuous cultivation in a selective environment.

In some embodiments, the host microorganism's biochemical network is attenuated or augmented to (1) ensure the intracellular availability of oxaloacetate, (2) create an NADPH imbalance that may only be balanced via the formation of one or more C6 building blocks, (3) prevent degradation of central metabolites, central precursors leading to and including C6 building blocks and (4) ensure efficient efflux from the cell.

In some embodiments, the anaplerotic reactions from glycolysis leading into the Krebs cycle to augment oxaloacetate are overexpressed in the host.

In some embodiments where the host microorganism uses the lysine biosynthesis pathway via meso-2,6-diaminopimelate, the genes encoding the synthesis of lysine from 2-oxoglutarate via 2-oxoadipate are gene dosed into the host organisms.

In some embodiments where the host microorganism uses the lysine biosynthesis pathway via 2-oxoadipate, the genes encoding the synthesis of lysine via meso-2,6-diaminopimelate are gene dosed into the host organisms.

In some embodiments, where pathways require excess NADPH co-factor in the synthesis of a C6 building block, a puridine nucleotide transhydrogenase gene such as UdhA is overexpressed in the host organisms (Brigham et al., *Advanced Biofuels and Bioproducts,* 2012, Chapter 39, 1065-1090).

In some embodiments, where pathways require excess NADPH co-factor in the synthesis of a C6 building block, a glyceraldehyde-3P-dehydrogenase gene such as GapN is overexpressed in the host organisms (Brigham et al., 2012, supra).

In some embodiments, where pathways require excess NADPH co-factor in the synthesis of a C6 building block, a gene encoding a malic enzyme, such as maeA or maeB, is overexpressed in the host (Brigham et al., 2012, supra).

In some embodiments, where pathways require excess NADPH co-factor in the synthesis of a C6 building block, a gene encoding a glucose-6-phosphate dehydrogenase such as zwf is overexpressed in the host (Lim et al., *Journal of Bioscience and Bioengineering,* 2002, 93(6), 543-549).

In some embodiments, where pathways require excess NADPH co-factor in the synthesis of a C6 building block, a gene encoding a fructose 1,6 diphosphatase such as fbp is overexpressed in the host (Becker et al., *Journal of Biotechnology,* 2007, 132, 99-109).

In some embodiments, where pathways require excess NADPH co-factor in the synthesis of a C6 building block, an endogenous gene encoding a triose phosphate isomerase (EC 5.3.1.1) is attenuated.

In some embodiments, where pathways require excess NADPH co-factor in the synthesis of a C6 building block, an endogenous gene encoding a glucose dehydrogenase such as the gene product of gdh is overexpressed in the host (Satoh et al., Journal of Bioscience and Bioengineering, 2003, 95(4), 335-341).

In some embodiments, endogenous genes encoding enzymes facilitating the conversion of NADPH to NADH are attenuated, such as the NADH generation cycle that may be generated via inter-conversion of a glutamate dehydrogenase in EC 1.4.1.2 (NADH-specific) and EC 1.4.1.4 (NADPH-specific).

In some embodiments, an endogenous gene encoding a glutamate dehydrogenase (EC 1.4.1.3) that can utilize both NADH and NADPH as co-factors is attenuated.

In some embodiments using hosts that naturally accumulate polyhydroxyalkanoates, one or more endogenous genes encoding polymer synthase enzymes can be attenuated in the host strain.

In some embodiments, β-oxidation enzymes degrading central metabolites and central precursors leading to and including C6 building blocks are attenuated.

In some embodiments, enzymes activating C6 building blocks via Coenzyme A esterification such as CoA-ligases are attenuated.

In some embodiments, the efflux of a C6 building block across the cell membrane to the extracellular media is enhanced or amplified by genetically engineering structural modifications to the cell membrane or increasing any associated transporter activity for a C6 building block.

Producing C6 Building Blocks Using a Recombinant Host

Typically, one or more C6 building blocks can be produced by providing a host microorganism and culturing the provided microorganism with a culture medium containing a suitable carbon source as described above. In general, the culture media and/or culture conditions can be such that the microorganisms grow to an adequate density and produce a C6 building block efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C6 building block. Once produced, any method can be used to isolate C6 building blocks. For example, C6 building blocks can be recovered selectively from the fermentation broth via adsorption processes. In the case of adipic acid and 6-aminoheptanoic acid, the resulting eluate can be further concentrated via evaporation, crystallized via evaporative and/or cooling crystallization, and the crystals recovered via centrifugation. In the case of hexamethylenediamine and 1,6-hexanediol, distillation may be employed to achieve the desired product purity.

EXAMPLES

Example 1

Enzyme Activity of ω-transaminase Using Adipate Semialdehyde as Substrate and Forming 6-aminohexanoate A nucleotide sequence encoding a His-tag was added to the genes from *Chromobacterium violaceum, Pseudomonas aeruginosa, Pseudomonas syringae, Rhodobacter sphaeroides,* and *Vibrio Fluvialis* encoding the ω-transaminases of SEQ ID NOs: 8, 9, 10, 11 and 13, respectively (see FIG. 20E and FIG. 20F) such that N-terminal HIS tagged ω-transaminases could be produced. Each of the resulting modified genes was cloned into a pET21a expression vector under control of the T7 promoter and each expression vector was transformed into a BL21[DE3] *E. coli* host. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanoate to adipate semialdehyde) were performed in a buffer composed of a final concentration of 50 mM HEPES buffer (pH=7.5), 10 mM 6-aminohexanoate, 10 mM pyruvate and 100 µM pyridoxyl 5' phosphate. Each enzyme activity assay reaction was initiated by adding cell free extract of the ω-transaminase gene product or the empty vector control to the assay buffer containing the 6-aminohexanoate and incubated at 25° C. for 24 h, with shaking at 250 rpm. The formation of L-alanine from pyruvate was quantified via RP-HPLC.

Figure 14:
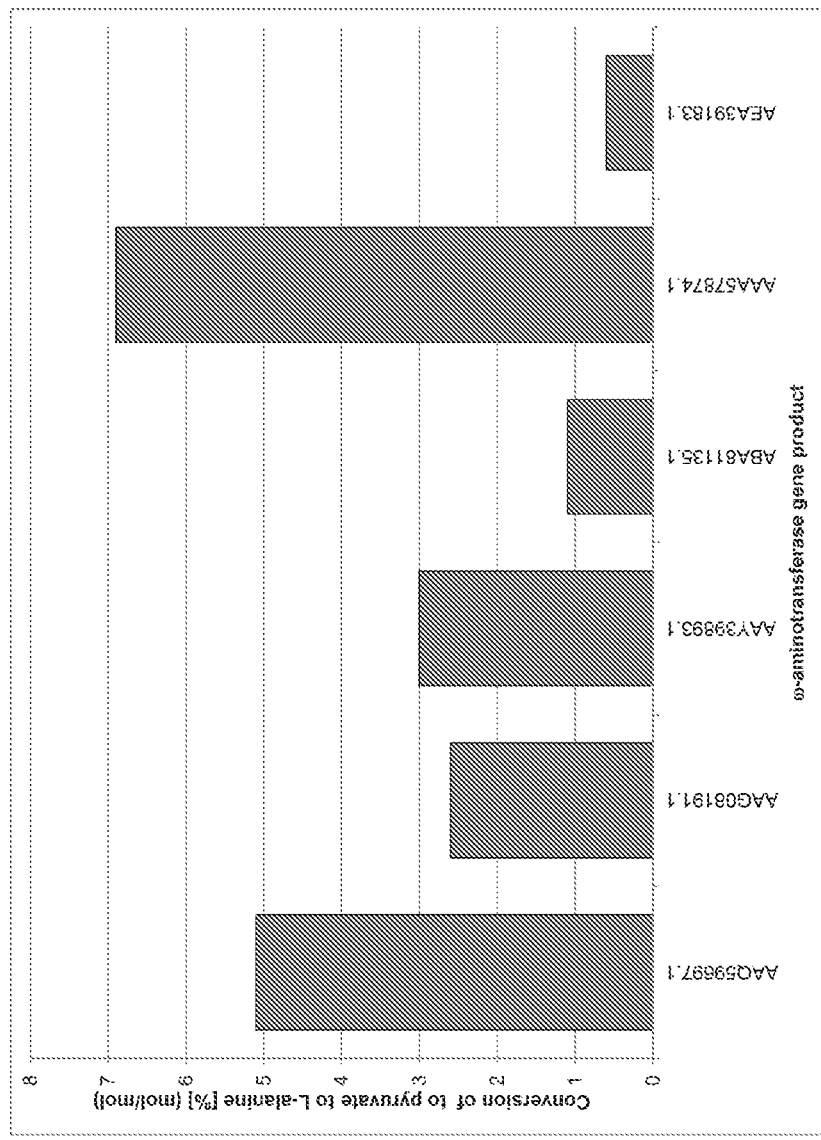
FIG. 14 is a bar graph summarizing the percent conversion after 4 hours of pyruvate to L-alanine (mol/mol) as a measure of the ω-transaminase activity of the enzyme only controls (no substrate).
Figure 15:
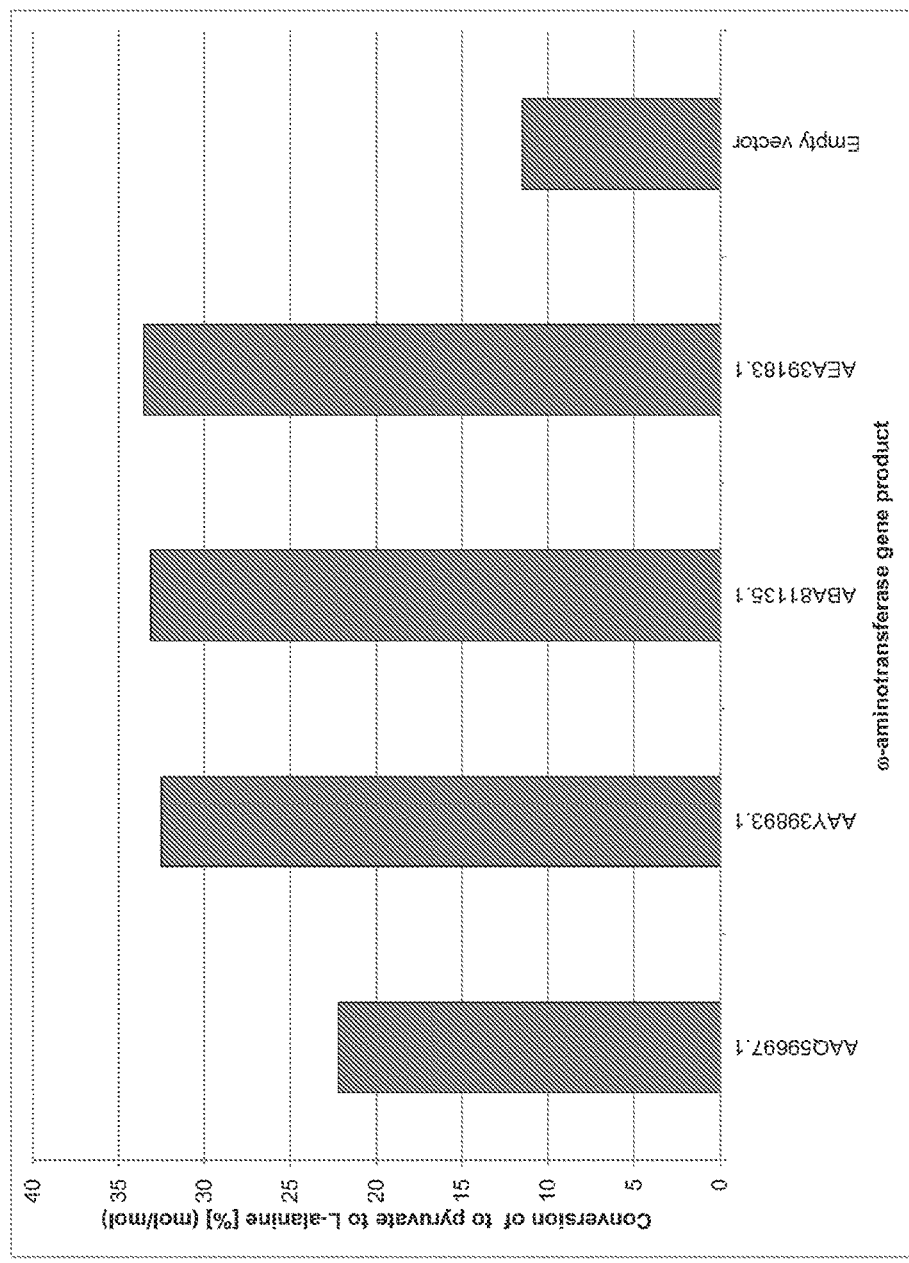
FIG. 15 is a bar graph of the percent conversion after 24 hours of pyruvate to L-alanine (mol/mol) as a measure of the ω-transaminase activity for converting 6-aminohexanoate to adipate semialdehyde relative to the empty vector control.

Each enzyme only control without 6-aminohexanoate demonstrated low base line conversion of pyruvate to L-alanine See FIG. 14. The gene product of SEQ ID NO 8, SEQ ID NO 10, SEQ ID NO 11 and SEQ ID NO 13 accepted 6-aminohexanote as substrate as confirmed against the empty vector control. See FIG. 15.

Enzyme activity in the forward direction (i.e., adipate semialdehyde to 6-aminohexanoate) was confirmed for the transaminases of SEQ ID NO 8, SEQ ID NO 9, SEQ ID NO 10, SEQ ID NO 11 and SEQ ID NO 13. Enzyme activity assays were performed in a buffer composed of a final concentration of 50 mM HEPES buffer (pH=7.5), 10 mM adipate semialdehyde, 10 mM L-alanine and 100 µM pyridoxyl 5' phosphate. Each enzyme activity assay reaction was initiated by adding a cell free extract of the ω-transaminase gene product or the empty vector control to the assay buffer containing the adipate semialdehyde and incubated at 25° C. for 4 h, with shaking at 250 rpm. The formation of pyruvate was quantified via RP-HPLC.

Figure 16:
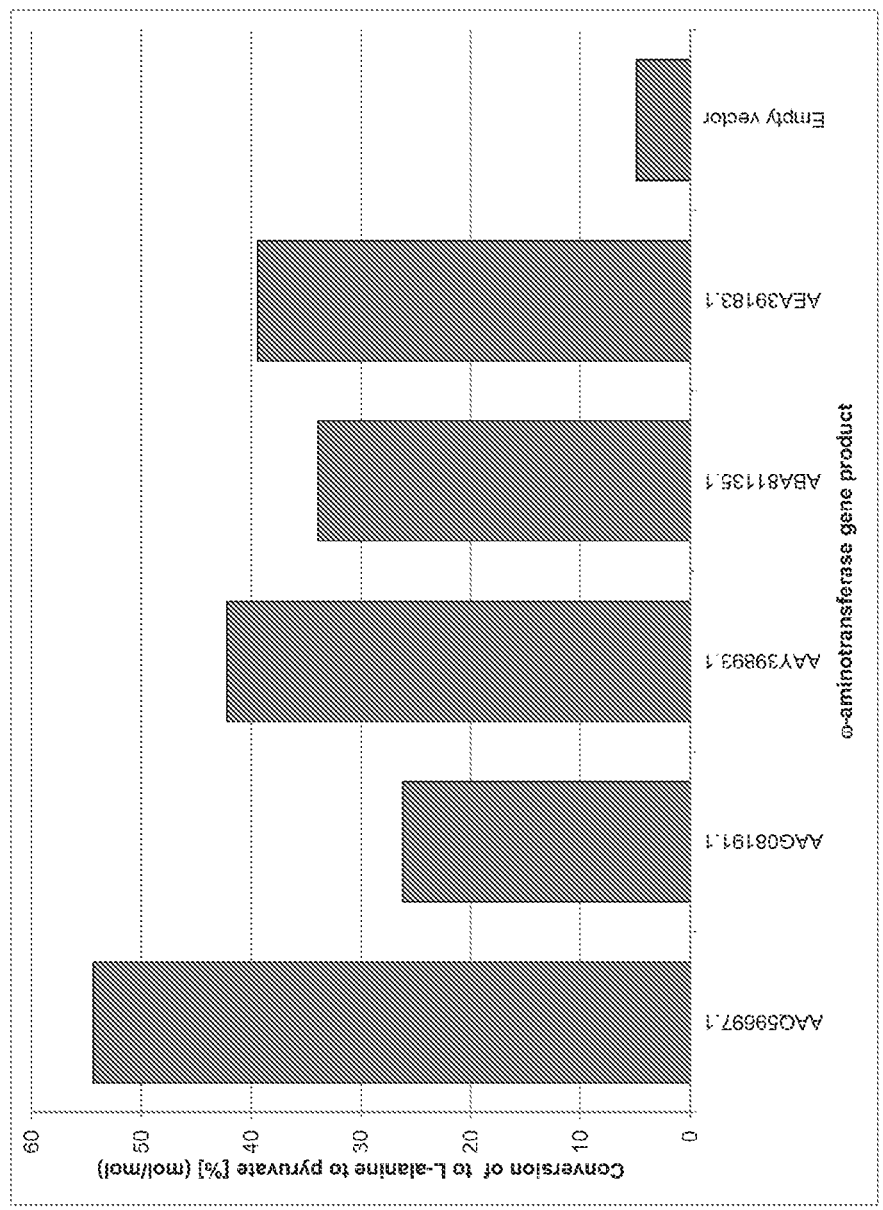
FIG. 16 is a bar graph of the percent conversion after 4 hours of L-alanine to pyruvate (mol/mol) as a measure of the ω-transaminase activity for converting adipate semialdehyde to 6-aminohexanoate relative to the empty vector control.

The gene product of SEQ ID NO 8, SEQ ID NO 9, SEQ ID NO 10, SEQ ID NO 11 and SEQ ID NO 13 accepted adipate semialdehyde as substrate as confirmed against the empty vector control. See FIG. 16. The reversibility of the ω-transaminase activity was confirmed, demonstrating that the ω-transaminases of SEQ ID NO 8, SEQ ID NO 9, SEQ ID NO 10, SEQ ID NO 11 and SEQ ID NO 13 accepted adipate semialdehyde as substrate and synthesized 6-aminohexanoate as a reaction product.

Example 2

Enzyme Activity of Carboxylate Reductase Using 6-hydroxyhexanoate as Substrate and Forming 6-hydroxyhexanal A nucleotide sequence encoding a His-tag was added to the genes from *Mycobacterium marinum, Mycobacterium smegmatis, Mycobacterium smegmatis, Segniliparus rugosus, Mycobacterium massiliense*, and *Segniliparus rotundus* that encode the carboxylate reductases of SEQ ID NOs: 3-7, respectively (see FIGS. 20A-20E) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter. Each expression vector was transformed into a BL21[DE3] *E. coli* host. Each resulting recombinant *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Figure 9:
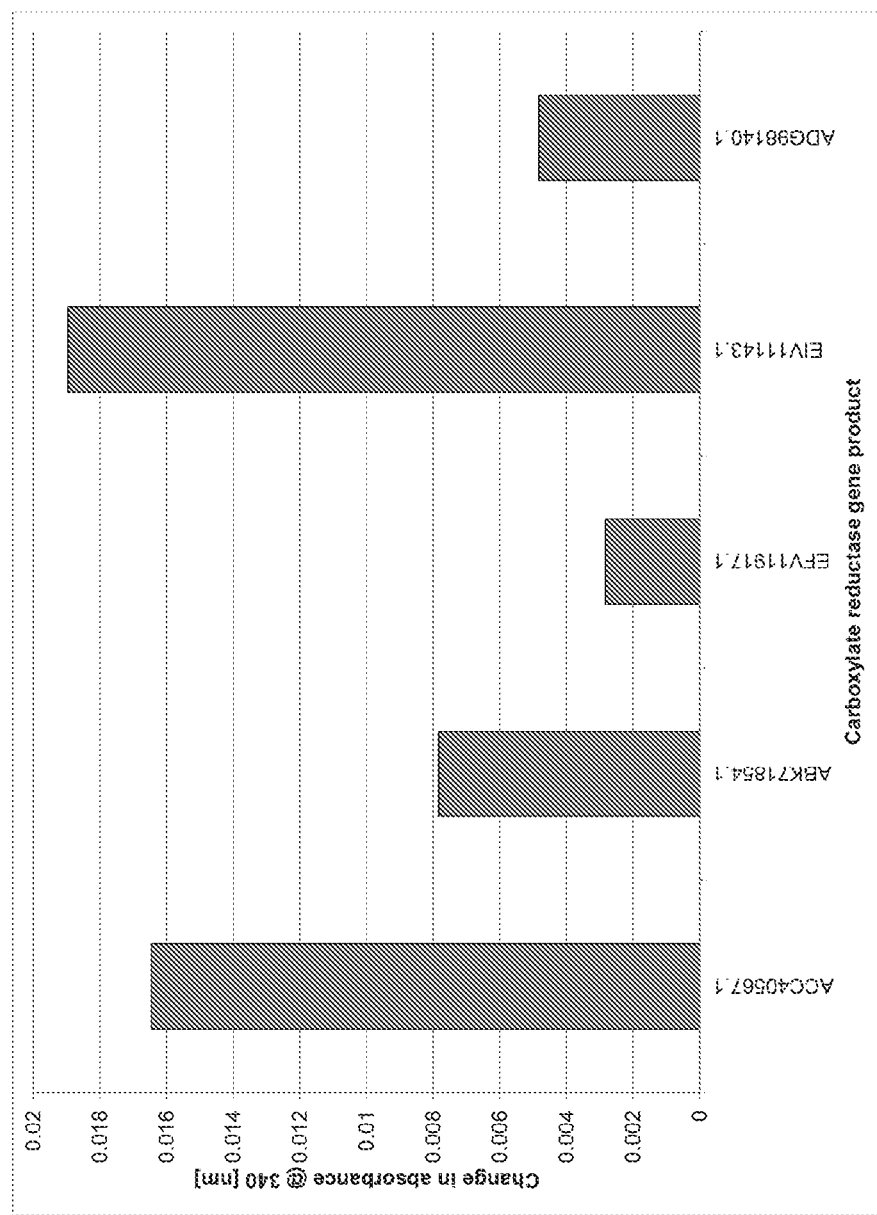
FIG. 9 is a bar graph summarizing the change in absorbance at 340 nm after 20 minutes, which is a measure of the consumption of NADPH and activity of carboxylate reductases relative to the enzyme only controls (no substrate).
Figure 10:
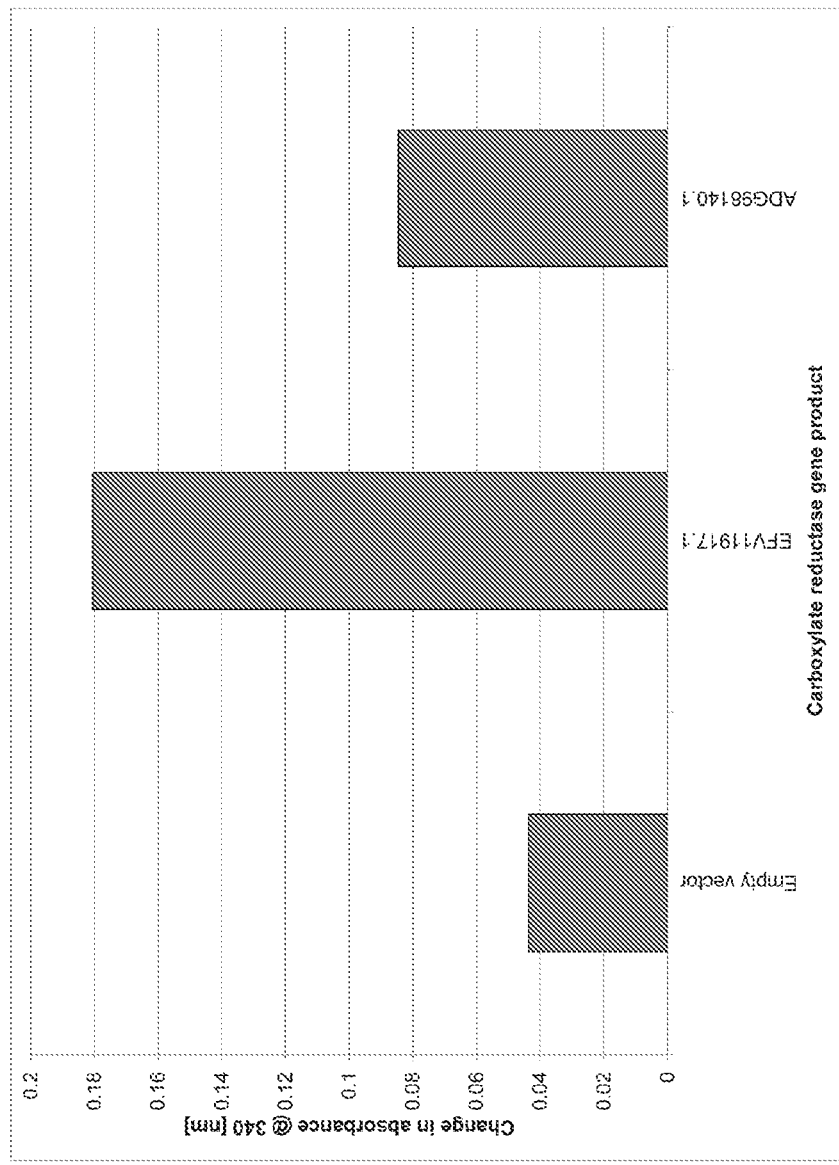
FIG. 10 is a bar graph of the change in absorbance at 340 nm after 20 minutes, which is a measure of the consumption of NADPH and the activity of carboxylate reductases for converting adipate to adipate semialdehyde relative to the empty vector control.

Enzyme activity (i.e., 6-hydroxyhexanoate to 6-hydroxyhexanal) assays were performed in triplicate in a buffer composed of a final concentration of 50 mM HEPES buffer (pH=7.5), 2 mM 6-hydroxyhexanal, 10 mM $MgCl_2$, 1 mM ATP, and 1 mM NADPH. Each enzyme activity assay reaction was initiated by adding purified carboxylate reductase and phosphopantetheine transferase or the empty vector control to the assay buffer containing the 6-hydroxyhexanoate and then incubated at room temperature for 20 min. The consumption of NADPH was monitored by absorbance at 340 nm. Each enzyme only control without 6-hydroxyhexanoate demonstrated low base line consumption of NADPH. See FIG. 9.

Figure 11:
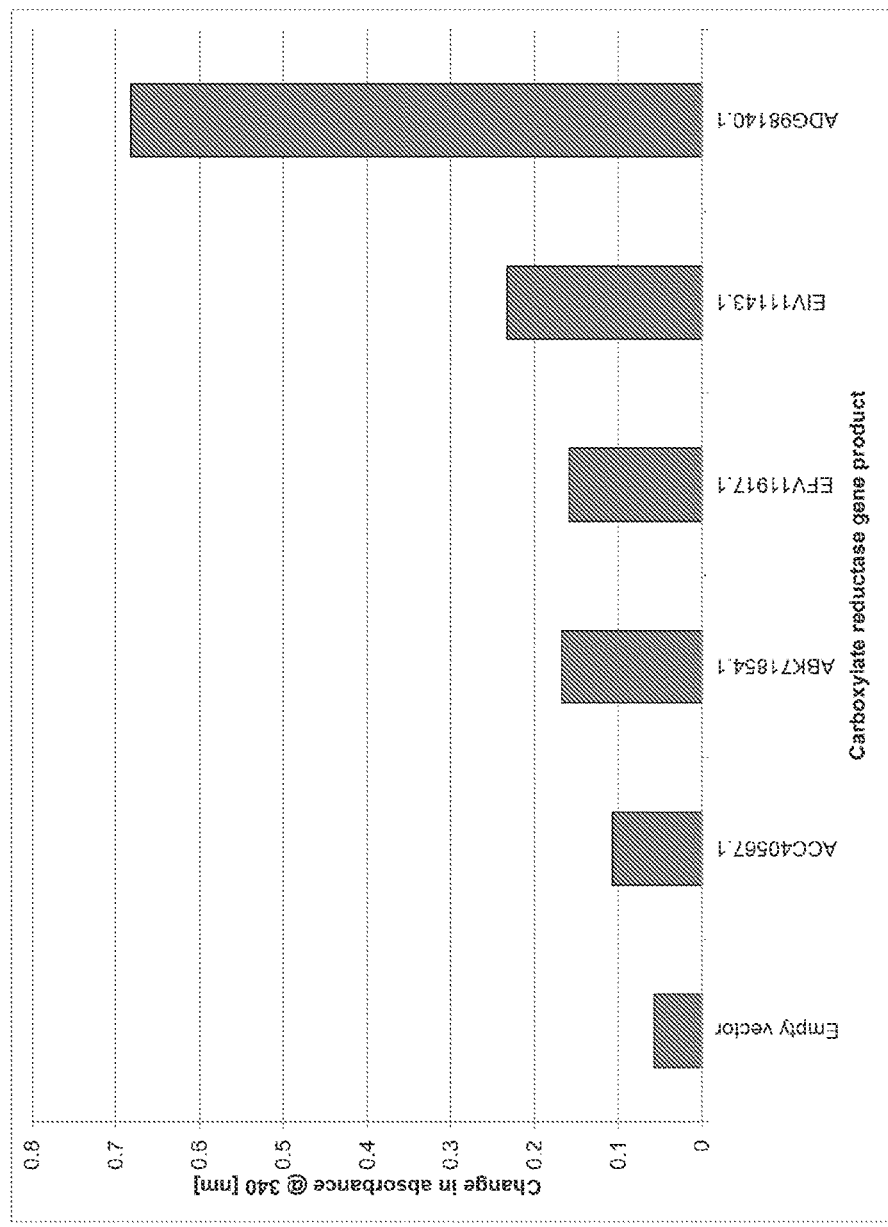
FIG. 11 is a bar graph of the change in absorbance at 340 nm after 20 minutes, which is a measure of the consumption of NADPH and the activity of carboxylate reductases for converting 6-hydroxyhexanoate to 6-hydroxhexanal relative to the empty vector control.

The gene products of SEQ ID NO 3-7, enhanced by the gene product of sfp, accepted 6-hydroxyhexanoate as substrate as confirmed against the empty vector control (see FIG. 11), and synthesized 6-hydroxyhexanal.

Example 3

Enzyme Activity of ω-transaminase for 6-aminohexanol, Forming 6-oxohexanol

A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* genes encoding the ωtransaminases of SEQ ID NOs: 8-13, respectively (see FIG. 20E and FIG. 20F) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanol to 6-oxohexanol) were performed in a buffer composed of a final concentration of 50 mM HEPES buffer (pH=7.5), 10 mM 6-aminohexanol, 10 mM pyruvate, and 100 µM pyridoxyl 5' phosphate. Each enzyme activity assay reaction was initiated by adding cell free extract of the ω-transaminase gene product or the empty vector control to the assay buffer containing the 6-aminohexanol and then incubated at 25° C. for 4 h, with shaking at 250 rpm. The formation of L-alanine was quantified via RP-HPLC.

Each enzyme only control without 6-aminohexanol had low base line conversion of pyruvate to L-alanine See FIG. 14.

Figure 19:
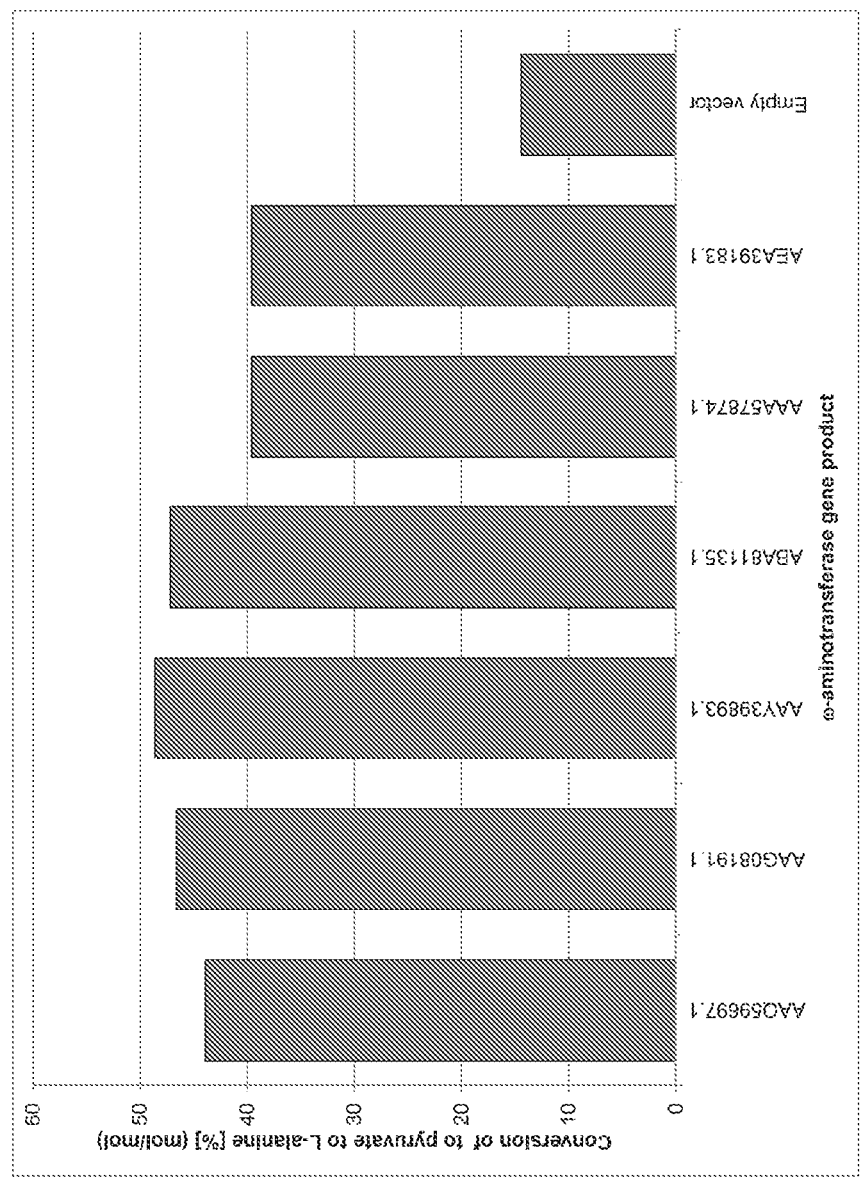
FIG. 19 is a bar graph of the percent conversion after 4 hours of pyruvate to L-alanine (mol/mol) as a measure of the ω-transaminase activity for converting 6-aminohexanol to 6-oxohexanol relative to the empty vector control.

The gene products of SEQ ID NO 8-13 accepted 6-aminohexanol as substrate as confirmed against the empty vector control (see FIG. 19) and synthesized 6-oxohexanol as reaction product. Given the reversibility of the ω-transaminase activity (see Example 1), it can be concluded that the gene products of SEQ ID 8-13 accept 6-aminohexanol as substrate and form 6-oxohexanol.

Example 4

Enzyme Activity of ω-transaminase Using Hexamethylenediamine as Substrate and Forming 6-aminohexanal A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* genes encoding the ω-transaminases of SEQ ID NOs: 8-13, respectively (see FIG. 20E and 20F) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., hexamethylenediamine to 6-aminohexanal) were performed in a buffer composed of a final concentration of 50 mM HEPES buffer (pH=7.5), 10 mM hexamethylenediamine, 10 mM pyruvate, and 100 μM pyridoxyl 5' phosphate. Each enzyme activity assay reaction was initiated by adding cell free extract of the ω-transaminase gene product or the empty vector control to the assay buffer containing the hexamethylenediamine and then incubated at 25° C. for 4 h, with shaking at 250 rpm. The formation of L-alanine was quantified via RP-HPLC.

Each enzyme only control without hexamethylenediamine had low base line conversion of pyruvate to L-alanine. See FIG. 14.

Figure 17:
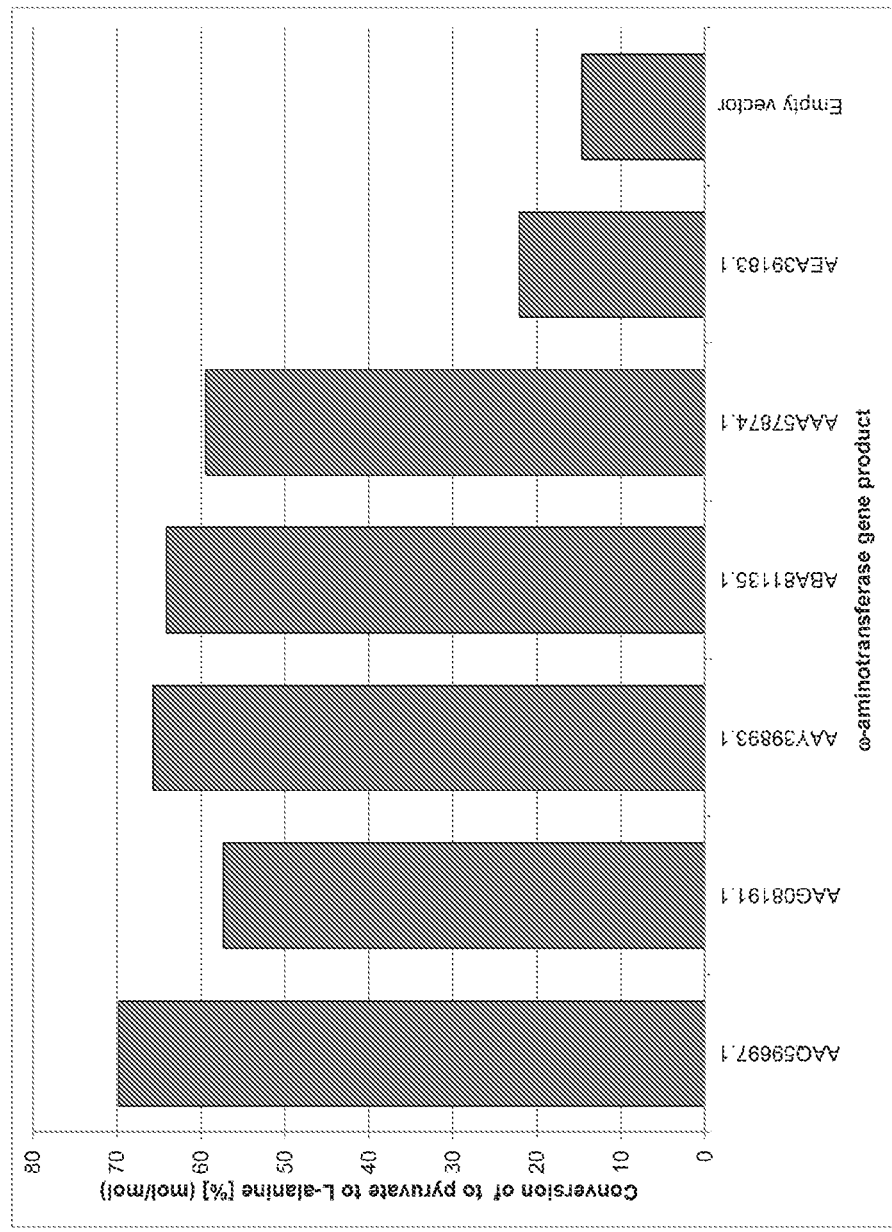
FIG. 17 is a bar graph of the percent conversion after 4 hours of pyruvate to L-alanine (mol/mol) as a measure of the ω-transaminase activity for converting hexamethylenediamine to 6-aminohexanal relative to the empty vector control.

The gene products of SEQ ID NO 8-13 accepted hexamethylenediamine as substrate as confirmed against the empty vector control (see FIG. 17) and synthesized 6-aminohexanal as reaction product. Given the reversibility of the ω-transaminase activity (see Example 1), it can be concluded that the gene products of SEQ ID NOs: 8-13 accept 6-aminohexanal as substrate and form hexamethylenediamine.

Example 5

Enzyme Activity of Carboxylate Reductase for N6-acetyl-6-aminohexanoate, Forming N6-acetyl-6-aminohexanal The activity of each of the N-terminal His-tagged carboxylate reductases of SEQ ID NOs: 5-7 (see Example 2, and FIGS. 20C-20E) for converting N6-acetyl-6-aminohexanoate to N6-acetyl-6-aminohexanal was assayed in triplicate in a buffer composed of a final concentration of 50 mM HEPES buffer (pH=7.5), 2 mM N6-acetyl-6-aminohexanoate, 10 mM MgCl$_2$, 1 mM ATP, and 1 mM NADPH. The assays were initiated by adding purified carboxylate reductase and phosphopantetheine transferase or the empty vector control to the assay buffer containing the N6-acetyl-6-aminohexanoate then incubated at room temperature for 20 min. The consumption of NADPH was monitored by absorbance at 340 nm. Each enzyme only control without N6-acetyl-6-aminohexanoate demonstrated low base line consumption of NADPH. See FIG. 9.

Figure 12:
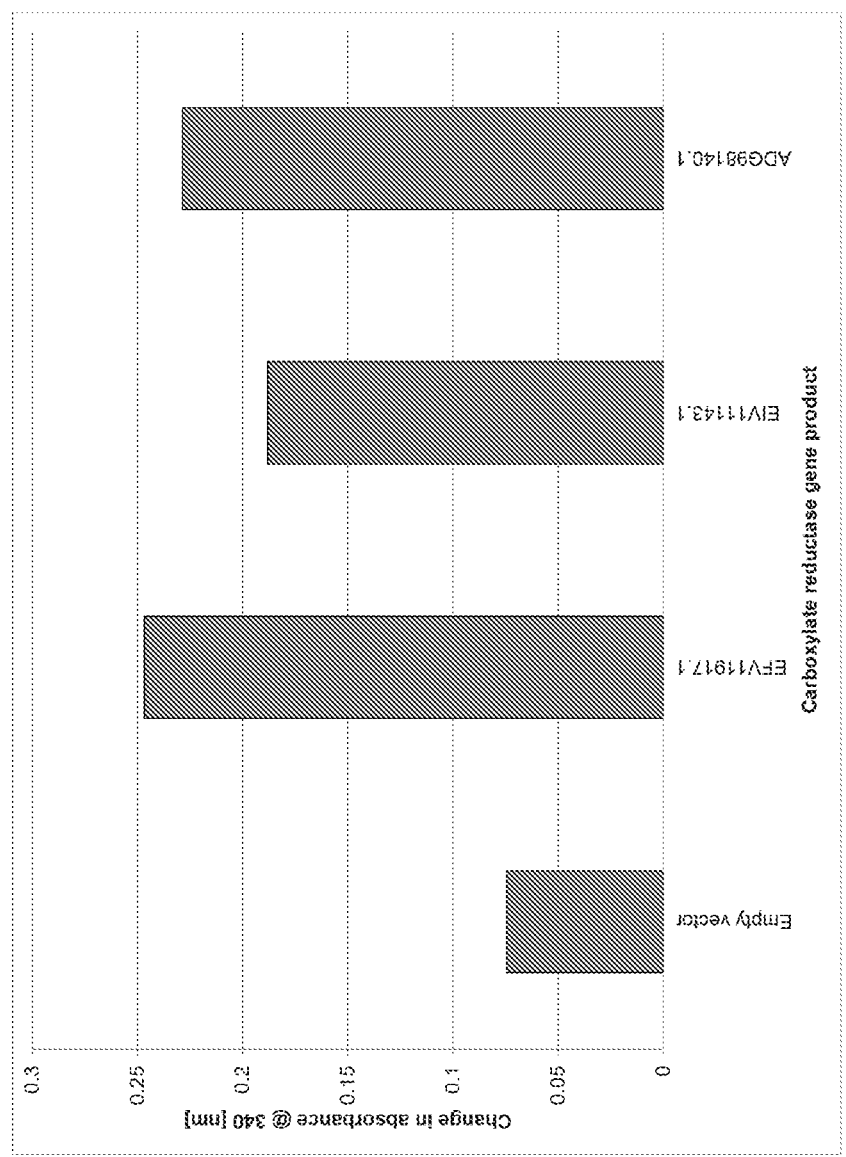
FIG. 12 is a bar graph of the change in absorbance at 340 nm after 20 minutes, which is a measure of the consumption of NADPH and the activity of carboxylate reductases for converting N6-acetyl-6-aminohexanoate to N6-acetyl-6-aminohexanal relative to the empty vector control.

The gene products of SEQ ID NO 5-7, enhanced by the gene product of sfp, accepted N6-acetyl-6-aminohexanoate as substrate as confirmed against the empty vector control (see FIG. 12), and synthesized N6-acetyl-6-aminohexanal.

Example 6

Enzyme Activity of ω-transaminase using N6-acetyl-1,6-diaminohexane, and Forming N6-acetyl-6-aminohexanal The activity of the N-terminal His-tagged ω-transaminases of SEQ ID NOs: 8-13 (see Example 4, and FIG. 20E and FIG. 20F) for converting N6-acetyl-1,6-diaminohexane to N6-acetyl-6-aminohexanal was assayed using a buffer composed of a final concentration of 50 mM HEPES buffer (pH=7.5), 10 mM N6-acetyl-1,6-diaminohexane, 10 mM pyruvate and 100 μM pyridoxyl 5' phosphate. Each enzyme activity assay reaction was initiated by adding a cell free extract of the ω-transaminase or the empty vector control to the assay buffer containing the N6-acetyl-1,6-diaminohexane then incubated at 25° C. for 4 h, with shaking at 250 rpm. The formation of L-alanine was quantified via RP-HPLC.

Each enzyme only control without N6-acetyl-1,6-diaminohexane demonstrated low base line conversion of pyruvate to L-alanine See FIG. 14.

Figure 18:
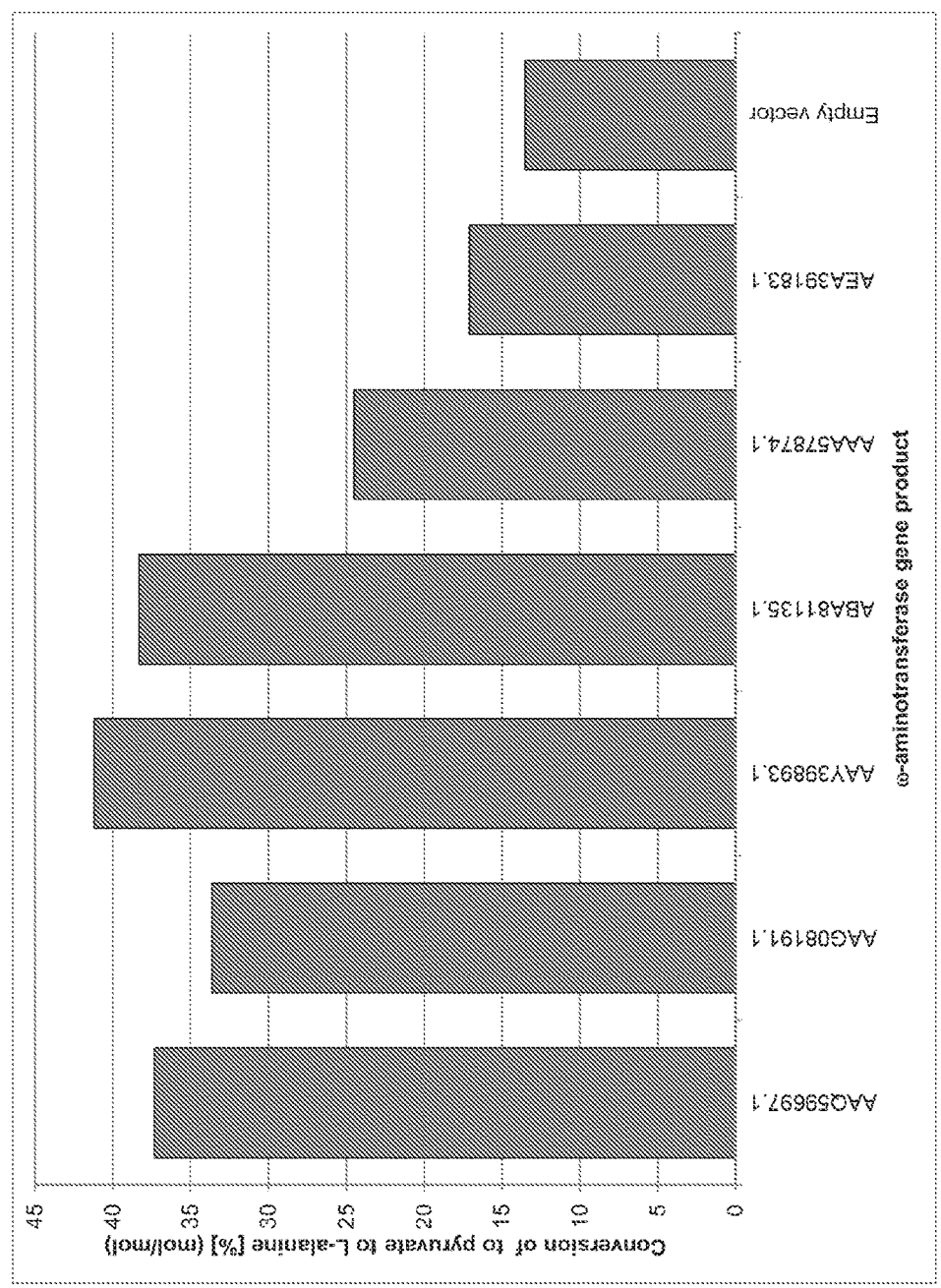
FIG. 18 is a bar graph of the percent conversion after 4 hours of pyruvate to L-alanine (mol/mol) as a measure of the ω-transaminase activity for converting N6-acetyl-1,6-diaminohexane to N6-acetyl-6-aminohexanal relative to the empty vector control.

The gene product of SEQ ID NO 8-13 accepted N6-acetyl-1,6-diaminohexane as substrate as confirmed against the empty vector control (see FIG. 18) and synthesized N6-acetyl-6-aminohexanal as reaction product.

Given the reversibility of the ω-transaminase activity (see example 1), the gene products of SEQ ID 8-13 accept N6-acetyl-6-aminohexanal as substrate forming N6-acetyl-1,6-diaminohexane.

Example 7

Enzyme Activity of Carboxylate Reductase Using Adipate Semialdehyde as Substrate and Forming Hexanedial The N-terminal His-tagged carboxylate reductase of SEQ ID NO 7 (see Example 2 and FIG. 20E) was assayed using adipate semialdehyde as substrate. The enzyme activity assay was performed in triplicate in a buffer composed of a final concentration of 50 mM HEPES buffer (pH=7.5), 2 mM adipate semialdehyde, 10 mM MgCl$_2$, 1 mM ATP and 1 mM NADPH. The enzyme activity assay reaction was initiated by adding purified carboxylate reductase and phosphopantetheine transferase or the empty vector control to the assay buffer containing the adipate semialdehyde and then incubated at room temperature for 20 min. The consumption of NADPH was monitored by absorbance at 340 nm. The enzyme only control without adipate semialdehyde demonstrated low base line consumption of NADPH. See FIG. 9.

Figure 13:
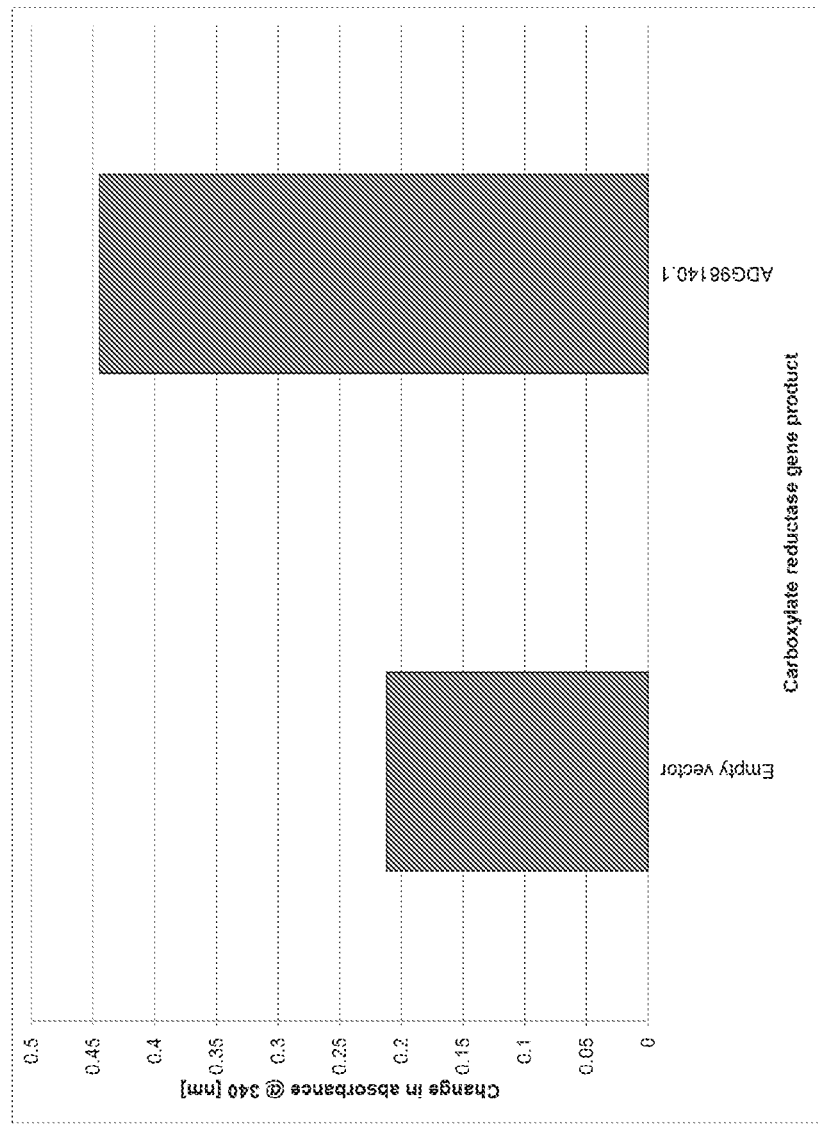
FIG. 13 is a bar graph of the change in absorbance at 340 nm after 20 minutes, which is a measure of the consumption of NADPH and activity of carboxylate reductases for converting adipate semialdehyde to hexanedial relative to the empty vector control.

The gene product of SEQ ID NO 7, enhanced by the gene product of sfp, accepted adipate semialdehyde as substrate as confirmed against the empty vector control (see FIG. 13) and synthesized hexanedial.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of biosynthesizing 2-aminopimelate in a recombinant host, the method comprising enzymatically converting 2,6-diaminopimelate to 2-aminopimelate using at least one polypeptide having an activity selected from 2-hydroxyacyl-CoA dehydratase activity, mutase activity, ammonia lyase activity, and enoate reductase activity, wherein said polypeptide having enoate reductase activity has at least 85% sequence identity to the amino acid sequence set forth in any one of SEQ ID NOs: 16-22, wherein said polypeptide having 2-hydroxyacyl-CoA dehydratase activity has at least 85% sequence identity to the amino acid sequence set forth in SEQ ID NO: 25 or SEQ ID NO: 28, wherein said polypeptide having mutase activity has at least 85% sequence identity to the amino acid sequence set forth in SEQ ID NO: 26, and wherein said polypeptide having ammonia lyase activity has at least 85% sequence identity to the amino acid sequence set forth in SEQ ID NO: 23, the method optionally further comprising using at least one polypeptide having an activity selected from diaminopimelate dehydrogenase activity, 2-hydroxycarboxylate dehydrogenase activity, CoA-transferase activity, and carboxylate reductase activity to enzymatically convert 2,6-diaminopimelate to 2-aminopimelate, wherein said polypeptide having diaminopimelate dehydrogenase activity is classified under EC 1.4.1.16, wherein said polypeptide having 2-hydroxycarboxylate dehydrogenase activity is classified under EC 1.1.1.337, wherein said polypeptide having CoA-transferase activity is classified under EC 2.8.3, and wherein said polypeptide having carboxylate reductase activity has at least 85% sequence identity to the amino acid sequence set forth in any one of SEQ ID NOs: 3-7.

2. The method of claim 1, wherein (S) 2-aminopimelate is biosynthesized.

3. The method of claim 1, said method comprising:
using said polypeptide having 2-hydroxyacyl-CoA dehydratase activity and said polypeptide having enoate reductase activity to enzymatically convert 2,6-diaminopimelate to 2-aminopimelate; or
using said polypeptide having mutase activity, said polypeptide having ammonia lyase activity, and said polypeptide having enoate reductase activity to enzymatically convert 2,6-diaminopimelate to 2-aminopimelate.

4. The method of claim 1, wherein (R) 2-aminopimelate is biosynthesized.

5. The method of claim 1, said method further comprising using at least one polypeptide having an activity selected from CoA ligase activity, CoA-transferase activity, carboxylate reductase activity, and aldehyde dehydrogenase activity to enzymatically convert 2,6-diaminopimelate to 2-aminopimelate, wherein said polypeptide having CoA ligase activity is classified under EC 6.2.1.5, wherein said polypeptide having CoA-transferase activity is classified under EC 2.8.3, wherein said polypeptide having carboxylate reductase activity has at least 85% sequence identity to the amino acid sequence set forth in any one of SEQ ID NOs: 3-7, and wherein said aldehyde dehydrogenase is classified under EC 1.2.1.-.

6. The method of claim 1, wherein the host is subjected to a cultivation strategy under aerobic or micro-aerobic cultivation conditions.

7. The method of claim 1, wherein the host is cultured under conditions of nitrogen, phosphate or oxygen limitation.

8. The method of claim 1, wherein the host is retained using a ceramic membrane to maintain a high cell density during fermentation.

9. The method of claim 1, further comprising a principal carbon source fed to the fermentation derived from a biological feedstock.

10. The method of claim 9, wherein the biological feedstock is or derives from monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

11. The method of claim 1, further comprising a principal carbon source fed to the fermentation derived from a non-biological feedstock.

12. The method of claim 11, wherein the non-biological feedstock is, or derives from, natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

13. The method of claim 1, wherein the host is a prokaryote selected from *Escherichia, Clostridia, Corynebacteria, Cupriavidus, Pseudomonas, Delftia, Bacillus, Lactobacillus, Lactococcus*, and *Rhodococcus*, or a eukaryote selected from *Aspergillus, Saccharomyces, Pichia, Yarrowia, Issatchenkia, Debaryomyces, Arxula*, and *Kluyveromyces*.

14. The method of claim 1, wherein the host exhibits tolerance to high concentrations of a C6 building block, and wherein the tolerance to high concentrations of a C6 building block is improved through continuous cultivation in a selective environment.

15. The method of claim 1, wherein the host comprises one or more of the following: the intracellular concentration of oxaloacetate for biosynthesis of a C6 building block is increased in the host by overexpressing recombinant genes forming oxaloacetate; wherein an imbalance in NADPH is generated that can be balanced via the formation of a C6 building block; wherein an exogenous lysine biosynthesis pathway synthesizing lysine from 2-oxoglutarate via 2-oxoadipate is introduced in a host using the meso 2,6 diaminopimelate pathway for lysine synthesis; wherein an exogenous lysine biosynthesis pathway synthesizing lysine from oxaloacetate to meso 2,6 diaminopimelate is introduced in a host using the 2-oxoadipate pathway for lysine synthesis; wherein endogenous degradation pathways of central metabolites and central precursors leading to and including C6 building blocks are attenuated in the host; or wherein the efflux of a C6 building block across the cell membrane to the extracellular media is enhanced or amplified by genetically engineering structural modifications to the cell membrane or increasing any associated transporter activity for a C6 building block.

16. A recombinant host cell comprising at least one exogenous nucleic acid encoding at least one polypeptide having an activity selected from 2-hydroxyacyl-CoA dehydratase activity, mutase activity, ammonia lyase activity, and enoate reductase activity, wherein said polypeptide having enoate reductase activity has at least 85% sequence identity to the amino acid sequence set forth in any one of SEQ ID NOs: 16-22, said polypeptide having 2-hydroxyacyl-CoA dehydratase activity has at least 85% sequence identity to the amino acid sequence set forth in SEQ ID NO: 25 or SEQ ID NO: 28, said polypeptide having mutase activity has at least 85% sequence identity to the amino acid sequence set forth in SEQ ID NO: 26, said polypeptide having ammonia lyase activity has at least 85% sequence identity to the amino acid sequence set forth in SEQ ID NO: 23, said host producing 2-aminopimelate from 2,6-diaminopimelate, the host optionally further comprising one or more exogenous polypeptides having an activity selected from aldehyde dehydrogenase activity, alcohol dehydrogenase activity, CoA-transferase activity, carboxylate reductase activity, α-aminotransferase activity, thioesterase activity, hydrolase activity, ω-transaminase activity, N-acetyltransferase activity, and deacylase activity, the host producing a product selected from adipic acid, adipate semialdehyde, 6-aminohexanoic acid, 6-hydroxyhexanoic acid, caprolactam, hexamethylenediamine, and 1,6-hexanediol, wherein said polypeptide having aldehyde dehydrogenase activity is classified under EC 1.2.1, wherein said polypeptide having alcohol dehydrogenase activity is classified under EC 1.1.1, wherein said polypeptide having CoA-transferase activity is classified under EC 2.8.3, wherein said polypeptide having carboxylate reductase activity has at least 85% sequence identity to the amino acid sequence set forth in any one of SEQ ID NOs: 3-7 wherein said polypeptide having α-aminotransferase activity classified under EC 2.6.1, wherein said polypeptide having thioesterase activity has at least 85% sequence identity to the amino acid sequence set forth in SEQ ID NO: 1 or SEQ ID NO: 2, wherein said polypeptide having hydrolase activity classified under EC 3.5.2, wherein said polypeptide having ω-transaminase activity has at least 85% sequence identity to the amino acid sequence set forth in any one of SEQ ID NOs: 8-13, wherein said polypeptide having N-acetyltransferase activity is classified under EC 2.3.1.32 and wherein said polypeptide having deacylase activity is classified under EC 3.5.1.17.

17. The host of claim 16, said host comprising said polypeptide having exogenous 2-hydroxyacyl-CoA dehydratase activity and said polypeptide having enoate reductase activity.

18. The host of claim 16, said host comprising said polypeptide having mutase activity, said polypeptide having ammonia lyase activity, and said polypeptide having enoate reductase activity.

19. The host of claim 16, said host further comprising at least one polypeptide having an activity selected from a) diaminopimelate dehydrogenase activity, 2-hydroxycarboxylate dehydrogenase activity, CoA-transferase activity, and carboxylate reductase activity, wherein said polypeptide having diaminopimelate dehydrogenase activity is classified under EC 1.4.1.16, wherein said polypeptide having 2-hydroxycarboxylate dehydrogenase activity is classified under EC 1.1.1.337, wherein said polypeptide having CoA-transferase activity is classified under EC 2.8.3, and wherein said polypeptide having carboxylate reductase activity has at least 85% sequence identity to the amino acid sequence set forth in any one of SEQ ID NOs: 3-7; or b) CoA ligase activity, CoA-transferase activity, carboxylate reductase activity, and aldehyde dehydrogenase activity, wherein said polypeptide having CoA ligase activity is classified under EC 6.2.1.5, wherein said polypeptide having CoA-transferase activity is classified under EC 2.8.3, wherein said polypeptide having carboxylate reductase activity has at least 85% sequence identity to the amino acid sequence set forth in any one of SEQ ID NOs: 3-7 and wherein said polypeptide having aldehyde dehydrogenase activity is classified under EC 1.2.1.

20. The host of claim 16, further comprising at least one exogenous polypeptide having an activity selected from 2-oxoacid decarboxylase activity classified under EC 4.1.1, α-aminoacid decarboxylase activity classified under EC 4.1.1, synthase activity, and activity of a dehydrogenase complex, wherein the polypeptide having 2-oxoacid decarboxylase activity is classified under EC 4.1.1.43. EC 4.1.1.71. EC 4.1.1.72, or EC 4.1.1.74 and has at least 85% sequence identity to the amino acid sequence set forth in SEQ ID NO: 34; the polypeptide having α-aminoacid decarboxylase activity is classified under EC 4.1.1.15, EC 4.1.1.17, or EC 4.1.1.18, or EC 4.1.1.19 and has at least 85% sequence identity to the amino acid sequence set forth in any one of SEQ ID NOs: 29-34; the polypeptide having synthase activity is classified under EC 2.2.1.6, or the polypeptide having the activity of a dehydrogenase complex comprises activities classified under EC 1.2.4.2 EC 1.8.1.4, or EC 2.3.1.61.

21. The host of claim 19, wherein the host cell further comprises at least one exogenous polypeptide having an activity selected from α-aminotransferase activity, 2-oxoacid decarboxylase activity, activity of a dehydrogenase complex, thioesterase activity, CoA-transferase activity, CoA-ligase activity, and aldehyde dehydrogenase activity, the host producing adipic acid, wherein said polypeptide having α-aminotransferase activity is classified under EC 2.6.1, wherein said polypeptide having 2-oxoacid decarboxylase activity has at least 85% sequence identity to the amino acid sequence set forth in SEQ ID NO: 34, wherein said polypeptide having the activity of a dehydrogenase complex is classified under EC 1.2.4.2, EC 1.8.1.4, or EC 2.3.1.61, wherein said polypeptide having thioesterase activity has at least 85% sequence identity to the amino acid sequence set forth in SEQ ID NO: 1 or SEQ ID NO: 2, wherein said polypeptide having CoA-transferase activity is classified under EC 2.8.3, wherein said polypeptide having CoA-ligase activity is classified under EC 6.2.1.5, and wherein said polypeptide having aldehyde dehydrogenase activity is classified under EC 1.2.1,
the host cell optionally further comprising at least one exogenous polypeptide having an activity selected from α-aminotransferase activity, 2-oxoacid decarboxylase activity, and synthase activity, the host producing adipate semialdehyde, wherein said polypeptide having α-aminotransferase activity is classified under EC 2.6.1-, wherein said polypeptide having 2-oxoacid decarboxylase activity has at least 85% sequence identity to the amino acid sequence set forth in SEQ ID NO: 34, and wherein said polypeptide having synthase activity is classified under EC 2.2.1.6.

22. The recombinant host of claim 16, wherein the host cell further comprises:
an exogenous polypeptide having α-aminoacid decarboxylase activity that has at least 85% sequence identity to the amino acid sequence set forth in any one of SEQ ID NOs: 29-34, the host producing 6-aminohexanoic acid; or
an exogenous ω-transaminase that has at least 85% sequence identity to the amino acid sequence set forth in any one of SEQ ID NOs: 8-13, the host producing 6-aminohexanoic acid;
the host cell optionally further comprising an exogenous polypeptide having hydrolase activity, wherein said polypeptide having hydrolase activity is classified under EC 3.5.2, the host producing caprolactam.

23. The recombinant host of claim 22, wherein the host cell further comprises one or more of an exogenous polypeptide having carboxylate reductase activity, N-acetyltransferase activity, ω-transaminase activity, or deacylase activity, the host producing hexamethylenediamine, wherein said polypeptide having carboxylate reductase activity has at least 85% sequence identity to the amino acid sequence set forth in any one of SEQ ID NOs: 3-7, wherein said polypeptide having N-acetyltransferase activity is classified under EC 2.3.1.32, wherein said polypeptide having ω-transaminase activity has at least 85% sequence identity to the amino acid sequence set forth in any one of SEQ ID NOs: 8-13, and wherein said polypeptide having deacylase activity is classified under EC 3.5.1.17.

24. The recombinant host of claim 21, wherein the host cell further comprises at least one exogenous polypeptide having carboxylate reductase activity and/or at least one exogenous polypeptide having r-transaminase activity, the host producing hexamethylenediamine, wherein said polypeptide having carboxylate reductase activity has at least 85% sequence identity to the amino acid sequence set forth in any one of SEQ ID NOs: 3-7 and wherein said polypeptide having ω-transaminase activity has at least 85% sequence identity to the amino acid sequence set forth in any one of SEQ ID NOs: 8-13.

25. The recombinant host of claim 16, wherein the host cell further comprises at least one exogenous polypeptide having an activity selected from α-aminotransferase activity, 2-oxoacid decarboxylase activity, alcohol dehydrogenase activity, and synthase activity, the host producing 6-hydroxyhexanoic acid, wherein said polypeptide having α-aminotransferase activity is classified under EC 2.6.1, wherein said polypeptide having 2-oxoacid decarboxylase activity has at least 85% sequence identity to the amino acid sequence set forth in SEQ ID NO: 34, wherein said polypeptide having alcohol dehydrogenase activity is classified under EC 1.1.1, and wherein said polypeptide having synthase activity is classified under EC 2.2.1.6, the host cell optionally further comprising:
at least one exogenous polypeptide having an activity selected from carboxylate reductase activity, ω-transaminase activity, and alcohol dehydrogenase activity, the host producing hexamethylenediamine, wherein said polypeptide having carboxylate reductase activity has at least 85% sequence identity to the amino acid sequence set forth in any one of SEQ ID NOs: 3-7, wherein said polypeptide having cg-transaminase activity has at least 85% sequence identity to the amino acid sequence set forth in any one of SEQ ID NOs: 8-13 and wherein said polypeptide having alcohol dehydrogenase activity is classified under EC 1.1.1; or an exogenous polypeptide having carboxylate reductase activity and/or an exogenous polypeptide having alcohol dehydrogenase activity, the host producing 1,6-hexanediol, wherein said polypeptide having carboxylate reductase activity has at least 85% sequence identity to the amino acid sequence set forth in any one of SEQ ID NOs: 3-7 and wherein said polypeptide having alcohol dehydrogenase activity is classified under EC 1.1.1.

26. A method of biosynthesizing 2-aminopimelate in a recombinant host, the method comprising enzymatically converting 2,6-diaminopimelate to 2-aminopimelate using at least one polypeptide selected from a polypeptide having the activity of an enoate reductase, classified under EC 1.3.1.31 or EC 1.6.99.1, or having at least 85% sequence identity to the amino acid sequence set forth in any one of SEQ ID NOs: 16-22; a polypeptide having the activity of a 2-hydroxyacyl-CoA dehydratase, classified under EC 4.2.1, or having at least 85% sequence identity to the amino acid sequence set forth in SEQ ID NO: 25 or SEQ ID NO: 28; a polypeptide having the activity of a mutase, classified under EC 5.4.3.2, or having at least 85% sequence identity to the amino acid sequence set forth in SEQ ID NO: 26; and a polypeptide having the activity of an ammonia lyase, classified under EC 4.3.1.14, or having at least 85% sequence identity to the amino acid sequence set forth in SEQ ID NO: 23, the method optionally further comprising using at least one polypeptide selected from a polypeptide having the activity of a diaminopimelate dehydrogenase or classified under EC 1.4.1.16; a polypeptide having the activity of a CoA-transferase, classified under EC 2.8.3, classified under EC 2.8.3.12, or having at least 85% sequence identity to the amino acid sequence of the gene product of thnH or gctAB; and a polypeptide having the activity of a carboxylate reductase, classified under EC 1.2.99.6, having at least 85% sequence identity to the amino acid sequence set forth in any one of SEQ ID NOs: 5-7, having at least 85% sequence identity to the amino acid sequence of the gene product of car and npt, or having at least 85% sequence identity to the amino acid sequence of the gene product of griC and griD.

27. The method of claim 26, wherein (S) 2-aminopimelate is biosynthesized.

28. The method of claim 26, said method comprising:
using said polypeptide having the activity of a 2-hydroxyacyl-CoA dehydratase, classified under EC 4.2.1, or having at least 85% sequence identity to the amino acid sequence set forth in SEQ ID NO: 25 or SEQ ID NO: 28 and said polypeptide having the activity of an enoate reductase, classified under EC 1.3.1.31 or EC 1.6.99.1, or having at least 85% sequence identity to the amino acid sequence set forth in any one of SEQ ID NOs: 16-22 to enzymatically convert 2,6-diaminopimelate to 2-aminopimelate; or using said a polypeptide having the activity of a mutase, classified under EC 5.4.3.2, or having at least 85% sequence identity to the amino acid sequence set forth in SEQ ID NO: 26, said polypeptide having the activity of an ammonia lyase, classified under EC 4.3.1.14, or having at least 85% sequence identity to the amino acid sequence set forth in SEQ ID NO: 23, and said polypeptide having the activity of an enoate reductase, classified under EC 1.3.1.31 or EC 1.6.99.1, or having at least 85% sequence identity to the amino acid sequence set forth in any one of SEQ ID NOs: 16-22 to enzymatically convert 2,6-diaminopimelate to 2-aminopimelate.

29. The method of claim 26, wherein (R) 2-aminopimelate is biosynthesized.

30. The method of claim 26, said method further comprising using at least one polypeptide selected a polypeptide having the activity of a CoA ligase, having the activity of a succinate-CoA ligase, or classified under EC 6.2.1.5, a polypeptide having the activity of a CoA-transferase, having the activity of a glutaconate CoA-transferase, classified under EC 2.8.3, classified under EC 2.8.3.12, having at least 85% sequence identity to the amino acid sequence of the gene product of thnH, or having at least 85% sequence identity to the amino acid sequence of the gene product of gctAB; a polypeptide having the activity of a carboxylate reductase, classified under EC 1.2.99.6, having at least 85% sequence identity to the amino acid sequence set forth in any one of SEQ ID NOs: 5-7, having at least 85% sequence identity to the amino acid sequence of the gene product of car and npt, or having at least 85% sequence identity to the amino acid sequence of the gene product of griC and griD, and a polypeptide having the activity of an aldehyde dehydrogenase, classified under EC 1.2.1, or classified under EC 1.2.1.3, EC 1.2.1.16, EC 1.2.1.20, EC 1.2.1.63, or EC 1.2.1.79 to enzymatically convert 2,6-diaminopimelate to 2-aminopimelate.

31. The method of claim 26, wherein the host comprises one or more of the following: the intracellular concentration of oxaloacetate for biosynthesis of a C6 building block is increased in the host by overexpressing recombinant genes forming oxaloacetate; wherein an imbalance in NADPH is generated that can be balanced via the formation of a C6 building block; wherein an exogenous lysine biosynthesis pathway synthesizing lysine from 2-oxoglutarate via 2-oxoadipate is introduced in a host using the meso 2,6 diaminopimelate pathway for lysine synthesis; wherein an exogenous lysine biosynthesis pathway synthesizing lysine from oxaloacetate to meso 2,6 diaminopimelate is introduced in a host using the 2-oxoadipate pathway for lysine synthesis; wherein endogenous degradation pathways of central metabolites and central precursors leading to and including C6 building blocks are attenuated in the host; or wherein the efflux of a C6 building block across the cell membrane to the extracellular media is enhanced or amplified by genetically engineering structural modifications to the cell membrane or increasing any associated transporter activity for a C6 building block.

32. The method of claim 26, said method comprising enzymatically converting 2,6-diaminopimelate to 2-aminopimelate using at least one polypeptide selected from: a polypeptide classified under EC 1.3.1.31 or EC 1.6.99.1; a polypeptide classified under EC 4.2.1; a polypeptide classified under EC 5.4.3.2; and a polypeptide classified under EC 4.3.1.14, the method optionally further comprising using at least one polypeptide selected from: a polypeptide classified under EC 1.4.1.16, a polypeptide classified under EC 2.8.3, and a polypeptide classified under EC 1.2.99.6.

33. The method of claim 26, said method comprising:
using said polypeptide classified under EC 4.2.1 and said polypeptide classified under EC 1.3.1.31 or EC 1.6.99.1 to enzymatically convert 2,6-diaminopimelate to 2-aminopimelate; or
using said polypeptide classified under EC 5.4.3.2, said polypeptide classified under EC 4.3.1.14, and said polypeptide classified under EC 1.3.1.31 or EC 1.6.99.1 to enzymatically convert 2,6-diaminopimelate to 2-aminopimelate.

34. The method of claim 26, said method further comprising using at least one polypeptide selected from a polypeptide classified under EC 6.2.1.5; a polypeptide classified under EC 2.8.3; a polypeptide classified under EC 1.2.99.6, and a polypeptide classified under EC 1.2.1 to enzymatically convert 2,6-diaminopimelate to 2-aminopimelate.

* * * * *

UNITED STATES PATENT AND TRADEMARK OFFICE
CERTIFICATE OF CORRECTION

| | |
|---|---|
| PATENT NO. | : 9,745,607 B2 |
| APPLICATION NO. | : 14/714164 |
| DATED | : August 29, 2017 |
| INVENTOR(S) | : Alex Van Eck Conradie et al. |

Page 1 of 1

It is certified that error appears in the above-identified patent and that said Letters Patent is hereby corrected as shown below:

On the Title Page

Item (71), Line 1, "INVISTA North America S.á r.l.," should read --INVISTA North America S.á.r.l.,--.

Item (74) Attorney, Agent, or Firm, "Finnegan Henderson, Farabow, Garrett & Dunner, LLP; Carla A. Mouta-Bellum" should read --William J. Simmons; Carla A. Mouta-Bellum, Ph.D.--.

In the Claims

Claim 20, Column 137, Line 30, "EC 4.1.1.43." should read as --EC 4.1.1.43,--.

Claim 20, Column 137, Line 31, "4.1.1.71." should read as --4.1.1.71,--.

Claim 20, Column 137, Line 40, "EC 1.2.4.2 EC 1.8.1.4," should read as --EC 1.2.4.2, EC 1.8.1.4,--.

Claim 24, Column 138, Line 39, "r-transaminase" should read as --ω- transaminase--.

Claim 25, Column 139, Line 1, "cg-transaminase" should read as --ω- transaminase--.

Signed and Sealed this
Nineteenth Day of December, 2017

Joseph Matal
*Performing the Functions and Duties of the
Under Secretary of Commerce for Intellectual Property and
Director of the United States Patent and Trademark Office*